United States Patent
Metcalf et al.

(10) Patent No.: US 11,832,601 B2
(45) Date of Patent: Dec. 5, 2023

(54) CYTOPLASMIC INCOMPATIBILITY FACTORS AND METHODS FOR CONTROLLING ANTHROPODS

(71) Applicants: VANDERBILT UNIVERSITY, Nashville, TN (US); YALE UNIVERSITY, New Haven, CT (US)

(72) Inventors: Jason Metcalf, Dexter, MI (US); Seth R. Bordenstein, Nashville, TN (US); Daniel Lepage, Centertown, MO (US); Sarah Bordenstein, Nashville, TN (US); Mark Hochstrasser, Hamden, CT (US); John F. Beckmann, New Haven, CT (US); Judith Ronau, Hamden, CT (US)

(73) Assignees: VANDERBILT UNIVERSITY, Nashville, TN (US); YALE UNIVERSITY, New Haven, CT (US)

( * ) Notice: Subject to any disclaimer, the term of this patent is extended or adjusted under 35 U.S.C. 154(b) by 0 days.

(21) Appl. No.: 16/307,982

(22) PCT Filed: Jun. 9, 2017

(86) PCT No.: PCT/US2017/036693
§ 371 (c)(1),
(2) Date: Dec. 7, 2018

(87) PCT Pub. No.: WO2017/214476
PCT Pub. Date: Dec. 14, 2017

(65) Prior Publication Data
US 2019/0216064 A1   Jul. 18, 2019

Related U.S. Application Data

(60) Provisional application No. 62/347,818, filed on Jun. 9, 2016.

(51) Int. Cl.
| | | |
|---|---|---|
| A01K 67/033 | (2006.01) |
| C12N 15/87 | (2006.01) |
| C12N 1/20 | (2006.01) |
| C07K 14/195 | (2006.01) |
| C12N 9/22 | (2006.01) |
| C12N 9/64 | (2006.01) |
| C12R 1/01 | (2006.01) |

(52) U.S. Cl.
CPC ...... *A01K 67/0337* (2013.01); *A01K 67/0339* (2013.01); *C07K 14/195* (2013.01); *C12N 1/205* (2021.05); *C12N 9/22* (2013.01); *C12N 9/6472* (2013.01); *C12N 15/87* (2013.01); *A01K 2217/052* (2013.01); *A01K 2217/206* (2013.01); *A01K 2227/706* (2013.01); *A01K 2267/02* (2013.01); *C07K 2319/21* (2013.01); *C12R 2001/01* (2021.05)

(58) Field of Classification Search
CPC .................................................. A01K 67/0337
See application file for complete search history.

(56) References Cited

U.S. PATENT DOCUMENTS

| 7,868,222 B1 | 1/2011 | Dobson |
| 2009/0042249 A1 | 2/2009 | Lubys |
| 2013/0209405 A1 | 8/2013 | Curtiss et al. |

FOREIGN PATENT DOCUMENTS

| WO | 2005042751 | 5/2005 | |
| WO | WO-2005042751 A1 * | 5/2005 | ......... C12N 15/8279 |
| WO | 2006008652 | 1/2006 | |

OTHER PUBLICATIONS

Beckmann et al. (2013, Insect Biochem. Mol. Biol., vol. 43, pp. 867-878) (Year: 2013).*
Chen et al. (2019, PNAS, vol. 116(44), pp. 22314-22321) (Year: 2019).*
Cini et al. (2014, J. Pest Sci., vol. 87, pp. 559-566) (Year: 2014).*
Klasson et al. (2008, Mol. Biol., Evol., vol. 25(9), pp. 1877-1887) (Year: 2008).*
International Preliminary Report on Patentability dated Dec. 20, 2018, from International Application No. PCT/US2017/036693, 11 pages.
International Search Report and Written Opinion dated Nov. 8, 2017, from International Application No. PCT/US2017/036693, 18 pages.
Beckmann, J.F. et al. "Detection of the Wolbachia Protein WPIP0282 in Mosquito Spermathecae: Implications for Cytoplasmic Incompatibility", Insect Biochem Mol Biol., Sep. 2013, 43(9), pp. 867-878.
Nikoh, N. et al. "Evolutionary origin of insect—Wolbachia nutritional mutualism", PNAS, Jul. 15, 2014, vol. 111, No. 28, pp. 10257-10262.
Beckmann, J.F. et al. "A Wolbachia Deubiquitylating Enzyme Induces Cytoplasmic Incompatibility", Nat Microbiol, 2:17007, 2017.
Rice, K.C. et al. "The *Staphylococcus aureus* cidAB Operon: Evaluation of Its Role in Regulation of Murein Hydrolase Activity and Penicillin Tolerance", Journal of Bacteriology, Apr. 2003, vol. 185, No. 8, pp. 2635-2643.

(Continued)

*Primary Examiner* — Anoop K Singh
*Assistant Examiner* — David A Montanari
(74) *Attorney, Agent, or Firm* — Meunier Carlin & Curfman LLC

(57) ABSTRACT

The disclosure relates to genetically modified bacteria, genetically modified arthropods, and methods for controlling and/or reducing arthropod populations.

4 Claims, 26 Drawing Sheets
Specification includes a Sequence Listing.

(56) References Cited

OTHER PUBLICATIONS

Hawkes, D.B. et al. "Cytochrome P450cin (CYP176A), Isolation, Expression, and Characterization", The Journal of Biological Chemistry, May 16, 2002, vol. 277, No. 31, pp. 27725-27732.

Makarova, K.S. et al. "Prokaryotic Homologs of Argonaute Proteins are Predicted to Function as Key Components of a Novel System of Defense Against Mobile Genetic Elements", Biology Direct, Aug. 25, 2009, vol. 4, No. 29, pp. 1-15.

Sutton, E.R. et al. "Comparative genome analysis of Wolbachia strain wAu", BMC Genomics 2014, 15:928, 15 pages.

Beckmann, J. F., Markowski, T. W., Witthuhn, B. A., & Fallon, A. M. (2013). Detection of the Wolbachia-encoded DNA binding protein, HU beta, in mosquito gonads. Insect biochemistry and molecular biology, 43(3), 272-279.

Pinto, S. B., Stainton, K., Harris, S., Kambris, Z., Sutton, E. R., Bonsall, M. B., Parkhill, J., & Sinkins, S. P. (2013). Transcriptional regulation of Culex pipiens mosquitoes by Wolbachia influences cytoplasmic incompatibility. PLoS pathogens, 9(10), e1003647.

Walker, T., Klasson, L., Sebaihia, M., Sanders, M. J., Thomson, N. R., Parkhill, J., & Sinkins, S. P. (2007). Ankyrin repeat domain-encoding genes in the wPip strain of Wolbachia from the Culex pipiens group. BMC biology, 5, 39.

Yamada, R., Iturbe-Ormaetxe, I., Brownlie, J.C. and O'Neill, S.L. (2011), Functional test of the influence of Wolbachia genes on cytoplasmic incompatibility expression in *Drosophila melanogaster*. Insect Molecular Biology, 20: 75-85.

\* cited by examiner a WD0631-like % aa identity

|        | WORiB | WORiC | WOHa1 | wNo |
|--------|-------|-------|-------|-----|
| WOMelB | 99    | 46    | 67    | 31  |
| WORiB  |       | 46    | 68    | 31  |
| WORiC  |       |       | 44    | 33  |
| WOHa1  |       |       |       | 31  |

WD0632-like % aa identity

|        | WORiB | WORiC | WOHa1 | wNo |
|--------|-------|-------|-------|-----|
| WOMelB | 99    | 30    | 62    | 29  |
| WORiB  |       | 30    | 62    | 29  |
| WORiC  |       |       | 31    | 36  |
| WOHa1  |       |       |       | 30  | b

| Strain | CI Type | Phage | Gene 1 | Gene 2 | Type |
|--------|---------|-------|--------|--------|------|
| wMel | Weak CI | WOMelB | WD0631 | WD0632 (Peptidase_C48) | Type I |
| wRi | Strong CI | WORiB | wRi_005370 | wRi_p05380 | Type I |
| wRi | Strong CI | WORiB | wRi_010030 | wRi_p10040 | Type I |
| wRi | Strong CI | WORiC | wRi_006720 | wRi_006710 | Type II |
| wHa | Strong CI | WOHa1 | wHa_02700 | wHa_02690 | Type I |
| wHa | Strong CI | WOHa1* | wHa_02280 | wHa_02270 | Type I |
| wNo | Intermediate CI | wNo | wNo_01990 (Cytochrome C552) | wNo_01980 (DUF 1703, TM) | Type III |

FIGURE 7 a
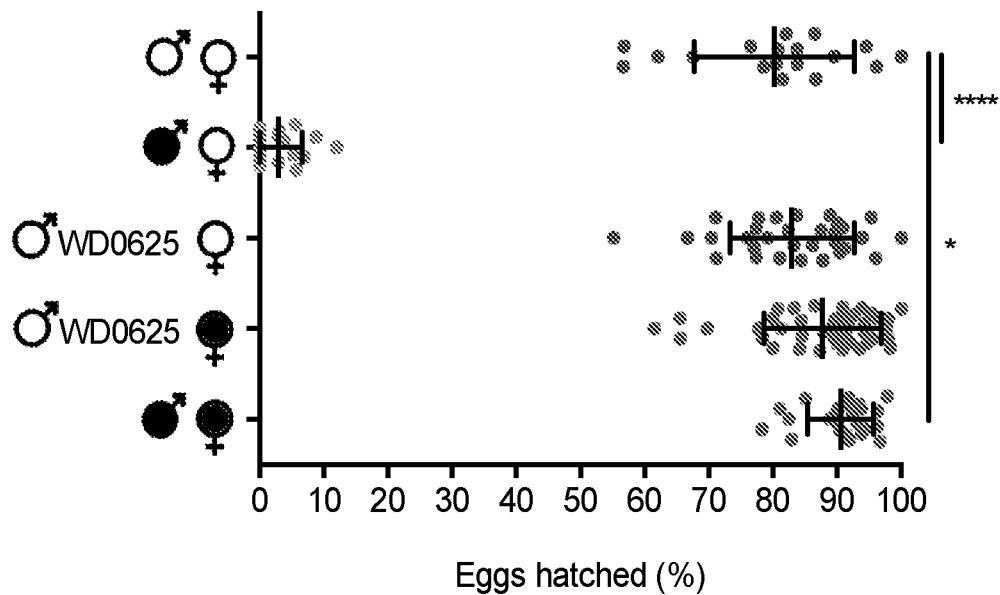
b
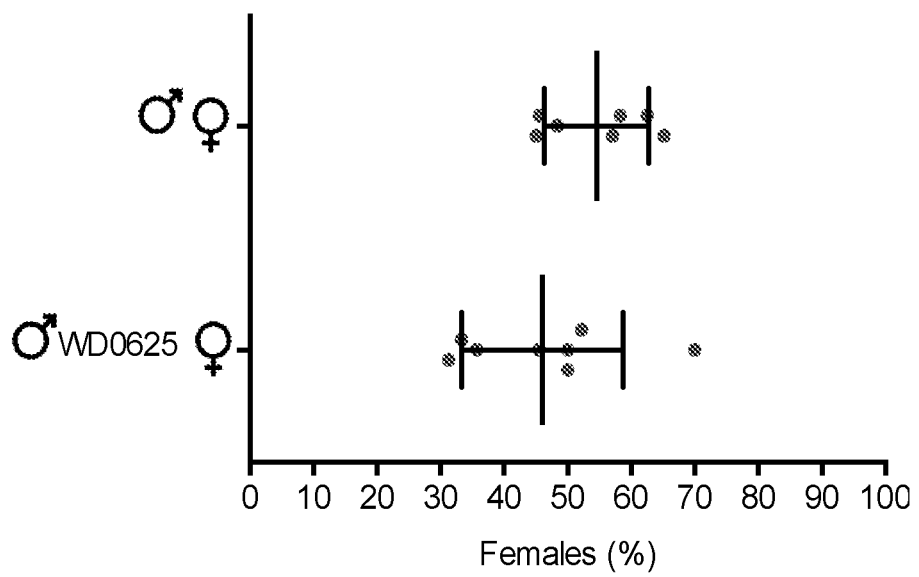
FIGURE 9

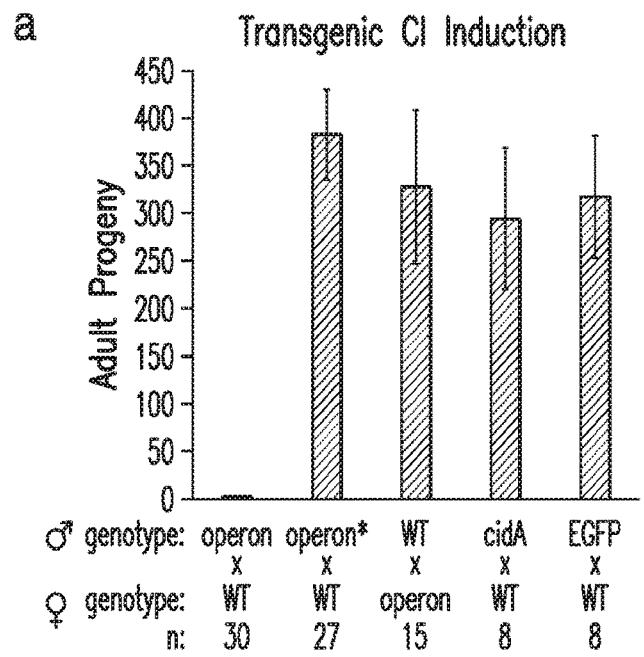
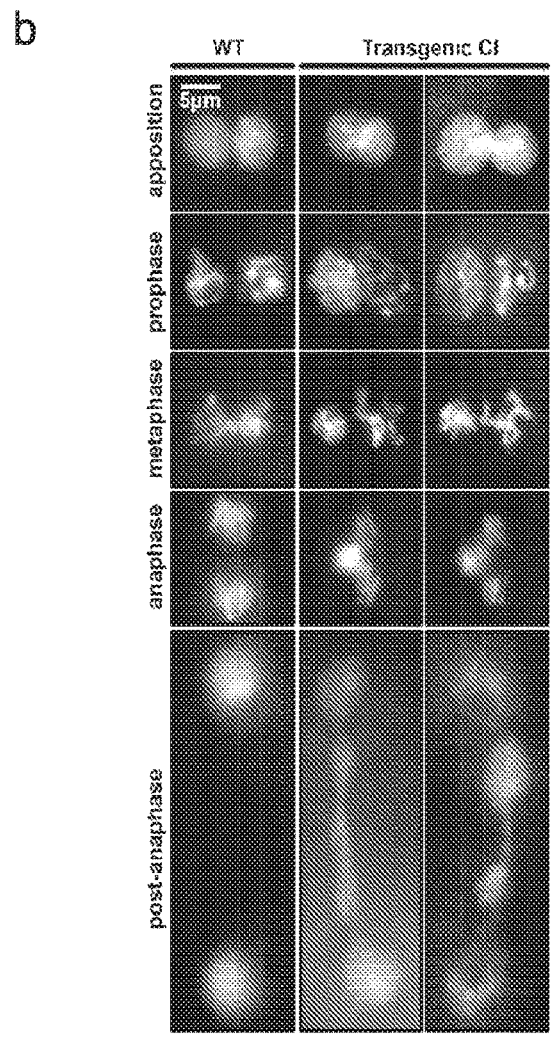
FIGURE 18

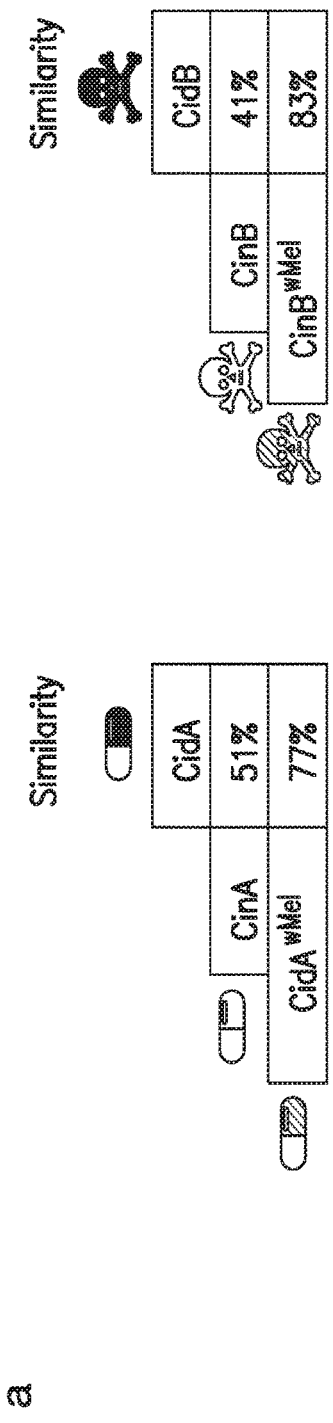
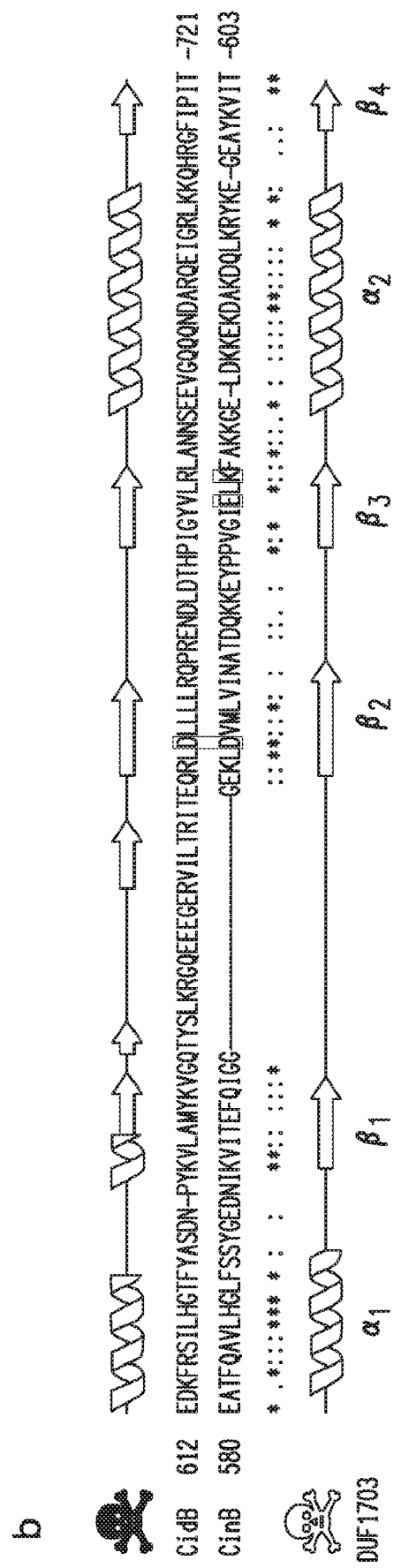
FIGURE 19

US 11,832,601 B2

CYTOPLASMIC INCOMPATIBILITY FACTORS AND METHODS FOR CONTROLLING ANTHROPODS

CROSS REFERENCE TO RELATED APPLICATIONS

This application is a national stage application filed under 35 U.S.C. § 371 of PCT/US2017/036693 filed Jun. 9, 2017, which claims the benefit of U.S. Provisional Patent Application Ser. No. 62/347,818 filed Jun. 9, 2016, which are is expressly incorporated herein by reference.

STATEMENT REGARDING FEDERALLY SPONSORED RESEARCH

This invention was made with government support under HD086833, GM007347, AI081322, DK020593, CA068485, GM053756, DK058404, DK059637 and EY008126 awarded by the National Institutes of Health, under 2014-67012-22268 awarded by the United States Department of Agriculture and under 1456778 and 1501398 awarded by the National Science Foundation. The Government has certain rights in the invention.

FIELD

The disclosure relates to genetically modified bacteria, genetically modified arthropods, and methods for controlling and/or reducing arthropod populations.

BACKGROUND

The genus *Wolbachia* is an archetype of maternally inherited intracellular bacteria that infect the germline of millions of invertebrate species worldwide and parasitically alter arthropod sex ratios and reproductive strategies to increase the proportion of infected females (the transmitting sex) in the population. The most common of these reproductive manipulations is cytoplasmic incompatibility (CI), typically expressed as embryonic lethality in crosses between infected males and uninfected females. This lethality is completely rescued by females infected with the same or a similar *Wolbachia* strain.

Cytoplasmic incompatibility (CI) has important applications in disease vector control, and is currently being used in field trials to drive the spread of Dengue-resistant mosquitoes in wild populations through the release of *Wolbachia*-infected females, and as a biological control mechanism to depress mosquito populations by releasing *Wolbachia*-infected males incompatible with wild females. Despite more than 40 years of research, the genes by which *Wolbachia* cause CI remain unknown.

SUMMARY

Disclosed herein are genetically modified bacteria and genetically modified arthropods useful for controlling and/or reducing populations of arthropods (for example, insects). For the first time, the inventors have identified the genes that encode the cytoplasmic incompatibility factors capable of reproducing the phenomena of cytoplasmic incompatibility. These genes are used to genetically modify bacteria and/or arthropods in order to produce sterile male arthropods and/or to replace a population of target arthropods.

In one aspect, provided herein is a genetically modified arthropod, said arthropod comprising:
 a bacterial operon encoding a cytoplasmic incompatibility factor or a variant thereof; and
 a promoter operably linked to the bacterial operon;
 wherein the expression of the cytoplasmic incompatibility factor in a male arthropod causes a reduction in viable offspring in comparison to a male arthropod lacking the cytoplasmic incompatibility factor.

In another aspect, provided herein is a method for controlling a population of target arthropods, comprising:
 providing a bacterial operon encoding a cytoplasmic incompatibility factor or a variant thereof, and a promoter operably linked to the bacterial operon;
 transforming a population of male arthropods with the bacterial operon; and
 releasing the male arthropods amongst a population of target arthropods, wherein the release of the male arthropods reduces the population of target arthropods.

In one aspect, provided herein is a genetically modified bacterium comprising:
 a bacterial operon encoding a cytoplasmic incompatibility factor or a variant thereof; and
 a promoter operably linked to the bacterial operon;
 wherein the bacterial operon occurs at a non-naturally occurring genomic location in the bacterium.

In another aspect, provided herein is an arthropod infected with a bacterium, wherein the bacterium comprises:
 a bacterial operon encoding a cytoplasmic incompatibility factor or a variant thereof; and
 a promoter operably linked to the bacterial operon;
 wherein the bacterial operon occurs at a non-naturally occurring genomic location in the bacterium.

In an additional aspect, provided herein is a method for controlling a population of target arthropods, comprising:
 providing a genetically modified bacterium comprising:
  a bacterial operon encoding a cytoplasmic incompatibility factor or a variant thereof, and
  a promoter operably linked to the bacterial operon;
 infecting a population of replacement arthropods with the genetically modified bacterium; and
 releasing the replacement arthropods amongst a population of target arthropods, wherein the release of the replacement arthropods reduces the population of target arthropods.

BRIEF DESCRIPTION OF THE DRAWINGS

The accompanying figures, which are incorporated in and constitute a part of this specification, illustrate several aspects described below.

FIG. 7. *Wolbachia* CI patterns correlate with WD0631/WD0632 operon similarity and copy number. (a) The % amino acid (aa) identity between homologs for each cif protein correlates with *Wolbachia* compatibility patterns. The only compatible cross, wMel males×wRi females, features a shared operon between WOMelB and WORiB. All other crosses are greater than 30% divergent and are bidirectionally incompatible. Each "% aa identity" value is based on the region of query coverage in a 1:1 BLASTp analysis. (b) CI strength, protein architecture and operon type are listed for each of the *Wolbachia* strains shown in FIG. 1*d*. (*) indicates the proteins are disrupted and not included in comparison analyses.

FIG. 9. WD0625 expression does not induce CI. Expression of WD0625 in uninfected males does not affect egg hatch rates (a) or sex ratios (b). Error bars indicate standard deviation. *=$P<0.05$, ***=$P<0.001$ by ANOVA with Kruskal-Wallis test and Dunn's multiple test correction.

FIG. 18. Induction of CI by transgenic cidA-cidB. a. *D. melanogaster* males carrying transgenic cidA-cidB are sterile when mated to WT (WCS) females (n=30). Males with transgenic cidA-cidB*harboring a CidB active-site mutation C1025A (operon*) are fully fertile (n=27). Females with the transgenic operon are fertile. CidA by itself has no effect on fertility, while no strain singly transgenic for cidB could be isolated. EGFP is a negative control. Error bars are standard deviations. b. CI-like defects in the male pronucleus initially appear in late prophase, during the first division of the apposed female and male pronuclei, and accrue through mitosis.

FIG. 19. Homology analysis of putative toxins and antidotes. a. Percent similarity using BLAST of the wPip CidA antidote and CidB toxin as queries against other antidotes and toxins. DUB-based operons from wPip and wMel *Wolbachia* strains share higher similarity and are more closely related than they are to the nuclease-type operon from wPip. b. Secondary structure predictions by Psipred shows an underlying conserved architecture between CidB and CinB. Both toxins show a homologous αββββαβ fold characteristic of the predicted DUF1703 nuclease. However, only CinB maintains a complete catalytic D-E-K triad (black boxes), and in CidB the αββββαβ fold is interrupted by an insertion. In CidB this nuclease-like fold is N-terminal to the additional DUB catalytic domain (FIG. 15c, dotted lines). This evidence is consistent with a duplication and divergence from a common CinB-like ancestral operon.

Lanes 1, 2 and 3 are His6-CidA, His6-CidB, and His6-CidA-CidB (full operon), respectively. b. Western blot analysis verifying that the co-pelleted species is CidB. CidB is C-terminally FLAG-tagged in lanes 4 and 6. c. His6 pull-downs show interactions of CinA to CinB. Lanes 1, 2 and 3 are His6-CinA, His6-CinB, and His6-CinA-CinB (full operon), respectively. d. Western blot analysis verifying that the co-pelleted species is CinB. FLAG tags are analogous to panel b.

Figure 22:
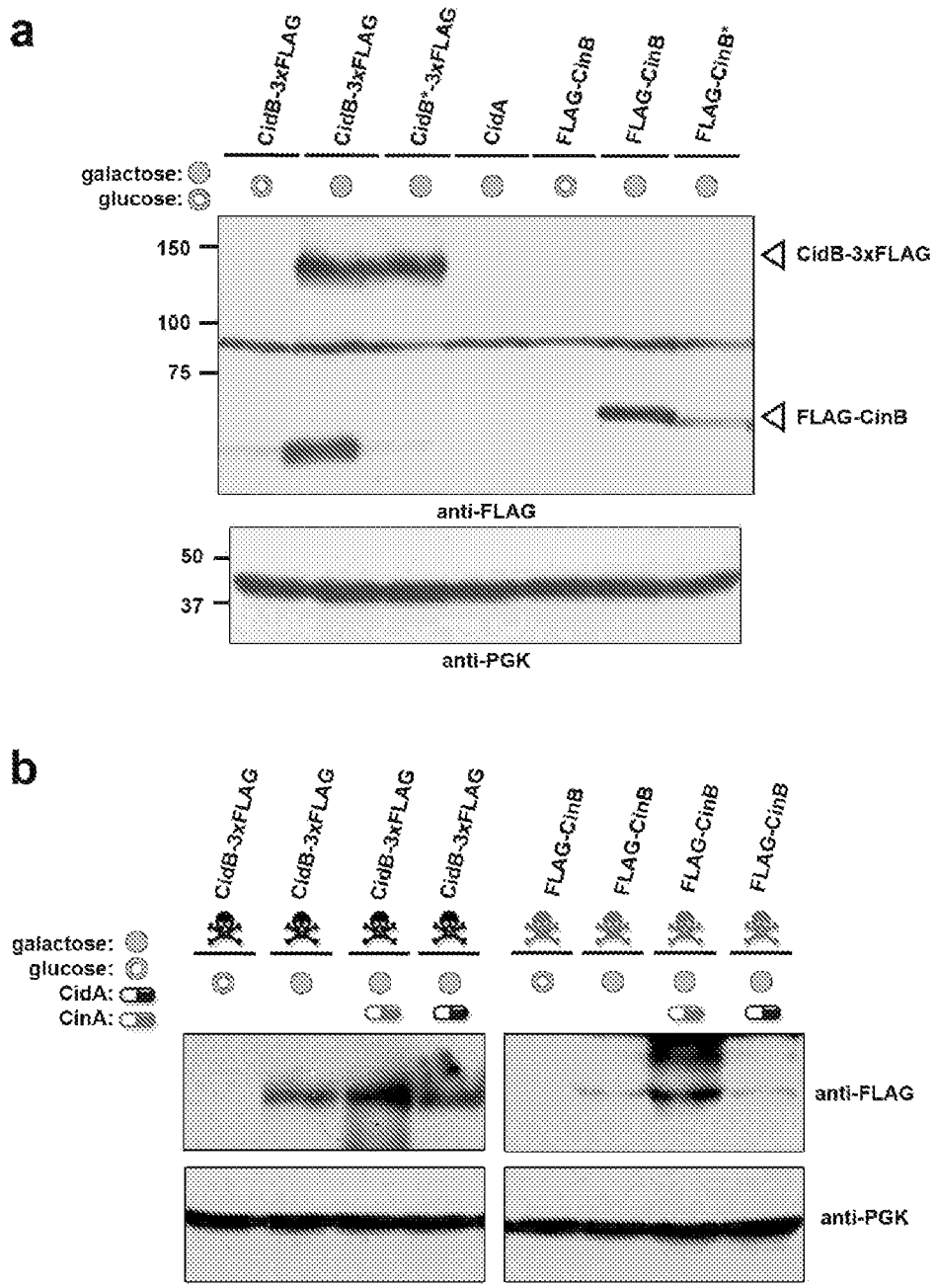

FIG. 22. Yeast heterologous protein expression controls. A. Western immunoblotting of FLAG-tagged CidB and CinB proteins expressed from the yeast 2-micron plasmid pYES2 (GAL1 promoter). Closed green circles indicate 2% galactose (induced) in the growth medium, open green circles, 2% glucose (repressed). CinB and the catalytically inactivated CidB* (C1025A) are expressed at similar levels. The catalytically inactivated mutant (D614A; E634A; K636A), CinB*, does appear to be expressed at lower levels, and this could account at least in part for decreased toxicity. However, when CinB was expressed from a low-copy (CEN) expression plasmid (FIG. 22b), the protein level is lower than CinB* expression from the high-copy vector, yet toxicity was still observed for CinB. This suggests that enzyme inactivation, rather than reduced protein amount, caused the reduced toxicity of the inactive nuclease. b. Western blotting of FLAG-tagged CidB and CinB proteins expressed from the low-copy pRS416 (GAL1) plasmid. Genes for the co-expressed putative antidotes were cloned into the high-copy 2-micron pRS425 (GAL1) vector. PGK is a loading control.

Figure 23:
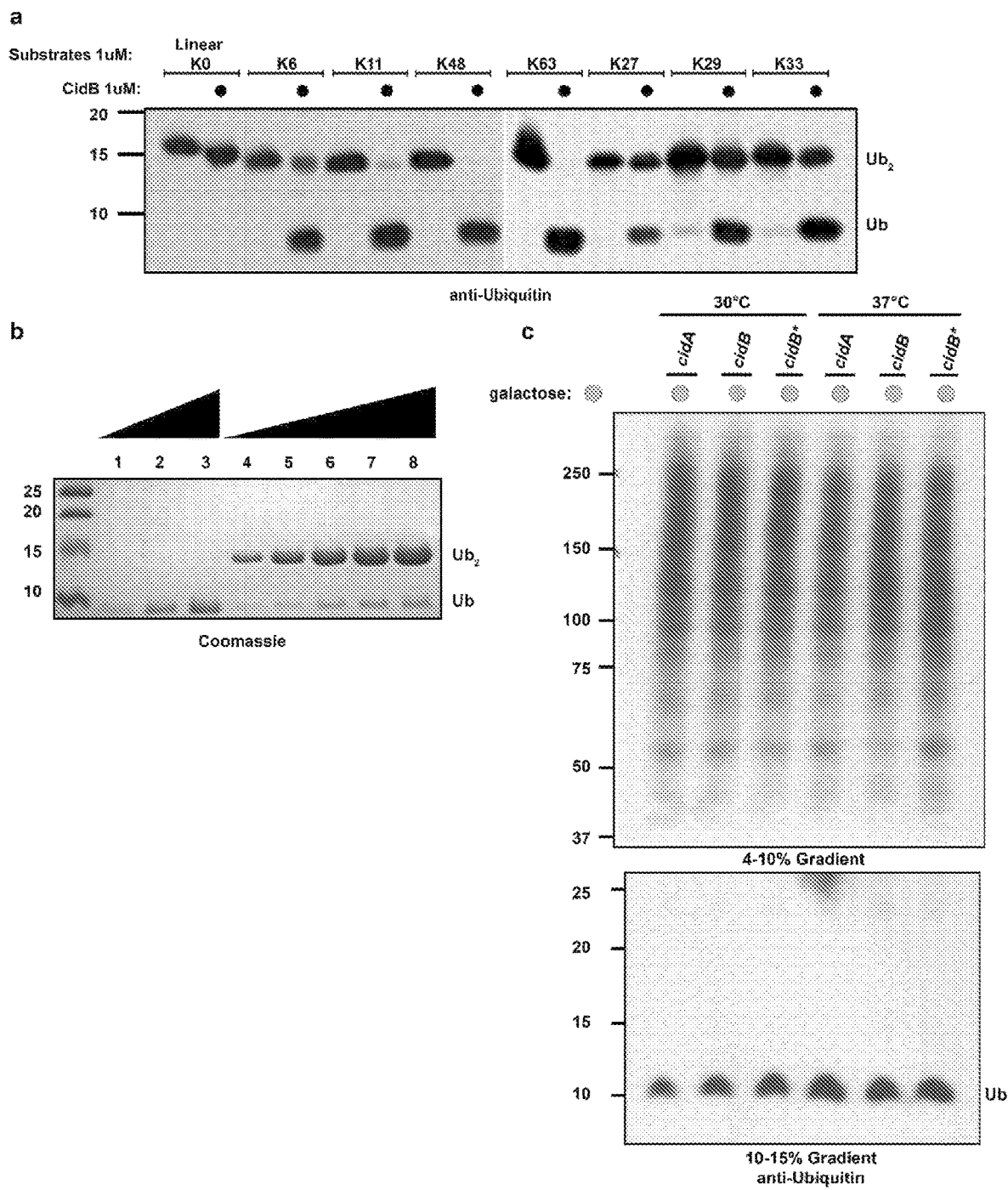

FIG. 23. Cleavage of ubiquitin dimers. a. Full length CidB cleaves all forms of lysine-linked (isopeptide-linked) diubiquitin, albeit with variable efficiency, but is inactive on linear Met1-linked diubiquitin. Digests of diubiquitin were performed overnight at 37° C. with enzyme and substrate both at 1 µM concentration. Similar results were observed with shorter digests of 1 or 4 h. b. Representative kinetic assay of diubiquitin cleavage. Lanes 1-3 are ubiquitin standards of 6, 20, and 40 µM, respectively. In lanes 4-8, 400 nM CidB (762-1143) was incubated with Lys48-linked diubiquitin ranging in concentration from 20 µM (lane 4) to 120 µM (lane 8). All Lys48-linked diubiquitin reactions were carried out at room temperature for 15 min. The amount of ubiquitin produced from each reaction was quantified by densitometry using ImageJ software. c. Total cellular ubiquitylation as measured by anti-ubiquitin immunoblotting in yeast extracts. Induction of GAL1-driven CidB expression did not change the pattern of ubiquitin conjugates when compared to cells with induced CidA or CidB* (negative controls). These results suggest CidB activity is likely limited to a small number of cellular substrates rather than affecting gross protein ubiquitylation. The same sample was run on two separate gradient gels of 4-10% and 10-15% gels to create maximal separation of high and low molecular weight ubiquitylated species. Induction temperatures of 30° C. and 37° C. in the presence of galactose for 4 h were utilized because toxicity is most apparent at 37° C.

Figure 24:
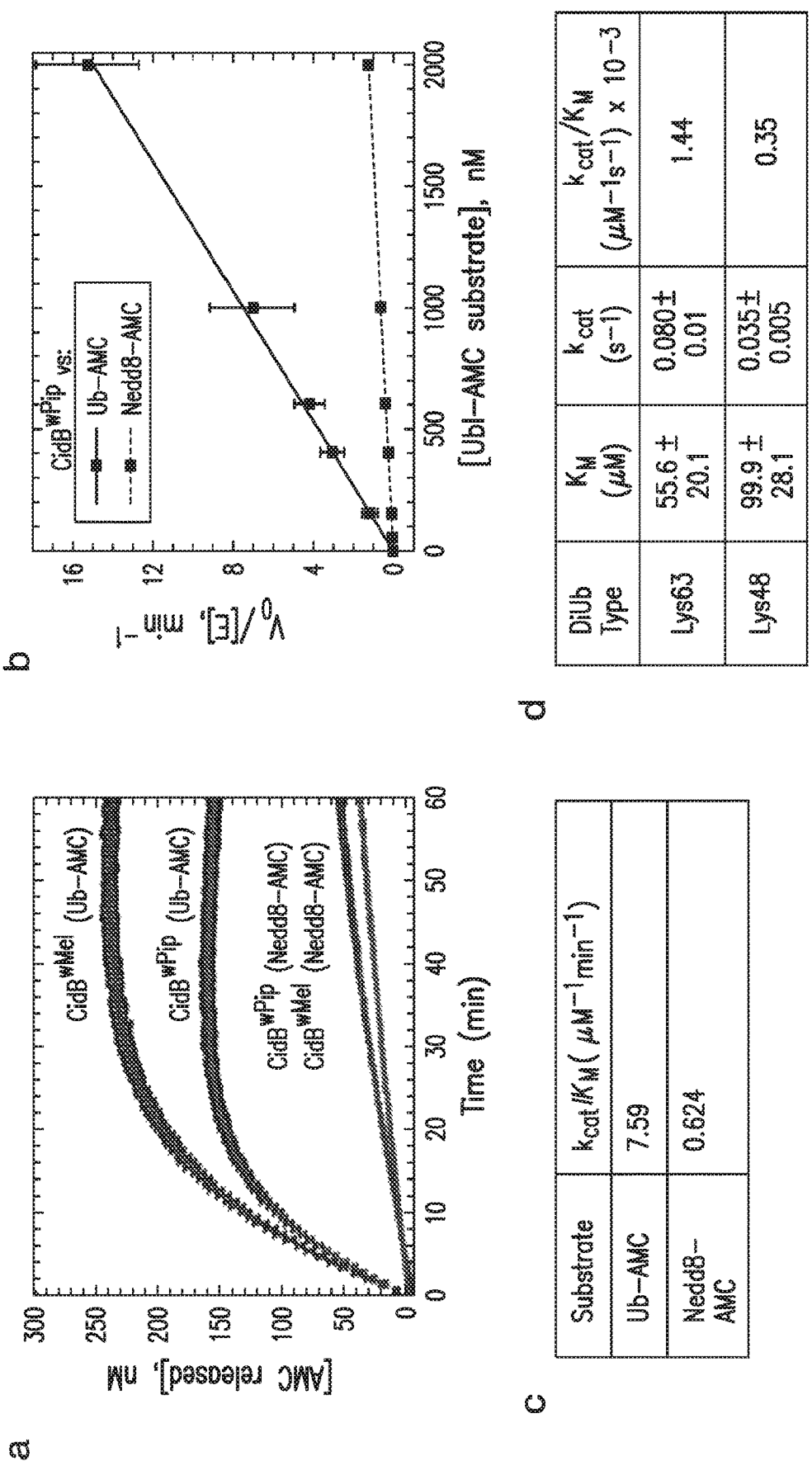

FIG. 24. Cleavage of Ub-AMC and Nedd8-AMC by wPip and wMel CidB enzymes. a. Progress curves of AMC release from Ub-AMC and Nedd8-AMC catalyzed by $CidB^{wPip}$ and $CidB^{wMel}$ are depicted. Enzyme (5 nM) was mixed with 400 nM of substrate, and the reactions proceeded at 30° C.; the enzymes share a similar preference for ubiquitin over the UBL Nedd8. The activity of $CidB^{wMel}$ is comparable to $CidB^{wPip}$. b. $CidB^{wPip}$ catalytic efficiency for hydrolyzing Ub-AMC is 11-fold greater than for Nedd8-AMC. c. As the kinetics from FIG. 24b exhibited a linear response over the substrate concentration range tested, which is typical of other DUBs toward the Ub-AMC substrate, the $k_{cat}/K_M$ values were determined by fitting the data to the equation: $v/[E]=k_{cat}/K_M[S]$. d. Steady-state kinetic parameters for $CidB^{wPip}$ cleavage of Lys63- and Lys48-linked ubiquitin dimers indicate a modest preference for Lys63-linked diubiquitin. This suggests that the physiological targets of $CidB^{wPip}$ might bear Lys63-polyubiquitin linkages and are less likely to be targets of Lys48-polyubiquitin-based proteasomal degradation.

Figure 25:
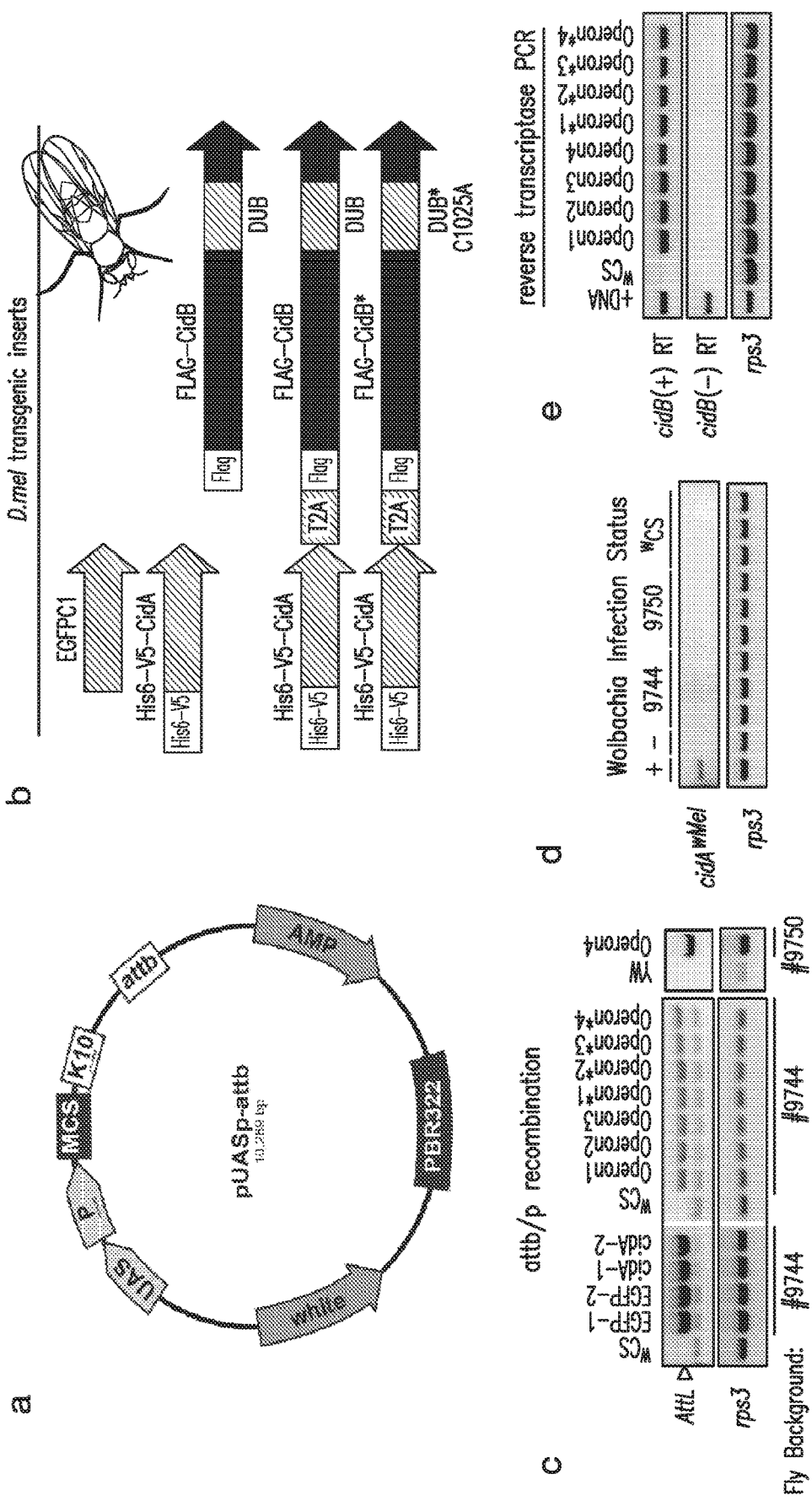

FIG. 25. Creation of transgenic D. melanogaster strains. a. pUASp-attB vector.[32,33] UAS is the GAL4 upstream activating element; P is the P-element basal germline promoter; and MCS is the multi-cloning site. K10 has 3'UTR sequences from the K10 terminator, and attB is the ΦC31 integrase recombination site. b. Five transgene injection constructs were created by heterologous gene insertion into pUASp-attB: four cidA-cidB-derived constructs and an EGFPC1 negative control. T2A is a viral peptide sequence that causes translation of two separate polypeptides from the fused ORFs by ribosome skipping, mimicking the bicistronic bacterial operon; no efficient IRES system has been described for D. melanogaster. No transgenic lines expressing $CidB^{wPip}$ alone could be established after 3 trials totaling 600 embryo microinjections, whereas all other constructs readily recombined into the Drosophila chromosome-3 attP site. c. Transgenic fly lines were created and screened for proper attB/attP recombination by PCR. "AttL" is a PCR product indicating correct recombination. Rps3 is a positive PCR control. The ʷCS and YW lanes are negative controls using genomic DNA from these two untransformed fly strains. Multiple transgenic fly lines were created for each construct. A total of four sterile "Operon" (cidA-cidB) lines were created in two different fly backgrounds bearing independent attP insertion sites (#9744 and #9750). Four independent lines with the catalytically inactive DUB (Operon*) were isolated in the #9744 background. All replicate lines showed the same phenotypes. d. Verification that lines used in transgenic crosses (#9744, 9750, and WCS) were uninfected with native Wolbachia strains. $CidA^{wMel}$ (WD_0631) is the antidote protein from the wMel Wolbachia strain. e. Reverse transcriptase-PCR analysis confirming transcription of the transgenic operons from the basal P-element promoter despite the absence of a Gal4 driver. DNA is a positive PCR control to show correct band size. RNA samples from pooled adult males were assayed with reverse transcriptase "(+) RT"-PCR to verify the presence of transcript; omission of reverse transcriptase, "(−) RT," served as a negative control for DNA contamination. The cDNAs were amplified with primers specific for $CidB^{wPip}$. Analysis of the fly Rps3 transcript was a positive control for RNA quality. As in panel c, the Operon and Operon* (cidA-cidB wPip) fly lines express active CidB and catalytically inactive CidB* (C1025A), respectively.

Figure 26:
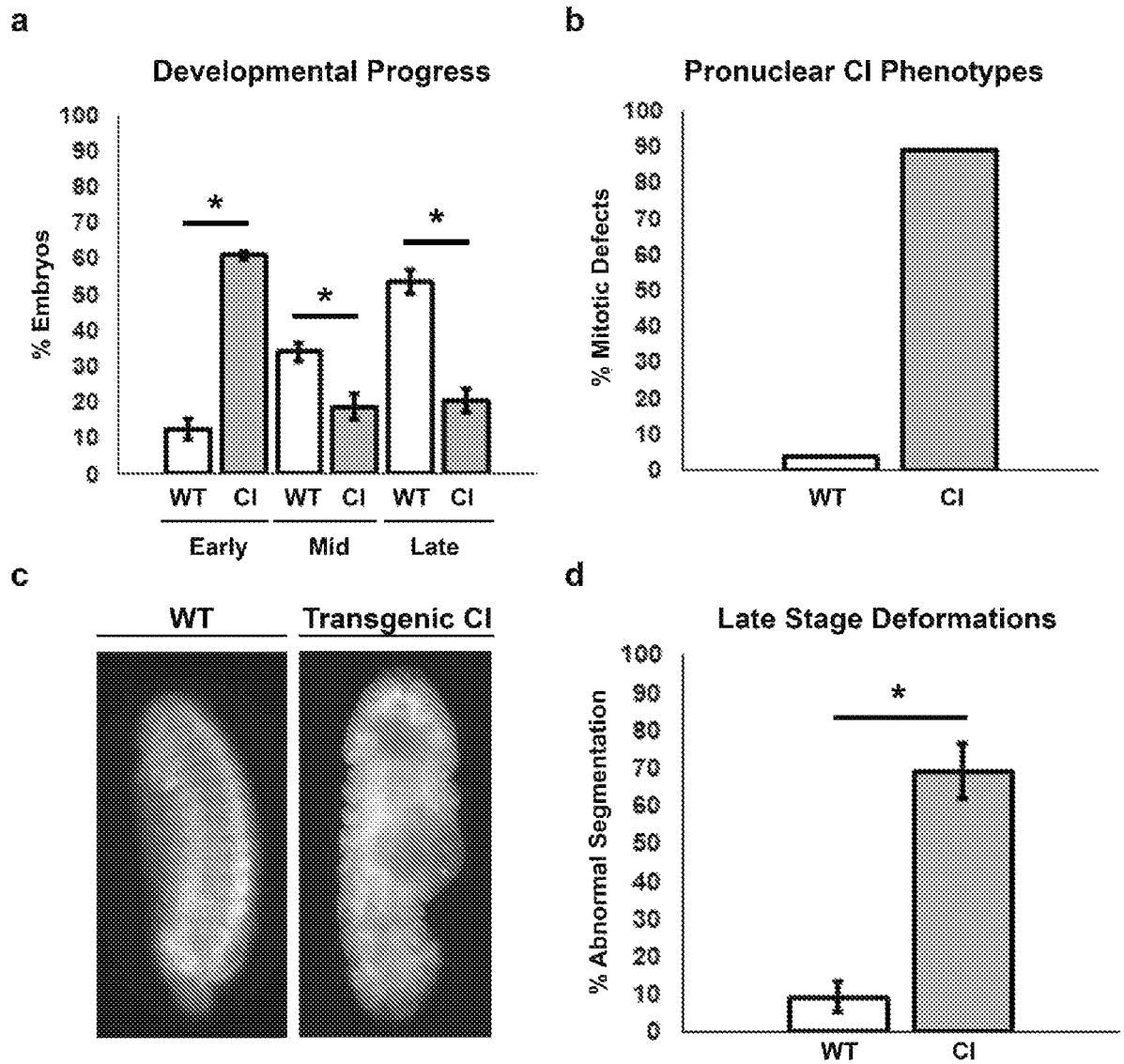

FIG. 26. Quantification of transgenic cidA-cidB embryo cytology. a. Developmental progress of transgenic ("CI") embryos. After 24 h, embryos were classified into three categories. Early, pre-blastoderm formation; Mid, blastoderm until segmentation stages; and Late, segmented stages. Quantification is based on three samples of approximately 200 embryos each. 60% of CI embryos arrested development in the early stage compared to 12% from the wild-type (WT) control. Significant p values<0.005 are indicated by (*). b. Quantification of transgenic cidA-cidB (CI) embryos' mitotic defects including uncondensed paternal chromosomes, delayed segregation of paternal chromosomes, or chromosomal bridging during the first cell cycle. 88% of CI embryos fixed and characterized during this stage exhibited these CI-like defects as compared to 3% in the WT control. Sample sizes of observed transgenic and WT embryos were 63 and 29, respectively. c. Examples of late-stage embryos; transgenic embryos that develop to the late stage show significant deformations of segmentation patterns including pinching, gaps in segmentation, and asymmetry. d. Of the 20% of transgenic CI embryos that develop to the late stage, 69% showed deformations and abnormal segmentation.

DETAILED DESCRIPTION

Disclosed herein are genetically modified bacteria and genetically modified arthropods useful for controlling and/or reducing populations of arthropods (for example, insects). For the first time, the inventors have identified the genes that encode the cytoplasmic incompatibility factors capable of reproducing the phenomena of cytoplasmic incompatibility. These genes are used to genetically modify bacteria and/or arthropods in order to produce sterile male arthropods and/or to replace a population of target arthropods.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

Terminology

As used herein, the article "a," "an," and "the" means "at least one," unless the context in which the article is used clearly indicates otherwise.

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" denotes single- or double-stranded nucleotide multimers of from about 2 to up to about 100 nucleotides in length. Suitable oligonucleotides may be prepared by the phosphoramidite method described by Beaucage and Carruthers, *Tetrahedron Lett.,* 22:1859-1862 (1981), or by the triester method according to Matteucci, et al., *J. Am. Chem. Soc.,* 103:3185 (1981), both incorporated herein by reference, or by other chemical methods using either a commercial automated oligonucleotide synthesizer or VLSIPS™ technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, *Biochemistry*, Third Ed., (1988), incorporated herein by reference for all purposes.

The term "polynucleotide" refers to a single or double stranded polymer composed of nucleotide monomers. In some embodiments, the polynucleotide is composed of nucleotide monomers of generally greater than 100 nucleotides in length and up to about 8,000 or more nucleotides in length.

The term "polypeptide" refers to a compound made up of a single chain of D- or L-amino acids or a mixture of D- and L-amino acids joined by peptide bonds.

The term "complementary" refers to the topological compatibility or matching together of interacting surfaces of a probe molecule and its target. Thus, the target and its probe can be described as complementary, and furthermore, the contact surface characteristics are complementary to each other.

The term "hybridization" refers to a process of establishing a non-covalent, sequence-specific interaction between two or more complementary strands of nucleic acids into a single hybrid, which in the case of two strands is referred to as a duplex.

The term "anneal" refers to the process by which a single-stranded nucleic acid sequence pairs by hydrogen bonds to a complementary sequence, forming a double-stranded nucleic acid sequence, including the reformation (renaturation) of complementary strands that were separated by heat (thermally denatured).

The term "melting" refers to the denaturation of a double-stranded nucleic acid sequence due to high temperatures, resulting in the separation of the double strand into two single strands by breaking the hydrogen bonds between the strands.

The term "target" refers to a molecule that has an affinity for a given probe. Targets may be naturally-occurring or man-made molecules. Also, they can be employed in their unaltered state or as aggregates with other species.

The term "promoter" or "regulatory element" refers to a region or sequence determinants located upstream or downstream from the start of transcription and which are involved in recognition and binding of RNA polymerase and other proteins to initiate transcription. Promoters need not be of bacterial origin, for example, promoters derived from viruses or from other organisms can be used in the compositions, systems, or methods described herein.

A polynucleotide sequence is "heterologous" to a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from naturally occurring allelic variants.

The term "recombinant" refers to a human manipulated nucleic acid (e.g. polynucleotide) or a copy or complement of a human manipulated nucleic acid (e.g. polynucleotide), or if in reference to a protein (i.e, a "recombinant protein"), a protein encoded by a recombinant nucleic acid (e.g. polynucleotide). In embodiments, a recombinant expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual,* Cold Spring Harbor Laboratory, Cold Spring Harbor, N.Y., (1989) or Current Protocols in Molecular Biology Volumes 1-3, John Wiley & Sons, Inc. (1994-1998)). In another example, a recombinant expression cassette may comprise nucleic acids (e.g. polynucleotides) combined in such a way that the nucleic acids (e.g. polynucleotides) are extremely unlikely to be found in nature.

For instance, human manipulated restriction sites or plasmid vector sequences may flank or separate the promoter from the second nucleic acid (e.g. polynucleotide). One of skill will recognize that nucleic acids (e.g. polynucleotides) can be manipulated in many ways and are not limited to the examples above.

The term "expression cassette" refers to a nucleic acid construct, which when introduced into a host cell, results in transcription and/or translation of a RNA or polypeptide, respectively. In embodiments, an expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In some embodiments, an expression cassette comprising a terminator (or termination sequence) operably linked to a second nucleic acid (e.g. polynucleotide) may include a terminator that is heterologous to the second nucleic acid (e.g. polynucleotide) as the result of human manipulation. In some embodiments, the expression cassette comprises a promoter operably linked to a second nucleic acid (e.g. polynucleotide) and a terminator operably linked to the second nucleic acid (e.g. polynucleotide) as the result of human manipulation. In some embodiments, the expression cassette comprises an endogenous promoter. In some embodiments, the expression cassette comprises an endogenous terminator. In some embodiments, the expression cassette comprises a synthetic (or non-natural) promoter. In some embodiments, the expression cassette comprises a synthetic (or non-natural) terminator.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) *J. Mol. Biol.* 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

The phrase "codon optimized" as it refers to genes or coding regions of nucleic acid molecules for the transformation of various hosts, refers to the alteration of codons in the gene or coding regions of polynucleic acid molecules to reflect the typical codon usage of a selected organism without altering the polypeptide encoded by the DNA. Such optimization includes replacing at least one, or more than one, or a significant number, of codons with one or more codons that are more frequently used in the genes of that selected organism. For example, the sequence of a heterologous gene expressed in *Wolbachia* may be "codon optimized" to optimize gene expression based on the preferred codon usage in *Wolbachia*.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, operably linked nucleic acids (e.g. enhancers and coding sequences) do not have to be contiguous. Linking is accomplished by ligation at convenient restriction sites. If such sites do not exist, the synthetic oligonucleotide adaptors or linkers are used in accordance with conventional practice. In embodiments, a promoter is operably linked with a coding sequence when it is capable of affecting (e.g. modulating relative to the absence of the promoter) the expression of a protein from that coding sequence (i.e., the coding sequence is under the transcriptional control of the promoter).

"Transformation" refers to the transfer of a nucleic acid molecule into a host organism (e.g. *Wolbachia* cell). In embodiments, the nucleic acid molecule may be a plasmid that replicates autonomously or it may integrate into the genome of the host organism. Host organisms containing the transformed nucleic acid molecule may be referred to as "transgenic" or "recombinant" or "transformed" organisms. A "genetically modified" organism (e.g. genetically modified arthropod) is an organism that includes a nucleic acid that has been modified by human intervention. Examples of a nucleic acid that has been modified by human intervention include, but are not limited to, insertions, deletions, mutations, expression nucleic acid constructs (e.g. over-expression or expression from a non-natural promoter or control sequence or an operably linked promoter and gene nucleic acid distinct from a naturally occurring promoter and gene nucleic acid in an organism), extra-chromosomal nucleic acids, and genomically contained modified nucleic acids.

The term "bacterial operon" as used herein refers to a gene or multiple genes transcribed from a single promoter which leads to the production of a single transcript in which one or more coding regions are linked.

The term "cytoplasmic incompatibility (CI) factor" or "cytoplasmic incompatibility (CI) gene" refers to the genes or the factors encoded by the genes from bacteria which provide a function that is required and/or beneficial to produce the natural genetic drive mechanism of cytoplasmic incompatibility (CI) used by various, unrelated bacterial infections (e.g., *Wolbachia* and Cardinium endosymbionts). "Cytoplasmic incompatibility (CI) factors" can include those factors that induce the CI and can also include those rescue factors that counteract the CI. In some embodiments, a single bacterial operon may encode multiple cytoplasmic incompatibility (CI) factors. In some embodiments, a single bacterial operon may encode a factor that induces the CI and can also encode a factor that can counteract the CI (for example, a rescue factor).

The term "variant" or "derivative" as used herein refers to an amino acid sequence derived from the amino acid sequence of the parent protein having one or more amino acid substitutions, insertions, and/or deletions. For example, a "cytoplasmic incompatibility (CI) factor variant" includes cytoplasmic incompatibility (CI) factor that may have a number of amino acid changes. In some embodiments, the variants may be greater than about 20%, greater than about 30%, greater than about 40%, greater than about 50%, greater than about 60%, greater than about 70%, greater than about 80%, greater than about 90%, or greater than about 95%, identical to the parent nucleic acid sequence or amino acid sequence.

*Wolbachia* and Cytoplasmic Incompatibility

*Wolbachia pipientis* is an obligate, intracellular α-proteobacteria and a member of the Rickettsiales family. These gram-negative bacteria are not culturable outside of host cells and, as a result, knowledge on *Wolbachia* symbiosis has only surged in the last two decades owing to readily available molecular techniques. Once considered an obscure bacterium in a few insect species, the most recent meta-analysis estimates that ~40% of all arthropod species are infected with *Wolbachia* as well as 47% of the Onchocercidae family of filarial nematodes.

The genus *Wolbachia* is an archetype of maternally inherited intracellular bacteria that infect the germline of millions of invertebrate species worldwide and parasitically alter arthropod sex ratios and reproductive strategies to increase the proportion of infected females (the transmitting sex) in the population. The most common of these reproductive manipulations is cytoplasmic incompatibility (CI), typically expressed as embryonic lethality in crosses between infected males and uninfected females. This lethality is completely rescued by females infected with the same or a similar *Wolbachia* strain. Despite more than 40 years of research, the genes by which *Wolbachia* cause CI remained unknown until the inventors isolated the genes encoding cytoplasmic instability factors from several strains of *Wolbachia*.

For the first time, the inventors have determined the genes encoding the cytoplasmic incompatibility factors capable of reproducing the phenomena of cytoplasmic incompatibility. These genes are used to genetically modify bacteria and/or arthropods in order to produce sterile male arthropods and/or to replace a population of target arthropods (for example, replacement of a target population with arthropods that are less susceptible to infectious agents or have a reduced capacity to transmit an infectious agent (for example, dengue virus or Zika virus)).

In one embodiment, the genes encoding the cytoplasmic incompatibility factors are from wMel, for example, WD0631 (SEQ ID NO:1) and/or WD0632 (SEQ ID NO:3). In one embodiment, the bacterial operon encodes the cytoplasmic incompatibility factor WD0631 (SEQ ID NO:2). In one embodiment, the bacterial operon encodes the cytoplasmic incompatibility factor WD0632 (SEQ ID NO:4). In one embodiment, the bacterial operon encodes the cytoplasmic incompatibility factors WD0631 and WD0632.

In one embodiment, the bacterial operon encodes a cytoplasmic incompatibility factor of the amino acid sequence SEQ ID NO:2. In one embodiment, the bacterial operon encodes a cytoplasmic incompatibility factor at least 60% identical (for example, at least 60%, at least 65%, at least 70%, at least 75%, at least 80%, at least 85%, at least 90%, at least 95%, at least 99%) to the amino acid sequence SEQ ID NO:2. In one embodiment, the bacterial operon encodes a cytoplasmic incompatibility factor of the amino acid sequence SEQ ID NO:4. In one embodiment, the bacterial operon encodes a cytoplasmic incompatibility factor at least 60% identical (for example, at least 60%, at least 65%, at least 70%, at least 75%, at least 80%, at least 85%, at least 90%, at least 95%, at least 99%) to the amino acid sequence SEQ ID NO:4.

In one embodiment, the genes encoding the cytoplasmic incompatibility factors are from *Wolbachia pipientis*, for example, CidA$^{wPip}$ (wPa_0282; SEQ ID NO:5), CidB$^{wPip}$ (wPa_0283; SEQ ID NO:7), CinA$^{wPip}$ (wPa_0294; SEQ ID NO:17), and/or CinB$^{wPip}$ (wPa_0295; SEQ ID NO: 19).

In one embodiment, the bacterial operon encodes the cytoplasmic incompatibility factor CidA$^{wPip}$ (wPa_0282; SEQ ID NO:6). In one embodiment, the bacterial operon encodes the cytoplasmic incompatibility factor CidB$^{wPip}$ (wPa_0283; SEQ ID NO:8). In one embodiment, the bacterial operon encodes the cytoplasmic incompatibility factors CidA$^{wPip}$ (wPa_0282) and CidB$^{wPip}$ (wPa_0283). In one embodiment, the bacterial operon encodes the cytoplasmic incompatibility factor CinA$^{wPip}$ (wPa_0294; SEQ ID NO: 18). In one embodiment, the bacterial operon encodes the cytoplasmic incompatibility factor CinB$^{wPip}$ (wPa_0295; SEQ ID NO:20). In one embodiment, the bacterial operon encodes the cytoplasmic incompatibility factors CinA$^{wPip}$ (wPa_0294) and CinB$^{wPip}$ (wPa_0295).

In one embodiment, the bacterial operon encodes a cytoplasmic incompatibility factor of the amino acid sequence SEQ ID NO:6. In one embodiment, the bacterial operon encodes a cytoplasmic incompatibility factor at least 60% identical (for example, at least 60%, at least 65%, at least 70%, at least 75%, at least 80%, at least 85%, at least 90%, at least 95%, at least 99%) to the amino acid sequence SEQ ID NO:6. In one embodiment, the bacterial operon encodes a cytoplasmic incompatibility factor of the amino acid sequence SEQ ID NO:8. In one embodiment, the bacterial operon encodes a cytoplasmic incompatibility factor at least 60% identical (for example, at least 60%, at least 65%, at least 70%, at least 75%, at least 80%, at least 85%, at least 90%, at least 95%, at least 99%) to the amino acid sequence SEQ ID NO:8.

In one embodiment, the bacterial operon encodes a cytoplasmic incompatibility factor of the amino acid sequence SEQ ID NO:18. In one embodiment, the bacterial operon encodes a cytoplasmic incompatibility factor at least 60% identical (for example, at least 60%, at least 65%, at least 70%, at least 75%, at least 80%, at least 85%, at least 90%, at least 95%, at least 99%) to the amino acid sequence SEQ ID NO:18. In one embodiment, the bacterial operon encodes a cytoplasmic incompatibility factor of the amino acid sequence SEQ ID NO:20. In one embodiment, the bacterial operon encodes a cytoplasmic incompatibility factor at least 60% identical (for example, at least 60%, at least 65%, at least 70%, at least 75%, at least 80%, at least 85%, at least 90%, at least 95%, at least 99%) to the amino acid sequence SEQ ID NO:20.

Figure 6:
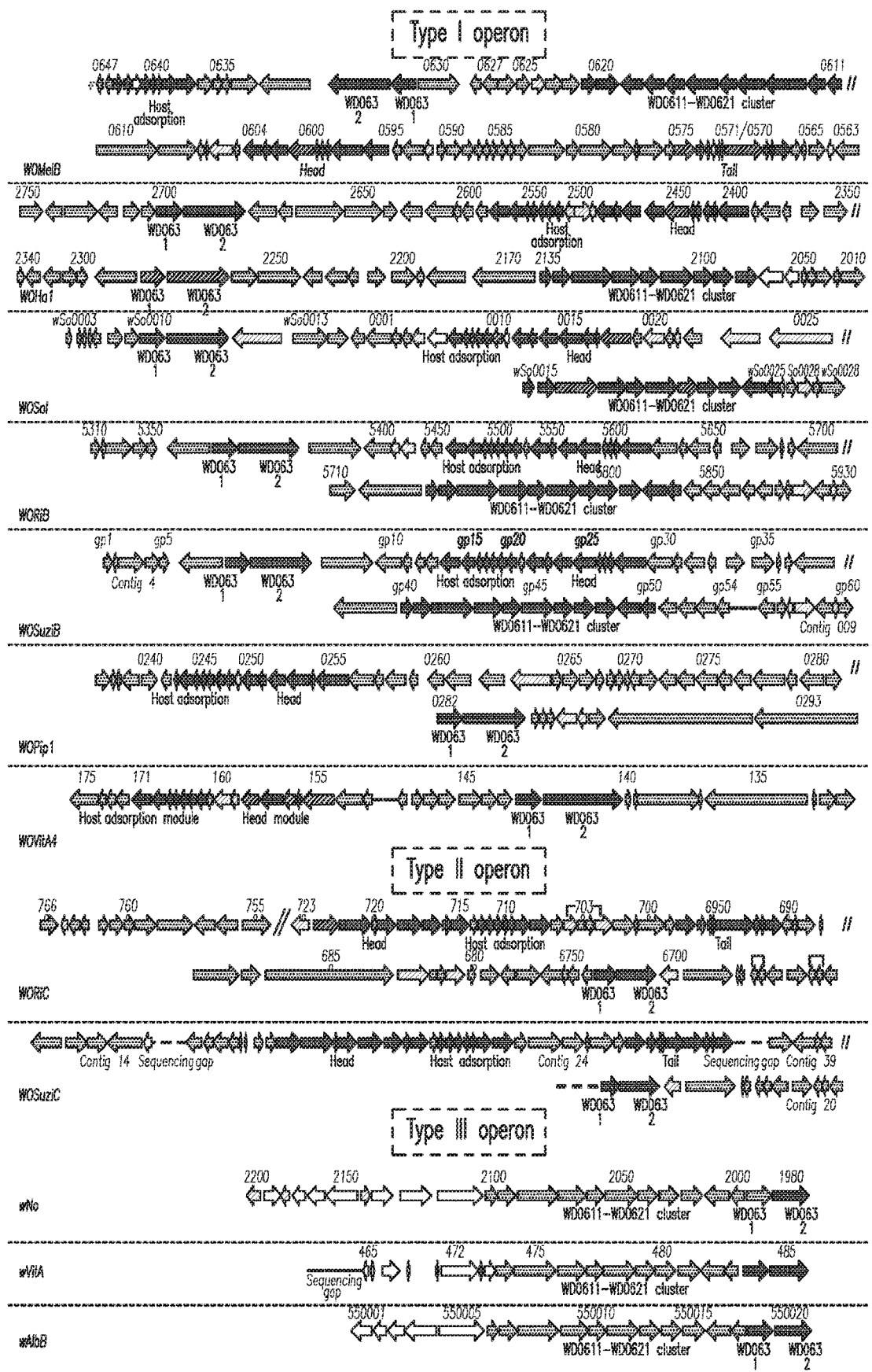
FIG. 6. WD0631/WD0632 operon is always associated with prophage WO regions. CI operons are labeled and colored pink. Structural modules are labeled as host adsorption, head or tail. The WD0611-WD0621 label highlights a conserved gene cluster that is often associated with the CI operon. Only one phage haplotype is shown per *Wolbachia* strain when multiple copies of the same operon type are present.

Additional examples of cytoplasmic incompatibility factors include homologues of WD0631 and WD0632 in additional *Wolbachia* strains including, but not limited to, WOMelB, WOHa1, WOSol, WORiB, WOSuziB, WOPip1, WOVitA4, WORiC, WOSuziC, wNo, wVitA, and/or wAlbB (See FIG. 6).

In some embodiments, a bacterial operon or a gene encoding a cytoplasmic incompatibility factor may be codon optimized, without changing the resulting polypeptide sequence. In some embodiments, the codon optimization includes replacing at least one, or more than one, or a significant number, of codons with one or more codons that are more frequently used in the genes of that selected arthropod. For example, the sequence of a bacterial operon or a gene encoding a cytoplasmic incompatibility expressed in, for example, an *Aedes* mosquito, may be "codon optimized" to optimize gene expression based on the preferred codon usage in *Aedes*.

Non-limiting examples of Type I bacterial operons, Type II bacterial operons, Type III bacterial operons, and additional homologues are listed in Table 1, Table 2, Table 3, and Table 4, respectively. Type I CI bacterial operons are Ulp1 type operons and were queried using WP0283 in Table 1. Type II CI bacterial operons are "No CTD" type operons and were queried using wRi_006170 in Table 2. Type III CI bacterial operons are DUF1703 type operons and were queried using wNo_01980 in Table 3. Additional homologues in Table 4 were queried by the gene listed in the table. Additional chromosomal Ulp1 containing loci are listed in Table 5.

TABLE 1

Non-limiting Examples of Type I CI Bacterial Operons

| cidA | cidB Locus tag | cidB Accession | Wolbachia strain | Insect Host | Query coverage | Identity |
|---|---|---|---|---|---|---|
| WP0282 | WP0283 | WP_012481788.1 | wPip | Culex pipiens quinquefasciatus Pel | 100% | 100% |
| | WP1291/ WP1292 | WP_012482028.1/ WP_012481788.1 | wPip | Culex pipiens quinquefasciatus Pel | 30% | 99% |
| (incomplete contig) | C1A_1260 | EEB55318.1 | wPipJHB | Culex quinquefasciatus JHB | 51% | 100% |
| C1A_1298 | C1A_1299 | EEB55179.1 | wPipJHB | Culex quinquefasciatus JHB | 61% | 97% |
| C1A_1302 | C1A_1300/ C1A_1301 | EEB55246.1 | wPipJHB | Culex quinquefasciatus JHB | 28/40% | 96/98% |
| C1A_1344 | C1A_1343 | EEB55169 & WP_007301817.1 | wPipJHB | Culex quinquefasciatus JHB | 23% | 99% |

TABLE 1-continued

Non-limiting Examples of Type I CI Bacterial Operons

| cidA | cidB Locus tag | cidB Accession | Wolbachia strain | Insect Host | Query coverage | Identity |
|---|---|---|---|---|---|---|
| | C1A_1356 | EEB55171.1 | wPipJHB | Culex quinquefasciatus JHB | 14% | 100% |
| (gap in contig) | C1A_RS07400 | WP_050751958.1 | wPipJHB | Culex quinquefasciatus JHB | 21% | 55% |
| WPM_01119 | WPM_01122 | CQD10800 & WP_012481788.1 | wPipMol | Culex pipiens Molestus | 30% | 99% |
| WD0631 | WD0632 | WP_010962722.1 | wMel | Drosophila melanogaster | 99% | 76% |
| WMELPOP_03523 | WMELPOP_03528 | ERN55637.1 & WP_038228284.1 | wMelPopcorn | Drosophila melanogaster | 99% | 76% |
| wRec0566 | wRec0567 | JQAM01000018.1* | wRec | Drosophila recens | | |
| wHa_02700 | wHa_02690 | YP_007888921.1 & WP_015588932.1 | wHa | Drosophila simulans | 100% | 67% |
| wHa_02280 | wHa_02270 | WP_041573504.1 | wHa | Drosophila simulans | 35% | 74% |
| wRi_05370 | wRi_p05380 | WP_041582611.1 | wRi | Drosophila simulans | 16% | 82% |
| wRi_010030 | wRi_p10040 | WP_041582611.1 | wRi | Drosophila simulans | 16% | 82% |
| WwSim0304 | WwSim0305/ WwSim0306 | EAL59981.1/ EAL59982.1 | wSim | Drosophila simulans | 16%/20% | 81%/66% |
| (incomplete contig) | WwSim0307 | EAL59913.1 | wSim | Drosophila simulans | 46% | 82% |
| (contig 004 - CAOU02000034.1*) | | WP_044471243.1 | wSuzi | Drosophila suzukii | 99% | 76% |
| (contig 005 - CAOU02000021.1*) | | WP_044471243.1 | wSuzi | Drosophila suzukii | 99% | 76% |
| (incomplete contig) | wAna0112 | EAL58062.1 | wAna | Drosophila ananassae | 16% | 78% |
| gwv_142 | gwv_141 | PRJDB1504* | wVitA | Nasonia vitripennis | | |
| wSo0010 | wSo0010 | AGK87078.1 | wSol | Ceratosolen solmsi | 100% | 67% |
| wBol1_RS02195 | wBol1_RS02190 | WP_019236548 | wBol1-b | Hypolimnas bolina | 100% | 93% |
| TV41_RS03095 | TV41_RS03090 | WP_064085577.1 | wDacB | Dactylopius coccus | 100% | 93% |
| (incomplete contig) | wGmm_0957/ wGmm_0598 | KDB19421.1/ KDB19420.1 | wGmm | Glossina morsitans morsitans | 22%/39% | 74%/44% |

TABLE 2

Non-limiting Examples of Type II CI Bacterial Operons

| cixA | cixB Locus tag | cixB Accession | Wolbachia strain | Insect Host | Query coverage | Identity |
|---|---|---|---|---|---|---|
| wRi_006720 | wRi_006710 | YP_002727222.1 & WP_012673227.1 | wRi | Drosophila simulans | 100% | 100% |
| (incomplete contig) | WwSim0727 | EAL59553 | wSim | Drosophila simulans | 34% | 100% |
| (incomplete contig) | WwSim0783 | EAL59591.1 | wSim | Drosophila sinulans | 28% | 100% |
| (contig 20 - CAOU02000023.1*) | (contig 20 - CAOU02000023.1*) | WP_044471251.1 | wSuzi | Drosophila suzukii | 100% | 99% |
| (incomplete contig) | wAna_0864/ wAna_0865 | WP_007549286.1/ WP_007549287.1 | wAna | Drosophila ananassae | 25%/74% | 100/100% |

TABLE 3

Non-limiting Examples of Type III CI Bacterial Operons

| cinA | cinB Locus tag | cinB Accession | Wolbachia strain | Insect Host | Query coverage | Identity |
|---|---|---|---|---|---|---|
| wNo_01990 | wNo_01980 | YP_007885511.1 & WP_015587805.1 | wNo | Drosophila simulans | 100% | 100% |
| WP0294 | WP0295 | YP_001975096.1 & WP_007302979.1 & CAQ54403.1 | wPip | Culex pipiens quinquefasciatus Pel | 98% | 31% |
| C1A_1254 | C1A_1253 | EEB55311.1 & WP_007302979.1 | wPipJHB | Culex quinquefasciatus JHB | 98% | 31% |
|  | WPM_01094 | CQD10626 & WP_007302979.1 | wPipMol | Culex pipiens Molestus | 98% | 31% |
| wAlbB_120005 | wAlbB_120006 | CCE77108.1 & WP_006012795.1 | wAlbB | Aedes albopictus | 98% | 31% |
| wAlbB_550019 | wAlbB_550020 | CCE77513.1 & WP_006014164.1 | wAlbB | Aedes albopictus | 100% | 99% |
| wBol1_RS01705 | wBol1_RS01710 (or WBOL1_01725) | WP_019236480 | wBol1-b | Hypolimnas bolina | 98% | 31% |
| gwv_484 | gwv_485 | PRJDB1504* | wVitA | Nasonia vitripennis |  |  |
| wUni_598 | wUni_599 | * | wUni | Muscidifurax uniraptor |  |  |

TABLE 4

Non-limiting Examples of Additional CI Bacterial Operons

| WP0282-like | WP0283-like | WP0283-like Accession | Description | Bacterial strain | Query | Query coverage | Identity |
|---|---|---|---|---|---|---|---|
| RGRA_RS0104630 | RGRA_RS0104635 | WP_024547315.1 | polymorphic, DUF1703 | Candidatus Rickettsia gravesii | wwNo_01980 | 41% | 28% |
| JS61_08060 | JS61_08070 | WP_024547315.1 | polymorphic | Rickettsia felis | wNo_01980 | 67% | 26% |
|  | CHV_RS01335 | WP_034576592.1 |  | Cardinium endosymbiont of Bemisia tabaci | wNo_01980 | 41% | 27% |
| WSTR_05295 | WSTR_05300 | WP_063631194.1 | polymorphic | Wolbachia of Laodelphax striatella | wNo_01980 | 95% | 24% |
| TV41_RS02770 | TV41_RS02775 | WP_064085536.1 | polymorphic, Ulp1 | Wolbachia of Dactylopius coccus | wNo_01980 | 87% | 25% |
|  | AlI_06850 | ABV79684.1 | polymorphic, Ulp1 | Rickettsia bellii | wPa_0283 (894-1177) |  |  |
|  | RPR_06665 | ACR47821.1 | polymorphic, Ulp1 | Rickettsia peacockii | wPa_0283 (894-1177) |  |  |

TABLE 5

Non-limiting Examples of Chromosomal Ulp1 Containing Loci

| Ulp1 containing locus tag | Accession | Wolbachia strain | Insect Host |
|---|---|---|---|
| WP1291 | YP_001976023.1 | wPip | Culex pipiens quinquefasciatus Pel |
| WPM_001053c | CDH88846.1 | wPipMol | Culex pipiens Molestus |
| wBm_0463 | YP_198293.1 | wBm | Brugia malayi |
| WRi_000250 | YP_002726686.1 | wRi | D. simulans |
| wHa_00230 | YP_007888701.1 | wHa | D. simulans |
| WD0027 | WP_010962314.1 | wMel | D. melanogaster |
| WMELPOP_00953 | ERN56121.1 | wMelPopcorn | D. melanogaster |
| wPAU_0024 | CDR78424.1 | wAu | D. Simulans |
| wNo_02560 | WP_015587858.1 | wNo | D. simulans |

Methods of Controlling Arthropod Populations: Sterile Insect Technique (SIT)

The concept of the sterile insect technique (SIT) was first discovered by Knipling in 1955 (Knipling, E. F. *J Econ Entomol* 48, 459-462 (1955)). SIT is the use of sterile males to suppress populations of insects. SIT works by periodic controlled releases of vast numbers of sterile male insects into wild populations. In principle, these sterile males outnumber and outcompete wild males for matings with wild females. If a female mates with a sterile male she will lay eggs that do not hatch. If the proportion of sterile males consistently exceeds the proportion of fertile males then each new generation's reproduction is suppressed. As the wild population numbers dwindle, SIT becomes more and more effective creating a negative feedback loop that ultimately eradicates the species in an area. One major advantage of SIT population suppression versus traditional insecticide treatment is that it is species specific and environmentally safe. Three major processes are necessary for the implementation of SIT: 1) a method of sterilization; 2) a method of sex separation; and 3) a method of dispersal. The invention herein relates to the first point and represents a unique method of sterilization.

The historical example of SIT is Knipling's and the USDA's rearing of irradiated sterile males to eradicate the New World Screwworm (*Cochliomya hominivorax*) in North America and Mexico (Bushland, R. C., et al. *Science* 122, 287-288 (1955)). Screwworm is a deadly livestock pest which causes myiasis (an infestation of parasitic fly larvae that feed on host tissues)(Lindquist, D. A., et al. *Med Vet Entomol* 6, 2-8 (1992)). Initial field tests were carried out in Florida starting in 1951 and later in 1954 on the island of Curacao (Baumhover, A. H. et al. *J Econ Entomol* 48, 462-466 (1955)). This initial program utilized gamma rays of cobalt to sterilize male pupae (Bushland, R. C. & Hopkins, D. E. *J Econ Entomol* 44, 725-731 (1951)). Adult flies were then dispersed over the island by weekly release from an airplane. After 6 months of releases, screwworm was completely eradicated from the island (Baumhove. Ah. *J Amer Med Assoc* 196, 240 (1966)). Using the same technique, screwworm was eradicated from Florida and the Southeast USA by 1959 (Baumhove. Ah. *J Amer Med Assoc* 196, 240 (1966); Baumhover, A. H., et al. *J Econ Entomol* 52, 1202-1206 (1959)) and entirely from North and Central America by 1995 (Baumhover, A. H. Baumhover: A Personal Account of Screwworm Eradication. *Pioneer Lecture presentation* (1997)). SIT based eradication of the screwworm was later replicated in Libya (1990) when a shipment of contaminated livestock caused an outbreak; the technique has been proven to be a useful suppression tactic for many insects (Lindquist, D. A., et al. *Med Vet Entomol* 6, 2-8 (1992)).

The physical quality or "fitness" of sterile insects produced for SIT is of paramount importance for the application.[9] One downside of canonical sterilization by irradiation is that many insects are not as resilient to this treatment as screwworm. For example, mosquitoes are more sensitive to irradiation and cannot be irradiated without significant fitness reductions and lethality (Benedict, M. Q. & Robinson, A. S. *Trends Parasitol* 19, 349-355 (2003); Dame, D. A., et al. Historical applications of induced sterilization in field populations of mosquitoes. *Malaria J* 8 (2009)). Thus, alternative means of sterilization are useful inventions for the development and application of SIT. Other methods of inducing sterility in insects include cytoplasmic incompatibility (CI), chromosomal disruptions, chemical sterilization, and sex ratio distortion (Benedict, M. Q. & Robinson, A. S. *Trends Parasitol* 19, 349-355 (2003)). CI is a conditional sterility induced by a secreted bacterial sperm toxin produced from *Wolbachia* infections in insect gonads (described above). Hannes Laven was the first to pioneer research on *Wolbachia* as a tool for SIT. He described how *Culex pipiens* mosquito isolates were sterile when mated with isolates from different regions of Europe (Laven, H. Chapter 7: Speciation and Evolution in Culex pipiens. 251 (Elsevier, 1967)). Realizing the potential, Laven isolated a strain of *Culex pipiens fatigans* (major vector of filariasis) which would be sterile when mated to the same species in Burma. Unbeknownst to Laven, his mosquito strain was infected with a corresponding strain of *Wolbachia* incompatible with the wild type populations in Burma. Despite not understanding the functionality of the sterility, Laven was able to use *Wolbachia* sterilized male mosquitoes to eradicate populations of the local mosquito vector in Burma (Laven, H. *Nature* 216, 383 (1967)).

Although the proof of principle has existed in the public domain with respect to *Wolbachia* mediated CI and SIT, it is important to note that the molecular mechanism and genetic system by which this happens had not been understood for over 60 years until the experiments described in this application were performed. Thus, the important distinction to be made between the invention disclosed herein and *Wolbachia* mediated SIT is that the inventors have identified the minimal molecular components from the *Wolbachia* genome that are sufficient to induce sterility by a transgenic means, independent of the *Wolbachia* bacterium. This last point importantly distinguishes the present invention from the invention described in U.S. Pat. No. 9,090,911 which describes a line of mosquito adapted by infection of variants of the *Wolbachia* strain wMel.

Figure 15:
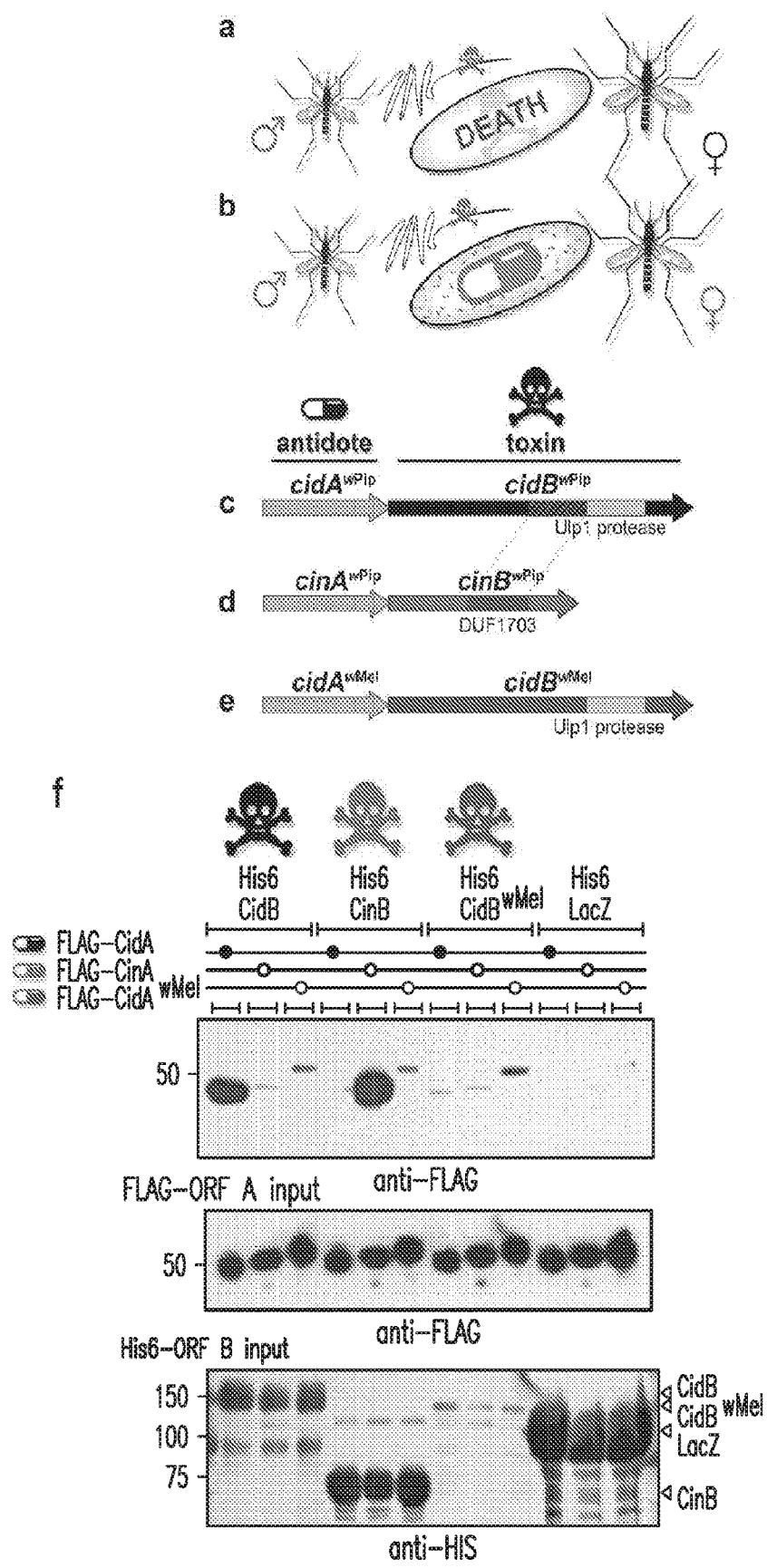
FIG. 15. Toxin-antidote hypothesis for CI. a. Crossing *Wolbachia*-infected males (red) with uninfected females (black) yields nonviable embryos due to a sperm-derived toxin. b. Crossing infected males and infected females rescues viability due to antidote in the infected egg. c. Operon from *Wolbachia* (wPip strain) proposed to induce CI through a toxin-antidote mechanism with CidA (wPa 0282) acting as antidote and CidB (wPa 0283) as toxin. d. Paralogous operon from wPip in which a putative DUF1703 nuclease, CinB (wPa 0295) is the toxin. e. Orthologous cidA-cidB operon from wMel. f. Pulldown assays of operon partners reveal interaction specificity. His6-tagged beta-galactosidase (LacZ) is a negative control.
Figure 16:
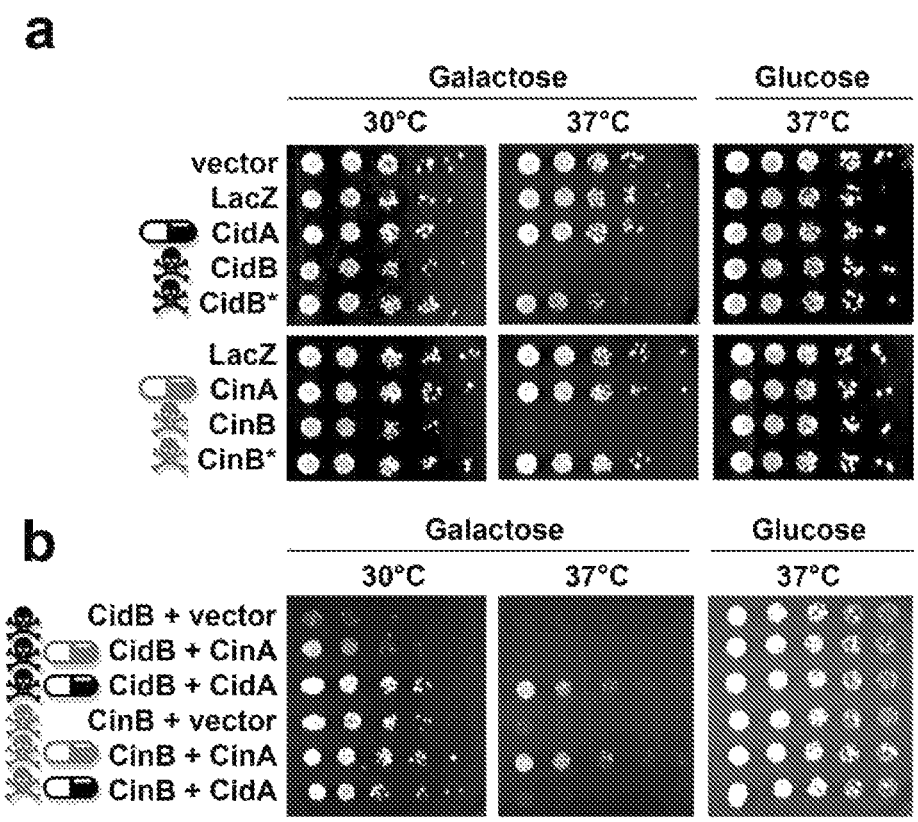
FIG. 16. Test of the toxin-antidote hypothesis in *Saccharomyces cerevisiae*. a. Expression of *Wolbachia* proteins from a galactose-inducible GAL1 promoter on minimal medium lacking uracil and containing galactose or glucose. Controls pYES2 (empty vector) and LacZ (negative control) cause no defects. Both CidB and CinB expression blocks yeast growth at high temperature. Inactivation of the Ulp1-like protease by a C1025A mutation (CidB*) or the putative DUF1703 nuclease by mutation of the D-E-K triad to A-A-A (CinB*) eliminates toxicity. b. Coexpression of "toxins" with different "antidotes" on minimal media lacking uracil and leucine shows growth rescue only with cognate partners. Vector is pRS425.

Therefore, the present application of these "bacterial operons" utilizes the cytoplasmic incompatibility genes or their derivatives within a construct able to be transgenically inserted into a pest insect for the purposes of inducing sperm sterilization. In one embodiment, the CidA/B$^{wPip}$ operon is used as it induces extremely high levels of CI nearing 100% sterility in *D. melanogaster* (FIG. 18; See Example 2). In some embodiments, the cidA/B$^{wMel}$ operon is used for application of SIT. Achieving a perfect 100% sterility is not entirely necessary for application of SIT (Dame, D. A., et al. Historical applications of induced sterilisation in field populations of mosquitoes. *Malaria J* 8 (2009)). Furthermore other "bacterial operons" including but not limited to CinA/B can be used in applications of SIT as the CinA/B operon was shown to exhibit toxin like properties in yeast comparable to the CidA/B operon (FIG. 16). In additional embodiments, many derivative "bacterial operons," including but not limited to, the examples seen in FIGS. 6, 7, and 15, can be used for sterilization of insects.

After sterilization, male insects could then be separated from female insects, delivered to the target site, and released for mating with wild females to eradicate a pest population.

Alterations to the system can be made to optimize sterilization effectiveness of the "bacterial operon". However, these optimizations do not change the essential composition of the "bacterial operon." These changes might include but are not limited to: 1) alterations of gene regulatory sequences as sterility was induced utilizing various promoters such as the nanos promoter of the Gal4/UAS system described in Example 1 or the P-element promoter described in Example 2; 2) the insertion of protein affinity tags, post/pre-translational modifications, or untranslated exons altering detectability, stability, localization, or structure of the "bacterial operon" proteins or their transcripts as evidenced by sterility induction by a His6-V5 tagged version of CidA with a FLAG tagged version of CidB in the Example 2. Furthermore, In this case the mRNA of the bacterial operon was also stabilized and localized into the germline by the K10 3' untranslated region of the last exon of the K10 gene (Rorth, P. *Mech Dev* 78, 113-118 (1998)); 3) Amino acids mutations/variants altering binding affinities between cognate operon pair proteins as FIG. 15F indicates that different amino acids regulate binding affinities of the cognate partner proteins; 4) alternative methods of driving expression of duel cognate partner proteins as two independent chromosomal insertions were utilized in Example 1 in contrast to an engineered eukaryotic operon with both open reading frames separated by the T2A insect peptide, which directs ribosomal translation of two separate proteins (Diao, F. & White, B. H. *Genetics* 190, 1139-1144 (2012)). 5) known transcriptional regulators including Gal4/UAS or others such as the tetracycline promoter and repressor for timed induction of expression.

The present method is uniquely different from other available genetic methods of sterilization such as Oxitec's patented RIDL technology (U.S. Pat. No. 9,125,388). In the cited patent and its published literature (Harris, A. F. et al. *Nat Biotechnol* 29, 1034-1037 (2011); Waltz, E. *Nat Biotechnol* 33, 792-793 (2015) an invention is described whereby biological control of an insect is achieved by the release of a dominant negative lethal gene under the control of transcriptional regulators. The unique difference with the method herein is the fact that the "bacterial operon" does not encode a dominant lethal gene. The "bacterial operons" instead sterilize sperm alone and effectively inhibit embryonic development and hatching of eggs. Evidence for this is provided in FIG. 18 (See Example 2) where sterility only occurs in "bacterial operon" transgenic males but not in transgenic females; also embryos resulting in crosses to "bacterial operon" transgenic males all die before egg hatch and exhibited extreme developmental deformities before larval emergence indicative of sperm defects. These phenotypes are in contrast to the dominant lethal approach which allows growth and development and only acts by killing larvae in a later developmental instar. Another distinction is that dominant lethal genes for SIT in one insect might not translate effectively into application for another genus of insect. The methods herein describe a cross compatible example of a platform technology capable of being applied to any insect genus. Proof of this lies in the fact that the "bacterial operon" CidA/B$^{wPip}$ derived from *Wolbachia* which infects and induces CI in mosquitoes was able to induce sterility in fruit flies as well as toxicity in a model eukaryote yeast. Thus, the invention's effectiveness and application is not limited by species of insect and need not be restricted to *Drosophila*.

Once released, the transgenic insertion can be used as a tracking marker distinguishing the modified sterile insects from wild insects. Thus the "bacterial operons" would provide an additional tool to monitor and characterize the spread or incompatibility of the released populations or other populations of insects containing the "bacterial operons." These markers can be detected by means such as standard polymerase chain reaction or antibody based detection. Furthermore, because the "bacterial operons" described underlie the reproductive barriers induced by wild strains of variant Wolbachias in insects, these markers can be used for determining and assessing mating compatibilities of any intraspecies insect strains in general. Thus, commercial testing, research, and reproductive compatibility assessment by characterization of these "bacterial operons" can be used as a pest management tool for agricultural companies seeking to eradicate or monitor the spread of a particular pest.

A separate application independent of SIT, but inherently related to sterilization of insect sperm is the sterilization of transgenic strains of insects for safety testing. Newly created strains of genetically modified organisms (GMOs) are able to prevent or repress the transmission of diseases like malaria (Ito, J., et al. *Nature* 417, 452-455 (2002); Jacobs-Lorena, M. *J Vector Borne Dis* 40, 73-77 (2003)). However, release of such GMO insects cannot be performed without substantial field and safety testing. Initial field tests are often first administered by sterilizing the GMO insects before release such that they will not pass on modified chromosomes onto the next generation in the wild (Benedict, M. Q. & Robinson, A. S. *Trends Parasitol* 19, 349-355 (2003)). This allows safe examination of off-target effects of GMOs. Thus, in additional methods disclosed herein, the bacterial operons can be used to sterilize the GMO for safety tests.

In one aspect, provided herein is a genetically modified arthropod, said arthropod comprising:
 a bacterial operon encoding a cytoplasmic incompatibility factor or a variant thereof; and
 a promoter operably linked to the bacterial operon;
 wherein the expression of the cytoplasmic incompatibility factor in a male arthropod causes a reduction in viable offspring in comparison to a male arthropod lacking the cytoplasmic incompatibility factor.

In another aspect, provided herein is a method for controlling a population of target arthropods, comprising:
 providing a bacterial operon encoding a cytoplasmic incompatibility factor or a variant thereof, and a promoter operably linked to the bacterial operon;
 transforming a population of male arthropods with the bacterial operon; and
 releasing the male arthropods amongst a population of target arthropods, wherein the release of the male arthropods reduces the population of target arthropods.

In one embodiment, the bacterial operon is from *Wolbachia*. In one embodiment, the bacterial operon is from wMel. In one embodiment, the bacterial operon encodes the cytoplasmic incompatibility factor WD0631. In one embodiment, the bacterial operon encodes the cytoplasmic incompatibility factor WD0632. In one embodiment, the bacterial operon encodes the cytoplasmic incompatibility factors WD0631 and WD0632.

In one embodiment, the bacterial operon is from *Wolbachia pipientis*. In one embodiment, the bacterial operon encodes the cytoplasmic incompatibility factor CidA$^{wPip}$ (wPa_0282). In one embodiment, the bacterial operon encodes the cytoplasmic incompatibility factor CidB$^{wPip}$ (wPa_0283). In one embodiment, the bacterial operon encodes the cytoplasmic incompatibility factors CidA$^{wPip}$ (wPa_0282) and CidB$^{wPip}$ (wPa_0283). In one embodiment, the bacterial operon encodes the cytoplasmic incompatibility factor CinA$^{wPip}$ (wPa_0294). In one embodiment, the bacterial operon encodes the cytoplasmic incompatibility factor CinB$^{wPip}$ (wPa_0295). In one embodiment, the bacterial operon encodes the cytoplasmic incompatibility factors CinA$^{wPip}$ (wPa_0294) and CinB$^{wPip}$ (wPa_0295).

In one embodiment, the bacterial operon is from *Cardinium*. In one embodiment, the bacterial operon is from *Rickettsia*.

In one embodiment, the bacterial operon encodes a deubiquitylase. In one embodiment, the bacterial operon encodes a nuclease.

In one embodiment, the reduction in viable offspring is greater than 50%. In one embodiment, the reduction in viable offspring is greater than 60%. In one embodiment, the reduction in viable offspring is greater than 70%. In one embodiment, the reduction in viable offspring is greater than 80%. In one embodiment, the reduction in viable offspring is greater than 90%. In one embodiment, the reduction in viable offspring is greater than 95%.

In one embodiment, the arthropod is an insect. In one embodiment, the insect is selected from the genera consisting of *Aedes, Culex* and *Anopheles*. In one embodiment, the insect is selected from the group consisting of *Aedes albopictus, Aedes aegypti* and *Aedes polynesiensis*. In one embodiment, the insect is *Drosophila suzukii*.

Methods of Controlling Arthropod Populations: Population Replacement

Another method for controlling pest and disease vector populations is a Population Replacement Strategy (PRS). Its goal is to replace wild pest or vector populations with those that are not competent to function as pests or vectors of human disease (Sinkins, 2004, *Insect Biochem Mol Biol*, 34, 723-9; Dobson, Brelsfoard and Dobson, 2009, *AsPac J. Mol. Biol. Biotechnol.*, 17, 55-63). Population Replacement is dependent on two pieces of technology:

1) A beneficial trait that is desired in the target arthropod
2) A genetic drive mechanism to spread the desired trait through the arthropod population (Sinkins and Gould, 2006, *Nat Rev Genet*, 7, 427-35).

The technology described by the inventors in the present disclosure addresses the second problem by utilizing bacterial operons that induce cytoplasmic incompatibility (CI), which is a natural genetic drive mechanism used by various, unrelated bacterial infections (e.g., *Wolbachia* and *Cardinium* endosymbionts).

A previously used approach involving population replacement in the control of disease vectors is the Eliminate Dengue project. This method uses the naturally occurring *Wolbachia* strain wMel to introduce both a desirable trait, the inhibition of mosquito vector competence for Dengue virus and other human pathogens (Walker et al., 2011, *Nature*, 476, 450-3; Aliota et al., 2016, *PLoS Negl Trop Dis*, 10, e0004677; Dutra et al., 2016, *Cell Host Microbe*), and the genetic drive mechanism of CI. This technique has had limited success in field trials, but requires massive mosquito releases (Hoffmann et al., 2011, Hoffmann et al., 2014) and the horizontal transfer of *Wolbachia* into hosts that are frequently inhospitable to stable infection (Hughes et al., 2011, *PLoS Pathog*, 7, e1002043; Hughes et al., 2014, *Proc Natl Acad Sci USA*, 111, 12498-503).

Figure 5:
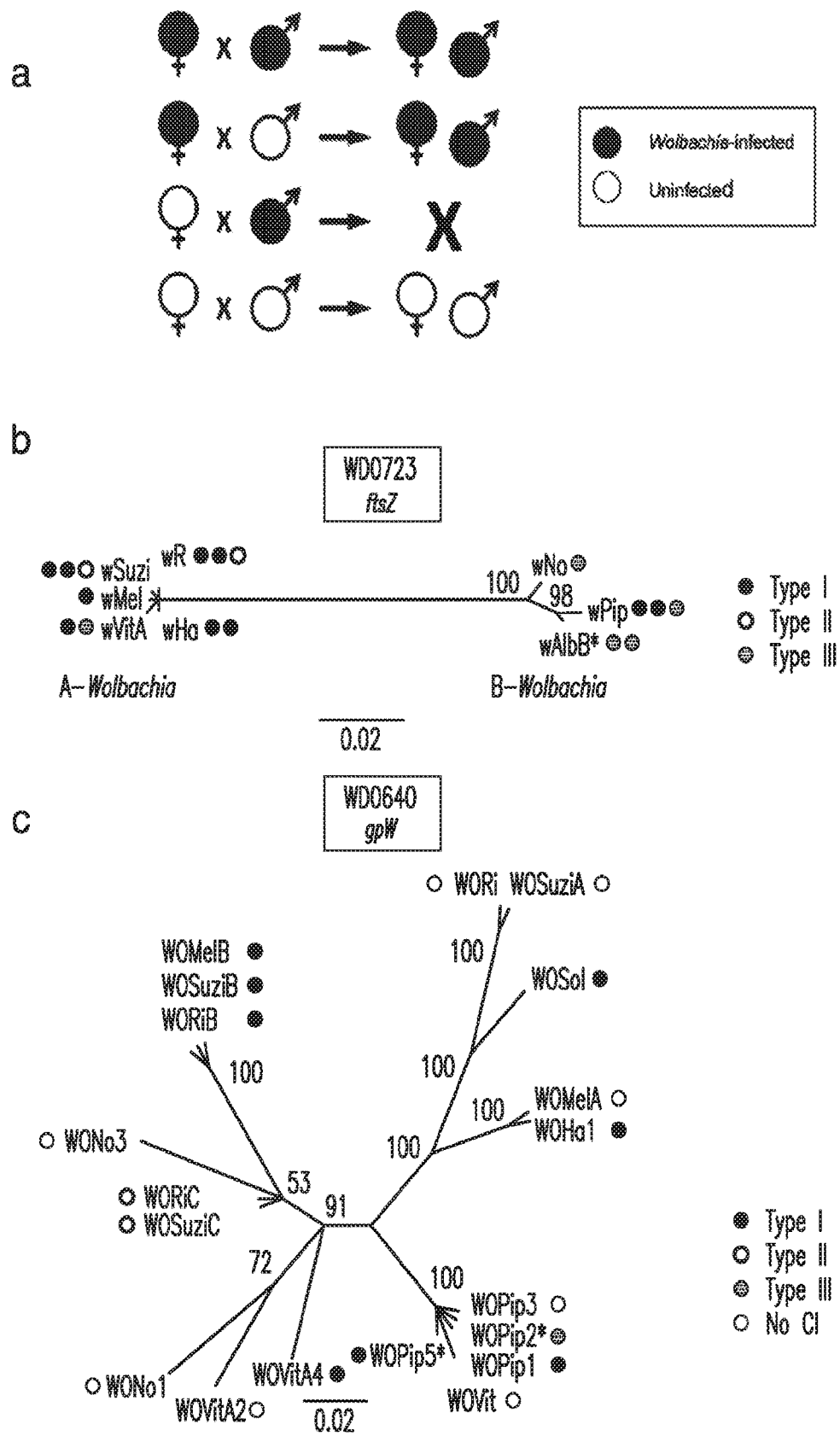
FIG. 5. CI and the evolution of *Wolbachia* or phage WO. (a) Diagram showing the effect of parental *Wolbachia* infection on progeny viability and infection status. CI occurs when males are *Wolbachia*-infected but females are not. *Wolbachia*-infected females are able to rescue the viability defect seen in CI crosses and favor spread of the infection through a population of mixed infection status. (b) Bayesian phylogenies based on a 393-aa alignment of WD0723, the wMel ftsZ gene, and its homologs and (c) a 70-aa alignment of WD0640, the phage WO gpW gene, and its homologs. Trees are based on JTT+G and CpRev+I models of evolution, respectively, and are unrooted. Consensus support values are shown at the nodes. (*) indicates that the CI operon is not included in FIG. 1. The WOPip5 operon is truncated while the WOPip2 and second wAlbB operons are highly divergent from WD0632.

Disclosed herein are methods for population replacement. The first includes generating CI-inducing males that do not harbor the classical bacteria required for CI such as *Wolbachia* (Zabalou et al., 2004, *Proc Natl Acad Sci USA*, 101, 15042-5) or Cardinium (Gotoh et al., 2007, *Heredity (Edinb)*, 98, 13-20; Penz et al., 2012, *PLoS Genet*, 8, e1003012) species. Historically, one of the major hurdles to utilizing a population replacement strategy has been the difficulty of transferring these CI-inducing organisms into new host species (Hughes et al., 2011, *PLoS Pathog*, 7, e1002043; Hughes et al., 2014, *Proc Natl Acad Sci USA*, 111, 12498-503). In fact, only three in 2,541 attempts led to transinfected *Aedes aegypti* after two years of cell-line adaptation (Walker et al., 2011, *Nature*, 476, 450-3). Moreover, once released in the population, the infection has to efficiently vertically transmit itself to the next generation and avoid the evolution of host suppression traits that eliminate the bacteria (Rasgon, 2008, *Adv Exp Med Biol*, 627, 114-25). The proposed technology circumvents these concerns by transgenically inserting the bacterial operons or their derivatives directly into the host nuclear genome, cytoplasmic genome (e.g., mitochondria), or into the genomes of various host-associated microorganisms (i.e., bacteria, viruses, archaea, protists) that are vertically inherited from parents to offspring. This technology would not be limited to just a handful of species, as Example 2 shows that bacterial operons derived from the *Wolbachia* infection of *Culex pipiens* are also effective in *Drosophila*. Further, FIGS. 5, 6, and 15 show examples of closely related bacterial operons that could be utilized in a broad range of animal species. This alleviates the current issues with inducing CI in novel hosts. It is important to note that utilizing CI bacterial operons instead of the CI-inducing bacteria relies on transgenic insertion of both the CI and "rescue" genes.

Some current uses of a PRS rely on one factor, such as an infection by *Wolbachia pipientis*, to provide both the beneficial trait and the genetic drive mechanism required for population replacement. The use of bacterial operons to induce CI, however, is an improvement to this approach as it de-couples the genetic drive mechanism from the desired trait being spread. This allows for a larger assortment of traits to be spread through PRS as they do not have to be provided by a technology or organism, such as a naturally occurring *Wolbachia* infection, that also induces CI. The bacterial operons could thus be utilized in conjunction with other technologies that may alter host fitness, lifespan, or disease resistance to propagate different desired traits through a population.

Figure 3:
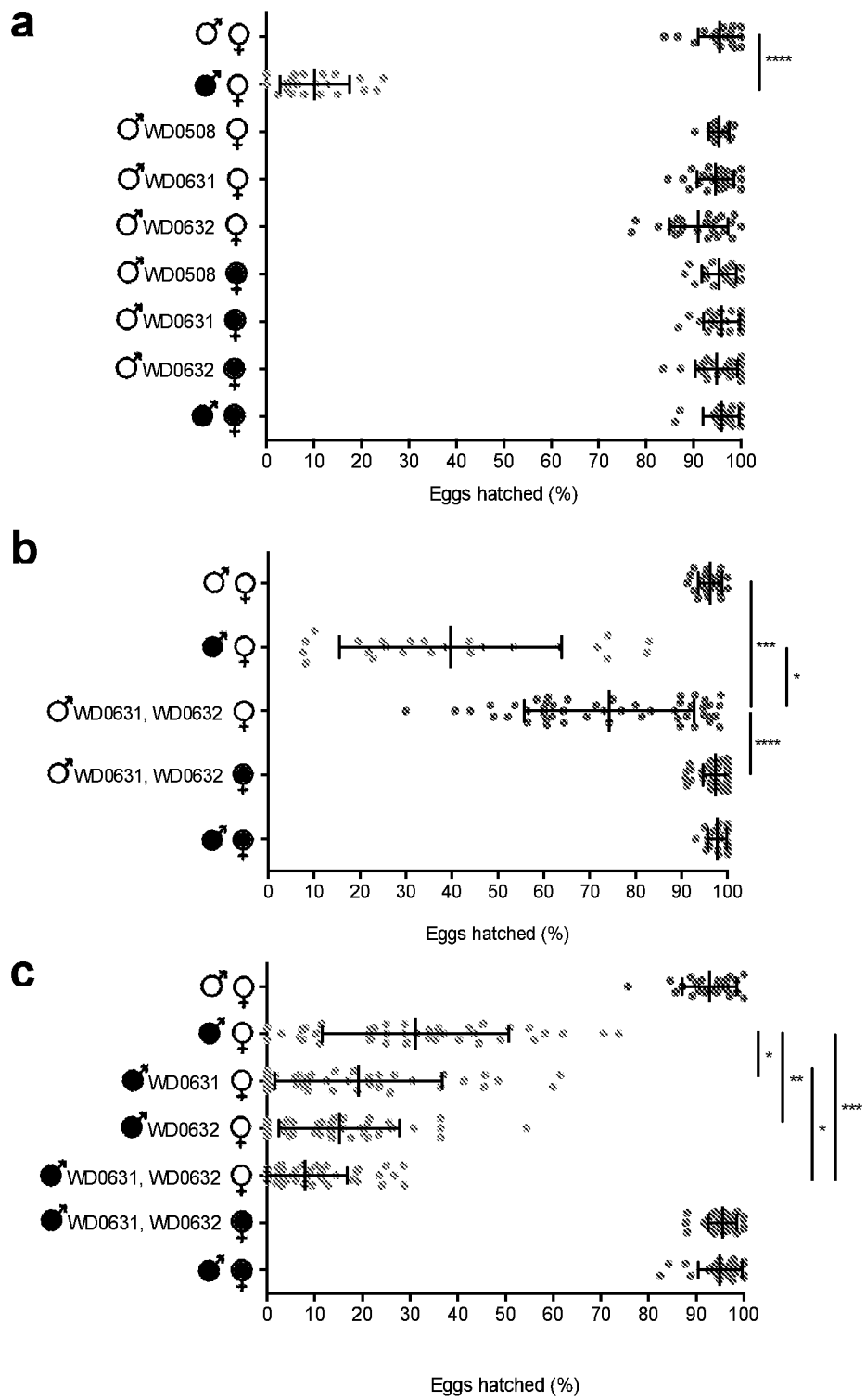
FIG. 3. Dual expression of WD0631 and WD0632 induces CI. Hatch rate assays are shown with either single-gene transgenic (a,c), or dual WD0631/WD0632 transgenic (b,c) *D. melanogaster*. Infection status is designated with filled-in symbols for a wMel-infected parent or open symbols for an uninfected parent. Transgenic flies are labeled with their transgene to the right of their gender symbol. Unlabeled gender symbols represent wild type flies. Data points are colored according to the type of cross, with blue indicating no *Wolbachia* infection, red indicating a CI cross with male-only wMel infections, and purple indicating a rescue cross with wMel-infected females. Error bars indicate standard deviation. *=$P<0.05$, =$P<0.01$, *=$P<0.001$, ****=$P<0.0001$ by ANOVA with Kruskal-Wallis test and Dunn's multiple test correction. Statistical comparisons are between all groups for panels a and b; comparisons for panel c are between CI crosses (red) only.

A second option disclosed herein is to utilize the bacterial operons in conjunction with current approaches. The current technology is described in U.S. Pat. No. 9,090,911 but, importantly, is reliant upon CI induced by *Wolbachia* strains that are also detrimental to the host (wMel-Pop (Nguyen et al., 2015, *Parasit Vectors*, 8, 563; Ritchie et al., 2015, *PLoS Negl Trop Dis*, 9, e0003930)) or which induce incomplete CI (wMel (Reynolds and Hoffmann, 2002, *Genet Res*, 80, 79-87)). In one embodiment, bacterial operon products are expressed within these animals by inserting the genes into the host nuclear genome, cytoplasmic genome (e.g., mitochondria), or into the genomes of various host-associated microorganisms, including *Wolbachia*. FIG. 3 (See Example 1) shows that expression of bacterial operon genes in *Wolbachia*-infected insects is able to increase the rate of CI. Further, bacterial operon genes have not been shown to be detrimental to hosts. This means that current approaches can be enhanced through usage of bacterial operons as CI would be stronger without sacrificing host health. This can greatly increase the rate of population replacement and reduce the number of released animals required (Chan and Kim, 2013, *Bull Math Biol*, 75, 1501-23; Engelstadter and Telschow, 2009, *Heredity (Edinb)*, 103, 196-207).

Several unfavorable aspects of current population replacement strategies are that the new population may lose its beneficial qualities (through mutation, adaptation, or some other process) or may become actively harmful (through mosquito overproliferation, enhancement of replication of other microbes including malaria (Hughes et al., 2014, *PLoS Pathog*, 10, e1004182) or West Nile virus (Dodson et al., 2014, *PLoS Negl Trop Dis*, 8, e2965), or acquired traits). In this situation the proposed bacterial operons can also be utilized to spread a new replacement strain. It is well established that, in the natural context, CI induced by *Wolbachia pipientis* is strain specific (Sinkins, 2004, *Insect Biochem Mol Biol*, 34, 723-9). It becomes possible then to utilize differential versions of the bacterial operons, such as those in FIGS. 6, 7, and 15, to perform multiple rounds of population replacement with new CI/rescue factor combinations, wherein the new strains induce a version of CI that cannot be rescued by the incumbent population. This provides a measure of control over the previously released populations and also allows for new benefits to be introduced as technology advances.

Alterations to the system can be made to optimize effectiveness of the "bacterial operon", as discussed in the section above discussing the sterile insect technique. Additionally, once released, the transgenic insertion can be used as a tracking marker distinguishing the insects containing the genetically modified bacterium from wild insects, as further discussed in the section above discussing the sterile insect technique.

Previous examples of population replacement strategies include using wMel or wMel-Pop in mosquitoes (U.S. Pat. No. 9,090,911), recombinant insect with dominant lethal gene (U.S. Pat. No. 9,125,388): wMel provided disease resistance (WO2013026994): transferring *Wolbachia* to induce CI (WO2006008652): using transformed *Wolbachia* for similar techniques (WO1994002591): see also U.S. Pat. No. 7,868,222.

Additional patents that discuss methods for gene drives and population replacement strategies include for example, WO2015105928, and WO2013131920A1, which include methods using homing endonucleases such as zinc finger nucleases (ZFNs), transcription activator-like effector nucleases (TALENs), and CRISPR systems, such as the CRISPR/Cas9 and CRISPR/Cpf1 systems. These gene drive systems may be used in combination with the bacterial operons disclosed herein (for example, encoding cytoplasmic incompatibility factors).

In one aspect, provided herein is a genetically modified bacterium comprising:
 a bacterial operon encoding a cytoplasmic incompatibility factor or a variant thereof; and
 a promoter operably linked to the bacterial operon;
 wherein the bacterial operon occurs at a non-naturally occurring genomic location in the bacterium.

In another aspect, provided herein is an arthropod infected with a bacterium, wherein the bacterium comprises:
 a bacterial operon encoding a cytoplasmic incompatibility factor or a variant thereof; and
 a promoter operably linked to the bacterial operon;
 wherein the bacterial operon occurs at a non-naturally occurring genomic location in the bacterium.

In an additional aspect, provided herein is a method for controlling a population of target arthropods, comprising:
 providing a genetically modified bacterium comprising:
  a bacterial operon encoding a cytoplasmic incompatibility factor or a variant thereof, and
  a promoter operably linked to the bacterial operon;
 infecting a population of replacement arthropods with the genetically modified bacterium; and
 releasing the replacement arthropods amongst a population of target arthropods, wherein the release of the replacement arthropods reduces the population of target arthropods.

In one embodiment, the bacterial operon is from *Wolbachia*. In one embodiment, the bacterial operon is from wMel. In one embodiment, the bacterial operon encodes the cytoplasmic incompatibility factor WD0631. In one embodiment, the bacterial operon encodes the cytoplasmic incompatibility factor WD0632. In one embodiment, the bacterial operon encodes the cytoplasmic incompatibility factors WD0631 and WD0632.

In one embodiment, the bacterial operon is from *Wolbachia pipientis*. In one embodiment, the bacterial operon encodes the cytoplasmic incompatibility factor CidA$^{wPip}$ (wPa_0282). In one embodiment, the bacterial operon encodes the cytoplasmic incompatibility factor CidB$^{wPip}$ (wPa_0283). In one embodiment, the bacterial operon encodes the cytoplasmic incompatibility factors CidA$^{wPip}$ (wPa_0282) and CidB$^{wPip}$ (wPa_0283). In one embodiment, the bacterial operon encodes the cytoplasmic incompatibility factor CinA$^{wPip}$ (wPa_0294). In one embodiment, the bacterial operon encodes the cytoplasmic incompatibility factor CinB$^{wPip}$ (wPa_0295). In one embodiment, the bacterial operon encodes the cytoplasmic incompatibility factors CinA$^{wPip}$ (wPa_0294) and CinB$^{wPip}$ (wPa_0295).

In one embodiment, the bacterial operon is from Cardinium. In one embodiment, the bacterial operon is from *Rickettsia*.

In one embodiment, the bacterial operon encodes a deubiquitylase. In one embodiment, the bacterial operon encodes a nuclease.

In one embodiment, the bacterium is *Wolbachia*. In one embodiment, the bacterium is Cardinium. In one embodiment, the bacterium is *Rickettsia*.

In one embodiment, the arthropod is an insect. In one embodiment, the insect is selected from the genera consisting of *Aedes*, *Culex* and *Anopheles*. In one embodiment, the insect is selected from the group consisting of *Aedes albopictus*, *Aedes aegypti* and *Aedes polynesiensis*. In one embodiment, the insect is *Drosophila suzukii*.

Arthropods and Infectious Disease Vectors

The inventors have identified a primary mechanism for CI involving cytoplasmic incompatibility factor proteins secreted into germline cells by resident bacteria and disclose herein new methods for control of arthropod (for example, insects) pests and disease vectors, such as mosquitoes transmitting the Dengue fever and Zika viruses.

In one embodiment, the arthropod is an insect. In one embodiment, the arthropod is a mosquito. In one embodiment, the mosquito is selected from the genera consisting of *Aedes*, *Culex* and *Anopheles*. In one embodiment, the mosquito is an *Aedes* mosquito. In one embodiment, the mosquito is an *Anopheles* mosquito. In one embodiment, the mosquito is a *Culex* mosquito. In one embodiment, the *Aedes* mosquito species is selected from the group consisting of *Aedes albopictus*, *Aedes aegypti* and *Aedes polynesiensis*. In one embodiment, the *Anopheles* mosquito species is *Anopheles gambiae*. In one embodiment, the *Culex* mosquito species is *Culex pipiens*.

In one embodiment, disclosed herein are methods for controlling or reducing populations of insects that transmit human or veterinary pathogens. In one embodiment, disclosed herein are methods for replacing a population of arthropods that transmit human or veterinary pathogens with a replacement arthropod population that is infected with a genetically modified bacteria (for example *Wolbachia*) that reduces the ability of the insect to transmit the pathogen. In one embodiment, the pathogen is selected from dengue virus, Zika virus, a malaria parasite (*Plasmodium* genus), West Nile virus, yellow fever virus, chikungunya virus, Japanese encephalitis, St. Louis encephalitis and Western and Eastern Equine Encephalitis viruses.

In one embodiment, disclosed herein are methods for controlling or reducing populations of insects that transmit trypanosomes including African sleeping sickness, Chagas disease, and Nagana. In one embodiment, the pathogen is *Trypanosoma cruzi*. In one embodiment, the pathogen is *Trypanosoma brucei*. In one embodiment, the insect is of the genus *Glossina*. In one embodiment, the insect is *Glossina morsitans*. In one embodiment, the insect is a Tsetse fly. In one embodiment, the insect is a kissing bug. In one embodiment, the insect is of the genus *Rodnius*. In one embodiment, the insect is *Rhodnius prolixus*.

In one embodiment, disclosed herein are methods for controlling or reducing populations of arthropods that transmit rickettsioses and pathogens within Anaplasmatacea including Rickettsias *rickettsii, africae, parkeri, sibirica, conorii, slovaca, peacockii, philipii, rickettsii* Hlp2, *heilongjiangensis, japonica, montanensis, massiliae, rhipicephali,* amblyommii, *helvetica, monacensis, buchneri, hoogstralli, felis, akari, australis, canadensis, prowazekii, typhi, bellii*. In one embodiment, the arthropod is a tick. In one embodiment, the arthropod is a tick of the genera *Amblyomma, Ixodes*, or *Rhipicephalus*. In one embodiment, the disease is epidemic typhus. In one embodiment, the disease is scrub typhus. In one embodiment, the disease is an Ehrlichiosis. In one embodiment, the pathogen is of the genus *Ehrlichia*. In one embodiment, the pathogen is of the genus *Anaplasma*. In one embodiment, the pathogen is of the genus Orientia. In one embodiment, the arthropod is a chigger of the genus *Leptotrombidium*. In one embodiment, the arthropod is a louse of the genus *Pediculus*. In one embodiment, the arthropod is a flea of the genus *Pulex*.

In one embodiment, the invention is useful for controlling sandflies that transmit leishmaniasis. In one embodiment, the insect is of the genus *Phlebotomus*. In one embodiment, the pathogen is of the genus *Leishmania*. In one embodiment, the pathogen is *Leishmania donovani, Leishmania infantum*, or *Leishmania Chagasi.*

In one embodiment, the insect is of various aphids including: *Acyrthosiphon kondoi, Brevicoryne brassicae, Rhopalosiphum maidis, Aphis gossypii, Aphis craccivora, Myzus persicae, Rhopalosiphum padi, Acyrthosiphon pisum, Rhopalosiphum rufiabdominalis, Metopolophium dirhodum, Aphis glycine, Therioaphis trifolii, Lipaphis erysimi, Rhopalosiphum padi.*

In one embodiment, the invention is useful for controlling the armyworm agricultural pest species including *Leucania convecta, Spodoptera exempta, Spodoptera Mauritia, Spodoptera exigua*, Mythimna separate, *Leucania stenographa.*

In one embodiment, the invention is useful for controlling pests of beans and beets. In one embodiment, the insect is either the Bean fly (*Ophiomyia phaseoli*), the Bean leafroller (*Omiodes diemenalis*), the Bean looper or *Mocis* (*Mocis alterna*), the Bean podborer (*Maruca vitrata*), the Bean spider mite (*Tetranychus ludeni*), the Beet webworm (*Spoladea recurvalis*), the Large Brown bean bug (*Riptortus serripes*), the Small Brown bean bug (*Melanacanthus scutellaris*)

In one embodiment, the invention is useful for controlling the Blue oat mite (*Penthaleus major*). In one embodiment, the invention is useful for controlling the Brown flea beetle (*Chaetocnema* sp.). In one embodiment, the invention is useful for controlling the Brown mirid (*Creontiades pacificus*). In one embodiment, the invention is useful for controlling the Brown shield bug (*Dictyotus caenosus*). In one embodiment, the invention is useful for controlling the Brown wheat mite (*Petrobia latens*). In one embodiment, the invention is useful for controlling the Bruchid, Cowpea (*Callosobruchus maculatus*).

In one embodiment, the invention is useful for controlling pests of Corn including: the Corn aphid (*Rhopalosiphum maidis*), and the Corn earworm (*Helicoverpa armigera*).

In one embodiment, the invention is useful for controlling pests of cotton including the Cotton aphid (*Aphis gossypii*), Cotton bollworm (*Helicoverpa armigera*), the Cotton harlequin bug (*Tectocoris diophthalmus*), the Cotton leafhopper (*Amrasca terraereginae*), the Cotton leafperforator (*Bucculatrix gossypii*), the Cotton looper (*Anomis flava*), the Cottonseed bug (*Oxycarenus luctuosus*), the Cotton seedling thrip (*Thrips tabaci*), the Cotton tipworm (*Crocidosema plebejana*), and the Cotton webspinner (*Achyra affinitalis*).

In one embodiment, the invention is useful for controlling the Diamondback moth (*Plutella xylostella*). In one embodiment, the invention is useful for controlling the Dried fruit beetle (*Carpophilus* spp.). In one embodiment, the invention is useful for controlling the Eastern false wireworm (*Pterohelaeus* spp.). In one embodiment, the invention is useful for controlling the *Etiella* moth (*Etiella behrii*). In one embodiment, the invention is useful for controlling the False wireworm (*Pterohelaeus* and *Gonocephalum* spp.). In one embodiment, the invention is useful for controlling the Flea beetles, Brown and Redheaded (*Chaetocnema* and *Nisostra* sp.). In one embodiment, the invention is useful for controlling the Flower beetle (*Carpophilus* spp.).

In one embodiment, the invention is useful for controlling various Grasshoppers and locusts including the Grasshopper, Wingless (*Phaulacridium vittatum*), the Locust, Australian plague (*Chortoicetes terminifera*), the Locust, Migratory (*Locusta migratoria*), the Locust, Yellow-winged (*Gastrimargus musicus*), the Locust, Spur-throated (*Austracris* (Noamdacris) *guttulosa*).

In one embodiment, the invention is useful for controlling the Greenhouse whitefly (*Trialeurodes vaporariorum*). In one embodiment, the invention is useful for controlling the Green peach aphid (*Myzus persicae*). In one embodiment, the invention is useful for controlling the Green mirid (*Creontiades dilutus*). In one embodiment, the invention is useful for controlling the Green vegetable bug (*Nezara viridula*). In one embodiment, the invention is useful for controlling the Green stink bug (*Plautia affinis*). In one embodiment, the invention is useful for controlling the Grey cluster bug (*Nysius clevelandensis*). In one embodiment, the invention is useful for controlling the *Helicoverpa* species (*armigera* and *punctigera*).

In one embodiment, the invention is useful for controlling planthoppers. In one embodiment, the insect is the small brown planthopper (*Laodelphax striatellus*). In one embodiment, the invention is useful for preventing the transmission of crop diseases like Rice White Stripe Virus. In one embodiment, the invention is useful for controlling vectors of plant pathogens.

In one embodiment, the invention is useful for controlling the Jassids and various leafhoppers including the Leafhopper, cotton (*Amrasca terraereginae*), the Leafhopper, lucerne (*Austroasca alfalfae*), the Leafhopper, maize (*Cicadulina bimaculata*), the Leafhopper, vegetable (*Austroasca viridigrisea*).

In one embodiment, the invention is useful for controlling the Loopers including the Looper, Brown pasture (*Ciampa arietaria*), the Looper, Castor oil (*Achaea janata*), the Looper, Cotton (*Anomis flava*), the Looper, Sugarcane (*Mocis frugalis*), the Looper, Soybean (*Thysanoplusia orichalcea*), the Looper, Tobacco (*Chrysodeixis argentifera*), the Looper, Vegetable (*Chrysodeixis eriosoma*).

In one embodiment, the invention is useful for controlling various Thrip pests including the Onion Thrip (*Thrips tabaci*), the Cotton seedling Thrip (*Thrips tabaci*), the Maize Thrip (*Frankliniella williamsi*), the Plague Thrip (*Thrips imaginis*), the tobacco Thrip (*Thrips tabaci*), the Tomato Thrip (*Frankliniella schultzei*), the Western flower Thrip (*Frankliniella orientalis*)

In one embodiment, the invention is useful for controlling various Mite pests including the Mite, Bean spider (*Tetrany-* chus ludeni), Mite, Brown wheat (*Petrobia latens*), Mite, Blue oat (*Penthaleus major*), Mite, Peanut (*Paraplonobia* spp.), Mite, Redlegged earth (*Halotydeus destructor*), Mite, Strawberry spider (*Tetranychus lambi*), and the Two-spotted mite (*Tetranychus urticae*).

In one embodiment, the invention is useful for controlling various whitefly pests including the Greenhouse whitefly (*Trialeurodes vaporariorum*), the Silverleaf whitefly (*Bemisia tabaci* biotype B and Australian native AN), and the Silverleaf whitefly (*Bemisia tabaci* biotype Q).

In one embodiment, the inventions is useful for controlling various fruit pests. In one embodiment, the arthropod is from the genera *Drosophila*. In one embodiment, the arthropod is *Drosophila suzukii*. *Drosophila suzukii*, commonly called the spotted-wing *drosophila*, is a vinegar fly closely related to *Drosophila melanogaster*. Unlike its vinegar fly relatives who are primarily attracted to rotting or fermented fruit, *D. suzukii* attacks fresh, ripe fruit by laying eggs under the soft skin. The larvae hatch and grow in the fruit, destroying the fruit's commercial value. The pest particularly (but not limited to) infests cherries, apples, apricots, persimmons, tomatoes, blueberries, grapes, nectarines, pears, plums, peaches, figs, raspberries and strawberries. Although *D. suzukii* is native to Southeast Asia, the fruit pest has recently invaded North and Central America as well as Europe, where it is expanding rapidly. Effective management of this pest is a challenge owing to the wide host range and short generation time. Therefore, monitoring and controlling *D. suzukii* is of great economic importance. However, traps and baits containing for instance apple cider vinegar, which are typically used for attracting vinegar flies such as *D. melanogaster*, are less efficient for attracting and trapping *D. suzukii*. In one embodiment, the insect is the Mexican Fruit Fly (*Anastrepha ludens*). In one embodiment, the insect is the Mediterranean Fruit Fly (*Ceratitis capitata*). In one embodiment, the insect is of the genus *Anastrepha, Bactrocera,* or *Ceratitis*. In one embodiment, the insect is a tephritid.

In one embodiment, the invention is useful for controlling various other agricultural pests including: the red-houldered leaf beetle (*Monolepta australis*), Native budworm (*Helicoverpa punctigera*), Native whitefly (*Bemisia tabaci*), Northern armyworm (*Mythimna separata*), Oat aphid (*Rhopalosiphum padi*), Onion thrip (*Thrips tabaci*), Pale cotton stainer bug (*Dysdercus sidae*), Pea aphid (*Acyrthosiphon pisum*), Pea blue butterfly (*Lampides boeticus*), Peanut mite (*Paraplonobia* spp.), Peanut scarab (*Heteronyx* spp.), Pea weevil (*Bruchus pisorum*), Pinkspotted bollworm (*Pectinophora scutigera*), Plague thrip (*Thrips imaginis*), Podsucking bugs (*Nezara viridula*), Redbanded shield bug (*Piezodorus oceanicus*), Redheaded flea beetle (*Nisotra* sp.), Redlegged earth mite (*Halotydeus destructor*), Redshouldered leaf beetle (*Monolepta australis*), Rice root aphid (*Rhopalosiphum rufiabdominalis*), Rose grain aphid (*Metopolophium dirhodum*), Rough bollworm (*Earias huegeliana*), Rutherglen bug (*Nysius vinitor*), Seed harvesting ants (*Pheidole* spp.), Scarab, Black sunflower (*Pseudoheteronyx* sp.), Scarab, Peanut (JPG, 20.4 KB) (*Heteronyx* sp.), Shoot flies (*Atherigona* sp.), Silverleaf whitefly (*Bemisia tabaci* biotype B and Australian native AN), Silverleaf whitefly (*Bemisia tabaci* biotype Q), Sitona weevil (*Sitona discoideus*), Solenopsis mealybug (*Phenacoccus solenopsis*), Sorghum midge (*Stenodiplosis sorghicola*), Sorghum head caterpillar (*Cryptoblabes adoceta*), Soybean leafminer (*Porphyrosela aglaozona*), Soybean looper (*Thysanoplusia orichalcea*), Soybean moth (*Aproaerema simplexella*), Spotted alfalfa aphid (*Therioaphis trifolii*), Spur-throated locust (*Austracris* (*Nomadacris*) *guttulosa*), Strawberry spider mite (*Tetranychus lambi*), Swarming leaf beetle (*Rhyparida* spp.), Tortrix (*Epiphyasa postvittana*), True wireworm (*Agrypnus* spp.), Vegetable weevil (*Listroderes difficilis*), Weed web moth (*Achyra affinitalis*), Whitegrub (*Heteronyx* spp.), Wingless cockroaches (*Calolampra* spp.), Wireworm, False (*Pterohelaeus* and *Gonocephalum* spp.), Wireworm, True (*Agrypnus* spp.), Yellow peach moth (*Conogethes punctiferalis*). In one embodiment, the insect is *Heteronychus arator*. In one embodiment, the insect is of the genus *Amnemus*. In one embodiment, the insect is of the genus *Pheidole*. In one embodiment, the invention is useful for controlling the Black field cricket (*Teleogryllus commodus, T. oceanicus, Lepidogryllus parvulus*), the Black field earwig (*Nala lividipes*), the Black leaf beetle (*Rhyparida nitida*), the Black sunflower scarab (*Pseudoheteronyx* sp.). In one embodiment, the invention is useful for controlling the Cowpea bruchid (*Callosobruchus maculatus*). In one embodiment, the invention is useful for controlling the Cricket, Black field (*Teleogryllus commodus, T. oceanicus, Lepidogryllus parvulus*). In one embodiment, the invention is useful for controlling the Crop mirid (*Sidnia kinbergi*). In one embodiment, the invention is useful for controlling the Cutworm (*Agrotis* spp.). In one embodiment, the invention is useful for controlling the Cabbage moth (*Plutella xylostella*). In one embodiment, the invention is useful for controlling the Castor oil looper (*Achaea janata*). In one embodiment, the invention is useful for controlling the Click beetle (*Agrypnus* spp.). In one embodiment, the invention is useful for controlling the Clover springtail (*Sminthurus viridis*). In one embodiment, the invention is useful for controlling the Cluster caterpillar (*Spodoptera litura*). In one embodiment, the invention is useful for controlling the Cockroach, Wingless (*Calolampra* spp.). In one embodiment, the invention is useful for controlling the Common grass blue butterfly (*Zizina labradus*). In one embodiment, the invention is useful for controlling the Legume webspinner (*Omiodes diemenalis*). In one embodiment, the invention is useful for controlling the Light brown apple moth (*Epiphyas postvittana*). In one embodiment, the invention is useful for controlling *Mocis trifasciata*. In one embodiment, the invention is useful for controlling *Pantydia* spp. In one embodiment, the invention is useful for controlling the Lucerne crownborer (*Zygrita diva*). In one embodiment, the invention is useful for controlling the Lucerne flea (*Sminthurus viridis*). In one embodiment, the invention is useful for controlling the Lucerne leafhopper (*Austroasca alfalfae*). In one embodiment, the invention is useful for controlling the Lucerne leafroller (*Merophyas divulsana*). In one embodiment, the invention is useful for controlling the Lucerne seed wasp (*Bruchophagus roddi*). In one embodiment, the invention is useful for controlling the Lucerne seed web moth (*Etiella behrii*).

In one embodiment, the invention is useful for controlling forestry and wildlife pests such as the emerald ash borer. In one embodiment, the insect is of the genus *Agrilus* or specifically *Agrilus planipennis*. In one embodiment, the invention is useful for pests of trees and lumber.

EXAMPLES

The following examples are set forth below to illustrate the results and methods according to the disclosed subject matter. These examples are not intended to be inclusive of all aspects of the subject matter disclosed herein, but rather to illustrate representative results and methods. These Example 1. *Wolbachia*-Induced Cytoplasmic Incompatibility is Caused by Prophage WO Genes The genus *Wolbachia* is an archetype of maternally inherited intracellular bacteria that infect the germline of millions of invertebrate species worldwide and parasitically alter arthropod sex ratios and reproductive strategies to increase the proportion of infected females (the transmitting sex) in the population. The most common of these reproductive manipulations is cytoplasmic incompatibility (CI), typically expressed as embryonic lethality in crosses between infected males and uninfected females. This lethality is completely rescued by females infected with the same or a similar *Wolbachia* strain. Despite more than 40 years of research[1], the genes by which *Wolbachia* cause CI remain unknown. Here, we use comparative genomic, transcriptomic, proteomic and transgenic approaches to elucidate two genes that are CI effectors. In the *Wolbachia* strain wMel, the phage WO[2]-encoded operon consisting of WD0631 and WD0632 recapitulates significant degrees of CI in transgenic male *Drosophila melanogaster* that express both genes. The transgene-induced CI causes cytological defects similar to wild type CI, and it is fully rescued by wMel-infected females. The discovery of these two cytoplasmic incompatibility factor genes (cifA and cifB) represents an important step forward in understanding the genetics of reproductive parasitism and has implications for symbiont-induced speciation[3,4] and control of agricultural pests[5] and disease vectors that spread dengue virus[6,7], Zika virus[8], and other human pathogens.

Figure 1:
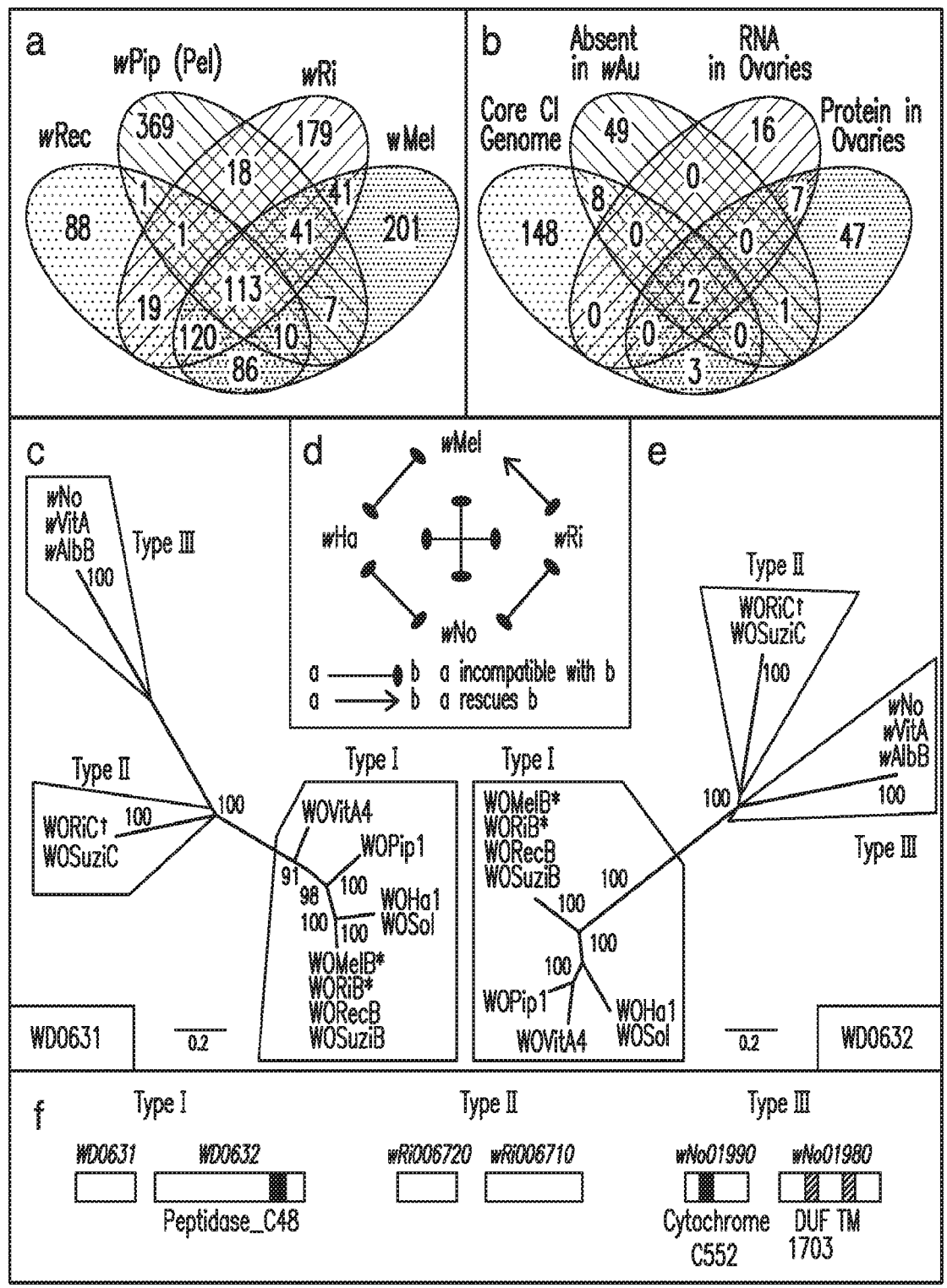
FIG. 1. Cytoplasmic incompatibility (CI) gene candidate selection and evolution. (a) Venn diagram illustrating unique and shared gene sets from four CI-inducing *Wolbachia* strains. The number of gene families in common between strains is indicated for each combination. (b) Venn diagram illustrating the number of unique wMel genes matching each criteria combination. Bayesian phylogenies of WD0631 (c) and WD0632 (e) and their homologs are shown based on a 256-aa alignment of WD0631 reciprocal BLASTp hits and a 462-aa alignment of WD0632 reciprocal BLASTp hits. When multiple similar copies of the same operon exist in the same strain, only one copy is shown. Consensus support values are shown at the nodes. Both trees are based on the JTT+G model of evolution and are unrooted. (d) CI patterns correlate with WD0631/WD0632 operon homology. wRi rescues wMel and both share a similar operon (*). The inability of wMel to rescue wRi correlates with an operon type (†) that is present in wRi but absent in wMel. Likewise, bidirectional incompatibility of all other crosses correlates to divergent operons. This diagram was adapted from *Bossan et. al*[51]. (f) Protein architecture of WD0631/WD0632 homologs is conserved for each clade and is classified according to the WD0632-like domain: Type I features Peptidase_C48; Type II lacks an annotated functional domain; and Type III features DUF1703. TM stands for transmembrane domain. For (c) and (e), the WO-prefix indicates a specific phage WO haplotype and the w-prefix refers to a "WO-like island," a small subset of conserved phage genes, within that specific *Wolbachia* strain.

We hypothesized that the genes responsible for CI (FIG. 5a) would be present in all CI-inducing *Wolbachia* strains but absent or divergent in strains that are mutualists or that do not induce CI; we also predicted that these genes would be relatively highly expressed in the gonads of infected insects. To elucidate CI effector candidates, we determined the core genome shared by the CI-inducing *Wolbachia* strains wMel, wRi, wPip (Pel), and the recently sequenced wRec, which helped narrow the list of candidate prophage WO genes associated with reproductive parasitism[9], while excluding the pan-genome of the mutualistic strain wBm. This analysis yielded 113 gene families representing 161 unique wMel genes (FIG. 1a, Supplementary Information 1a). Next we streamlined this candidate list by comparing it to (i) homologs of genes previously determined by comparative genomic hybridization to be absent or divergent in the strain wAu[10], which does not induce CI, (ii) homologs to genes that are highly expressed at the RNA level in wVitA-infected *Nasonia vitripennis* ovaries, and (iii) homologs detected at the protein level in wPip (Buckeye)-infected ovaries of *Culex pipiens* mosquitoes. Remarkably, only two genes, those whose wMel locus tags are WD0631 and WD0632, were shared among all four gene subsets (FIG. 1b, Supplementary Information 1b-d). Notably, the homolog of WD0631 in the *Wolbachia* strain wPip, wPa_0282, was found at the protein level in the fertilized spermathecae of infected mosquitoes, lending support to the gene's role in reproductive manipulation[11].

We analyzed the evolution and predicted protein domains of these two genes and found that homologs of both genes are always associated with prophage WO in the *Wolbachia* chromosome[12], and they codiverged into three distinct phylogenetic groups that we designate type I, II, and III (FIG. 1c, e, Supplementary Information 1e). These relationships are not recapitulated in the phylogeny of the *Wolbachia* cell division gene ftsZ, which exhibits the typical bifurcation of A and B *Wolbachia* (FIG. 5b), or in the phylogeny of phage WO baseplate assembly gene gpW (FIG. 5c). This suggests that WD0631 and WD0632 are evolving under different evolutionary pressures than the core *Wolbachia* genome and active phage WO haplotypes.

Type I genes are the most prevalent amongst sequenced *Wolbachia* strains, and are always associated with large but incomplete phage WO regions that are missing important tail genes likely needed for active phage (FIG. 6). Although the function of type I WD0631 homologs are unknown, type I WD0632 homologs contain a peptidase_C48 domain (FIG. 1f), a key feature of Ulp1 (ubiquitin-like-specific protease) proteases[11], which catalyze the maturation of small ubiquitin-like modifier (SUMO) propeptides and can play a role in regulating cell cycle progression in eukaryotes[13]. A number of bacteria and viruses are known to usurp SUMOylation pathways in the manipulation of their hosts[14,15]. Type II WD0631 and WD0632 homologs are located within more complete phage haplotypes (FIG. 6), but the WD0632 homologs are truncated and lack recognized protein domains (FIG. 1f). Notably, all *Wolbachia* strains that contain type II homologs invariably contain at least one other copy of the operon that is type I and intact. Type III WD0631 homologs possess a cytochrome C552 domain involved in nitrate reduction, while type III WD0632 homologs contain a domain of unknown function (DUF1703) and a transmembrane domain (FIG. 1f). The functions of these domains are less well understood, but DUF1703 likely possesses nuclease activity and was previously found in a selfish genetic element that mediates embryonic lethality in Tribolium beetles[17].

Consistent with these genes' role in CI, the degree of relatedness and presence or absence of shared operons of WD0631 and WD0632 between *Wolbachia* strains correlates with known patterns of bidirectional incompatibility (FIG. 1d). Among the strains wRi, wHa, and wNo, only wRi is able to rescue wMel-induced CI[18,19]. We postulate that this is due to the fact that wRi and wMel share a highly related type I operon (99% amino acid identity), and thus likely also have a shared rescue factor, while wRi has an additional type II operon that may explain its ability to induce CI against wMel. Meanwhile, wHa has at most a 67% identity in the amino acid sequence of these proteins when compared to wMel, while wNo contains a type II operon that is only 31% identical (FIG. 7a). Additionally, the strength of CI varies considerably between different *Wolbachia* strains, and the relative degree of offspring lethality correlates with the number of copies of the WD0631/WD0632 operon that are present in each strain (FIG. 7b). Those strains with only one copy, such as wMel, have a comparatively weak CI phenotype, while those with two or three copies of the operon, such as wRi and wHa, cause strong CI[19].

Figure 2:
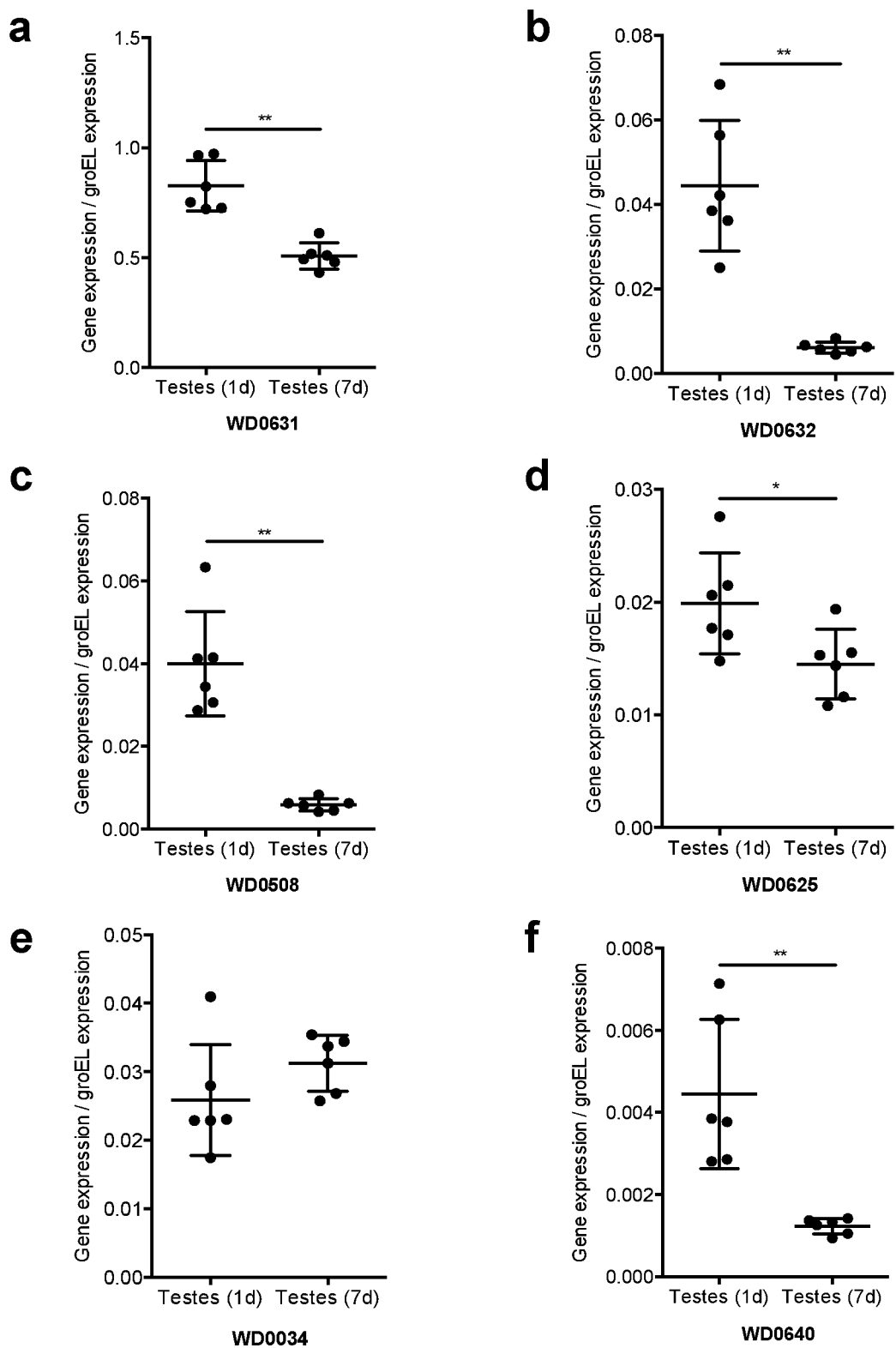
FIG. 2. Expression of CI effector candidates decrease as males age. (a-f) Expression of each gene in one-day-old and seven-day-old wMel-infected *D. melanogaster* testes, as determined by quantitative RT-PCR, is shown relative to groEL. Error bars indicate standard deviation. *=$P<0.05$, **=$P<0.01$ by Mann-Whitney U test.
Figure 8:
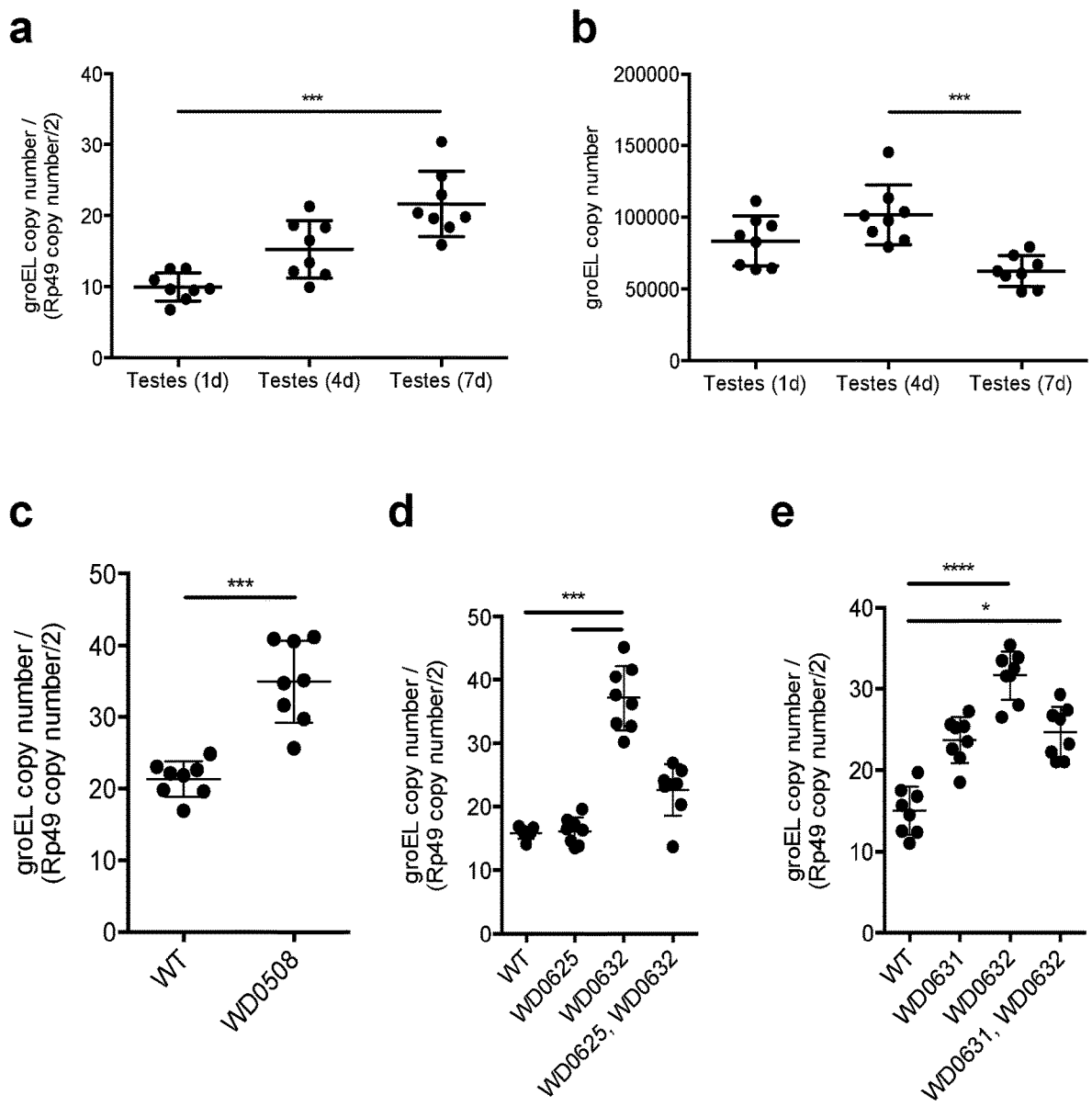
FIG. 8. *Wolbachia* titers in wild type and transgenic lines. (a) Relative *Wolbachia* titers do not decrease with age. DNA copy number of wMel groEL gene is shown normalized to *D. melanogaster* Rp49 gene copy number in testes at the indicated ages. (b) Absolute *Wolbachia* titers do not decrease with male age. (c-e) Relative *Wolbachia* titers are increased in WD0508, WD0631, or WD0632 transgenic lines. This does not occur in the WD0625 transgenic line nor does there appear to be an additive effect. Titers determined by real-time PCR detecting absolute copy number of wMel groEL gene compared to absolute copy number of the *D. melanogaster* Rp49 gene. Error bars show standard deviation. *=$P<0.05$, *=$P<0.001$, **=$P<0.0001$ by ANOVA with Kruskal-Wallis test and Dunn's multiple test correction. Two-tailed Mann-Whitney U test used for (c).
Figure 10:
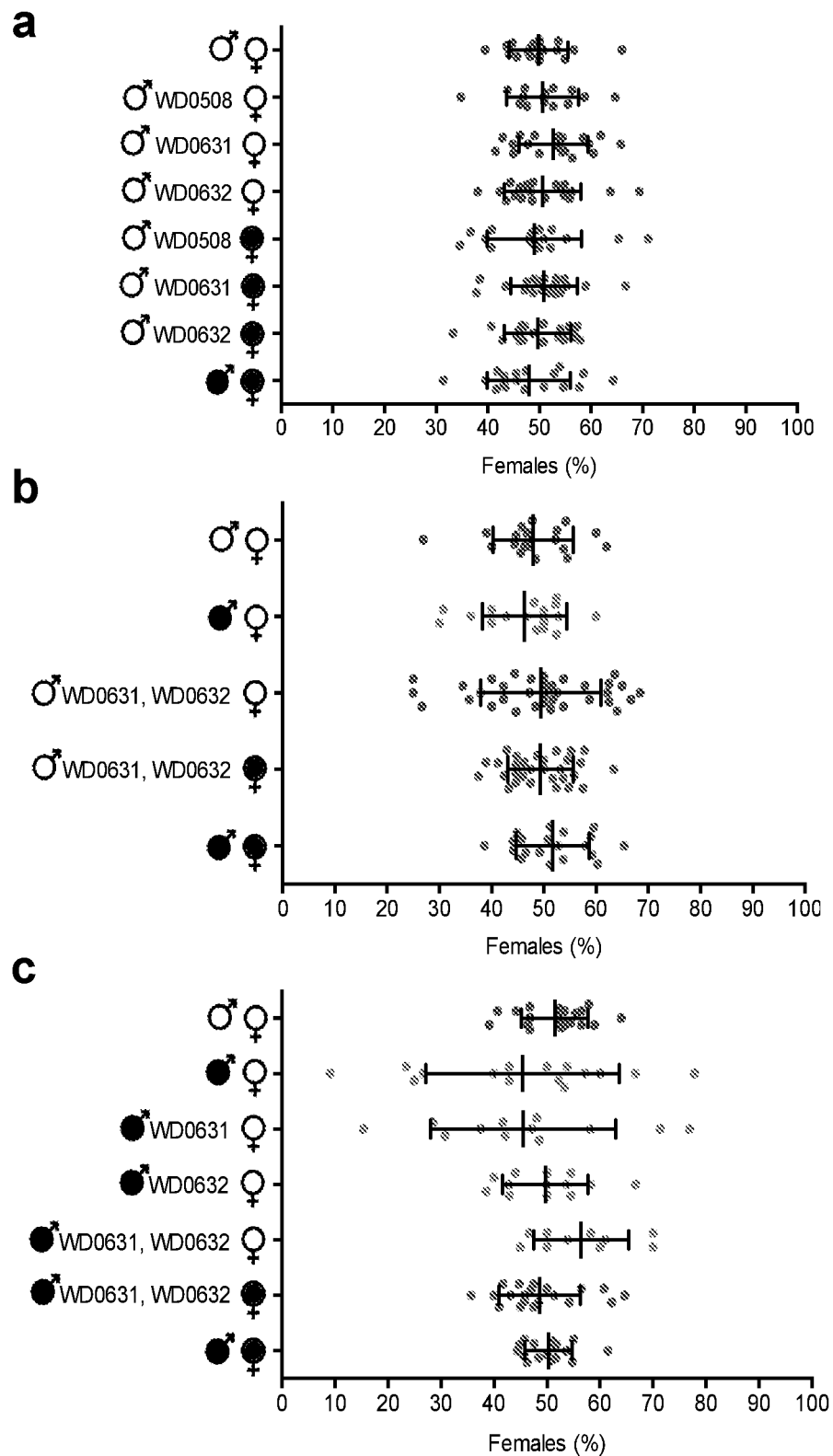
FIG. 10. Expression of CI effector candidates does not alter sex ratios. (a-c) Graphs correspond to the same crosses as FIG. 3. Infection status is designated with filled in symbols for a wMel-infected parent or open symbols for an uninfected parent. Transgenic flies are labeled with their transgene to the right of their gender symbol. Unlabeled gender symbols represent WT flies. Data points are colored according to the type of cross, with blue indicating no *Wolbachia* infection, red indicating a CI cross with male-only wMel infections, and purple indicating a rescue cross with wMel-infected females. Error bars indicate standard deviation.

Given the many lines of evidence in support of these two genes, we next examined WD0631 and WD0632 for their functional role in CI, as well as control wMel genes that were not correlated with CI. These control genes are WD0034, which encodes a PAZ (Piwi, Argonaut, and Zwille) domain containing protein, and two prophage WO genes—WD0508, which encodes a putative transcriptional regulator, and WD0625, which encodes a DUF2466 domain likely acting as a nuclease or regulatory protein. We first examined the expression of CI effector candidates in the testes of wMel-infected, one-day-old and seven-day-old *D. melanogaster* males. Since the magnitude of CI is known to decrease dramatically between newly emerged and one-week-old males[20], we predicted that a CI effector would be expressed at a lower level in older male testes. Indeed, while WD0631 and WD0632 are expressed at different levels, both show a significantly lower transcription level in older versus younger males (FIG. 2a,b), as measured relative to the *Wolbachia* housekeeping gene groEL. Both phage-encoded control genes, WD0508 and WD0625, also exhibited this pattern, but the non-phage gene WD0034, did not (FIG. 2c-e). WD0640, which encodes phage WO structural protein gpW, was also reduced in older males, suggesting that phage genes in general are relatively downregulated in seven-day-old testes (FIG. 2f). The phenomenon of decreased CI in older males is not due to decreases in *Wolbachia* titer over time, as the copy number of *Wolbachia* groEL relative to *D. melanogaster* Rp49 increases as males age, and there is no significant difference in the absolute *Wolbachia* gene copies between one-day-old and seven-day-old males (FIG. 8a,8b).

To directly test the function of these genes in CI, we generated transgenic *D. melanogaster* that express the candidate genes alone under the direction of an upstream activating sequence (UAS), since *Wolbachia* itself cannot be genetically transformed. We utilized a nanos-Gal4 driver line for tissue-specific expression predominantly in the germline[21,22]. CI was determined by measuring the percentage of embryos that hatched into larvae. While wild type (WT) CI between infected males (less than one day old) and uninfected females led to significantly reduced hatch rates, transgene-expressing, uninfected males with each of the four candidate genes did not affect hatch rates when crossed to uninfected females (FIG. 3a, FIG. 9a). In addition, none of the four genes had an effect on sex ratios (FIG. 9b, 6). There are no phenotypic effects despite confirmed expression of each transgene in the testes (FIG. 11a-d).

Figure 11:
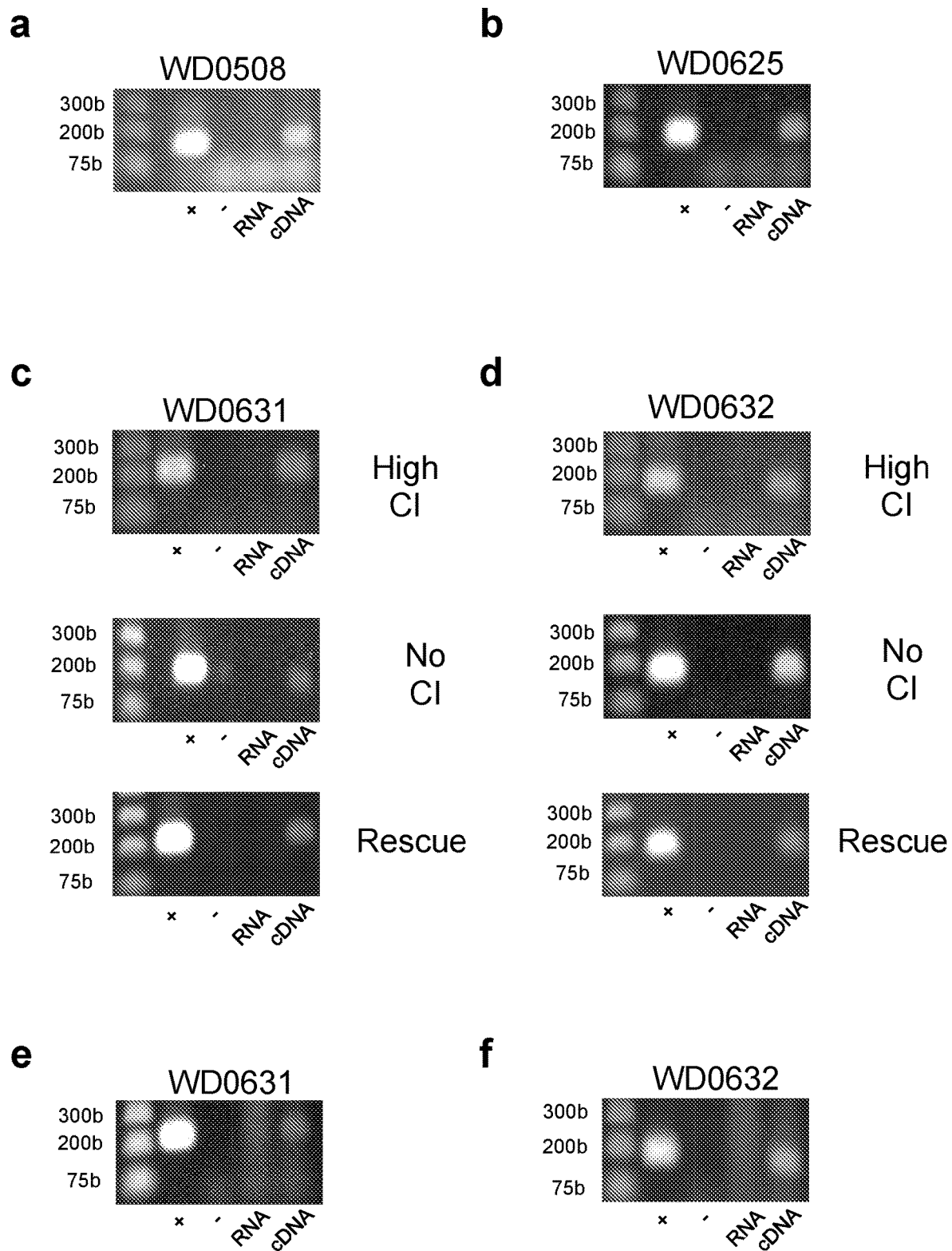
FIG. 11. CI effector candidates are expressed in testes from transgenic flies. WD0508 (a) and WD0625 (b) are expressed in testes as evident by PCR performed against cDNA generated from dissected males utilized in FIG. 3*a*. (c,d) WD0631 and WD0632 are expressed in the testes from transgenic males inducing high CI, no CI, or rescued CI. Testes were removed from males used in FIG. 3*b*. (e,f) WD0631 and WD0632 are expressed in ovaries from transgenic females. Ovaries were dissected from females utilized in FIG. 14*a*.

As WD0631 and WD0632 are adjacent genes natively expressed as an operon[11], we reasoned that dual transgene expression of WD0631 and WD0632 in males may be required to induce CI. Indeed, dual expression significantly reduced hatch rates (74.2±18.5%) in comparison to that of uninfected males (96.2±2.5%) when mated to uninfected females (FIG. 3b). While this level of CI is incomplete, several crosses with transgenic males yielded hatch rates at levels comparable to the median hatch rate of WT CI (39.8±24.2%). It is possible that full induction of CI requires other factors or that our transgenic system does not express the genes at the ideal time, place, or amount to induce complete CI, though the genes do have confirmed expression in adult testes (FIG. 11c,d). Importantly, the observed defects are fully rescued by wMel-infected females (FIG. 3b), indicating that these genes are bona fide *Wolbachia*-induced CI genes rather than genes that artificially reduce hatch rates through off target effects. We provisionally name them here cytoplasmic incompatibility factors, cifA and cifB, for WD0631 and WD0632, respectively.

Figure 12:
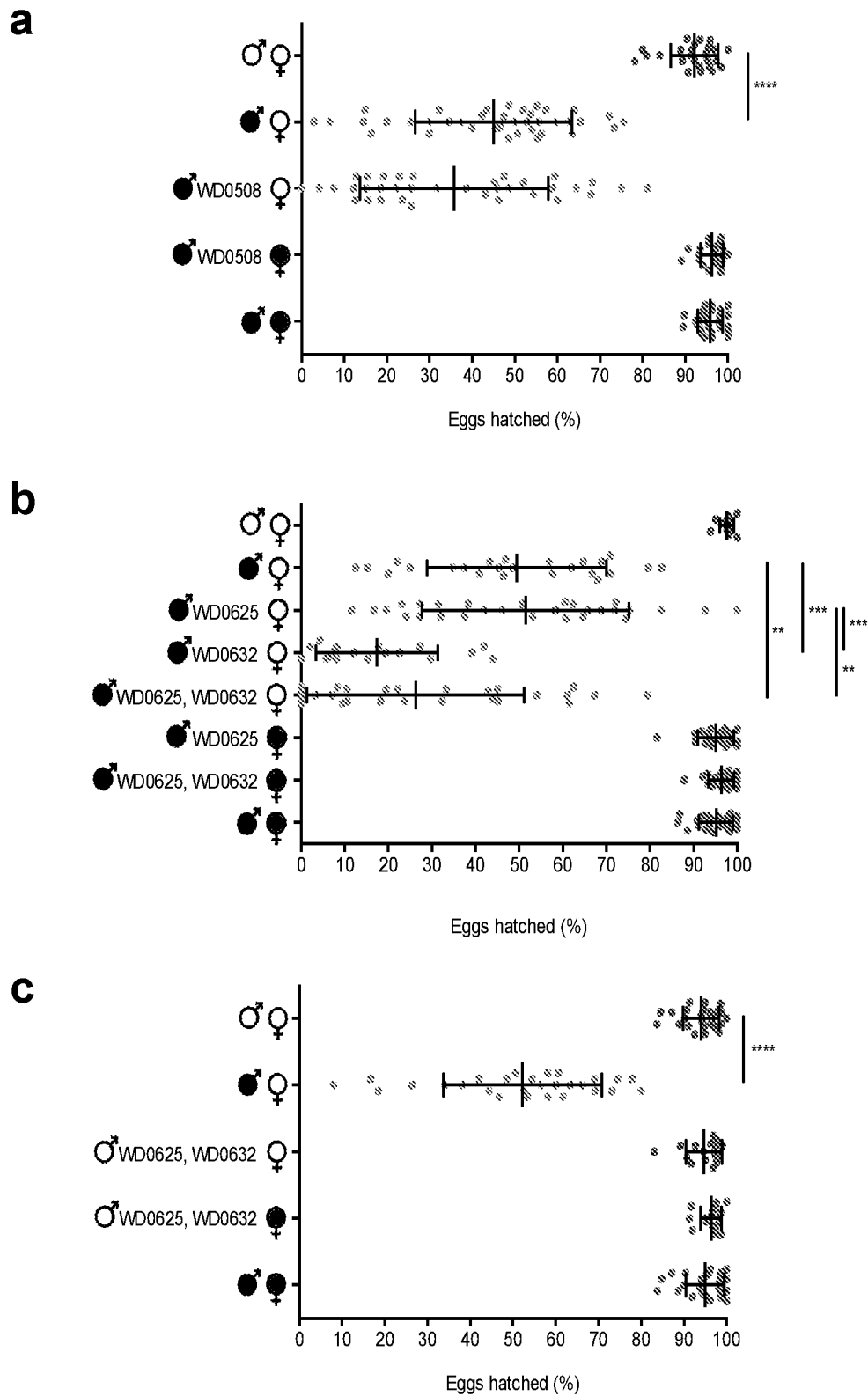
FIG. 12. Transgenic expression of genes other than WD0631/WD0632 has no effect on hatch rates. (a) The WD0508 transgene does not increase CI in infected males. (b) Addition of WD0625 to WD0632 in wMel-infected males does not lower hatch rates further than WD0632 alone. (c) WD0625/WD0632 dual expression cannot induce CI. Infection status is designated with filled in symbols for a wMel-infected parent or open symbols for an uninfected parent. Transgenic flies are labeled with their transgene to the right of their gender symbol. Unlabeled gender symbols represent wild type flies. Data points are colored according to the type of cross, with blue indicating no *Wolbachia* infection, red indicating a CI cross with male-only wMel infections, and purple indicating a rescue cross with wMel-infected females. Error bars indicate standard deviation. =P<0.01, *=P<0.001, ****=P<0.0001 by ANOVA with Kruskal-Wallis test and Dunn's multiple test correction.

To test if the genes enhance WT CI levels that are naturally incomplete in *D. melanogaster*, we expressed WD0631 or WD0632 separately in wMel-infected male flies and found that hatch rates decreased significantly compared to WT CI crosses (FIG. 3c). In this context, we reason that both genes are adding to the quantity of CI effector molecules in wMel-infected tissues. This effect is not seen when control genes are expressed in wMel-infected males (FIG. 12a,b). Moreover, dual expression of the genes in wMel-infected flies reduces hatch rates still further than either gene alone, yet remains fully rescuable by wMel-infected females (FIG. 3c). Adding WD0625 to WD0632 in wMel-infected males does not increase CI beyond WD0632 alone (FIG. 12b), and the combination of WD0625 and WD0632 in uninfected males has no effect on hatching (FIG. 12c), indicating that the combination of WD0631 and WD0632 is uniquely required for induction of CI and that these findings are not an artifact of the transgenic system.

Figure 13:
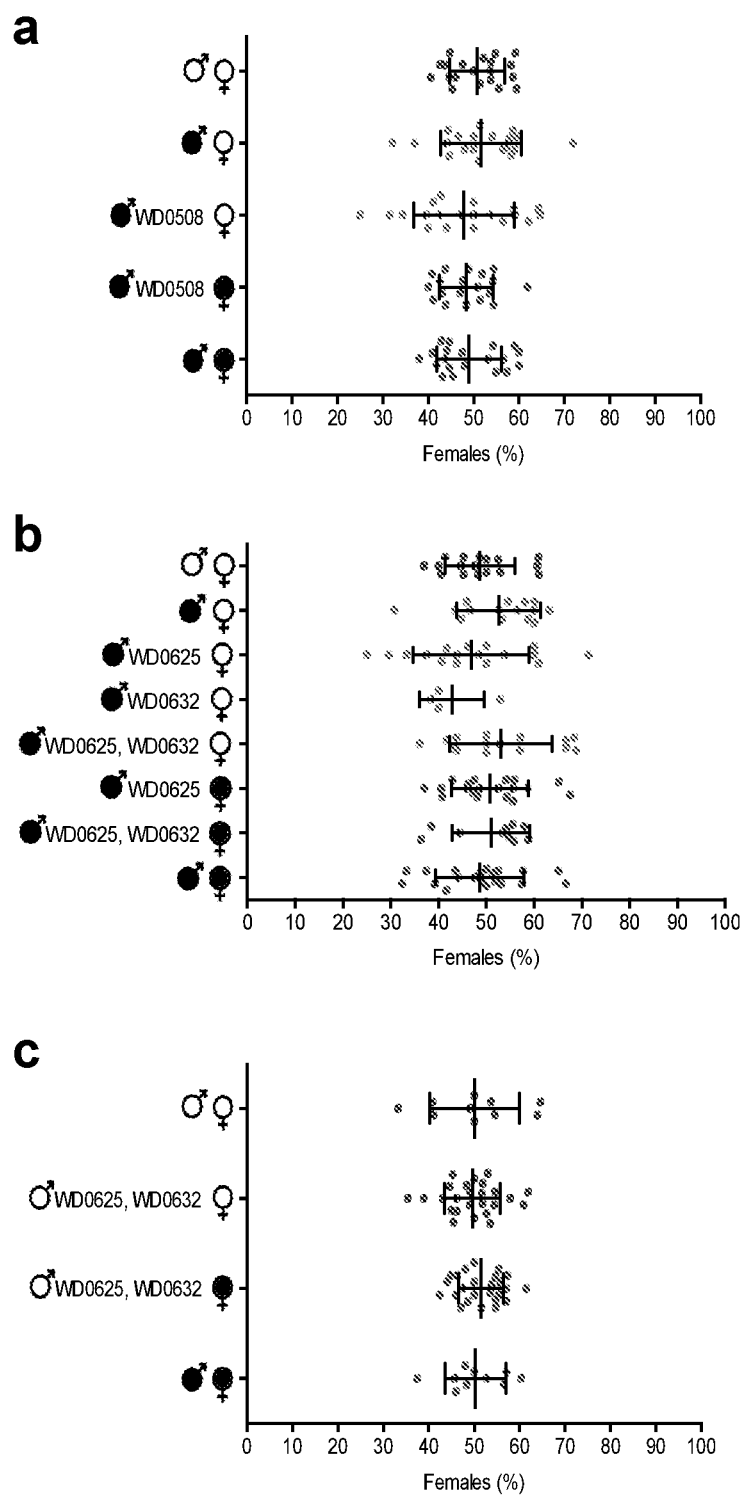
FIG. 13. Transgenic expression of genes other than WD0631/WD0632 has no effect on sex ratios. (a-c) Infection status is designated with filled in symbols for a wMel-infected parent or open symbols for an uninfected parent. Transgenic flies are labeled with their transgene to the right of their gender symbol. Unlabeled gender symbols represent wild type flies. Data points are colored according to the type of cross, with blue indicating no *Wolbachia* infection, red indicating a CI cross with male-only wMel infections, and purple indicating a rescue cross with wMel-infected females. Error bars indicate standard deviation. Statistics performed by ANOVA with Kruskal-Wallis test and Dunn's multiple test correction.

To rule out the possibility that enhancement of CI in the infected transgenic lines is due to an increase in *Wolbachia* titers, we monitored symbiont densities by measuring amplicons of single copy genes from *Wolbachia* and *D. melanogaster*. Although there were some differences in *Wolbachia* titers between the infected transgenic lines (FIG. 12c-e), these differences did not correlate with changes in the magnitude of CI, suggesting that decreased offspring viability was due to the direct effect of the transgenes rather than increased *Wolbachia* proliferation. Most notably, densities are significantly increased in control transgene WD0508 lines (FIG. 12c), but there is no effect on CI (FIG. 3a). Finally, none of these gene combinations had any effect on the sex ratios of offspring (FIG. 13).

Figure 4:
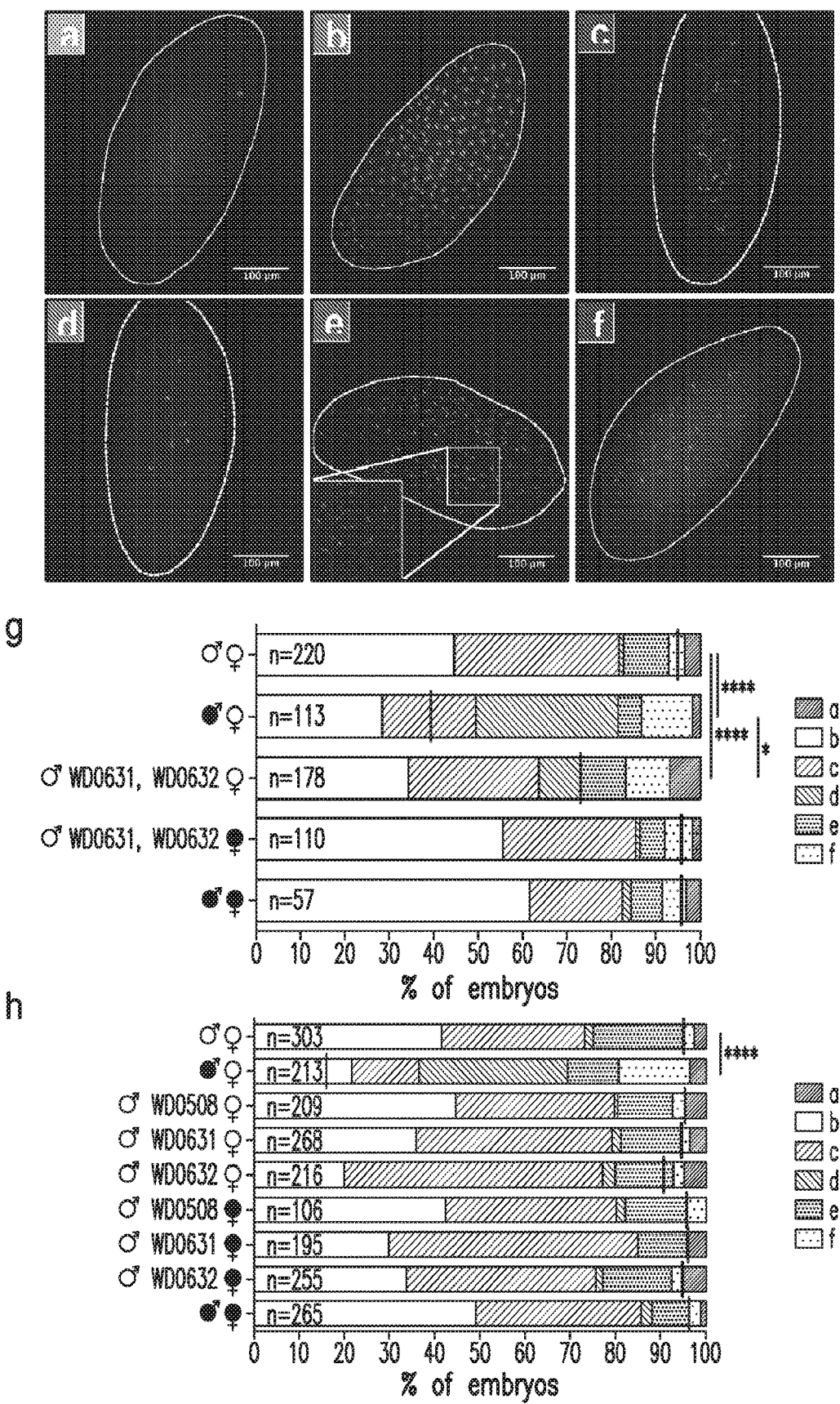
FIG. 4. Dual expression of WD0631 and WD0632 recapitulates cytological defects associated with CI. Representative embryo cytology is shown for (a) unfertilized embryos, (b) normal embryos at one hour of development, (c) normal embryos at two hours of development, and three different mitotic abnormalities: (d) failure of cell division after two to three mitoses, (e) chromatin bridging, and (f) regional mitotic failure. (g) The number of embryos with each cytological phenotype resulting from crosses of dual-expressing WD0631/WD0632 males and uninfected females along with control crosses were counted. Infection status is designated with filled in symbols for a wMel-infected parent or open symbols for an uninfected parent. Transgenic flies are labeled with their transgene to the right of their gender symbol. Unlabeled gender symbols represent wild type flies. Black lines on each graph indicates mean hatch rate for the cross. *=$P<0.05$, ****=$P<0.0001$ by two-tailed Fisher's exact test comparing normal (phenotypes b and c) to abnormal (phenotypes a, d, e, and f) for each cross. (h) Quantitation of cytological defects in crosses utilizing WD0508, WD0631, or WD0632 uninfected males.

Next, we determined the similarity between the cytological defects observed during embryonic development in *Wolbachia*-induced CI versus CI from dual WD0631/WD0632 expressing transgenic flies. Although CI is classically recognized to cause failure of the first mitotic division[23,24], nearly half of the embryonic arrest in incompatible crosses occurs during advanced developmental stages in *Drosophila simulans*[25], a result that was first reported in *Aedes* polinesiensis mosquitoes[26]. We examined embryos resulting from uninfected, wMel-induced CI, and transgenic crosses after one to two hours of development and binned their cytology into one of six phenotypes. While a few embryos in each cross were unfertilized (FIG. 4a), most embryos in WT crosses were either in normal late-stage preblastoderm (FIG. 4b), or in the syncytial blastoderm stage (FIG. 4c)[27]. In the CI induced by wMel, embryos had one of three defects: arrest of cellular division after two to three mitotic divisions (FIG. 4d), arrest throughout development associated with moderate to extensive chromatin bridging as is classically associated with strong CI in *D. simulans*[24] (FIG. 4e), or arrest associated with regional failure of division in one segment of the embryo (FIG. 4f). After blindly scoring the number of embryos demonstrating each phenotype, we determined that arrest phenotypes d, e, and f were significantly more common in the offspring of dual WD0631/WD0632 transgenic males mated to uninfected females, but that these abnormalities were rescued in embryos from wMel-infected females (FIG. 4g). These effects were not seen with control gene WD0508 or with singular expression of WD0631 or WD0632 (FIG. 4h). These data again validate that *Wolbachia*-induced CI is recapitulated in dual WD0631/WD0632 transgenic flies.

Figure 14:
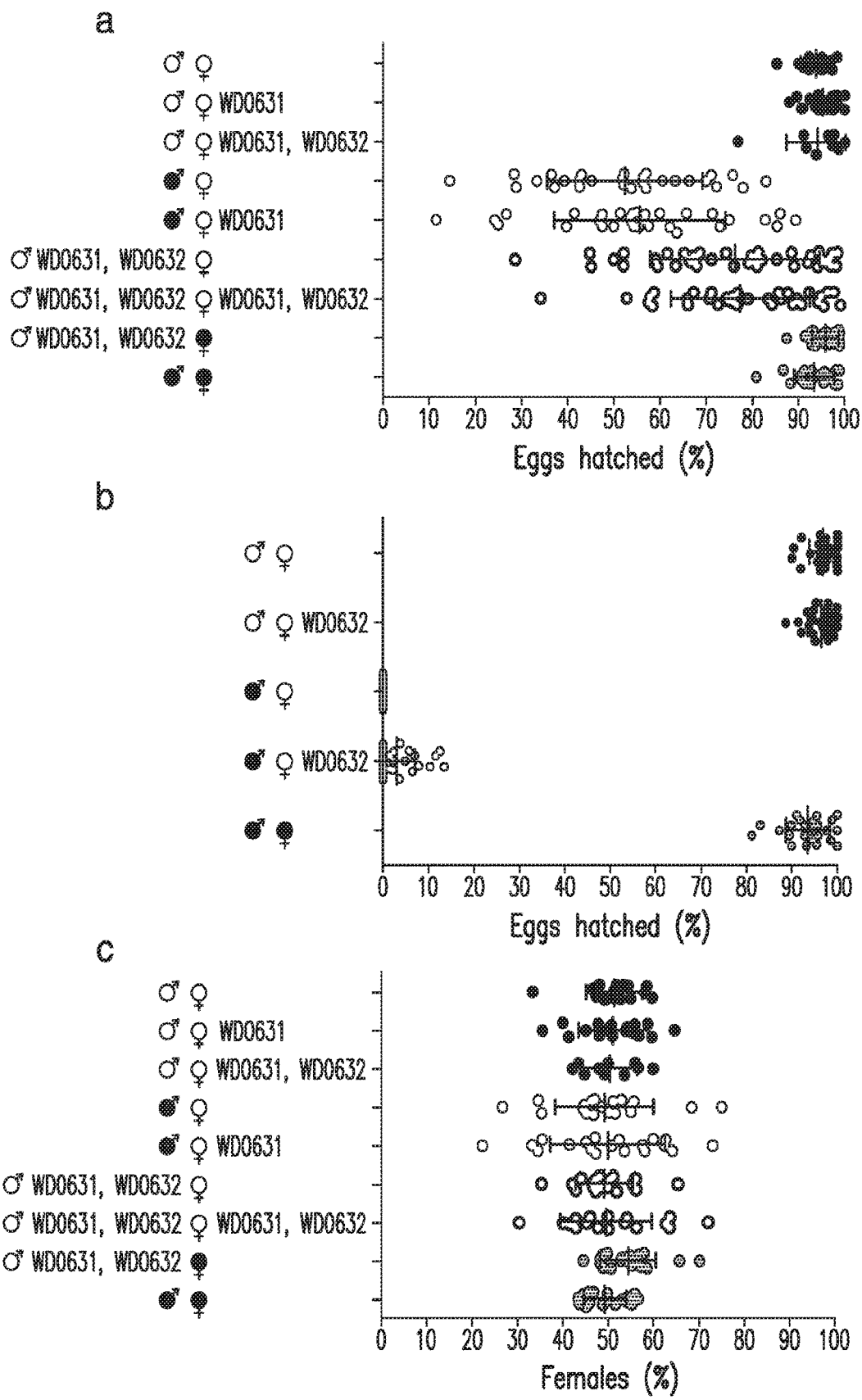
FIG. 14. WD0631/WD0632 expression in females cannot rescue CI. (a, b) Hatch rates and (c) sex ratios for the indicated crosses are shown. Single expression or dual expression of WD0631 and WD0632 in uninfected females does not reduce embryo hatching or rescue wild-type or induced CI defects. Infection status is designated with shading for a wMel-infected parent or no shading for an uninfected parent. Transgenic flies are labeled with their transgene to the right of their gender symbol. Unlabeled gender symbols represent WT flies. Data points are colored according to the type of cross, with blue indicating no *Wolbachia* infection, red indicating a CI cross with male-only wMel infections, and purple indicating a rescue cross with wMel-infected females. Error bars indicate standard deviation. Statistics performed by ANOVA with Kruskal-Wallis test and Dunn's multiple test correction.

Finally, we evaluated whether WD0631 and WD0632 can rescue CI. Neither WD0631 nor WD0632, whether alone or combined, had an effect on hatch rates when expressed in uninfected females (FIG. 14a,b). WD0631- or WD0632-expressing females could not rescue wMel-induced CI, nor could WD0631/WD0632 dual-expressing females rescue CI induced by dual transgenic males (FIG. 14a,b), despite confirmed expression in ovaries (FIG. 11e,f). Transgene expression also had no effect on sex ratios (FIG. 14c). These data suggest that different genes underlie CI and rescue.

This study identifies, for the first time, genes that are responsible for inducing CI. While protein domain predictions suggest that the mechanism may involve nuclease or ubiquitin-modifying activity, the molecular basis of CI is further elucidated in a companion publication by Beckmann, et al, co-submitted with this manuscript. The discovery of CI effector genes is the first inroad to solving the genetic basis of reproductive parasitism, a phenomenon induced worldwide in an estimated hundreds of thousands to millions of arthropod species[28]. The genes also have major implications for studying microbe-assisted speciation, because these genes likely underlie the CI-induced hybrid lethality observed between closely related species of *Nasonia* and *Drosophila*[29,30]. Finally, these genes are important for arthropod pest or vector control strategies, as they could potentially be used as an alternative or adjunctive strategy to current *Wolbachia*-based paradigms aimed at controlling agricultural pests or curbing arthropod-borne transmission of infectious diseases[5-8].

Methods

Comparative Genomics and Transcriptomics

MicroScope[31] was used to select the set of genes comprising the core genomes of CI-inducing *Wolbachia* strains wMel [NC 002978.6][32], wRi [NC_012416.1][33], wPip (Pel) [NC_010981.1][34], and the recently sequenced wRec [RefSeq 1449268][9], while excluding the pan-genome of the mutualistic strain wBm [NC_006833.1][35], using cutoffs of 50% amino acid identity and 80% alignment coverage. wAu microarray data were obtained from the original authors[10] and genes that were present in CI-inducing strains wRi and wSim but absent or divergent in the non-CI strain wAu were selected.

For ovarian transcriptomics, one-day old females from wVitA infected-*Nasonia vitripennis* 12.1 were hosted as virgins on *Sarcophaga bullata* pupae for 48 hours to stimulate feeding and oogenesis. Females were then dissected in RNase-free 1×PBS buffer, and their ovaries were immediately transferred to RNase-free Eppendorf tubes in liquid nitrogen. Fifty ovaries were pooled for each of three biological replicates. Ovaries were manually homogenized with RNase-free pestles, and their RNA was extracted using the RNeasy Mini Kit (Qiagen) according to the manufacturer's protocol for purification of total RNA from animal tissues. After RNA purification, samples were treated with RQ1 RNase-free DNase (Promega), and ethanol precipitation was performed. PCR of RNA samples with *Nasonia* primers NvS6KQTF4 and NVS6KQTR4[36] confirmed that all samples were free of DNA contamination. RNA concentrations were measured with a Qubit 2.0 Fluorometer (Life Technologies) using the RNA HS Assay kit (Life Technologies), and approximately 5 µg of total RNA from each sample was used as input for the MICROBEnrich Kit (Ambion) in order to enrich for *Wolbachia* RNA in the samples. Microbially-enriched RNA was then ethanol-precipitated, and rRNA was depleted from the samples using the Ribo-Zero Magnetic kit (Illumina) according to manufacturer's protocol. Approximately 1.5 µg of microbially-enriched, rRNA-depleted RNA for each replicate was shipped to the University of Rochester Genomics Research Center for sequencing. Library preparation was performed using the Illumina ScriptSeq v2 RNA-Seq Library Preparation kit, and all samples were run multiplexed on a single lane of the Illumina HiSeq2500 (single-end, 100 bp reads). Raw reads were trimmed and mapped to the wVitA genome (PRJDB1504) in CLC Genomics Workbench 8.5.1 using a minimum length fraction of 0.9, a minimum similarity fraction of 0.8, and allowing one gene hit per read. With all three replicates combined, a total of 364,765 reads out of 41,894,651 (0.87%) mapped to the wVitA genome with the remaining reads mapping to the *N. vitripennis* host genome (GCF_000002325.3). All *Wolbachia* genes with greater than or equal to five RNA-seq reads, with the exception of the 16S and 23S RNA genes, were selected. For non-wMel data sets, the closest homologs in wMel were found using blastp in Geneious Pro v5.5.6[37].

Protein Extraction and Mass Spectrometry

Protein was extracted from *Culex pipiens* tissues as described previously[11]. Ovaries from 30 wPip (Buckeye)-infected mosquitoes were dissected in 100% ethanol and collected in a 1.5 ml tube filled with 100% ethanol. Pooled tissues were sonicated at 40 mA for 10 seconds in a Kontes GE 70.1 ultrasonic processor, and trichloroacetic acid (TCA) was added to a final concentration of 10% (v/v). After centrifugation at 13,000 rpm in a microcentrifuge, pellets were washed with acetone:water (9:1), dried, and stored at −20° C. Samples were directly submitted to the University of Minnesota's Center for Mass Spectrometry and Proteomics for iTRAQ (isobaric tagging for relative and absolute quantification) analysis. Proteins were sorted according to their relative abundance as determined by the number of spectra from the single most abundant peptide. Because proteins can often produce varying amounts of detectable tryptic peptides depending upon protein size and lysine/arginine content, we counted only the single most abundant peptide for each protein. This quantification is justified by previous reports[11] showing that the two most abundant proteins are the *Wolbachia* surface protein (WSP; gi|190571332) and another putative membrane protein (gi|190570988). Only proteins with at least three unique peptides (95% confidence) detected were reported, and using this criterion the false discovery rate was zero.

Gene Expression Assays

Expression of CI candidates was tested with RT-qPCR on pools of 20 pairs of testes from one-day-old and seven-day-old virgin males. RNA was extracted with the Qiagen RNeasy mini kit, DNase treated with TURBO DNase (Life Technologies) and cDNA was generated with Superscript III Reverse Transcriptase (Invitrogen). Delta delta Ct analysis against the housekeeping gene groEL was used to determine relative gene expression.

Evolutionary Analyses

WD0631 and WD0632 were used as queries to perform a BLASTp search of NCBI's nonredundant (nr) protein sequence database with algorithm parameters based on a word-size of six and BLOSUM62 scoring matrix[38]. Homologs were selected based on the satisfaction of three criteria: (i) E-value≤$10^{-20}$, (ii) query coverage greater than 60%, and (iii) presence in fully sequenced *Wolbachia* and/or phage WO genomes. FtsZ and gpW proteins were identified for all representative *Wolbachia* and phage WO genomes, respectively. Protein alignments were performed using the MUSCLE plugin[39] in Geneious Pro v8.1.7[37]; the best models of selection, according to the corrected Akaike Information Criteria (AICc)[40], were estimated using the ProtTest server[41]; and phylogenetic trees were built using the MrBayes plugin[42] in Geneious. Putative functional domains were identified using NCBI's BLASTP, Wellcome Trust Sanger Institute's PFAM database[43] and EMBL's Simple Modular Architecture Research Tool (SMART)[44].

Fly Rearing

*D. melanogaster* were reared on standard cornmeal and molasses based media. Stocks were maintained at 25 C while virgin flies were stored at room temperature. During virgin collections, stocks were kept at 18 C overnight and 25 C during the day. *Wolbachia* uninfected lines were generated through tetracycline treatment for three generations. Briefly, tetracycline was dissolved in ethanol and then diluted in water to a final concentration of 1 mg/mL. 1 mL of this solution was added to 50 mL of media (final concentration of 20 ug/mL). Freshly treated media was used for each generation. Infection status was confirmed with PCR using Wolb_F and Wolb_R3 primers[45], and flies were reared on untreated media for at least three additional generations before being utilized.

Transgenic Flies

Each CI candidate gene was cloned into the pTIGER plasmid for transformation and expression in *D. melanogaster*[46]. pTIGER was designed for targeted integration into the *D. melanogaster* genome using PhiC31 integrase[47] and tissue-specific, inducible expression through the Gal4-UAS system[48]. Cloning was performed using standard molecular biology techniques and plasmids were purified and sequence-confirmed before injection. At least 200 *D. melanogaster* embryos were injected per gene by Best Gene, Inc (Chino Hills, CA), and transformants were selected based on w+ eye color. Isogenic, homozygous lines were maintained when possible, or isogenic heterozygous flies were maintained when homozygous transgenics were inviable (WD0625/CyO). WD0508 and WD0631 insertion was carried out with the $y^1$ M{vas-int.Dm}ZH-2A w*; P{CaryP}attP40 line. WD0625 was inserted into BSC9723 with the genotype: $y^1$ M{vas-int.Dm}ZH-2A w*; PBac{y+-attP-3B}VK00002. WD0632 insertion was done using BSC8622 with the genotype: $y^1$ $w^{67c23}$; P{CaryP}attP2.

*Wolbachia* Titers

For FIG. 8*c-e*, brothers of those used in the corresponding hatch rates were utilized. Testes were dissected from males in cold PBS. Pools of testes from 15 males were used for each sample, and DNA was extracted using the Gentra Puregene Tissue kit (Qiagen). Quantitative PCR was performed on a Bio-Rad CFX-96 Real-Time System using iTaq Universal SYBR Green Supermix (Bio-Rad). Absolute quantification was achieved by comparing all experimental samples to a standard curve generated on the same plate. The Rp49 standard template was generated using the same primers as those used to determine quantity while the groEL standard template was generated using groELstd_F and groELstd_R primers that we designed. qPCR conditions: 50 C 10 min, 95 C 5 min, 40× (95 C 10 sec, 55 C 30 sec), 95 C 30 sec. Followed by melt curve analysis (0.5 C steps from 65-95 C for 5 sec each). To obtain a more accurate *Wolbachia*:host cell ratio, it was assumed that each host cell has two copies of Rp49 and each *Wolbachia* cell has one copy of groEL.

Hatch Rate Assays

Parental females, unless expressing a transgene, were WT $y^1w^*$ flies (wMel-infected or uninfected) and aged for 2-5 days before crossing. Parental males were created by crossing nanos-Gal4 virgin females (wMel-infected or uninfected) with either WT or UAS-candidate gene-transgenic males. Only the first males emerging from these crosses were used to control for the older-brother effect associated with CI[20]. In assays to determine whether CI was increased, virgin males were aged for 3-4 days before crossing to reduce the level of WT CI. In these experiments, care was taken to match the age of males between experimental and control crosses. In all other assays, virgin males were used within 30 hours of emergence. 32-64 individual crosses were used for each crossing condition. To perform the hatch rate assays, a single male and single female were placed in an 8 oz, round bottom, polypropylene *Drosophila* stock bottle. A grape juice-agar plate with a small amount of yeast mix (1 part water: 2 parts dry yeast) smeared on top was placed in the bottle opening and affixed with tape. Grape juice-agar plates consist of the lids from 35×10 mm culture dishes (CytoOne). 12.5 g of agar is mixed in 350 mL of ddH2O and autoclaved. In a separate flask, 10 mL of ethanol is used to dissolve 0.25 g tegosept (methyl 4-hyrdoxybenzoate). 150 mL of Welch's grape juice is added to the tegosept mix, combined with the agar, and poured into plates.

Hatch rate bottles were placed in a 25 C incubator overnight (~16 hours). After this initial incubation the grape plates were discarded and replaced with freshly yeasted plates. After an additional 24 hours the adult flies were then removed and frozen for expression analysis and the embryos on each plate were counted. These plates were then incubated at 25 C for 36 hours before the number of unhatched embryos was counted. Larvae were moved from these plates and placed in vials of fly media with one vial being used for each individual grape plate to be assayed for sex ratios at adulthood. A total of 10-20 vials were used for each cross type. Any crosses with fewer than 25 embryos laid were discarded from the hatching analysis while vials with fewer than 10 adults emerging were discarded from the sex ratio analysis. Statistical analysis and outlier removal, utilizing the ROUT method, were performed using Graphpad Prism v6 software.

Transgene RT-PCR

Pools of six pairs of testes or ovaries were dissected from parents utilized in hatch rate assays. In samples designated "High CI" and "No CI", the males correspond to crosses that had low or normal hatch rates, respectively. For all other samples the flies utilized were chosen at random. RNA was extracted using the Direct-zol RNA MiniPrep Kit (Zymo), DNase treated with DNA-free (Ambion, Life Technologies) and cDNA was generated with SuperScript VILO (Invitrogen). 30 cycles of PCR were performed against positive controls (extracted DNA), negative controls (water), RNA, and cDNA with the following conditions: 95 C 2 min, 30× (95 C 15 sec, 56 C 30 sec, 72 C 30 sec), 72 C 5 min.

Embryo Imaging

Embryos were collected in a fashion similar to hatch rate assays except bottles contained 60-80 females and 15-20 males. After an initial 16 hours of mating, fresh grape plates were added and embryos were removed after 60 minutes. The embryo-covered plates were then placed in the incubator at 25 C for a further 60 minutes to ensure each embryo was at least 1 hour old. Embryos were then moved to a small mesh basket and dechorionated in 50% bleach for 1-3 minutes. These were then washed in embryo wash solution (7% NaCl, 0.5% Triton X-100) and moved to a small vial with ~2 mL heptane. An equal amount of methanol was added to the vial and then vigorously shaken for 15 seconds. The upper heptane layer, and most of the methanol, was then removed and the embryos moved to fresh methanol in a 1.5 mL microcentrifuge tube. Embryos were stored overnight at 4° C. for clearing. The old methanol was then removed and replaced with 250 uL of fresh methanol along with 750 uL of PBTA (1×PBS, 1% BSA, 0.05% Triton X-100, 0.02% sodium azide). After inverting the tube several times, the solution was removed and replaced with 500 uL PBTA. Embryos were then rehydrated for 15 minutes on a rotator at room temperature. After rehydrating, the PBTA was replaced with 100 uL of a 10 mg/mL RNase solution and incubated at 37° C. for 2 hours. The RNase was then removed and embryos were washed several times with PBS followed by a final wash with PBS-Azide (1x PBS, 0.02% sodium azide). After removing the PBS-Azide, embryos were mounted on glass slides with ProLong Diamond Antifade (Life Technologies) spiked with propidium iodide (Sigma-Aldrich) to a final concentration of 1 ug/mL. Imaging was performed at the Vanderbilt Cell Imaging Shared Resource using a Zeiss LSM 510 META inverted confocal microscope. All scores were performed blind and image analysis was done using ImageJ software[49].

REFERENCES CITED IN EXAMPLE 1

1 Yen, J. H. & Barr, A. R. New hypothesis of the cause of cytoplasmic incompatibility in *Culex pipiens* L. *Nature* 232, 657-658 (1971).
2 Kent, B. N. & Bordenstein, S. R. Phage WO of *Wolbachia*: lambda of the endosymbiont world. *Trends in microbiology* 18, 173-181 (2010).
3 Brucker, R. M. & Bordenstein, S. R. Speciation by symbiosis. *Trends in ecology & evolution* 27, 443-451 (2012).
4 Shropshire, J. D. & Bordenstein, S. R. Speciation by Symbiosis: the Microbiome and Behavior. *MBio* 7 (2016).
5 Zabalou, S. et al. *Wolbachia*-induced cytoplasmic incompatibility as a means for insect pest population control. *Proceedings of the National Academy of Sciences of the United States of America* 101, 15042-15045 (2004).
6 O'Connor, L. et al. Open release of male mosquitoes infected with a wolbachia biopesticide: field performance and infection containment. *PLoS Negl Trop Dis* 6, e1797 (2012).
7 Walker, T. et al. The wMel *Wolbachia* strain blocks dengue and invades caged *Aedes aegypti* populations. *Nature* 476, 450-453 (2011).
8 Dutra, Heverton Leandro C. et al. *Wolbachia* Blocks Currently Circulating Zika Virus Isolates in Brazilian *Aedes aegypti* Mosquitoes. *Cell Host & Microbe*, doi: 10.1016/j.chom.2016.04.021.
9 Metcalf, J. A., Jo, M., Bordenstein, S. R., Jaenike, J. & Bordenstein, S. R. Recent genome reduction of *Wolbachia* in *Drosophila* recens targets phage WO and narrows candidates for reproductive parasitism. *PeerJ* 2, e529 (2014).
10 Ishmael, N. et al. Extensive genomic diversity of closely related *Wolbachia* strains. *Microbiology* 155, 2211-2222 (2009).
11 Beckmann, J. F. & Fallon, A. M. Detection of the *Wolbachia* protein WPIP0282 in mosquito spermathecae: implications for cytoplasmic incompatibility. *Insect biochemistry and molecular biology* 43, 867-878 (2013).
12 Bordenstein, S. R. & Bordenstein, S. R. Novel eukaryotic association module in phage WO genomes from *Wolbachia*. *Nature Communications* (2016).
13 Li, S. J. & Hochstrasser, M. A new protease required for cell-cycle progression in yeast. *Nature* 398, 246-251 (1999).
14 Wimmer, P. & Schreiner, S. Viral Mimicry to Usurp Ubiquitin and SUMO Host Pathways. *Viruses* 7, 4854-4872 (2015).
15 Wimmer, P., Schreiner, S. & Dobner, T. Human pathogens and the host cell SUMOylation system. *Journal of virology* 86, 642-654 (2012).
16 Knizewski, L., Kinch, L. N., Grishin, N. V., Rychlewski, L. & Ginalski, K. Realm of PD-(D/E)XK nuclease superfamily revisited: detection of novel families with modified transitive meta profile searches. *BMC Struct Biol* 7, 40 (2007).
17 Lorenzen, M. D. et al. The maternal-effect, selfish genetic element Medea is associated with a composite Tc1 transposon. *Proceedings of the National Academy of Sciences of the United States of America* 105, 10085-10089 (2008).
18 Zabalou, S. et al. Multiple rescue factors within a *Wolbachia* strain. *Genetics* 178, 2145-2160 (2008).
19 Poinsot, D., Bourtzis, K., Markakis, G., Savakis, C. & Mercot, H. *Wolbachia* transfer from *Drosophila melanogaster* into *D. simulans*: Host effect and cytoplasmic incompatibility relationships. *Genetics* 150, 227-237 (1998).
20 Yamada, R., Floate, K. D., Riegler, M. & O'Neill, S. L. Male development time influences the strength of *Wolbachia*-induced cytoplasmic incompatibility expression in *Drosophila melanogaster*. *Genetics* 177, 801-808 (2007).
21 Rorth, P. Gal4 in the *Drosophila* female germline. *Mechanisms of development* 78, 113-118 (1998).
22 White-Cooper, H. Tissue, cell type and stage-specific ectopic gene expression and RNAi induction in the *Drosophila* testis. *Spermatogenesis* 2, 11-22 (2012).
23 Serbus, L. R., Casper-Lindley, C., Landmann, F. & Sullivan, W. The genetics and cell biology of *Wolbachia*-host interactions. *Annual review of genetics* 42, 683-707 (2008).
24 Landmann, F., Orsi, G. A., Loppin, B. & Sullivan, W. *Wolbachia*-mediated cytoplasmic incompatibility is associated with impaired histone deposition in the male pronucleus. *PLoS pathogens* 5, e1000343 (2009).
25 Callaini, G. & Riparbelli, M. G. Fertilization in *Drosophila melanogaster*: centrosome inheritance and organization of the first mitotic spindle. *Dev Biol* 176, 199-208 (1996).
26 Wright, J. D. & Barr, A. R. *Wolbachia* and the normal and incompatible eggs of *Aedes polynesiensis* (Diptera: Culicidae). *Journal of invertebrate pathology* 38, 409-418 (1981).
27 Bate, M. & Arias, A. M. *The Development of Drosophila Melanogaster*. (Cold Spring Harbor Laboratory Press, 1993).
28 Zug, R. & Hammerstein, P. Still a host of hosts for wolbachia: analysis of recent data suggests that 40% of terrestrial arthropod species are infected. *PloS one* 7, e38544 (2012).
29 Jaenike, J., Dyer, K. A., Cornish, C. & Minhas, M. S. Asymmetrical reinforcement and *Wolbachia* infection in *Drosophila*. *PLoS biology* 4, e325 (2006).
30 Bordenstein, S. R., O'Hara, F. P. & Werren, J. H. *Wolbachia*-induced incompatibility precedes other hybrid incompatibilities in *Nasonia*. *Nature* 409, 707-710 (2001).
31 Vallenet, D. et al. MicroScope: a platform for microbial genome annotation and comparative genomics. *Database: the journal of biological databases and curation* 2009, bap021 (2009).
32 Wu, M. et al. Phylogenomics of the reproductive parasite *Wolbachia pipientis* wMel: a streamlined genome overrun by mobile genetic elements. *PLoS biology* 2, E69 (2004).
33 Klasson, L. et al. The mosaic genome structure of the *Wolbachia* wRi strain infecting *Drosophila simulans*. *Proc Natl Acad Sci USA* 106, 5725-5730 (2009).
34 Klasson, L. et al. Genome evolution of *Wolbachia* strain wPip from the *Culex pipiens* group. *Mol Biol Evol* 25, 1877-1887 (2008).
35 Foster, J. et al. The *Wolbachia* genome of *Brugia malayi*: endosymbiont evolution within a human pathogenic nematode. *PLoS biology* 3, e121 (2005).
36 Bordenstein, S. R. & Bordenstein, S. R. Temperature affects the tripartite interactions between bacteriophage WO, *Wolbachia*, and cytoplasmic incompatibility. *PloS one* 6, e29106 (2011).

37 Kearse, M. et al. Geneious Basic: an integrated and extendable desktop software platform for the organization and analysis of sequence data. *Bioinformatics* 28, 1647-1649 (2012).

38 Johnson, M. et al. NCBI BLAST: a better web interface. *Nucleic acids research* 36, W5-9 (2008).

39 Edgar, R. C. MUSCLE: multiple sequence alignment with high accuracy and high throughput. *Nucleic acids research* 32, 1792-1797 (2004).

40 Hurvich, C. M. & Tsai, C.-L. A Corrected Akaike Information Criterion for Vector Autoregressive Model Selection. *Journal of Time Series Analysis* 14, 271-279 (1993).

41 Abascal, F., Zardoya, R. & Posada, D. ProtTest: selection of best-fit models of protein evolution. *Bioinformatics* 21, 2104-2105 (2005).

42 Ronquist, F. et al. MrBayes 3.2: efficient Bayesian phylogenetic inference and model choice across a large model space. *Systematic biology* 61, 539-542 (2012).

43 Finn, R. D. et al. The Pfam protein families database: towards a more sustainable future. *Nucleic acids research* 44, D279-285 (2016).

44 Letunic, I., Doerks, T. & Bork, P. SMART 7: recent updates to the protein domain annotation resource. *Nucleic acids research* 40, D302-305 (2012).

45 Casiraghi, M., Anderson, T. J., Bandi, C., Bazzocchi, C. & Genchi, C. A phylogenetic analysis of filarial nematodes: comparison with the phylogeny of *Wolbachia* endosymbionts. *Parasitology* 122 Pt 1, 93-103 (2001).

46 Ferguson, S. B., Blundon, M. A., Klovstad, M. S. & Schupbach, T. Modulation of gurken translation by insulin and TOR signaling in *Drosophila*. *Journal of cell science* 125, 1407-1419 (2012).

47 Groth, A. C., Fish, M., Nusse, R. & Calos, M. P. Construction of transgenic *Drosophila* by using the site-specific integrase from phage phiC31. *Genetics* 166, 1775-1782 (2004).

48 Southall, T. D., Elliott, D. A. & Brand, A. H. The GAL4 System: A Versatile Toolkit for Gene Expression in *Drosophila*. *CSH protocols* 2008, pdb top49 (2008).

49 Schneider, C. A., Rasband, W. S. & Eliceiri, K. W. NIH Image to ImageJ: 25 years of image analysis. *Nature methods* 9, 671-675 (2012).

50 Vizcaino, J. A. et al. 2016 update of the PRIDE database and its related tools. *Nucleic acids research* 44, D447-456 (2016).

51 Bossan, B., Koehncke, A. & Hammerstein, P. A new model and method for understanding *Wolbachia*-induced cytoplasmic incompatibility. *PloS one* 6, e19757 (2011).

Example 2. A *Wolbachia* Deubiquitylating Enzyme Induces Cytoplasmic Incompatibility

*Wolbachia* are obligate intracellular bacteria[1] that infect many arthropods, including nearly two-thirds of all insect species.[2] These symbionts often manipulate host reproduction to enhance their inheritance through the female germline. The most common reproductive alteration is cytoplasmic incompatibility (CI),[3-5] wherein eggs from uninfected females fail to develop when fertilized by sperm from *Wolbachia*-infected males. By contrast, if female and male partners are both infected, the resulting embryos are viable. CI is a potent gene-drive mechanism that impacts population structure[6] and speciation,[7] but its molecular mechanism remained unknown. In this example, we show a *Wolbachia* deubiquitylating enzyme (DUB) contributes directly to CI. The CI-inducing DUB, CidB, is a cysteine protease encoded in a two-gene operon; the other protein, CidA, binds CidB. Binding affinity is highest between cognate partners of cidA-cidB-related operons from different *Wolbachia* strains. In transgenic fruit flies, the cidA-cidB operon mimics CI when sperm introduce the DUB into eggs; an operon with a catalytically inactive DUB does not induce sterility. Toxicity is recapitulated in yeast by CidB alone: DUB activity is required for toxicity but is rescued by coexpressed CidA, suggesting a toxin-antidote relationship between CidB and CidA. A related operon from the same *Wolbachia* strain, wPip, involves a putative nuclease (CinB) rather than a DUB; analogous binding, toxicity and rescue in yeast were observed. These results identify a primary mechanism for CI involving toxin and antidote-like proteins secreted into germline cells by resident bacteria and suggest potential new methods for control of insect pests and disease vectors, such as mosquitoes transmitting the Dengue fever and Zika viruses.

The mechanism of CI is frequently modeled as a toxin-antidote (modification-rescue) system in which sperm carry a *Wolbachia* toxin[8,9] that can be conditionally rescued in the egg by a *Wolbachia*-encoded antidote (FIG. 15a, b).[5,10-13] Normally, upon fertilization the sperm-derived pronucleus undergoes nuclear envelope breakdown and exchanges protamines for maternal histones.[14] Subsequently, male and female pronuclei juxtapose (but do not fuse) and undergo DNA replication prior to the first zygotic mitosis. Chromosomes condense, align at metaphase, and separate in anaphase.[15] In CI crosses, paternal chromatin fails to condense properly for the first cell cycle. This induces lethal missegregation and bridging of paternal DNA at anaphase.[16-18]

*Wolbachia* themselves are removed from sperm in the later stages of spermatid differentiation.[11] Therefore, in a previous proteomic search, we looked for *Wolbachia* (wPip strain) proteins associated with *Wolbachia*-modified mosquito sperm deposited in the spermathecae of female mosquitoes following mating. We identified the *Wolbachia* protein WPA0282.[19] The wPa_0282 gene is part of a two-gene operon (FIG. 15c). Given our identification (see below) of the second gene product, WPA0283, as a CI-inducing DUB, we have renamed the genes cidA (wPa_0282) and cidB (wPa_0283). Ubiquitin is a small protein that posttranslationally modifies many proteins and has many functions.[20] Protein ubiquitylation is highly dynamic, and is reversed by many different cellular DUBs.[21] Phenotypic evidence from diverse *Wolbachia* strains suggests that the toxin and antidote functionalities of CI arise from at least two independent genes.[10] Moreover, most toxin-antidote systems studied in bacteria are organized as simple two-gene operon structures (5'-antidote-toxin-3').[22,23] Therefore, we hypothesized that the cidA-cidB operon products might be the executers of CI.

As *Wolbachia* strains diverge within a host species, they accumulate mutations in their corresponding CI systems and become bidirectionally incompatible,[3,24] suggesting that their respective toxin-antidote genes have evolved mutually exclusive specificities.[10] Interestingly, *Wolbachia* genomes from *Culex pipiens* mosquitoes show extensive genetic duplication and divergence of the putative toxin-antidote operon, potentially accounting for multiple incompatibilities. *Wolbachia* strain wPip, for example, has two related operons (FIG. 15c, d). The second operon encodes proteins related to CidA and CidB, but the putative toxin includes what appears to be a functional nuclease domain (DUF1703)[25] rather than a C48/Ulp1-like DUB motif (FIG. 15d); we have therefore renamed the two genes in this operon as cinA (wPa_0294) and cinB (wPa_0295). The putative toxins from both operons, CidB and CinB, appear to share a common nuclease ancestor (FIG. 19; FIG. 15c, dotted lines), but the apparent nuclease active-site residues are not maintained in CidB. Importantly, the predicted enzymatic competence of the toxin components of these operons correlates with ability to induce CI in diverse *Wolbachia* strains.

Figure 20:
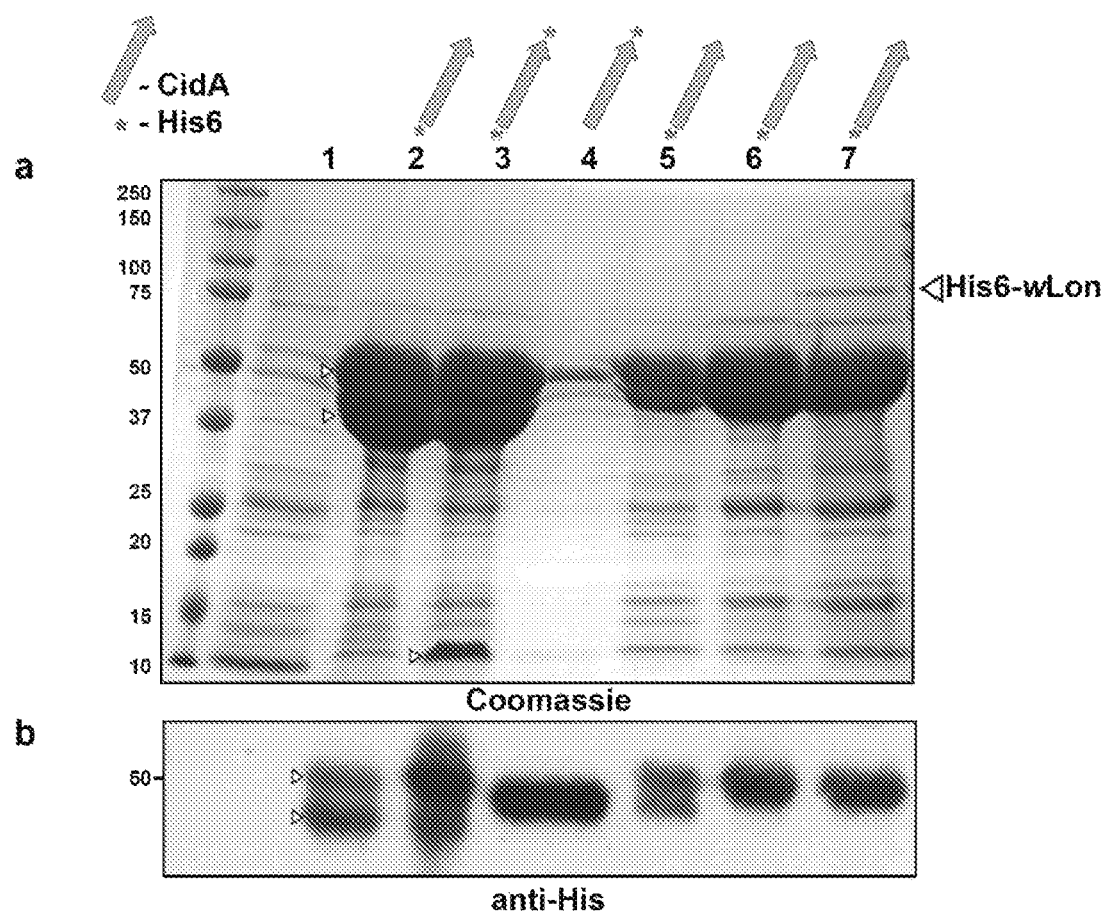
FIG. 20. His6 pulldowns of recombinant CidA shows C-terminal cleavage by *E. coli* Lon protease but not *Wolbachia* Lon protease. a. Coomassie SDS-PAGE analysis of recombinant CidA protein expression. Lane 1, pBadB vector; 2, N-terminally tagged His6-CidA (#AX1); 3, doubly tagged His6-CidA-His6 (#AW1); 4, C-terminally tagged CidA-His6 (#Y10); 5, a codon-optimized variant of N-terminally tagged His6-CidA (#AS1); 6, N-terminally tagged His6-CidA in BL21-AI cells with a deletion of the ion protease gene (#N15); and 7, N-terminally tagged His6-CidA coexpressed with His6-tagged *Wolbachia* Lon Protease (#BN5). Switching expression of recombinant proteins from TOP10F' cells to BL21-AI cells (which lack Lon protease) eliminated the doublet (Lane 6). Because Lon often regulates toxin-antidote systems, tested *Wolbachia*'s own Lon protease was tested, but it did not cleave CidA (lane 7). Subsequent expression of CidA and other proteins was always performed in BL21-AI or Rosetta cells lacking Lon. b. Anti-His6 immunoblot corroborates the Coomassie staining patterns.
Figure 21:
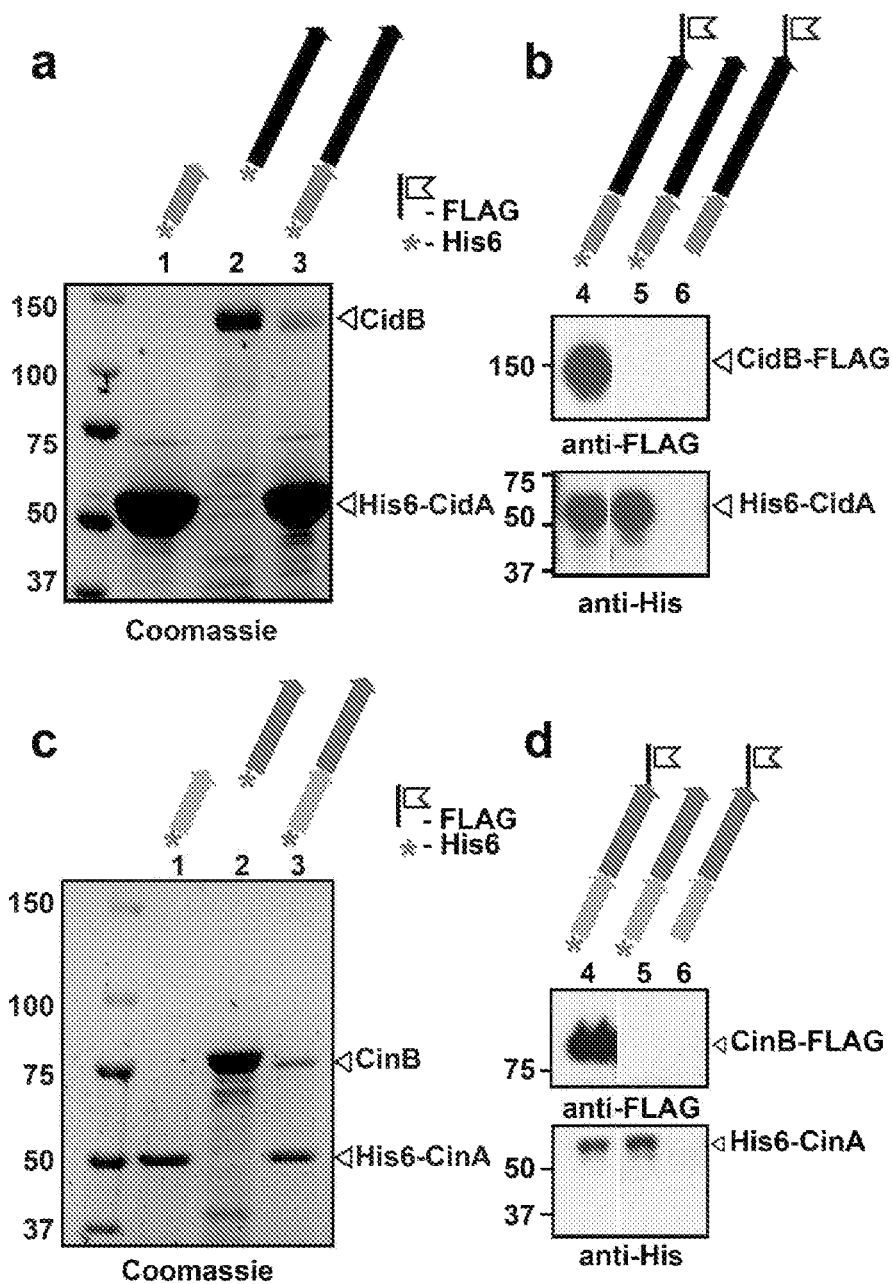
FIG. 21. Interaction of toxin-antidote proteins. a. His6 pulldowns reveal binding interactions of operon partners.

In many toxin-antidote systems, toxin and antidote bind one another.[23] We therefore expressed recombinant tagged constructs of the cidA-cidB operon proteins (FIG. 20, 21) and examined their interactions. Pulldown of His6-tagged CidA from extracts of *E. coli* expressing both His6-CidA and CidB brought down the CidB protein (FIG. 22a, b). We observed similar binding of the cognate partners His6-CinA and CinB (FIG. 22c, d). If differential affinity of operon-encoded toxins and antidotes accounts for bi-directional incompatibility, then the putative toxin-antidote pairs expressed from the same operon would be predicted to associate preferentially relative to their noncognate partners[26] from other operons. To test this, we purified His6-tagged copies of CidB, CinB, and CidB$^{wMel}$ (the latter is from a *Wolbachia* strain isolated from *Drosophila melanogaster*). These putative toxin proteins were incubated with extracts of the corresponding FLAG-tagged antidote variants, and binding was assessed (FIG. 15f). Binding was indeed much stronger between the cognate proteins from each operon. These results are consistent with a model in which operon-specific differences in toxin-antidote binding underlie the bidirectional incompatibilities and partial rescues seen in genetic crosses with different *Wolbachia* strains.

When divergent CI-causing *Wolbachia* strains are introduced into different insects by microinjection, CI is recapitulated.[27-30] This indicates that *Wolbachia* CI factors can operate in a broad range of hosts. To test the toxin-antidote model for CI in a heterologous eukaryotic host, we expressed the Cid and Cin proteins in the yeast *Saccharomyces cerevisiae* (FIG. 16). The putative toxins CidB and CinB both caused temperature-sensitive growth inhibition when introduced into yeast. Growth was rescued by coexpression of the cognate antidotes, CidA and *CinA*, respectively. When the predicted cysteine protease active site in CidB[31] was mutated from Cys to Ala (CidB* in FIG. 16a), toxicity was lost. Similarly, upon mutation of the predicted nuclease catalytic residues in CinB (CinB*, FIG. 16a), temperature-sensitive lethality was no longer observed. Changes in toxin protein levels cannot account for the loss of toxicity, at least in the case of CidB* (FIG. 22). Importantly, only the cognate antidotes rescued growth when coexpressed with the toxins (FIG. 16b). Toxicity and rescue for both operons was seen in two different yeast backgrounds (BY4741 and W303a). These results show first, that the *Wolbachia*-encoded proteins can behave as toxin-antidote pairs in vivo; second, that toxicity depends on enzymatic activity (see below) of the CidB and CinB proteins; and finally, that suppression of toxicity in vivo correlates with protein binding preferences in vitro.

Figure 17:
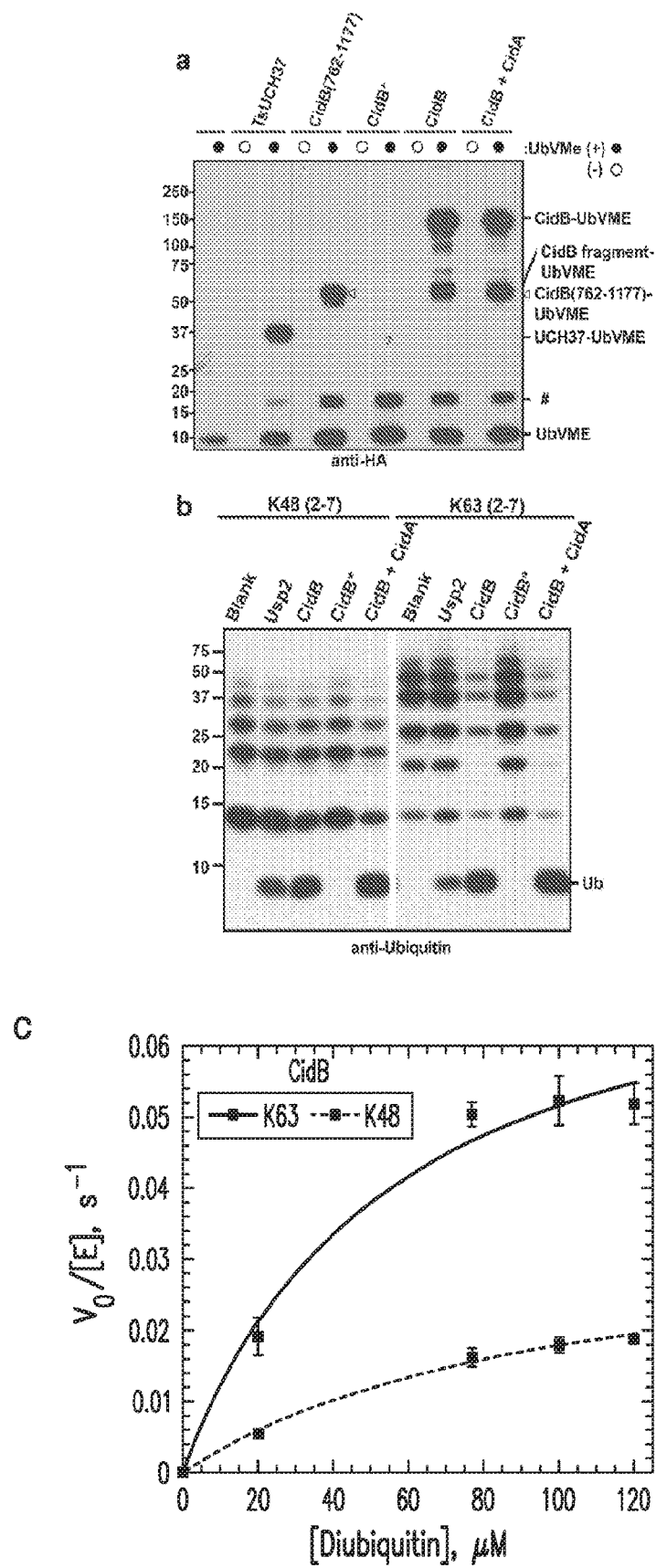
FIG. 17. CidB is a DUB. a. Anti-HA immunoblot examining DUB reactivity with the HA-tagged suicide inhibitor, Ub-VME. Ub-VME reacts with wild-type and truncated CidB proteins but not the C1025A catalytic mutant (CidB*). TsUCH37 is a positive control.[40] CidA at 100-fold molar excess does not inhibit Ub-VMe reactivity. (#) is putative UbVME$_2$ b. Anti-ubiquitin (Ub) immunoblot of K48- and K63-linked ubiquitin chains showing cleavage by CidB. Usp2 is a positive control.[41] Enzyme and substrate were 50 nM and 500 nM, respectively, and reactions were at 37° C. for 1 h. c. CidB has a ~4-fold preference for K63-Ub dimers compared to K48-linked dimers.

Next, we sought to characterize the enzymatic activity of CidB. We initially expected it to be a protease specific for the SUMO ubiquitin-like protein (UBL) since it bears a C48/Ulp1-like domain;[31] however, the purified protein did not cleave fluorogenic SUMO-AMC or SUMO-peptide fusions (data not shown). By contrast, both full-length and a truncated C48/Ulp1-like domain-bearing version of CidB reacted with the suicide inhibitor HA-ubiquitin-vinyl methyl ester (HA-Ub-VME) (FIG. 17a). Enzyme activity was tested against polyubiquitin chains with isopeptide linkages (C-terminal ubiquitin carboxyl group linked to a ubiquitin lysine F-amino group) involving either Lys48 or Ly63 residues or against ubiquitin dimers linked through each of the seven different ubiquitin lysines. CidB cleaved the isopeptide bonds in all of them and had a preference for Lys63 linkages in quantitative assays (FIG. 17b, c; FIG. 23). The enzyme did not cleave Met1-linked (linear) diubiquitin even after overnight incubation. Finally, both CidB and CidB$^{wMel}$ cleaved Ub-AMC, and to a much lesser extent, the UBL Nedd8-AMC (FIG. 24). The CidB-C1025A catalytic mutant was inactive against Ub-AMC (data not shown). Despite the ability to cleave multiple substrates in vitro, CidB appears to have a restricted substrate range in cells, as bulk ubiquitin conjugates in yeast were not detectably altered by CidB expression (FIG. 23c).

Because CidA binds CidB and suppresses CidB toxicity in yeast, we tested whether CidA inhibited CidB DUB activity. A 100-fold molar excess of CidA failed to inhibit CidB modification by Ub-VMe or cleavage of Ub chains (FIG. 17a, b, last lane of each panel); Ub-AMC hydrolysis also was not blocked (data not shown). CidA must block toxicity in yeast by some other means, such as control of its localization. This would have the advantage that the related CidA and CinA antidotes could be deployed against toxins with diverse enzymatic functions, such as those with DUB and nuclease domains.

To test the ability of the cidA-cidB operon to induce CI in an insect in the absence of *Wolbachia* infection, we cloned expression constructs into the germline-optimized pUASp-attB vector[32,33] for transgenic insertion into *D. melanogaster* by the site-directed ΦC31 integrase[34] (FIG. 25). The multiple independent transgenic flies each had a fusion of the cidA-cidB ORFs linked by a T2A viral peptide sequence that causes ribosomal skipping such that CidA and CidB are produced as separate proteins[35] (FIG. 25b). After transgenesis we verified attB/P recombination by PCR, confirmed that our fly lines were not infected by native *Wolbachia* strains, and verified transgene expression by reverse-transcription PCR (FIG. 25c-e). Males expressing the transgenic operon displayed a fully penetrant sterility in matings with wild-type females (four biological replicates with two independent attP insertion sites; FIG. 18a; FIG. 25). Females transgenic for the cidA-cidB operon were fertile, indicating that the operon caused male-specific sterility. Importantly, mutational inactivation of the CidB DUB (CidB-C1025A) in transgenic inserts failed to cause male sterility, linking CidB enzyme activity to sterility (FIG. 18a, "operon*"). Attempts to rescue the CI-like phenotype with transgenic females expressing either CidA alone or the full operon were not successful.

To verify that cidA-cidB specifically induced CI rather than an alternative form of sterility, we determined whether embryos from crosses with cidA-cidB transgenic males recapitulated established CI cytological and embryonic defects (FIG. 18b). These defects include impaired male pronuclear chromatin condensation at metaphase and delayed chromosome separation and bridging at anaphase. All were observed in the transgenic crosses. Of the embryos observed during the first post-fertilization mitosis, 88% showed these CI-like defects compared to only 3% in WT crosses (FIG. 25). Of embryos that were left to develop for 24 hours, 60% arrested "early," prior to blastoderm formation. Of the 20% of embryos that developed to segmentation, 69% showed segmentation deformities[36] (FIG. 25c, d). These specific developmental defects recapitulate those of CI embryos.[11,15-18,36,37] Thus, the defects produced by cidA-cidB expression in males closely mimic the established developmental abnormalities in CI-inducing crosses from *Wolbachia*-infected males.

Research on CI was pioneered 63 years ago in intraspecific crosses of the mosquito *C. pipiens*,[3,38] and intracellular *Wolbachia* infections were described over 90 years ago.[1] The *Wolbachia*-CI link was made in 1971,[4] but the molecular mechanism has remained obscure. Our data provide strong evidence that the *Wolbachia* cidA-cidB operon is responsible for CI. The most parsimonious interpretation of our yeast and transgenic fly data is an adaptation of the modification-rescue framework first proposed by Hurst[13] and Werren[12] in which CidB would be the modifier or toxin and CidA would function as the rescue factor or antidote. *Wolbachia* bacteria have a type IV secretion system that could translocate the CidA and CidB proteins into the host cytoplasm.[39] In analogy to many toxin-antidote systems in free-living bacteria, we propose that within the fertilized egg of an incompatible cross, CidA is rapidly inactivated or degraded. Unless CidA is supplied by a maternal *Wolbachia* infection in the egg's cytoplasm, the paternally supplied CidB enzyme toxin will become active. However, CidA alone, might not be sufficient for rescue in the egg; additional *Wolbachia* or host factors might be required, possibly for co-localization of the toxin and antidote. The exact targets of the CidB DUB enzyme (and putative CinB nuclease) and the detailed molecular pathway of cidA-cidB-induced CI also remain to be determined.

*Wolbachia* Genomics Supports a Role for the cidA-cidB Operon in CI The lock-and-key model, originally proposed as the toxin-antidote model by Hurst 1991,[13] has gained traction as the model that best describes the phenomenology of CI in insects.[10] Our toxin-antidote operon fits all tenets of the lock-and-key model: i) lock and key functions are genetically distinct (FIG. 15c-e); ii) independent sets of locks and keys exist;[19] iii) pairs of locks and keys interact in a specific or preferential manner (FIGS. 15f, 16b); and iv) locks and keys are co-evolving/diverging from a common ancestor (FIG. 19).[19] Although we have not proven antidote function for the CidB orthologs in an insect host, genomic evidence supports our molecular specification of the lock-and-key hypothesis.

Different strains of *Wolbachia* show different reproductive phenotypes. *Wolbachia* that infect *Drosophila simulans* show five different CI phenotypes. Specifically, three strains exhibit mutual bi-directional incompatibilities (different locks/toxins)—wRi, wHa, and wNo;[26] each strain has a unique toxin variant: one with an unknown enzymatic function (WRI_RS03365), one with a C48/Ulp1-like cysteine protease domain (WHA_RS01430), and one with the DUF1703 putative nuclease domain (wNo_01980), respectively. Different enzymatic toxin domains can rationalize these incompatibilities. A fourth strain, wAu, which is unable to induce or rescue CI lacks the operon altogether.[50] Finally, all sequenced genomes from so-called A and B strains that induce CI have orthologs to the putative wPip CI operon, and all strains of *Wolbachia* not observed to induce CI (wAu, wOo, and wBm) lack an orthologous operon.[19] Therefore, all the assembled genomes of *Wolbachia* show a correlation between their CI phenotypes and cid/cin operon structures.

A full-length CidB structure, rather than simply presence of the DUB domain, appears to be necessary for CI. BLAST analysis of the Ulp1-like CidB domain shows that small truncated orthologs of the enzymatic Ulp1-like domain are present in non-inducing CI strains as well as non-CI inducing Rickettsial relatives. We make a distinction between these small truncated versions and full-length genes. The small versions are exemplified by the paralogous wPa_1291 of wPip, which encodes just the Ulp1-like domain and lacks possibly important N-terminal residues, an operon structure, or an associated antidote. Notably, when we analyzed wPa_1291 (which encodes residues equivalent to 894-1177 of CidB), we found that it would not induce toxicity in yeast (data not shown). This suggests that N-terminal residues and possibly even the hypothetical antidote are important for toxin localization and CI induction.

In Beckmann and Fallon (2013), a toxin-antidote hypothesis was postulated in which CidA acted as toxin and CidB as antidote. This was because we had detected CidA in mature mosquito sperm purified from spermathecae.[19] Our analyses in yeast and *Drosophila* (FIGS. 16 and 18) now suggest the opposite, namely, that CidB acts as toxin and CidA as antidote. Although CidB had not been detected within sperm, this does not repudiate our new formulation. Because CidA binds to CidB, it is possible that the CidA antidote might even play a role in localizing CidB within the mature sperm or in the zygote. We were unable to generate a transgenic line expressing just the CidB enzyme. In contrast, all other constructs could be readily inserted into the fly genome. We suspect that CidB, by itself, was killing the injected flies. The CidA protein might mitigate unwanted side effects of CidB expression. Further investigation of molecular interactions and localization of the putative toxin and antidote proteins will be needed.

Bacterial DUBs are Secretion System Effectors that Modulate Host Ubiquitin Systems Prokaryotic ubiquitin-like protein (UBL) proteases (ULPs) and DUBs are frequently encoded by pathogenic gram-negative and obligate intracellular bacteria.[21] This is intriguing because prokaryotes do not have their own full ubiquitin-proteasome system.[51] All identified bacterial DUBs specifically tested for secretion have been shown to be secreted as effector proteins. Type III secretion system (T3SS) substrates include ChlaOTU (*Chlamydia*), a DUB which is thought to interact with intrinsic cellular immunity/autophagy systems regulated by ubiquitin;[52] XopD (*Xanthomonas*) a SUMO protease which affects modification of important plant transcription factors by the UBL SUMO;[53-55] and SseL (*Salmonella*), a DUB that was shown to be a virulence factor important for regulation of cytotoxicity in macrophages.[56] A Type IV secretion system (T4SS) substrate is SdeA (*Legionella*), which is essential for virulence in protozoan hosts.[57] No reports describe an intrabacterial function for any prokaryotic ULP or DUB. Because the CidA protein was detected in spermathecal tissues not known to harbor endogenous *Wolbachia* infections, secretion of the protein is suggested.[19] Interestingly, the cidA-cidB operon was shown to be incorporated into WO prophage genomes,[58] making the translated proteins' escape from cells by phage-induced bacterial lysis, or incorporation into transmissible viral particles, another possibility. Overall, these data strongly suggest secretion of the CidA and CidB proteins, although this remains to be proven.

The CidB enzyme showed no activity toward mammalian SUMO1-AMC or SUMO2-AMC substrates or toward yeast SUMO (Smt3) fusions. Because XopD from *Xanthomonas* specifically targeted plant SUMO isoforms and would not cleave SUMO from other species,[59] we thought it possible that the CidB enzyme might specifically cleave *Culex* mosquito SUMO and not other isoforms. We cloned the mosquito SUMO as a fusion substrate with ubiquitin and tested this protein for cleavage by CidB; it did not cleave and was also inactive toward ISG15-AMC. CidB showed weak activity toward Nedd8-AMC; its $k_{cat}/K_M$ for Nedd8-AMC was determined to be 0.69 $\mu M^{-1}$ $min^{-1}$ (FIG. 24). By comparison, the $k_{cat}/K_M$ for Ub-AMC hydrolysis was 7.59 $\mu M^{-1}$ min⁻¹. CidB$^{wMel}$ had a similar preference for ubiquitin over Nedd8 (FIG. 24). These data imply that CidB specifically targets ubiquitin linkages rather than UBL conjugates; weak cross reactivity with Nedd8 is more likely an off-target effect due to the close sequence similarity of Nedd8 and ubiquitin.[21] All these data support the hypothesis that the major biological effects of CidB are mediated by its activity against ubiquitin conjugates. Identification of its critical in vivo substrates will be needed to test this model.

We investigated the ability of CidB to cleave all seven possible ubiquitin-C-terminus-lysine linkages in ubiquitin dimers as well as the linear Met1-ubiquitin linkage because different ubiquitin chains of different linkages are associated with different cellular pathways.[60] CidB displayed activity towards all of the lysine-linked diubiquitins but was unable to cleave linear diubiquitin in 1 h or overnight at 37° C. Other DUBs, mainly from the USP family, such as USP7 and USP28, are similarly active against multiple chain linkages but not linear diubiquitin.[41] Of all the possible linkages explored in our diubiquitin panel digest (FIG. 23a), CidB appeared to have the highest activity toward Lys48 and Lys63. The Lys48 polyubiquitin linkage often signals for substrate degradation by the proteasome, whereas Lys63 linkages are typically involved in certain DNA repair pathways and endocytosis.[21] The preference of CidB for K63 ubiquitin dimers over K48 dimers is relatively modest (~4-fold), so we cannot conclude which chain types might be most relevant to CI induction, although K63 chain-modified (or monoubiquitylated) substrates appear most likely.

It has been speculated that CI targets a core conserved biochemical machinery involved in mitosis because delays in chromosome condensation and bridging are, without exception, observed in insects ranging from mosquitoes (*Culex* and *Aedes*), fruitflies (*Drosophila*), and wasps (*Nasonia*).[11,15] Furthermore, artificial transfection of heterologous *Wolbachia* strains into diverse hosts still results in induction of CI (wAlbB into *Anopheles stephensi*;[27] wRi into *Drosophila melanogaster*;[28] wMel into *Aedes aegypti*).[29]

Our data with heterologous expression of the *Wolbachia* cid and cin genes in yeast fully support this idea of broad host range. Similarly, we could induce robust transgenic CI in *Drosophila* flies with an operon from a *Wolbachia* strain that normally infects *Culex* mosquitoes. This CI-like effect over a broad host range also means that the transgenic operon might be utilized in many different insect pests or disease vectors to limit their populations.

Finally, CidB is not the only means of inducing CI. There are redundant paralogous operons, such as in wPip. In the case of wNo, which lacks a functional cidA-cidB operon, CI may be induced by virtue of the orthologous DUF1703 nuclease-type operon. The DUF1703 domain has previously been implicated in insect sterility.[63] Likewise, in wPip both paralogous operons might induce CI simultaneously, creating multi-directional incompatibility dynamics (peptides were detected from both operon systems in an ovarian proteome).[62]

In accord with the lock-and-key model, the two paralogous operons appear to share a common ancestor. Not only does conservation of sequence suggest this, but secondary structure predictions from Psipred[64] show that the CidB proteins share an underlying CinB-related secondary structure immediately preceding the DUB domain (FIG. 19; αββαβ).[25] In contrast to the CinB-type operons, the CidB catalytic operons do not maintain conservation of the D-E-K catalytic triad predicted to coordinate a metal ion for nuclease activity. However, the underlying structural skeleton suggests that a common ancestor was a nuclease form which then diverged by addition of the DUB domain at its C-terminus and mutational drift of the nuclease active site.

Interestingly, a divergent version of the apparent CI toxin from *Rickettsia gravesii* has both a DUF1703 nuclease and a DUB domain (WP_024547315.1). This ortholog may be an evolutionary "missing link" between the paralogous forms diverging in *Wolbachia*. Furthermore, another known CI-inducing bacterium, the phylogenetically distant Cardinium hertigii, was shown to possess a USP-type DUB in its genome, making it a possibility that Cardinium uses this effector to induce CI by a similar pathway.[65]

Methods

DNA Manipulation

DNA was purified from *Wolbachia*-infected insects according to Beckmann and Fallon 2012.[42] Genes from cid and cin operons were cloned from DNA of wPip-infected *C. pipiens* Buckeye mosquitoes[19] and from YW wMel-infected *D. melanogaster* flies. PCR products were amplified using PhusionHF DNA polymerase (New England Biolabs), gel-purified, and ligated into various plasmid vectors, including the pBAD (ThermoFisher; arabinose induction), pET (ThermoFisher; IPTG induction), pCold-GST (gift from Chittaranjan Das; IPTG induction) and pGEX (GE Healthcare; IPTG induction) *E. coli* expression vectors. All plasmid inserts were fully sequenced at the Yale Keck Foundation DNA sequencing facility. Point mutations were introduced by QuikChange mutagenesis (Stratagene). Further modifications such as truncations or tag additions were carried out using SLIM.[43]

Protein Purification for Pulldown Analysis of His6-Tagged Proteins

The procedure followed was a slight modification of the Dynabeads manufacturer's protocol (Novex). Recombinant proteins were expressed in *E. coli* strains BL21-AI (ThermoFisher) or Rosetta DE3 (Novagen). Large (2 L) or small (100 ml) cultures were grown in Luria Broth (LB) at 37° C. with vigorous shaking to 0.5 OD at $\lambda_{600\ nm}$ and induced by either 0.02% arabinose (pBAD) or 1 mM IPTG (pET). Protein induction in most cases was allowed to proceed overnight at 18° C. Cell pellets were resuspended in binding wash buffer (50 mM sodium phosphate [pH 8.0]; 300 mM NaCl; 0.01% Tween-20; 5 mM β-mercaptoethanol; 10 mM imidazole) and lysed by either sonication or French press. Cell lysates were incubated for 10-60 min at 4° C. with HisPur cobalt resin or Ni-NTA agarose resin (both Qiagen).

For His6-tagged protein pulldown assays, bead-bound tagged proteins were incubated with bacterial extracts containing bait protein for 1 h at 4° C. The resin was washed, and bound proteins were eluted at 4° C. with 1 bead volume of elution buffer containing 300 mM imidazole. For large-scale purifications of His6-tagged proteins, eluates isolated by the same method were concentrated to ~0.3 ml in a 10 Kda cutoff concentrator (Amicon). Protein concentrations were determined either by densitometry on a Syngene G:box with GeneTools software using BSA as a standard or by Bradford assay (Bio-Rad). We note that in FIG. 15f, protein loading of the CidB$^{wMel}$ toxin was lower than the others because it expressed at very low levels.

Purification of Proteins for Kinetic Assays

To obtain purified enzymes for kinetic analysis of DUB activity, CidB (762-1143) and CidB$^{wMel}$ (797-1128) were overproduced as glutathione-S-transferase (GST) fusions in *E. coli* with minor modifications to the protocol described previously.[44] Briefly, large-scale cultures were grown to late exponential phase in LB and were induced with 0.3 mM IPTG. Following induction at 37° C. for 4 h, cells were harvested and lysed with a French press. Proteins were purified by GST-affinity chromatography using glutathione agarose (Thermo Scientific). After removal of the GST tag with PreScission protease (GE Biosciences), the protein was further purified by size-exclusion chromatography using a HiLoad Superdex S75 PG column (GE Biosciences) in a buffer consisting of 50 mM Tris-HCl (pH 7.6), 150 mM NaCl, and 1 mM DTT. All protein samples were concentrated, aliquoted, flash frozen, and stored at −80° C. until use. Prior to use, concentrations were carefully determined both spectrophotometrically at 280 nm and by BCA Assay (Thermo Scientific).

Lys63-linked and Lys48-linked ubiquitin dimers were synthesized enzymatically using Lys63Arg, Lys48Arg, and Asp77 (mouse) ubiquitin mutants according to a previously described method.[44,45] Enzymes required for formation of Lys63 diubiquitin were human E1 (pGEX6P1 vector), Uev1a (pGEX6P1), Ubc13 (pGEX6P1), Lys63Arg ubiquitin (pET26b), and Asp77 ubiquitin (pET26b). These were purified separately and mixed in a reaction buffer containing 80 mM Tris-HCl (pH 7.6), 20 mM ATP, 20 mM MgCl$_2$, and 1 mM DTT. Synthesis of Lys48 diubiquitin used a reaction consisting of human E1, CDC34 (pET16b), Lys48Arg ubiquitin (pET26b) and Asp77 ubiquitin. All reactions proceeded overnight at room temperature and were quenched by addition of a 10-fold excess of Buffer A [50 mM NaOAC (pH 4.5)]. Unreacted ubiquitin and enzymes utilized for the reaction were separated from newly formed diubiquitin using MonoS cation-exchange chromatography (GE Biosciences). Lys63- and Lys48-linked ubiquitin dimers were eluted using a linear gradient of Buffer A mixed with Buffer B [50 mM NaOAc (pH 4.5), 1 M NaCl], and then buffer exchanged to 50 mM Tris-HCl (pH 7.6), 150 mM NaCl, 1 mM DTT. All diubiquitin samples were concentrated, aliquoted, flash frozen, and stored at −80° C. until use.

SDS-Polyacrylamide Gel Electrophoresis and Western Immunoblotting

Standard SDS-PAGE gel analysis was carried out in a range of gel concentrations. Proteins were either stained with GelCode Blue (ThermoFisher) or transferred to PVDF Immobilon-P transfer membranes (0.45 µM pore size) (SigmaAldrich) for immunoblot analysis.[46] Antibodies utilized for immunoblotting were: mouse anti-tetraHis (Qiagen, 1:4,000); mouse anti-FLAG M2 (Sigma, 1:10,000); rabbit anti-ubiquitin (Dako, 1:1000); mouse 16B12 anti-HA (BAbCo Covance, 1:1000); and mouse anti-PGK (yeast phosphoglycerate kinase) (Molecular Probes, 1:20,000). Secondary antibodies used were: sheep anti-mouse NA931V (GE Healthcare, 1:10,000) and donkey anti-rabbit NA934V (GE Healthcare, 1:5,000). Membranes used for anti-His blotting required blocking of nonspecific binding with 3% BSA and extensive washing. Other immunoblot analyses used 5% milk for blocking.

Diubiquitin Cleavage Assays

Chain cleavage assays were carried out using CidB (762-1143) following a previously published protocol.[44] Briefly, 250 nM CidB was incubated in a reaction buffer of 50 mM Tris (pH 7.6), 20 mM KCl, 5 mM MgCl$_2$, and 1 mM DTT with Lys63-linked diubiquitin concentrations ranging from 20-120 µM. In assays using Lys48-linked diubiquitin, 400 nM CidB was used. All reactions were carried out at room temperature for 10 min (Lys63 reactions) or 15 min (Lys48 reactions) and were quenched by the addition of 5×SDS-PAGE sample buffer. Ubiquitin standards ranging from 6-40 µM were used to generate a standard curve, enabling quantification of ubiquitin produced from each diubiquitin cleavage reaction using ImageJ software.[47] To account for the release of two ubiquitin moieties (P and P') from a single reaction, the initial rates of each reaction were divided by 2. All kinetic data were analyzed with Kaleidagraph Version 4.1.3b1 and could be fit to the Michaelis-Menten equation: $V_i=(V_{max}[S])/(K_M+[S])$ where [S] is the concentration of substrate. We also tested reactivity of full length CidB with all seven potential ubiquitin lysine linkages by incubating 1 µM enzyme with 1 µM diubiquitin for 3 h or overnight at 37° C. using the Ub$_2$ Explorer Panel (LifeSensors). Lastly, we incubated 50 nM CidB with 500 nM mixtures of Lys63-linked or Lys48-linked polyubiquitin chains (ranging in size from 2-7 ubiquitins; Boston Biochem) for times of 20 min to 4 h at 37° C. Error bars are standard deviations.

Ubiquitin-AMC and UBL-AMC Hydrolysis Assays

Ubiquitin (Ub) and ubiquitin-like protein (UBL) with C-terminal 7-amido-4-methylcoumarin adducts (Ub-AMC and UBL-AMC) were used for hydrolysis assays as described previously.[40] Briefly, a CidB fragment encompassing the DUB domain (residues 762-1143) was diluted to a final concentration of 5 nM in reaction buffer (50 mM Tris, pH 7.6, 0.5 mM EDTA, 0.10% bovine serum albumin, 5 mM DTT). Prior to addition of the Ub or UBL-linked AMC substrate (Ub-AMC, NEDD8-AMC, SUMO1/2-AMC, and ISG15-AMC; Boston Biochem), the enzyme was pre-incubated at 30° C. for 5 min, and all reactions proceeded at 30° C. Apart from the ISG15-AMC substrate (excitation/emission 380 nm/460 nm), hydrolysis of the Ub/UBL-AMC substrates as a function of time was monitored via excitation/emission at 345 nm/445 nm using a SynergyMix plate reader (BioTek, Winooski, VT). A standard curve comprising AMC (Sigma Aldrich) concentrations ranging from 0-50 nM was prepared in reaction buffer to allow quantification of the amount of hydrolyzed substrate. Despite testing human ISG15-AMC and SUMO1/2-AMC with several concentrations of CidB (up to 400 nM), we failed to detect any AMC release. Substrate concentrations ranging from 50 nM to 2 µM were mixed with 5 nM and 25 nM CidB in Ub-AMC and Nedd8-AMC assays, respectively. Initial velocities were extrapolated from the linear portion of the curve and plotted as a function of substrate concentration. As the catalytic activity exhibited a linear response to substrate over the concentration range tested, data could not be fit to the Michaelis-Menten equation. Data were instead fit to the equation $v/[E]=k_{cat}/K_M[S]$, where [E] and [S] are the concentrations of enzyme and substrate, respectively. All enzymatic assays were carried out in triplicate and analyzed using Kaleidagraph Version 4.1.3b1. Error bars are standard deviations.

Generation of a Covalent CidB-UbVME Adduct

To test for formation of a covalent complex between CidB and the suicide DUB inhibitor UbVME, 5 µM CidB was mixed with 1 µM HA-UbVME (a gift from Michael Sheedlo and Chittaranjan Das, Purdue University). After adjusting the pH to 8, reactions were carried out for 4 h at 37° C. and quenched by mixing with 5×SDS sample buffer, and the products were run on a gradient SDS-PAGE gel. Following electrotransfer to a PVDF filter, the filter was incubated, as outlined above, with anti-HA antibodies, followed by secondary antibody.

Yeast Methods

Analysis of yeast growth that is displayed in figures utilized the BY4741 strain background. Rescue experiments were replicated in the W303a background. DNA fragments used for expression in yeast were subcloned from E. coli vectors by restriction digest or PCR amplification and ligated into yeast vectors. The 2-micron plasmids pYES2 (URA3) and p425GAL (LEU2) both had the GAL1 promoter and CYC1 terminator and were utilized for galactose-induced expression of *Wolbachia* genes in yeast.[48] Expression from the low-copy CEN vector pRS416 was also utilized. For serial dilutions of yeast cells, cultures were grown overnight in non-inducing minimal synthetic media lacking either uracil, leucine, or both depending upon the plasmid(s) used for expression. Cells were pelleted by centrifugation, washed with sterile water, and spotted in 5-fold serial dilution from an initial 0.05 $OD_{600}$ concentration on solid minimal SD media containing either 2% galactose or glucose and lacking either uracil, leucine, or both. Plates were placed at 30, 32, 34, and 37° C. for 3 d.

*Drosophila* Genetic Analysis

An initial cidA-T2A-cidB operon construct was synthesized and codon optimized for *Drosophila* by Genscript and cloned into the pUC57 vector (FIG. 25b). Genes were then subcloned from the mother construct into the pUASp-attB vector[32,33] by PCR and restriction digest. The full-length operon construct pUASp-attB-cidA-T2A-cidB was unstable in TOP10F' bacterial cells and prone to degradation. The plasmid was stabilized in CopyCutter EPI400 cells (Epicentre). All constructs for transgenesis in the pUASp-attB vector were fully sequenced and verified to lack spurious mutations.

DNA constructs were sent to BestGene for microinjection of *D. melanogaster* embryos. Fly backgrounds #9744 and #9750 (containing attP insertion sites on the $3^{rd}$ chromosome) were chosen for site-directed attP/B integration by the ΦC31 integrase. Red-eyed flies were selected and screened by BestGene. Upon receipt of transgenic lines, we independently verified attP/B integration by PCR using primers 509 (5'-GGGCGTGCCCTTGAGTTCTCTC-3'; SEQ ID NO:21) and 510 (5'-CGAGGATCGCATACCGCACTG-3'; SEQ ID NO:22) (#9744; 0.5 kb product) or 509 (5'-GGGCGTGCCCTTGAGTTCTCTC-3'; SEQ ID NO:23) and 511 (5'-AACGCTTTGCTTTCTCGCTG-3'; SEQ ID NO:24) (#9750; 0.7 kb product), which amplified a product only if site-specific recombination had occurred. We also verified that our #9744, #9750, and WCS strains were uninfected with native *Wolbachia* isolates that might interfere with crossing data. This was done using PCR to amplify the $cidA^{wMel}$ gene. As a positive DNA control, we amplified a ~200 bp product of *D. melanogaster* rps3. The basal P-element promoter in pUASp-attB induced sufficient expression to induce phenotypes without a Gal4 driver. This was confirmed by reverse transcription-PCR (RT-PCR) analysis carried out by purifying RNA with TRIzol reagent (Ambion) according to the manufacturer's specifications from pools of 20 male flies. RNA was further purified with by RNeasy (Qiagen) and treated with DNase I. Complementary DNA was synthesized using the iSCript cDNA Synthesis Kit (BioRad), and the cDNA was used as template for PCR reactions with primers that amplified either CidB or rps3.

Flies were maintained at room temperature on a standard diet. For CI analysis, two males (<3 d old) were mated to 10 virgin females in an individual tube. 1 tube of 12 flies was one N. Adult flies were removed after 10 days of egg laying, and fecundity was assessed by counting eclosions of adult progeny. In the case of the crosses that led to sterility, flies were allowed to lay eggs until they died in the tube; they never produced offspring. To assess the cytology of early embryos resulting from an incompatible cross with cidA-cidB transgenic males, ~300 virgin female $^w$CS flies were placed in a collection container with ~100 transgenic cidA-cidB males and put on apple juice plates with yeast paste for 2 d. Embryos were then collected by a brush and sieve every 15 min, dechorionated in 50% bleach, and fixed immediately in a solution of 5 ml heptane, 2 ml 2.5×PBS, 500 µl 0.5 M EDTA, and 1 ml of 37% fresh formaldehyde. The fixing solution (10 ml) was kept in a clear glass scintillation vial to allow visualization of liquid phase layers and eggs. Vitelline membranes were removed by replacing the heptane top layer with 2 volumes of methanol and vigorous shaking. Sunken de-vitellinated embryos were collected with a Pasteur pipette, washed three times with methanol, and stored overnight at 4° C. before they were rehydrated with PBTA[49] and stained with Hoechst 33342 dye (ThermoFisher Scientific) at 1:1000 in PBTA. Stained embryos were washed and mounted on glass slides and sealed under a cover slip with nail polish. Microscopic analysis of the embryos was performed on a Zeiss Axioskop microscope using a 100×/1.4 NA objective lens.

Variations in the cytological quantifications are shown as the standard deviation of the mean of triplicate samples of 200 embryos (FIG. 25a). Polar bodies were used as a landmark. Images where polar bodies were not observed were excluded from the data (FIG. 25b). Images were captured by AxioVision Re.4.8 software and adjusted for contrast and assembled in Photoshop (Adobe). The images confirmed that the cidA-cidB transgenic males, while sterile, mated and successfully fertilized eggs. In cases where nuclei were not well visualized in a single plane of focus, a Z-stack maximum projection was created in ImageJ.

Crosses aimed at testing rescue of cidA-cidB-induced lethality were performed by first creating various heterozygous [GAL4; UAS-CidA] flies. These were generated by crossing [yw; UAS-CidA] homozygous virgin females with male driver strains that are expected to express Gal4 during oogenesis: #4442: nanos-Gal4, #32551: ubiquitin-Gal4, #44241: oskar-Gal4, #7062: MATα-Gal4 (all transgenes on the $2^{nd}$ chromosome), or #31777: MTD-Gal4, which has many Gal4 inserts on all three chromosomes including nanos-Gal4, nanos-Gal4:VP16, and otu-Gal4. These double heterozygotes were then mated with cidA-cidB males to test fecundity. Fly stocks were obtained from the Bloomington Stock Center or were gifts.

REFERENCES CITED IN EXAMPLE 2

1 Hertig, M. & Wolbach, S. B. Studies on *Rickettsia*-like micro-organisms in insects. *J Med Res* 44, 329-U322 (1924).
2 Werren, J. H., Baldo, L. & Clark, M. E. *Wolbachia*: master manipulators of invertebrate biology. *Nat Rev Microbiol* 6, 741-751 (2008).
3 Laven, H. *Chapter 7: Speciation and Evolution in Culex pipiens.* 251 (Elsevier, 1967).
4 Yen, J. H. & Barr, A. R. New hypothesis of the cause of cytoplasmic incompatibility in *Culex pipiens* L. *Nature* 232, 657-658 (1971).
5 Bourtzis, K., Braig, H. R., and Karr, T. L. *Chapter 14 Cytoplasmic Incompatibility*. Vol. 1 (CRC Press, 2003).
6 Turelli, M. & Hoffmann, A. A. Rapid spread of an inherited incompatibility factor in California *Drosophila*. *Nature* 353, 440-442 (1991).
7 Bordenstein, S. R., O'Hara, F. P. & Werren, J. H. *Wolbachia*-induced incompatibility precedes other hybrid incompatibilities in *Nasonia*. *Nature* 409, 707-710 (2001).
8 Clark, M. E., Veneti, Z., Bourtzis, K. & Karr, T. L. *Wolbachia* distribution and cytoplasmic incompatibility during sperm development: the cyst as the basic cellular unit of CI expression. *Mech Dev* 120, 185-198 (2003).

9 Presgraves, D. C. A genetic test of the mechanism of Wolbachia-induced cytoplasmic incompatibility in Drosophila. Genetics 154, 771-776 (2000).

10 Poinsot, D., Charlat, S. & Mercot, H. On the mechanism of Wolbachia-induced cytoplasmic incompatibility: confronting the models with the facts. BioEssays: news and reviews in molecular, cellular and developmental biology 25, 259-265 (2003).

11 Serbus, L. R., Casper-Lindley, C., Landmann, F. & Sullivan, W. The Genetics and Cell Biology of Wolbachia-Host Interactions. Annual review of genetics 42, 683-707 (2008).

12 Werren, J. H. Biology of Wolbachia. Annu Rev Entomol 42, 587-609 (1997).

13 Hurst, L. D. The Evolution of Cytoplasmic Incompatibility or When Spite Can Be Successful. J Theor Biol 148, 269-277 (1991).

14 Loppin, B., Dubruille, R. & Horard, B. The intimate genetics of Drosophila fertilization. Open biology 5 (2015).

15 Tram, U., Ferree, P. M. & Sullivan, W. Identification of Wolbachia—host interacting factors through cytological analysis. Microbes and infection Institut Pasteur 5, 999-1011 (2003).

16 Callaini, G., Dallai, R. & Riparbelli, M. G. Wolbachia-induced delay of paternal chromatin condensation does not prevent maternal chromosomes from entering anaphase in incompatible crosses of Drosophila simulans. Journal of cell science 110 (Pt 2), 271-280 (1997).

17 Reed, K. M. & Werren, J. H. Induction of paternal genome loss by the paternal-sex-ratio chromosome and cytoplasmic incompatibility bacteria (Wolbachia): a comparative study of early embryonic events. Molecular reproduction and development 40, 408-418 (1995).

18 Ryan, S. L. & Saul, G. B., 2nd. Post-fertilization effect of incompatibility factors in Mormoniella. Molecular & general genetics: MGG 103, 29-36 (1968).

19 Beckmann, J. F. & Fallon, A. M. Detection of the Wolbachia protein WPIP0282 in mosquito spermathecae: implications for cytoplasmic incompatibility. Insect biochemistry and molecular biology 43, 867-878 (2013).

20 Hochstrasser, M. Ubiquitin-dependent protein degradation. Annual review of genetics 30, 405-439 (1996).

21 Ronau, J. A., Beckmann, J. F. & Hochstrasser, M. Substrate specificity of the ubiquitin and Ubl proteases. Cell research (2016).

22 Zielenkiewicz, U. & Ceglowski, P. Mechanisms of plasmid stable maintenance with special focus on plasmid addiction systems. Acta biochimica Polonica 48, 1003-1023 (2001).

23 Yamaguchi, Y., Park, J. H. & Inouye, M. Toxin-antitoxin systems in bacteria and archaea. Annual review of genetics 45, 61-79 (2011).

24 O'Neill, S. L. & Karr, T. L. Bidirectional incompatibility between conspecific populations of Drosophila simulans. Nature 348, 178-180 (1990).

25 Knizewski, L., Kinch, L. N., Grishin, N. V., Rychlewski, L. & Ginalski, K. Realm of PD-(D/E)XK nuclease superfamily revisited: detection of novel families with modified transitive meta profile searches. BMC structural biology 7, 40 (2007).

26 Mercot, H. & Charlat, S. Wolbachia infections in Drosophila melanogaster and D. simulans: polymorphism and levels of cytoplasmic incompatibility. Genetica 120, 51-59 (2004).

27 Bian, G. et al. Wolbachia invades Anopheles stephensi populations and induces refractoriness to Plasmodium infection. Science 340, 748-751 (2013).

28 Boyle, L., O'Neill, S. L., Robertson, H. M. & Karr, T. L. Interspecific and intraspecific horizontal transfer of Wolbachia in Drosophila. Science 260, 1796-1799 (1993).

29 Ye, Y. H. et al. Wolbachia Reduces the Transmission Potential of Dengue-Infected Aedes aegypti. PLoS neglected tropical diseases 9, e0003894 (2015).

30 Xi, Z., Khoo, C. C. & Dobson, S. L. Wolbachia establishment and invasion in an Aedes aegypti laboratory population. Science 310, 326-328 (2005).

31 Li, S. J. & Hochstrasser, M. A new protease required for cell-cycle progression in yeast. Nature 398, 246-251 (1999).

32 Rorth, P. Gal4 in the Drosophila female germline. Mech Dev 78, 113-118 (1998).

33 Takeo, S. et al. Shaggy/glycogen synthase kinase 3beta and phosphorylation of Sarah/regulator of calcineurin are essential for completion of Drosophila female meiosis. Proceedings of the National Academy of Sciences of the United States of America 109, 6382-6389 (2012).

34 Groth, A. C., Fish, M., Nusse, R. & Calos, M. P. Construction of transgenic Drosophila by using the site-specific integrase from phage phiC31. Genetics 166, 1775-1782 (2004).

35 Diao, F. & White, B. H. A novel approach for directing transgene expression in Drosophila: T2A-Gal4 in-frame fusion. Genetics 190, 1139-1144 (2012).

36 Callaini, G., Riparbelli, M. G., Giordano, R. & Dallai, R. Mitotic defects associated with cytoplasmic incompatibility in Drosophila simulans. J Invertebr Pathol 67, 55-64 (1996).

37 Landmann, F., Orsi, G. A., Loppin, B. & Sullivan, W. Wolbachia-mediated cytoplasmic incompatibility is associated with impaired histone deposition in the male pronucleus. PLoS pathogens 5, e1000343 (2009).

38 Laven, H. [Reciprocally differentiable crossing of mosquitoes (Culicidae) and its significance for plasmatic heredity]. Z Indukt Abstamm Vererbungsl 85, 118-136 (1953).

39 Rances, E., Voronin, D., Tran-Van, V. & Mavingui, P. Genetic and functional characterization of the type IV secretion system in Wolbachia. Journal of bacteriology 190, 5020-5030 (2008).

Morrow, M. E. et al. Stabilization of an unusual salt bridge in ubiquitin by the extra C-terminal domain of the proteasome-associated deubiquitinase UCH37 as a mechanism of its exo specificity. Biochemistry 52, 3564-3578 (2013).

41 Ritorto, M. S. et al. Screening of DUB activity and specificity by MALDI-TOF mass spectrometry. Nat Commun 5, 4763 (2014).

42 Beckmann, J. F. & Fallon, A. M. Decapitation Improves Detection of Wolbachia pipientis (Rickettsiales: Anaplasmataceae) in Culex pipiens (Diptera: Culicidae) Mosquitoes by the Polymerase Chain Reaction. J Med Entomol 49, 1103-1108 (2012).

43 Chiu, J., March, P. E., Lee, R. & Tillett, D. Site-directed, Ligase-Independent Mutagenesis (SLIM): a single-tube methodology approaching 100% efficiency in 4 h. Nucleic acids research 32, e174 (2004).

44 Shrestha, R. K. et al. Insights into the mechanism of deubiquitination by JAMM deubiquitinases from cocrystal structures of the enzyme with the substrate and product. Biochemistry 53, 3199-3217 (2014).

Sheedlo, M. J. et al. Structural basis of substrate recognition by a bacterial deubiquitinase important for dynamics of phagosome ubiquitination. *Proceedings of the National Academy of Sciences of the United States of America* 112 (2015).

46 Mruk, D. D. & Cheng, C. Y. Enhanced chemiluminescence (ECL) for routine immunoblotting: An inexpensive alternative to commercially available kits. *Spermatogenesis* 1, 121-122 (2011).

47 Schneider, C. A., Rasband, W. S. & Eliceiri, K. W. NIH Image to ImageJ: 25 years of image analysis. *Nat Methods* 9, 671-675 (2012).

48 Guthrie, C. a. F., G. Guide to yeast genetics and molecular biology. *Methods Enzymol* 194, 1-863 (1991).

49 Sullivan, W., Ashburner, M., and Hawley, R. S. *Drosophila Protocols*. (Cold Spring Harbor Laboratory Press, 2000).

50 Sutton, E. R., Harris, S. R., Parkhill, J. & Sinkins, S. P. Comparative genome analysis of *Wolbachia* strain wAu. *BMC genomics* 15, 928 (2014).

51 Iyer, L. M., Burroughs, A. M. & Aravind, L. The prokaryotic antecedents of the ubiquitin-signaling system and the early evolution of ubiquitin-like beta-grasp domains. *Genome biology* 7, R60 (2006).

52 Furtado, A. R. et al. The chlamydial OTU domain-containing protein ChlaOTU is an early type III secretion effector targeting ubiquitin and NDP52. *Cellular microbiology* 15, 2064-2079 (2013).

53 Hotson, A., Chosed, R., Shu, H., Orth, K. & Mudgett, M. B. *Xanthomonas* type III effector XopD targets SUMO-conjugated proteins in planta. *Molecular microbiology* 50, 377-389 (2003).

54 Kim, J. G., Stork, W. & Mudgett, M. B. *Xanthomonas* type III effector XopD desumoylates tomato transcription factor SlERF4 to suppress ethylene responses and promote pathogen growth. *Cell host & microbe* 13, 143-154 (2013).

55 Noel, L., Thieme, F., Nennstiel, D. & Bonas, U. Two novel type III-secreted proteins of *Xanthomonas campestris* pv. vesicatoria are encoded within the hrp pathogenicity island. *Journal of bacteriology* 184, 1340-1348 (2002).

56 Rytkonen, A. et al. SseL, a *Salmonella* deubiquitinase required for macrophage killing and virulence. *Proceedings of the National Academy of Sciences of the United States of America* 104, 3502-3507 (2007).

57 Bardill, J. P., Miller, J. L. & Vogel, J. P. IcmS-dependent translocation of SdeA into macrophages by the *Legionella pneumophila* type IV secretion system. *Molecular microbiology* 56, 90-103 (2005).

58 Bordenstein, S. R. & Bordenstein, S. R. Lateral genetic transfers between eukaryotes and bacteriophages. *bioRxiv*, doi:10.1101/049049 (2016).

59 Chosed, R. et al. Structural analysis of *Xanthomonas* XopD provides insights into substrate specificity of ubiquitin-like protein proteases. *The Journal of biological chemistry* 282, 6773-6782 (2007).

60 Kulathu, Y. & Komander, D. Atypical ubiquitylation—the unexplored world of polyubiquitin beyond Lys48 and Lys63 linkages. *Nature reviews. Molecular cell biology* 13, 508-523 (2012).

61 Tracey, W. D., Jr., Ning, X., Klingler, M., Kramer, S. G. & Gergen, J. P. Quantitative analysis of gene function in the *Drosophila* embryo. *Genetics* 154, 273-284 (2000).

62 Beckmann, J. F. *Molecular Mechanism of Wolbachia Induced Cytoplasmic Incompatibility* PhD thesis, University of Minnesota, (2014).

63 Lorenzen, M. D. et al. The maternal-effect, selfish genetic element Medea is associated with a composite Tc1 transposon. *Proceedings of the National Academy of Sciences of the United States of America* 105, 10085-10089 (2008).

64 McGuffin, L. J., Bryson, K. & Jones, D. T. The PSIPRED protein structure prediction server. *Bioinformatics* 16, 404-405 (2000).

65 Penz, T. et al. Comparative genomics suggests an independent origin of cytoplasmic incompatibility in Cardinium hertigii. *PLoS genetics* 8, e1003012 (2012).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

TABLE 6

Sequences of CI Factors

| Gene | Locus tag | Seq. type | Length | (5'-3') or (N-C) |
| --- | --- | --- | --- | --- |
| cidA | WD0631 | nucleotide | 1425 bp | ATGCCAATAGAAACAAAACGTCAGGCTGAAGTGCTTAAAAAGCTA CAAGATGTGATAAAACATACAGATCGTGACATTGCGGCTGGAAGA AAGTTAGCTATTAAAAGGTGGGTCAGACCTATATAGAGTATATC AAACTTTTTAAGGATGATAAGCTGGAATTCTTATATAATGTTTTC GAGATGAAGGTTGTTGGTTAGGTACAAGGTTAAATAATACTGTTTT AGGTCAGAAATTGACTGAAGAGAAAATAGGAGAAATCGATAACC CACTACCAAGGTATGGTATGGCATCTAGGTACTGTATAACGGGCA AGATAGGTGATTTTTTCAACAAACAGTTTGTACTCTCTAGAGGTCA ATTTACTTCAGAAGAGGTAGATAGTCAAGGTAATCCGATCAGTGA TCAATATGTAAGAAACATTCTGCTATCATCCATGAAGAGAAATGG TCCTGTGTTTGATTTCTGGATCGATAGAGAATCTGGGGAATTAAAG AAGTATGATGCAGTAGAAGGTTTTGACAGTACTGTAAAACTTAAG TGGAGCGAAGGGGTAGAGTATTTTTATAATCAGTTAGAGGAAAAA GATAAGGAGAAGAAGCTTACAGAAGCTATTGTTGCTCTTTCTCGTC CTCAATCTGTTAAGAGAGACGCTCCTATTTTAGATTTTTGTGTAAG GAATATAGGCGATAAAGATACTCTTTTACAGAAATTATTGCAGAA AGATAAGGGAGTATATTTCCTTCTTGCTGAATTAATAGAGTCATGT TTTTTTGATACGGTTCATGATTTGGTACAGTGCTGGTGTTATAAAG |

TABLE 6-continued

Sequences of CI Factors

| Gene | Locus tag | Seq. type | Length | (5'-3') or (N-C) |
|---|---|---|---|---|
| | | | | GCGTTTCAGCAGGAGGAGACTGTTCGGACAAGATATTCTCACAGC<br>AAGACTATGAACTTTTTCTTTATTCACTTTCAAATGTGATGTTGAA<br>AAATCCTGAGTTAAGTGTTCAAGCTAGATCCCTTATTATGGAGATT<br>TGGAAATGTGAACGCTTTGCTGAATACAGAGAGACCTCTGTTAAT<br>ACTTCTAATTATACAGTTCCTATAAAGAGTGTACTTGGGGGATTAA<br>TCATTAATTGGAAACGAGAAGATGTTTGTAAGCCCGATAGGGAAA<br>TAGAGAAAGAAGAAATATTAGATATGATTTCATTTGCCAAAGGTT<br>GCTTTCCTGAAAAGTTTGACCTTTTTAAAGAAGTCATGATAGAAAA<br>TCTTAGAATATGTGGTAGGGAAGGAAAGAGGAAAGGTGTAGATTA<br>CGGCAAGTTTGCAGAAGAGTTATTTCTTCAGTTAGAGAAAGTAAC<br>TTTACCTTCTGTAGGTGATGGTCCTTGGAATAATTTGCGGTCTCAA<br>TCTAAGGTATCTTTGCCACTTGATGGTTCTGGTGATGGCCCACAGT<br>CTGAGTTTGAAGCTCCTAGTGTGAGTGGTATTTCTGGTTCTCATAA<br>GAAAAGAAGAATCTAG (SEQ ID NO: 1) |
| cidA | WD0631 | amino acid | 474 aa | MPIETKRQAEVLKKLQDVIKHTDRDIAAGRKLAIKRWVETYIEYIKLF<br>KDDKLEFLYNVFRDEGCWLGTRLNNTVLGQKLTEEKIGEIDNPLPRY<br>GMASRYCITGKIGDFFNKQFVLSRGQFTSEEVDSQGNPISDQYVRNIL<br>LSSMKRNGPVFDFWIDRESGELKKYDAVEGFDSTVKLKWSEGVEYF<br>YNQLEEKDKEKKLTEAIVALSRPQSVKRDAPILDFCVRNIGDKDTLLQ<br>KLLQKDKGVYFLLAELIESCFFDTVHDLVQCWCYKGVSAGGDCSDKI<br>FSQQDYELFLYSLSNVMLKNPELSVQARSLIMEIWKCERFAEYRETSV<br>NTSNYTVPIKSVLGGLIINWKREDVCKPDREIEKEEILDMISFAKGCFP<br>EKFDLFKEVMIENLRICGREGKRKGVDYGKFAEELFLQLEKVTLPSVG<br>DGPWNNLRSQSKVSLPLDGSGDGPQSEFEAPSVSGISGSHKKRRI<br>(SEQ ID NO: 2) |
| cidB | WD0632 | nucle-otide | 3501 bp | GTGGATGGAGATCTTGATGGTTTTAGACAAGAGTTTGAATCCTTTT<br>TAGATCAATGTCCATTTTTCTTGTATCATGTAAGTACAGGACGTTT<br>CCTTCCTGTATTCTTTTTCAGTATGTTTGCTACTGCTCATGATGCTA<br>ATATCTTAAAAGCAAATGAGAGAGTGTATTTTCGTTTTGATAATCA<br>TGGTATTGATACAGGTGGTAGAAATAGAAATACAGGGAACCTAAA<br>AGTCGCTGTTTATCATGACGGACAGCAAGTTGTCAGATGCTACAGT<br>ATTTCTGATCGTCTTAATAGTGATGGGTTAAGGTTCAGTACAAGGG<br>AAAGAAATGCTCTAGTGCGAGAGATTAGAGGGCAAAATCCAAATT<br>TAAGGGAAGAAGACCTAAATTTTGAGCAATACAAAGTATGCATGC<br>ATGGAAAGGGCAAGAGTCAGGGAGAGGCGATTGCAACAGTATTC<br>GAGGTGATTCGTGAAAAAGATTCTCAAGGTAGAGATAGATTTGCT<br>AAATATTCAGCGTCTGAGATTAGCCTTCTTAGGCATATAGAACGCA<br>ATAGGCTTAATGGGATTAATGCGCCTGCGCCACGCAGTTTGTTGAC<br>AGTTAAGGAAATAGGAAGTATACGACTCAATCAAGATCAGAGAGT<br>ACAGCTTGGTCATTTGGTCAATTTTGTGCAAGTTGCACCGGGTCAG<br>CAAGGGATTTTCAGTTTTATGGAAGTGCTAGCAAGTAACCAAAAA<br>ATAAATATAGAACGTGGAATAAATGAAGGAATTTTGCCATACATA<br>ACTCGAATCTATCGTAGTTACCTAGGCAGCCTACAAAATGACATTC<br>AAAATCGCAGTCAAAAGTTTGAGAGTCACGGATTTTTCTTAGGTTT<br>GTTGGCAAATTTTATTCATCTCTACACAATAGATATTGACCTTGAC<br>TTGTCTCCTGGAAATTCATATGTTGCTTTTCTTATATGTCATCAGGC<br>AGAGAGAGAAAACATTCCTATCGTTATTAATGTTACTAGATGGAG<br>GACATCGTCTGATATTGCATTAAACCGCGCTAGAGCTGATGCTAA<br>AAGATTACATGTTTCTTCATTTATATCTATTCACACTGAATCAAGA<br>AATGCTGTTTGTATTGGATTAAATTTTAATCTGAATATAGATCCTTT<br>TAGTATTGATACAGTAGAGTTTTTAGAGAATAGATTTCCTTTGGTA<br>CAAAGATTATTTGAGTGTTTGGAGGATGAAGGAATTAGAGAAAAT<br>ATTAGAGATTTCTTGCTTCAACATCTTCCTAACGAAATACCAAGAA<br>ATGCAGAGAATTATAACAGAATATTTGATTGCATAACTGGTTTTGC<br>TTTTGGGAATAGTATTTTAGAAGAGTTCAGATTAGTAAACGCAGTT<br>CAACAACGTGTAAGAAAGTATATATTTAGATATGGTGATGAGAAT<br>CATGCTTTAACCATGGTCTTCCATACTCAAGGTTCTGATATAGTTA<br>TACTTCATATTAGAGATAACAACGCTGTACAACAAGGAGCCATCA<br>ATTTACAAGATCTTAATGTTGACGGAAATAATGTTCATGTACGGGA<br>AGTTTCATGCACACTTAATAATCAACTTGGCCTTAATATTCATACA<br>GATAACCTTGGTTTATATCACAATTACCAAAATAATAATGCAAATA<br>ATTTTCTTGGTGGTAATCTTGTGCAAGTGCCTAATGCTGGAAATGT<br>GCATAATGCTTTAAATCAAGTTATGAATGATGGCTGGCAAGATAG<br>ATTTCAGCATCAAGAATTATTTAGAAACATTTCTGCAGTATTAATG<br>CCAGAAGATACGCATGGCAATATGATAATAGATGTAAATAGCAAA<br>GATAAGTTTCGTCTATACTACATGGTACATTTATGCTAGTGATA<br>ATCCTTATAAAGTGCTTGCTATGTATAAAGTTGGTCAAACATATAG<br>TTTAAAAAGGTGGCAGGAAGAAGAAGGAGAAAGGGTAATACTTA<br>CAAGAGTTACAGAACAGAGACTAGGTCTTCTATTATTAAGACAAC<br>CTACAGCAGATACTCACCCAATTGGATATGTATTAGGATTTGCTGA<br>TAATGCAGAAGAAGTAGAACAGGAGCAAGACGAGGCAAGGTACA<br>AAATAACAGAATTGATGAGCAAACAAGGGGATATTTGCCTATTA<br>CTTCTGGAAATGAGGTGGTTTTGTCTTATGCTGTATTTAATAGAGG |

TABLE 6-continued

Sequences of CI Factors

| Gene | Locus tag | Seq. type | Length | (5'-3') or (N-C) |
|---|---|---|---|---|
| | | | | TGCACAGAGAGCAGAAGACTTTATATCTCTTCCACAACAAGCAGT<br>GTATGTACATAGACTTGATCGTCGTGGTCATGACTCAAGACCAGA<br>AGTATTAGTGGGACCTGAAAGTGTTATTGATGAAAATCCACCAGA<br>AAATCTATTGTCAGATCAAACTCGTGAAAATTTCAGGCGCTTTTAC<br>ATGGAAAAAAGACCAGGACAGAACTCGATTTTTTTGCTTGATATA<br>GATGATAATCTGCACGTTCCATTTAGTTACTTGCAAGGTACTAGAG<br>CACAGGCAATAGAAACATTAAGGTCAAGAATAAGGGGAGGTGGT<br>ACTTCTACAGCACAAGGAATATTACAACAAATAAACACTATCCTT<br>CGTAGAAACAACGCTCGTGAAATAGAAGATGTGCATAATCTACTT<br>GCACTAGACTTTGCAACAGAAAATCAAAATTTCCGTTATTGGCTAC<br>AAACTCATGACATGTTTTTCGCTGCACGACAATATACTTTCCATGA<br>TGATCGATCTAATCCAACTAATGATCGTCATGATTTTGCAATAACT<br>TCAGTAGGAGTCGATGGAAATCAAAATGATCCAACAGGTAGGGAC<br>TTATTAAGTAGTAACATAGATAACTTTAAACAAAAAGTAGATTCG<br>GGTGAAAAAGATAGATTAACTGCTATTATTAATGTAGGTAATCGT<br>CATTGGGTTACATTAGTTATTGTCCACCAAAATGGAAATTATTATG<br>GGTATTATGCTGATTCACTTGGTCCAGATAGTCGTATTGACAATAA<br>TATTCGAGGAGCTTTAAGAGAATGTGATATTAGCGATGATAATGT<br>CCATGATGTTTCCGTTCATCAGCAAACAGATGGCCATAATTGTGGC<br>ATATGGGCATACGAAAATGCTAGGGATATTAACCAAGCTATTGAT<br>CAAGCTTTACAGGGAAATAGTAACTTTGGAGAGAAAGGTGAAGGT<br>ATTATAGGTTATATACGTGGTCTTCTTAGTGCAGGAATTGGAAATG<br>ACACTAGACAACCTCAAAGAAATGAACAATACTTTAGAAATCGGA<br>GAAGAAATATTTCACAATTATTCCAAAATGATTCTCTATCTTCTCC<br>TAGGGGTAGATTGATTCAAGGTCGTCCAGGAATTCAACATGAAAT<br>TGATCCATTACTATTACAATTTTTAGAACTCCAATATCCACAGCGT<br>GGAGGTGGGGGAGCATTGCAATTAGGCGGAGAAAGAGTGATATC<br>AATTGATTTTGGTCCGCAATCTGTATTGGATGAAATTGATGGAGTG<br>AATAGAGTTTATGATCAATGGTAGAGGCAGTAGGTAG<br>(SEQ ID NO: 3) |
| cidB | WD0632 | amino acid | 1166 aa | MDGDLDGFREFESFLDQCPFFLYHVSTGRFLPVFFFSMFATAHDANI<br>LKANERVYFRFDNHGIDTGGRNRNTGNLKVAVYHDGQQVVRCYSIS<br>DRLNSDGLRFSTRERNALVREIRGQNPNLREEDLNFEQYKVCMHGKG<br>KSQGEAIATVFEVIREKDSQGRDRFAKYSASEISLLRHIERNRLNGINA<br>PAPRSLLTVKEIGSIRLNQDQRVQLGHLVNFVQVAPGQQGIFSFMEVL<br>ASNQKINIERGINEGILPYITRIYRSYLGSLQNDIQNRSQKFESHGFFLG<br>LLANFIHLYTIDIDLDLSPGNSYVAFLICHQAERENIPIVINVTRWRTSS<br>DIALNRARADAKRLHVSSFISIHTESRNAVCIGLNFNLNIDPFSIDTVEF<br>LENRFPLVQRLFECLEDEGIRENIRDFLLQHLPNEIPRNAENYNRIFDCI<br>TGFAFGNSILEEFRLVNAVQQRVRKYIFRYGDENHALTMVFHTQGSDI<br>VILHIRDNNAVQQGAINLQDLNVDGNNVHVREVSCTLNNQLGLNIHT<br>DNLGLYHNYQNNNANNFLGGNLVQVPNAGNVHNALNQVMNDGWQ<br>DRFQHQELFRNISAVLMPEDTHGNMIIDVNSKDKFRSILHGTFYASDN<br>PYKVLAMYKVGQTYSLKRWQEEEGERVILTRVTEQRLGLLLLRQPTA<br>DTHPIGYVLGFADNAEEVEQEQDEARYKITELMSKQRGYLPITSGNEV<br>VLSYAVFNRGAQRAEDFISLPQQAVYVHRLDRRGHDSRPEVLVGPES<br>VIDENPPENLLSDQTRENFRRFYMEKRPGQNSIFLLDIDDNLHVPFSYL<br>QGTRAQAIETLRSRIRGGGTSTAQGILQQINTILRRNNAREIEDVHNLL<br>ALDFATENQNFRYWLQTHDMFFAARQYTFHDDRSNPTNDRHDFAIT<br>SVGVDGNQNDPTGRDLLSSNIDNFKQKVDSGEKDRLTAIINVGNRHW<br>VTLVIVHQNGNYYGYYADSLGPDSRIDNNIRGALRECDISDDNVHDV<br>SVHQQTDGHNCGIWAYENARDINQAIDQALQGNSNFGEKGEGIIGYI<br>RGLLSAGIGNDTRQPQRNEQYFRNRRRNISQLFQNDSLSSPRGRLIQG<br>RPGIQHEIDPLLLQFLELQYPQRGGGGALQLGGERVISIDFGPQSVLDE<br>IDGVNRVYDHSNGRGSR (SEQ ID NO: 4) |
| cidA | WP0282 | nucleotide | 1476 bp | ATGCCAACACAGAAAGAGCTTCGGGATACGATGTCCAAAAAATTA<br>CAGGAAGCTATTAAACATCCAGATCCAGCAGTTGTTGCCGGGAGG<br>AAGTCAGCTATCAAGAGATGGGTGGGAGTCCTTCAAGATAACTTT<br>ATGGAGCACATAAAATACTTTAAGGGTGATAAGTTGAAGTTTTTG<br>CACAATGTATTTCAAGATGAAGGTTGCTGGTCAGGTGTAAGGTTG<br>GATAATGCTGCTTTAGGTCAAAGGTTTACTGAAGAAAAATAGGT<br>GGAATAGATAATCCACTTGCAAATATGAGATGGCTTGTAGTTACT<br>GTGTGGTGGATAAAATTCATCCTCTCTTTCAAAAAAGATTTGAATC<br>TTATAGGAACAAGTTTCCTCCTGGTGCATTTGATGGTAAAACTGAA<br>ACTGAATTTGGCAAATACGTACGAAACTCGTTACTAGATAGCATA<br>AAGAGGGAAGGTCCTGTATTTGATTTCTGGATTGATAGAGAATCT<br>GGGGAATTAAAGAAGTATGATGCAGTAGAAGGTTTTGACAGTGCT<br>GTAAAATTTAAGTGGAGTGAAGGGGTAGAGTATTTTTATAATCATT<br>TAAAAGAAGAAGATAAGGAAAAGAAGCTCACAGAAGCTATTCTT<br>GCTCTTTCTCGCGTTCAATCTGTTGAGAAAGACGCCCCTATTTTAG<br>ATTTTTGTGTAAATAAGATAGTCGATAAAGATACTCTTTTACAGAA<br>ATTATCACAGAAAGATAAGGAGTATATTCCCTTTTTGCTGAATTA<br>ATAGAGTCATGTTTTTTTGATACGGTTCATGATTTGGTACAGTGCT |

TABLE 6-continued

Sequences of CI Factors

| Gene | Locus tag | Seq. type | Length | (5'-3') or (N-C) |
|------|-----------|-----------|--------|------------------|
| | | | | GGTGTTATAAAGAAGTTTCAGCAGGAGGAGACCATTCAGAGAAAA<br>TATTCTCACAGCGAGACTATGAGCTTTTTCTTTCCTCTCTTTCAGAC<br>ACAATGTTGAAAAATCCTGAGTTAAGCGTTCAAGCTAGATCTCTTA<br>TTATGGAATTTTGGGAATGTGGTAGCTTGTATCAATACAGAAAAG<br>CTGCTGTTAATACTTCTAATTATACAGTTCCTACAAGTGGTGTATTT<br>GCAGAGTTAATAGTCAATTGGAGACGAGAAGACATTTATAAGACT<br>GATGAAGAAAAGAAATAGAGAAAAAAGAAATATTAGATATGAT<br>GTCATTTGCCAAAGATTGCTTTCCTGAAAAGTTTGAGCTCTTTAAA<br>AAACTAATAATAAGAGACCTTAGATTATGCGGTAGGGAAGGTAAA<br>AGAGTAAATGTAGATTACGGTCTGTTTGCAGAAGAATTATTCTCTG<br>AGTTAGAGAAAACAATTTTACCACCTGGTCCTGTAGGTGATGGTCC<br>TTGCAGTAATTTGCGATCACGATCTAAAGCTCATGGTAGTAAGAA<br>AACAACTTTGCCAGTTGATGATAGTCCGCAGTCTGAGCTTGGAACT<br>CCTAGTGTAAGTGGTGTTTCTTCTTATAAGAAAAAAAGCGTCTTTA<br>CGCTTAGTGGTAATAAGTAA (SEQ ID NO: 5) |
| cidA | WP0282 | amino acid | 491 aa | MPTQKELRDTMSKKLQEAIKHPDPAVVAGRKSAIKRWVGVLQDNFM<br>EHIKYFKGDKLKFLHNVFQDEGCWSGVRLDNAALGQRFTEEKIGGID<br>NPLRKYEMACSYCVVDKIHPLFQKRFESYRNKFPPGAFDGKTETEFG<br>KYVRNSLLDSIKRKGPVFDFWIDRESGELKKYDAVEGFDSAVKFKWS<br>EGVEYFYNHLKEEDKEKKLTEAILALSRVQSVEKDAPILDFCVNKIVD<br>KDTLLQKLSQKDKGVYSLFAELIESCFFDTVHDLVQCWCYKEVSAGG<br>DHSEKIFSQRDYELFLSSLSDTMLKNPELSVQARSLIMEFWECGSLYQ<br>YRKAAVNTSNYTVPTSGVFAELIVNWRREDIYKTDEEKEIEKKEILDM<br>MSFAKDCFPEKFELFKKLIIRDLRLCGREGKRVNVDYGLFAEELFSEL<br>EKTILPPGPVGDGPCSNLRSRSKAHGSKKTTLPVDDSPQSELGTPSVSG<br>VSSYKKKSVFTLSGNK (SEQ ID NO: 6) |
| cidB | WP0283 | nucleotide | 3525 bp | ATGAGTAATGGTGATGGACTTATTAGGAGTTTGGTGGATGGAGAT<br>CTTGAAGGATTCAGACAAGGATTTGAATCTTTTTTAGATCAATGTC<br>CATCTTTCTTGTATCATGTAAGTGCAGGTCGTTTCCTTCCTGTATTC<br>TTTTTTAGTATGTTTTCTACTGCACATGATGCTAATATCTTAAATGC<br>AAATGAGAGAGTCTATTTTCGTTTTGATAACCATGGTGTTAATCCA<br>CGTAATGGTGAAAATCGAAATACGGCAAACCTAAAAGTTGCTGTT<br>TATCGTGACGGACAGCAAGTTGTCAGATGCTACAGTATTTCTGATC<br>GTCCTAATAGTGATGGGTTGAGGTTCAGTACAAGGGAGAGAAATG<br>CTCTAGTACAAGAGATTAGACGGCAAAATCCAAATTTAAGGGAAG<br>AAGACCTAAATTTTGAGCAATACAAAGTATGCATGCACGGAAAGG<br>GCAAGAGTCAGGGAGAGGCAATTGCAACGGTATTCGAGGTAATTC<br>GTGAAAAGATCGTCAAGGTAGGGATAAATTTGCCAAATATTCAG<br>CATCTGAGGTTCATTTCTTGAGGCAACTCTTTAGAAATCACAGATT<br>AACAATTAAGGAAATAGAAGGAAGACAACTCAATCAAAATCAGC<br>TCAGACAACTTGGTAGGTCAGTCAATTTTACACGAGTAGAACCAG<br>GTCAGCAGAGGATTGACAACTTTATGGAAATGCTAGCAAGTAACC<br>AAAGACAAGATGTAAGGGATTCTCTCCGAGGAGATATTTTAGAAT<br>ATGTAACTGATACCTATAACAATTATAGGGCACAGATAGAAAATA<br>ATATTGAAGGTCGCAGTCAAAAGTTTGAGAGTCATGGGTTTTTATT<br>AGGTTTCTTAGCAAATTTTAGTCATCGCTACACAATAGGCGTCGAT<br>CTTGACTTATCTCCTAGAAACTCACATGTTGCATTTCTTGTACGTCA<br>TCAAGTAGAAAGAGAAAATATTCCTATTGTTATTAATCTTGCTACA<br>AGGGCACCGCCCTATATCGCATTAAACCGCGCCAGAAGTCACGCT<br>GAAAGATTGCATGTTTTTTCATTTATACCTATCCATACTGAATCAA<br>GAAATACTGTCTGTGTTGGATTAAATTTTAATTTAAATCTAGATCC<br>TTTTAGTGTTGATACAGTAGGGCTTCAACAGGATAGATTTCCTTTA<br>GTACAAAGATTATTTGAGTGTTTGGAGAATGAAGGAATTAGAGAA<br>AATATTAGAGATTTCTTGCTTCACCATCTTCCTGCTGAAATACCAA<br>GAAATGCAGAGAATTATGATAGAATATTTGATTGCATAACTGGTTT<br>TGCTTTTGGGAATAGTGCTTTTGATAGGCACCCTTTAGAACTAGAA<br>GAGGAAGACGAAGCACCTATAACAAAGTACATATTTAGACATGGT<br>GATGAGGGTTTAAGATGTTTAACTATGGTCTTTCATGCTGAAGGTT<br>CTGATATAGTTATACTTCATATTAGAGCTCACGATGCGCAACAACA<br>AGGAGCCATCAATTTACAGACTCTTAATGTTAATGGAAATGATGTT<br>CATGTGTGGGAAGTTTCATGCACACTTAATAATCAACTTGAACTAG<br>ATATTGATCTACCAAATGACCTTGGTTTATATCACGATTACCAAAA<br>TAATAATGCAAATAATTTTCTTGCTGGTGATCTTGTACAAGTGCCC<br>AATACTGAAAATGTACATAATACTTTAAATCAAGTTGTGAATGAT<br>GGCTGGAAAAATATAGCTCAGCATAGAGGATTATTTCAAGAGATC<br>TCTGGAGCATTGATGCCGCTTGTGGATACAATAAATGTTAATAGTG<br>AGGATAAGTTCCGTTCTATACTACATGGTACATTTTATGCTAGTGA<br>TAATCCTTATAAAGTCTTGCTATGTATAAAGTTGGTCAACATAT<br>AGTTTAAAAAGGGGCAGGAAGAAGAAGGAGAAAGGGTAATACT<br>CACAAGAATTACAGAACAGAGATTAGATCTTTTATTATTAAGACA<br>ACCTAGAGAGAATGACCTAGATACTCACCCAATTGGATATGTGTT<br>AAGACTTGCTAATAATGCAGAAGAAGTAGGACAACAGCAAAATG<br>ATGCGAGACAAGAAATCGGAAGACTTAAGAAACAACACAGAGGA |

TABLE 6-continued

Sequences of CI Factors

| Gene | Locus tag | Seq. type | Length | (5'-3') or (N-C) |
|---|---|---|---|---|
| | | | | TTTATACCTATTACTTCTGGAAATGAGGTGGTTTTGTTTCCTATTGT<br>GTTTAATAGAGATGCACACGAAGCAGGTAATCTTATACTTTTCCCA<br>GAAGGGATAGGAAGAGAAGAGCATGTACACAGGCTTGATCGTCAT<br>GTTCGCAGCTCAAGACCAGGAGGATTAGTGGGACCTGAAAGTGTT<br>ATTGATGAAAATCCACCAGAAGGTCTATTATCAGATCAGACTCGT<br>GAAAACTTTAGGCGTTTTTACGAAGAAAAAGCACCAGGACAAAAT<br>TCGATTTTTTGCTTGATATAGGCGACAATCTACATGTTCCCTTTAG<br>TTACTTGCAAGGTACTAGAGCACAGGTAATAGAAACATTAAAGTC<br>AAGAATAAGGGGAGGTGGTACTCCTACAGCACAAGGAATATTACA<br>ACAAATAAATGCTATCCTTCGTAGAAACAACGCTCGTGAGATAGA<br>AGATGTGCATGATCTACTTGCACTAGACTTTGCAACAGATAATCAA<br>AATTATCGTTATTGGCTACAAACTCATGACATGTTTTTCGCTGCAC<br>GACAATATACTTTCCTTGATAATCAATCTCATTCAACTAATGATCA<br>TTATGGTTTTGAAATAACTTCAGTAGGAGTCGATGGAAATCAAAA<br>TGATCCAACAGGTAGGGGCTTATTAAGTAGTCACATAACTAACTTT<br>AAACAAAAAGTAGATTCGGGTGAAAAAGATAGATTAATTGCTATT<br>ATTAATGTAGGTAATCGTCATTGGGTTACATTAGTTATTGTACACC<br>AAAATGGAAATTATTATGGGTATTATGCTGATTCACTTGGTCCAGA<br>TAGTGGTATTGACAATAATATTCGAGGAGCTTTAAGAGAATGTGA<br>TATTAACGATGATAATGTCCATAATATTTCCGTTCATCAGCAAACA<br>GATGGCCATAATTGTGGCATATGGGTATACGAAAATGCTAGGGAT<br>ATTAACCAAGCTATTGATCAAGCTTTACAGGGAAATAATAACTTTG<br>GAGAGAAAGGTGAAGGTATTATAGGTTATATACGTGGTCTTCTTA<br>GTGCAGGCATTGGAAATGACACTAGACAACCTCGAAGAAATGAAC<br>AATACTTTGAAGATCGGAGAAGAGATATTTCACAATTACTCCAAA<br>ATGATCCTAACTTACCTTCTCGCCGGAGTGATTTAATTCAAGCTCA<br>TCCAGGAATTCAACATGAAATTGATCCATTACTATTACAATTTTTA<br>GGACTCCAATACCCACAGCGTGGAGGTGGAGGAGCATTACAATTA<br>GGCGGAGAAAGAGTGATATCAATTGATTTTGGTAACCCGCAGTCT<br>GCATTAGATAAAATTGATGGAGTGAGTAGAGTTTATAACCATAGC<br>AATAGTAGAGGTAGTAGGTAG (SEQ ID NO: 7) |
| cidB | WP0283 | amino acid | 1174 aa | MSNGDGLIRSLVDGDLEGFRQGFESFLDQCPSFLYHVSAGRFLPVFFF<br>SMFSTAHDANILNANERVYFRFDNHGVNPRNGENRNTANLKVAVYR<br>DGQQVVRCYSISDRPNSDGLRFSTRERNALVQEIRRQNPNLREEDLNF<br>EQYKVCMHGKGKSQGEAIATVFEVIREKDRQGRDKFAKYSASEVHF<br>LRQLFRNHRLTIKEIEGRQLNQNQLRQLGRSVNFTRVEPGQQRIDNFM<br>EMLASNQRQDVRDSLRGDILEYVTDTYNNYRAQIENNIEGRSQKFES<br>HGFLLGFLANFSHRYTIGVDLDLSPRNSHVAFLVRHQVERENIPIVINL<br>ATRAPPYIALNRARSHAERLHVFSFIPIHTESRNTVCVGLNFNLNLDPF<br>SVDTVGLQQDRFPLVQRLFECLENEGIRENIRDFLLHHLPAEIPRNAEN<br>YDRIFDCITGFAFGNSAFDRHPLELEEEDEAPITKYIFRHGDEGLRCLT<br>MVFHAEGSDIVILHIRAHDAQQQGAINLQTLNVNGNDVHVWEVSCTL<br>NNQLELDIDLPNDLGLYHDYQNNNANNFLAGDLVQVPNTENVHNTL<br>NQVVNDGWKNIAQHRGLFQEISGALMPLVDTINVNSEDKFRSILHGT<br>FYASDNPYKVLAMYKVGQTYSLKRGQEEEGERVILTRITEQRLDLLL<br>LRQPRENDLDTHPIGYVLRLANNAEEVGQQQNDARQEIGRLKKQHR<br>GFIPITSGNEVVLFPIVFNRDAHEAGNLILFPEGIGREEHVHRLDRHVRS<br>SRPGGLVGPESVIDENPPEGLLSDQTRENFRRFYEEKAPGQNSIFLLDI<br>GDNLHVPFSYLQGTRAQVIETLKSRIRGGGTPTAQGILQQINAILRRNN<br>AREIEDVHDLLALDFATDNQNYRYWLQTHDMFFAARQYEFLDNQSH<br>STNDHYGEEITSVGVDGNQNDPTGRGLLSSHITNFKQKVDSGEKDRLI<br>AIINVGNRHWVTLVIVHQNGNYYGYYADSLGPDSGIDNNIRGALREC<br>DINDDNVHNISVHQQTDGHNCGIWVYENARDINQAIDQALQGNNNF<br>GEKGEGIIGYIRGLLSAGIGNDTRQPRRNEQYFEDRRRDISQLLQNDPN<br>LPSRRSDLIQAHPGIQHEIDPLLLQFLGLQYPQRGGGGALQLGGERVIS<br>IDFGNPQSALDKIDGVSRVYNHSNSRGSR (SEQ ID NO: 8) |
| cixA | wRi_06720 | nucleotide | 1371 bp | ATGCCAAAAAGATGGAGCGTCATGCTGCAGTGCTTAGTAAGTTA<br>AAGAGTGTTATTCAACATACAGATTCCAAGGTCATGGCTGAAAGG<br>CGTTCAGCTATTGAAAGATGGGTAAAAACTTACATTAGGCAGGTA<br>GAATATCTTAAAGATGATAAGCTACAATTCTTATACAACATATTTC<br>GCGATGAAAGTTGTTGGTCAGGTACGAGATTGAACAATACAATCT<br>TAGGACAGAGGTTACTGAAGAAAAAATAGGCGAAATAAAGAAC<br>CCTCTTCCTATATATGATATGGCATGTCGATACTGCGTGATAGATA<br>AAATTCCTTTGCTCTTTCAGAAGCAGTTTGAATCTTACAAAAGTAG<br>CTTCTCTTCTGAAGAGATAGATGATGATGGTAAGCCTGCAACTAGC<br>AATAACAAATATGTAAAGAGTGAGTTGTTGGGTTATATGAAGAGT<br>CAAGACCCTGTATTTAGCTTTTGGGTTGATAAAAAATCTGGAGAAT<br>TTAAGAAGCATGTCAGCGCAACAGAAGGATTTAAGAAAGCTATAG<br>AACTTAAGTGGAGCGAAGGAGTAGAAATATTTTTATAGCCTTCTAA<br>ATGAAAAGAAAGAGAAAGAGAAAGGAAAATTACTGATGCAGTT<br>ACTATATTATCCTCTGTTCAATGTGACCATAATGGTGCTGTTACTTT<br>AGACTTTTGTCTTAGTAAAATGAGCGATCAAGCAAAAAACAAGCT<br>GTTTAAAGATTCTGAGCTATCAAAAAAAGATAAGGAGTGTACTC |

TABLE 6-continued

Sequences of CI Factors

| Gene | Locus tag | Seq. type | Length | (5'-3') or (N-C) |
|---|---|---|---|---|
| | | | | TCTCTTTAGCGCGTTGATACATCAAGGTTTTTTTGATACGATGCAA<br>GCTATACTTCCGATGTTTAAAGATAAAATACTGGAGGATAAGATA<br>CTTTCACCTAGGAGTTATACTCTTCTTCTCTCCTCACTTTCGGACAT<br>GATGCTCGAAAATTCTGAGTCAACTATTCAAGCTAGGGAAGCTAT<br>AATGAACCTTATAAAGTGTGGTAATTTCAATAATCATGAGGGGCG<br>TGAGGAAAAAGCTGCGGTATTTTTTTCTAATGGAAGGGTTCCGATT<br>AAGCGTGCGCTTGCAGGATTGATTGTCGATTGGCAACTTGGTTGTA<br>CAAAAAAGGAAGAGGTGTTAAAGGTACTACAGTTTGCCAAAGAGT<br>TTTGTGCAGTTGAAAGTTTTATGTATTTTAAAAAATCTGTTGTTGAT<br>AACCTAAAAATGGTTGGTAGGGATGGTATGAGAAAAATATAGAC<br>TATGGTAAATTAGCAGAAAAGTTGTTTGCTGAATTAGATACGGTAT<br>CCGTGCCTAACGGAAGAGGTGATTTTGGTGGAGCTGGTGACCCAC<br>AGTCTACACTAGGAAGCACTGAAGTTAGTAGTTTTTCTGGTCGCAA<br>TAAGTAG (SEQ ID NO: 9) |
| cixA | wRi_06720 | amino acid | 456 aa | MPKKMERHAAVLSKLKSVIQHTDSKVMAERRSAIERWVKTYIRQVE<br>YLKDDKLQFLYNIFRDESCWSGTRLNNTILGQRFTEEKIGEIKNPLPIY<br>DMACRYCVIDKIPLLFQKQEESYKSSFSSEEIDDDGKPATSNNKYVKS<br>ELLGYMKSQDPVFSFWVDKKSGEFKKHVSATEGFKKAIELKWSEGV<br>EYFYSLLNEKERERERKITDAVTILSSVQCDHNGAVTLDFCLSKMSDQ<br>AKNKLFKDSELSKKDKGVYSLFSALIHQGFFDTMQAILPMFKDKILED<br>KILSPRSYTLLLSSLSDMMLENSESTIQAREAIMNLIKCGNFNNHEGRE<br>EKAAVFFSNGRVPIKRALAGLIVDWQLGCTKKEEVLKVLQFAKEFCA<br>VESFMYFKKSVVDNLKMVGRDGMRKNIDYGKLAEKLFAELDTVSVP<br>NGRGDFGGAGDPQSTLGSTEVSSFSGRNK (SEQ ID NO: 10) |
| cixB | wRi_06710 | nucleotide | 2265 bp | ATGCATGGGTTAGTTAGAAGTTTAATAAATGGAAATTGTGGAGAA<br>TTCACGGAAAAGTTTGAATATTTCTTGGATTCATGTCCATCTTTTCT<br>GCATTCAGTTGGCAAAGATCACTTTTTTCCTGCGTTCTTTTTTGGCA<br>TGTTTGCTACTGCACATGATTCTGGTGTTGCAAACAATGATGAAAG<br>AATCTTCTTTCGTTTTGATAATGATCCAGGTAGTCCTGGAAGGGGA<br>AATCTAAAGGTTGCAATTCTAACAACTGATGGAAATAACAGAAGA<br>GTTGTAAGGTGCTATACTATTGCTGACAGAGAGAATAGCTACGGT<br>TCTAGGTTTAGCCAGCAGGAAAGGGAGCAGCTGGAAGGTATCCTG<br>CGAGATGAAGAGCTTGAATGGCAAGAGTATAAAACATTTATATGG<br>GCGGATAATCAAGGTGAAGATGAAGAAGAGGAAGCAGTAAGATG<br>TAGGATATTTCAGGCAGGACAAGGGCCGTTTACTGGAAATCATGC<br>ATCTTATTTAACTCGTAGACATAGTTTTCAAGAGATTACCAGAACA<br>CCTGGGCTGCAAAATAATTATTTACCGGATTTGATGAATCAGCTAG<br>AAAGTGATGATGCAGATGATGTACACGACACTACTGAGGAAGTGT<br>TTCAGCATATTATTGGTGTCTACGATAGATATAGTCAGGCATTGGA<br>CTTCTATGGTAGAGAGTCTGACTATCATGGTTTTGTTTCCGGTGTTT<br>TGATGCATTTTAGATATCGCAATGTAGCCAATATTTACCTTGAGCT<br>GTTTGTAGGTGGTGGATATGCAGATATTACTTCTATTGTACGTGGT<br>ACACAGAGGTTAATTAATTCTGTTCCCTGTGTAACTGAACTTAAGG<br>CAGGCAGAAGAGCAGATAGGAATGCTGGCCGTGCATTAGAGCAG<br>GCTGGAAATTATGTTAATGGATGTCCCGTTTCATCCATATCTATTC<br>CAACATTATCACCAAGAGCTGTCTCCGCTGGAGTGAATTTCGATTT<br>TGGTAACCCAGGACGTTTACAGCTTGGTGTGAGGGCTTTTTTAGCA<br>AAAGGTTCTTCTTTAATGGAAAGATTATTTGAACCTGTAGAGGATG<br>AGGAGATTGGAGAAAATGTTAGGGATTATCTACTCCATCCAGCCT<br>TTGGTGTACCTGCTGTACCAGGTATTAGGAATAGGGGTGGTGTTAA<br>CGCTAGAGATAGAAGAATATTTCTCTATACAAGTGGATTTGCTTTC<br>GCAAGTATTGCATTTGCAAAAGGAACTGTGCCAATAGAAGGAAAT<br>CGTGCAATAGTAGATAAGCACTTGTTTCACTATGACGGTAATGCA<br>AAAATGTTAGATGAGCAAAGATACAATACACAAGTAAATATTGGA<br>GATCGTGCTTTGACTATGGTTTTGCATGTATCACGAGGTAGAGACC<br>AGAAGGAGGAGGTGATCGTATTTCATGTTCGCCACGTATTGGCTA<br>ATCAACTTTTTCCGGACAATGGATTGGATCTATCGCGTTGGCCGAA<br>TGCTATGGTACATGAAGTGGTGTGTAATTTGACCATAAATAGAAG<br>GACAAGAGGAGTAAATGATAATCTTGGTTTAACTGTTAATGTAGA<br>AACATTTGACTCGCCTGCTGACTACCTGCTTGATAGAGGTAATCAG<br>CCTTTTCAAGGTGAGCTTTTACGAATAGGTGGCGTTAGTAATGTGC<br>ATCGCGCTGCAAATGTAATGATGAATACTGGCTGGGAAAATGAAG<br>ATCCAGACAGTCATGAACGGTTTTACCAAGCAATTTCCAACGTGCT<br>AAATCCACCCCAGCCAAATAATGCAGGACTCCAATCATTAGCATG<br>GGTAGTGAACAGAGATAATGCTAGAGAAGCTGGGTTTCATGCTGC<br>ATTGCATGGATTATTTTACACTTGCGATAATCCTGCTAGGGTAGTT<br>AGTGAATTTCAGGTTGGAGGAGGAGGAAAGTTAGACTTAGTATTG<br>TCACGAGCTATAGGAAGGATGGGAGGTACTTATCCGATTGGAACA<br>GAGCTAAAGTTTGCTGCCACTGAAGCAGACGTACAAAATAGAGAA TABLE 6-continued Sequences of CI Factors

| Gene | Locus tag | Seq. type | Length | (5'-3') or (N-C) |
|------|-----------|-----------|--------|------------------|
| | | | | GAAGAAGCAGATGAACAGGTGGAGGGTTATCTGCAGAGTAGAGG<br>GTTTGATCGCATTACTGATGGAGATAAAATGGTTTTCTCGTATGCC<br>GTATTTAATGATCAAGCGCCAGCACCAGCACAAAATGTCCCAAAT<br>ACCCTTATAGCAGTTAGTAATGTTCTACGCATAAAAGATAACTTAG<br>GAATTGACACTGTGGACGACTTTCCTTATAGATAA (SEQ ID NO: 11) |
| cixB | wRi_06710 | amino acid | 754 aa | MHGLVRSLINGNCGEFTEKFEYFLDSCPSFLHSVGKDHFFPAFFFGMF<br>ATAHDSGVANNDERIFFRFDNDPGSPGRGNLKVAILTTDGNNRRVVR<br>CYTIADRENSYGSRFSQQEREQLEGILRDEELEWQEYKTFIWADNQGE<br>DEEEEAVRCRIFQAGQGPFTGNHASYLTRRHSFQEITRTPGLQNNYLP<br>DLMNQLESDDADDVHDTTEEVFQHIIGVYDRYSQALDFYGRESDYH<br>GFVSGVLMHFRYRNVANIYLELFVGGGYADITSIVRGTQRLINSVPCV<br>TELKAGRRADRNAGRALEQAGNYVNGCPVSSISIPTLSPRAVSAGVNF<br>DFGNPGRLQLGVRAFLAKGSSLMERLFEPVEDEEIGENVRDYLLHPAF<br>GVPAVPGIRNRGGVNARDRRIFLYTSGFAFASIAFAKGTVPIEGNRAIV<br>DKHLFHYDGNAKMLDEQRYNTQVNIGDRALTMVLHVSRGRDQKEE<br>VIVFHVRHVLANQLFPDNGLDLSRWPNAMVHEVVCNLTINRRTRGV<br>NDNLGLTVNVEITDSPADYLLDRGNQPFQGELLRIGGVSNVHRAANV<br>MMNTGWENEDPDSHERFYQAISNVLNPPQPNNAGLQSLAWVVNRD<br>NAREAGFHAALHGLFYTCDNPARVVSEFQVGGGGKLDLVLSRAIGR<br>MGGTYPIGTELKFAATEADVQNREEEADEQVEGYLQSRGFDRITDGD<br>KMVFSYAVFNDQAPAPAQNVPNTLIAVSNVLRIKDNLGIDTVDDFPY<br>R (SEQ ID NO: 12) |
| cinA | wNo_01990 | nucleotide | 1473 bp | ATGCCAAAAGTAAAACTAAACGTGGAACGGAAGATTTGAAGGG<br>TAATGCAGGCCCAAGCAAAAGATCTCGTCTCAGTTCTGATCCTAA<br>AAAAAATAAAGAGATTATCTCTAGCAAAGTAATAAGTAAGCTGAA<br>GGATGTTGTTAAAGGTGATAGAACTTCAGCTATTGAGGAATGGGT<br>CAAGGCTCACCCTGTCACAGTAGAGGGTCTAATCGTTGAGCAATC<br>GGACCTCTTATGTAATGCGTTTCGTGATGAATCTTGTTGGTCAGGT<br>GCGACACTAGATGTTGCTAAATTGGTAGGAGAATTAGCTAAATCA<br>GGTGTGTTGAATCCATTTGCTATATATAAAATAGCATGTATTGAGT<br>GTGTAGAGAGTGAAATTAAGCAATTATTTGACAAGGCGTTAGAGT<br>CTTTTAGATCTGACTTATCTCATAAAGGTGCATGTGAGGAAGATAG<br>GAATTTAGCTTGCAGTGATAAGCTTGCAAGAGTTGAATTGTTAAGT<br>TCCATGGGAAGACGTGATCCTGTTTTCAATTTCTGGATTGATCAAG<br>AATCAGGTAACCTTAGAGAAAATATAGAAGCAGAAGATGGATTTA<br>ATAAGGCTGTAGATTTCAAGTGGAGTAAGGGAGTGGAACACTTCT<br>ATAATCGTCTGTGTTCTGAAGAAAAATTAGTGAAAGAAGAGAGAG<br>AAAAATTGCTAGTTTCTGCTATTGCAAAATTATCTCCATTGCAATC<br>TAGCTATAAACTTGCTTCTACCTTAAATTCCCTTCTAGGTAAAGTC<br>ATAAGCGCAAAAGTAGATCATAAGTCACTACTTGGGCTACCGAAT<br>AAGAGAGATAGGGGTGTGATCTATCGTCCTCTTAGTTACTTAGTAG<br>AGCACGGTTTTCTTTGCACAACTAAGTATGTTATCCAGTACTTGAG<br>CGAGGGATGTTCAAGATCTGAAGTAGAGAAAATGCTTTCACCTAG<br>AGGATATGCACATCTTCTCTCATCGCTTTCATTTGTTGTAGTTTCTA<br>AAGATTATGACTTGGATAACAGGAATGAAGCAAGGTCAGCTATTA<br>GCAGTCTTTGGGAATCTAGTGTATTTAACCAAAATAAAATAAATGT<br>TGTCGATCCTTTTAAAGATAGGATTGCTTTTGTTGCAATGGAAAAT<br>GCAATTTCAAATTTGATTGTAGATCAGGAGAACAGTAAGGATACT<br>CAAAGTGCTGGCGATGGTGAAAAAGTTGATTTGGTCTTGAGTATTT<br>TAAAGTTTGCTAAAGATTGTTGTTCAGACAAAAGCTTTAAATCATT<br>AAAAGCGAGGATAGCAAATAGTTTAGATAAAACAAGGAATTCTAA<br>GATGATAGATGCAACTAGCTCCTGCAATTTAATAGAAGAGTTGTG<br>TAAGTCAGCGAGAAATTTGAATTATTCTCTGCTAGCACTGAAGGT<br>CCTCAATCTACGTTAGTGGGTACTAATGTTAGTATTTCGCCTGCTG<br>CAGTTGTTAACAAATAG (SEQ ID NO: 13) |
| cinA | wNo_01990 | amino acid | 490 aa | MPKSKTKRGTEDLKGNAGPSKRSRLSSDPKKNKEIISSKVISKLKDVV<br>KGDRTSAIEEWVKAHPVTVEGLIVEQSDLLCNAFRDESCWSGATLDV<br>AKLVGELAKSGVLNPFAIYKIACIECVESEIKQLFDKALESFRSDLSHK<br>GACEEDRNLACSDKLARVELLSSMGRRDPVFNFWIDQESGNLRENIE<br>AEDGFNKAVDFKWSKGVEHFYNRLCSEEKLVKEEREKLLVSAIAKLS<br>PLQSSYKLASTLNSLLGKVISAKVDHKSLLGLPNKRDRGVIYRPLSYL<br>VEHGFLCTTKYVIQYLSEGCSRSEVEKMLSPRGYAHLLSSLSFVVVSK<br>DYDLDNRNEARSAISSLWESSVFNQNKINVVDPFKDRIAPVAMENAIS<br>NLIVDQENSKDTQSAGDEKVDLVLSILKFAKDCCSDKSFKSLKARIA<br>NSLDKTRNSKMIDATSSCNLIEELCKSARNLNLFSASTEGPQSTLVGT<br>NVSISPAAVVNK (SEQ ID NO: 14) |
| cinB | wNo_01980 | nucleotide | 2091 bp | ATGCATGGTAATAATGAAGATCGTGAATTAGTTAGGGCTTTATTAA<br>GTGGAGGTTGTGATGAGTTTAGTAGACAATTTGTAGGTTTTTTAAA<br>CAACTGTCCATCTTTTTGCATTCGGCTAATAAGCCTGGCTTTTTC<br>CTACATTCTTTTTTGGTATGTTTTCTACTGCACATGATGCAGGTATA<br>TTAGTTGAAGGTGAAAGAGTCTATTTTCGTTTTGACAATTATGGAA |

TABLE 6-continued

Sequences of CI Factors

| Gene | Locus tag | Seq. type | Length | (5'-3') or (N-C) |
|---|---|---|---|---|
| | | | | ATCTAAAAGTTGCTGTTCTCACTAATAAAGAAAATAGAAGAATAG
TCAGGTGTTATACTGTTGCTGATAATGAGAACAGCCCTGGGTCAA
GGTTTAGTGCAGAAGAGAAGCAGCAGGTAGAAGAGAATCTTCCAC
AAGAATTACAGGAAGATGAGGATCTGGATTGGGAAGAGTATAAA
ATATTTCGGTTTGGAGAAGAATGTAGGTTTATTCATGAAATAGATA
GATTTCCTCAACGTGATGAACCTGGAGCTCCAATTTTTCATGAAAT
TAACCCAATCAGAGAACAAGGTGAATTGTTAGACCTGATGAGTGA
GTTGGCAAATGACGATACAGGAGAAGTGCGTACTAATGTTAAAAG
AATTTTGGAATATGTTATTGATATCCATGATGAACATGAAGATAGC
TTAGTGTTTCGTGCAGAGTCTGACTACCACGGTTTTCTGTGTGGGT
TTTTAGTAAATTTTAGATACCGAGCTTTGGCTGATTTCTACCCAGA
GCTACTTATAGGAAAAGGTTATGCAGATGTTGTTTTGCTTGTTCGT
GGTGTTGATCAGACAAATGATTCGGTTCCAATTATAATTGAGTTGA
AGGTTGGTGATGAGGAAGGATTAGAGCAAGCTAAAGATTATGCTA
AAAGTTGTTCTGTTTCGTCTTTGCCTATTCATACCTCATCACCAAGT
GCTGTTTGTGTAGCGTTAAATTTTCAATTACGTGGAGGTGCTGGTC
TCCGAACTTCTGTGCAGGCCTTTTCAGAAGGTGGTCTTTCCTTAAT
ACCGGGTTTACTACATCCTCATGGAAATGGAGTTAGGGGAAATGT
AAAACGTTTTTTACAACCCATAGCATCAGAGTTCACTCAATCGCCT
CATTGTAACACTTTTTCCTGTACTTCATCGTTTGTTTTTGGAAATGT
TTTATCTACAAGGAGGGACTTAGAAACAAATGATGGGCGGGAGGT
AAGGGTTACCAAGTATCTATTTAACCACTCTCAGGGAGAGAAAAT
GAAACGTACAGGTGGTAGAGGAGATGCAGCAGATATTGTAAGCCA
TGCGTTAACTTTAGCTCTATTTTTATCAAATATTGGTTTTGTTGTGC
TTCACATTTTTCGTCGTTTAAAGTGGCAGACTTTACCAGACAAGGC
ATTGAACCTGTCGTTACTGCCTCAAGCCACAGATGATGCTAAGGTG
CGTCAAGTACTTTGTGAAGTAGATGTCCAGGGTCATCTGGAAGTG
GCTTCTGCAAAGAAATTCGAATCACTACGTGCTTACTCACGTTCTC
ATAGTGAAGGTTATTTCGAGGGAAGGTTTTCAGAACAAATGGGTA
ATGTTAGGAATTTACATCAACTTGCAGATCAGTTGATGAGTGCTGA
GCCTAATTTTGGTAATGATGGTAATGTTAATGGTGAGTACAGGGCT
AGGTATGAAGTTTTATTTAATGAGATTTCTCGTCTGTTGTCTCCGTT
ATTAAATGGAAACCGTCTACTCGTGAACAATGAAGCTAAATTTCA
GGCTTTGTTGCGTGGAATATTTCAAAATTGCGATAATCCTGCCAAG
GTAATTATTGAGTTCCAGCTACAGAGAGGAAGGAAAATAGACCTA
GTATTATCAAAATCTGCGGAAAATGATGATACTCATCCAATTGGA
ATAGAGTTGAAGTATGCTAACACCGCAGAACAAGTTGAACGAAAA
AGGGTGGAGGCAAATCGACAGTTAAGTGAATACGAATTTTGTGGA
GGATGCAAGCGTATTACTGGGGGAGATGCGATGGTTTTGTTATAC
GCTATATTAAATGCTGTAGGACAAGAGCAGGATCTGATATTGATT
GGTGGGCTTCGTAGAGCATCTGGGTTTTCTAGATGA (SEQ ID
NO: 15) |
| cinB | wNo_01980 | amino acid | 696 aa | MHGNNEDRELVRALLSGGCDEFSRQFVGFLNNCPSFLHSANKPGFFP
TFFFGMFSTAHDAGILVEGERVYFRFDNYGNLKVAVLTNKENRIVR
CYTVADNENSPGSRFSAEEKQQVEENLPQELQEDEDLDWEEYKIFRF
GEECRFIHEIDRFPQRDEPGAPIFHEINPIREQGELLDLMSELANDDTGE
VRTNVKRILEYVIDIHDEHEDSLVFRAESDYHGFLCGFLVNFRYRALA
DFYPELLIGKGYADVVLLVRGVDQTNDSVPIIIELKVGDEEGLEQAKD
YAKSCSVSSLPIHTSSPSAVCVALNFQLRGGAGLRTSVQAFSEGGLSLI
PGLLHPHGNGVRGNVKRFLQPIASEFTQSPHCNTFSCTSSFVFGNVLST
RRDLETNDGREVRVTKYLFNHSQGEKMKRTGGRGDAADIVSHALTL
ALFLSNIGFVVLHIFRRLKWQTLPDKALNLSLLPQATDDAKVRQVLCE
VDVQGHLEVASAKKFESLRAYSRSHSEGYFEGRFSEQMGNVRNLHQ
LADQLMSAEPNFGNDGNVNGEYRARYEVLFNEISRLLSPLLNGNRLL
VNNEAKFQALLRGIFQNCDNPAKVIIEFQLQRGRKIDLVLSKSAENDD
THPIGIELKYANTAEQVERKRVEANRQLSEYEFCGGCKRITGGDAMV
LLYAILNAVGQEQDLILIGGLRRASGFSR (SEQ ID NO: 16) |
| CinA<sup>wPip</sup> | wPa_0294 | nucleotide | | ATGGAATCTGGTTTGGATCACAATTACAATAAAATACTTGATATAT
TAAAAGGTGCTATTAAAGGCGACGATAATCAAGTTAAAGCAAGAA
AACACCTTAGAGTAGAAAGATGGTTGAGGGCTTATATTCAATTAA
TTGAAGATTTTGATGAGGAAAACTAATTTTTTTTTCTGATATATT
CTCTGATAATTCTTGTTGGGATGGAATAAAATTAAAGAATAAAGC
TGTTGGTGAAAGGCTAACTGAAGAAAAAAATAAAAATGGAAAAG
AAAATCCGCTTGATCTTGCAGATAGATATTACTTGGCATGTAAATA
TTGTCTAGAAGATAAGATTCCTGGATTATTTGAACAAGTATTTATG
AGATTTAAGAGAAGTGCCTTTGAAGAAGATGGATCTGATGATGAT
CTGAGAAGAGAATTATTGGAAAATATCGAAGAAACTAGCCCTATA
GAAGCTTTCTGGTCTTTTCTTATTGATAAGCAGATTGGAAAACTAA
ACGAATATAAATCAGTTGAAGGTTTGCAAAAATCCATACAGATAA
ATTCTAATAAAAACTGGGAAGAAGGTATAGAGTTCTTCTATAATA
AATTACACAATGATTCCAGTATTTCTAGTCAAGATAAAGATGATCT
GTTAATTGAAGCAGCTTTATCTGCAGTAAAGGGTTACAAAGAAGT
AGACACCATAGAGTTTTGCCTGTCTAAAATGGATGATGAGCAAAA |

TABLE 6-continued

Sequences of CI Factors

| Gene | Locus tag | Seq. type | Length | (5'-3') or (N-C) |
|---|---|---|---|---|
| | | | | GAAAAAATTACTAGATAGAGATTATAAGGAAAATACTTATTATGC<br>AGTGTTGAATGTGCTAGTAGGTCAGTATTACTTTGATTCTTTTATG<br>GAATTAAGCCGATTGTGTAGTCAGATTGAATGTGAACGTTACACA<br>ACTTTTTTATCTTCATTATCAGATCAAGTACTGAAGAATCCAGATC<br>TGTCTGAAGAAACAAAAAAATGTATGATGAATGTTTGGGAACGTA<br>TAATAAAATTAAAAACTCAAGACCGCGGGGAGCAATCTATTTCCT<br>CTATTTTTGTAGACTATTCAGTTACATATACAATAGCAAATTTAAT<br>TGTGGATCCAAGTAGACAAGGGGTAAGTAAAGAAGAAATATTAG<br>GGAAGATATTAAAGCACGTAAAAGAAATGAGTGGTGAAGAGATG<br>ATAAAGGTTAAAGATTCTGTATTAAGTAAAATTCAGTTATTTCATG<br>GGGGTAAAAAATTGCAGTTAGGAGAACAAGTATTTTCTAAATTAG<br>CTCAAGAAGCTTCTAAAGAATCAATTTTGCGTGAAGCTGGTGATA<br>CTTTGCCACAGTCAAGTCTCAGTACGACTGATACCCCATATAATAT<br>AAAATCTTTAAGCCATAGCAAATAG (SEQ ID NO: 17) |
| CinA<sup>wPip</sup> | wPa_0294 | amino acid | | MESGLDHNYNKILDILKGAIKGDDNQVKARKHLRVERWLRAYIQLIE<br>DFDEEKLIFFSDIFSDNSCWDGIKLKNKAVGERLTEEKNKNGKENPLD<br>LADRYYLACKYCLEDKIPGLEEQVFMRFKRSAFEEDGSDDDLRRELL<br>ENIEETSPIEAFWSFLIDKQIGKLNEYKSVEGLQKSIQINSNKNWEEGIE<br>FFYNKLHNDSSTSSQDKDDLLIEAALSAVKGYKEVDTIEFCLSKMDDE<br>QKKKLLDRDYKENTYYAVLNVLVGQYYFDSFMELSRLCSQIECERYT<br>TFLSSLSDQVLKNPDLSEETKKCMMNVWERIIKLKTQDRGEQSISSIFV<br>DYSVTYTIANLIVDPSRQGVSKEEILGKILKHVKEMSGEEMIKVKDSV<br>LSKIQLFHGGKKLQLGEQVFSKLAQEASKESILREAGDTLPQSSLSTTD<br>TPYNIKSLSHSK (SEQ ID NO: 18) |
| CinB<sup>wPip</sup> | wPa_0295 | nucleotide | | ATGCCAAGTAATGTCAAGCCGCTTGAGTTGGTACAGCTTCTGTTAA<br>TGAGAAATAAATCAAAAGACGAGTTCCTAGATTTTCAAAAAAGGT<br>TCCAATCGTTTATCAATCAATCTCCTTCTTTTTTGCATTCAGTTGGA<br>AAGCCAGGCTTTTTCCCTAGTTTCTTTTTTGGTATGTTTGCTACTGT<br>ATTAGACACAGAACTTGCTACTAAAATTGGTATTAAAAAACTTCAT<br>TTTCGTTTTGATGATAATAGAACTTTAAAAATAGCTATATTAACTA<br>ATGAGGGACTTAAGTGTATAACGATGTCTGATCAAGTTGATGGTA<br>ACATGCATCTAAAGTTCTCTCAAGGAGAGTTAGAAAAAATAGCAC<br>AGAAATGGAAAATGGGAGCAGAGTTTGATAAACTAGAAAAAGAA<br>GAGCATGAAATAACAATTACAGGAAAAGAAGTAAAGCACGGAAA<br>GGTTGATCCAGCTTTTAGTAAAAAGACTGATTATTCACAAAAAGG<br>TTTTACAGAAATAGAAAAAGATCGTGACCAACAAGACCTAGAGAG<br>CTTAATTTCAAAATTGAGTAATCAAGATTTCGAAGAAGTAAAAAA<br>GAACGCTAGAAGAATGTTTAATTATATTACAAATGTCTATAAGAA<br>ATATGAAAAGAAACTCTATTTAGCGGTAAAGAATCAAGTCATCA<br>TGGGTTTTTAGCTGGGTTTTTGATAAATTTTAAGTATCGTTTTCACC<br>TAAAACTTTATCTCGAATTATTTGCTGGAAAAGGTTACGCAGACAT<br>TATTTTGCTTGTGCGCGGTTCTGATAAGTCGCTAAGCTCTATTCCTA<br>TTATTATTGAGCTTAAAGCAGGTACTGGTGAGATAAGTACAGTGA<br>TAAAAGCATTGAAGCAAGCACAAGATTATGTTAAGGGCTCTTTTTC<br>TAACTCTATAAGAATGATTACTATAGCTAATGAAGCTATTTGTGTA<br>GGATTAAATTTTGACATGGTTCATCACGAAAATGTTAAAATTGATG<br>TAGAAAATTTTCTTAGTCGAGAAGGTAATTCTGTAATAGAAAAGTT<br>ACTTGGCACTGAAGCAACGAATGCTGAGGTGATAAGAACACAGCT<br>AGAGTATCTTTACTATGGAATTGTTTGGAGCAATGGTGGAAGTGAT<br>AATATTAATTATGTCAGCAGAATGATCTTAGGTCAGCTAGTACTTA<br>TTTCTAATATTATTAAGCGTGAAAAGTTAGGTAAACATATTTTTAT<br>TTATGATCAAAATGATAAAATGGTTACTGGATCACAGAAACGCCC<br>AGAAGCAGCAAAAGAAAGTATTGAGGATTGTGTTACAACTATAGT<br>GCTAACTTTAGGTAAGAAGGTGCTTATACTCAACATAAATGAAAA<br>AAATGAATTTGCATTGAGAGTGCCAGATAATAAAGGAATTCCTAT<br>TGAAAAATATTAGGAGAATTCAAAACGTCAATGACATAAAGATACA<br>AGAAATAACCTGTAACTTATACAGTACGCCTAGTAATAAGAATCC<br>ATTTGATCAGTACTGTAATAAGAATAAGGGAATTACAGTAAATAC<br>GTATGACTCATTGGACAAATACAAAAGAGGTAAAGAAATTTTACA<br>AGGTAATTTTACTCGAATTGTGGAAAATAAAAAATTTAAAGCAGC<br>TTTGAGCAAAGCTATAGAATCTGGTAAATATGATGATTACAAAAA<br>ACTATTTGAAGAAATTCTCTATATACTACATCCTTTCAAATCATTA<br>ATAAGCAATGAGGCTACATTTCAAGCTGTATTGCATGGTTTATTTA<br>GTAGCTACGGAGAAGATAATATAAAAGTTATTACTGAATTTCAAA<br>TAGGTGGTGGAGAGAAGTTGGATGTTATGTTGGTTATAAATGCTA<br>CTGATCAAAAAAAAGAATACCCCCAGTTGGAATAGAGCTAAAAT<br>TTGCTAAGAAAGGAGAATTGGATAAAAAAGAAAAAGATGCTAAG<br>GACCAGTTGAAAAGATATAAAGAAGGTGAAGCGTATAAGGTAATT<br>ACTGATGCTGGCAAAGTGAAACTGATATATGCTGTTTTTAATAAAG<br>GTGCAACAGATGAAGGTTCCCTTATAAAAATTGGTAATGAGTTTGT<br>AGAGGTAGATGTAAGACATAGCTCTGTGGTTGCTTTTGGTCAACA<br>GCCAGGTAGTCTCCAACAACCTTATGTTAAACAAGCAGGTCTATCT<br>CGAGCAGTTAATCAGTGA (SEQ ID NO: 19) |

TABLE 6-continued

Sequences of CI Factors

| Gene | Locus tag | Seq. type | Length | (5'-3') or (N-C) |
|---|---|---|---|---|
| CinB<sup>wPip</sup> | wPa_0295 | amino acid | | MPSNVKPLELVQLLLMRNKSKDEFLDFQKRFQSFINQSPSFLHSVGKP GFFPSFFFGMFATVLDTELATKIGIKKLHFRFDDNRTLKIAILTNEGLK CITMSDQVDGNMELKFSQGELEKIAQKWKMGAEFDKLEKEEHEITIT GKEVKHGKVDPAFSKKTDYSQKGFTEIEKDRDQQDLESLISKLSNQD FEEVKKNARRMFNYITNVYKKYEKETLFSGKESSHHGFLAGFLINFK YRFHLKLYLELFAGKGYADIILLVRGSDKSLSSIPIIIELKAGTGEISTVI KALKQAQDYVKGSFSNSIRMITIANEAICVGLNFDMVHHENVKIDVE NFLSREGNSVIEKLLGTEATNAEVIRTQLEYLYYGIVWSNGGSDNINY VSRMILGQLVLISNIIKREKLGKHIFIYDQNDKMVTGSQKRPEAAKESI EDCVTTIVLTLGKKVLILNINEKNEFALRVPDNKGIPIENIRRIQNVNDI KIQEITCNLYSTPSNKNPFDQYCNKNKGITVNTYDSLDKYKRGKEILQ GNFTRIVENKKFKAALSKAIESGKYDDYKKLFEEISHILHPFKSLISNE ATFQAVLHGLFSSYGEDNIKVITEFQIGGGEKLDVMLVINATDQKKEY PPVGIELKFAKKGELDKKEKDAKDQLKRYKEGEAYKVITDAGKVKLI YAVFNKGATDEGSLIKIGNEFVEVDVRHSSVVAFGQQPGSLQQPYVK QAGLSRAVNQ (SEQ ID NO: 20) |

TABLE 7

Codon Optimized Sequences of CI Factors

| wMel CifA optimized\|631 | ATGCCCATTGAGACAAAGCGCCAGGCCGAGGTGCTGAAGAAGCTGCAGGATGT GATTAAGCATACAGACCGCGATATTGCCGCCGACGCAAGCTGGCCATCAAGC GCTGGGTGGAGACATACATCGAGTATATTAAGCTGTTCAAGGATGACAAGCTG GAGTTCCTGTACAACGTGTTTCGCGACGAGGGATGCTGGCTGGGCACCCGCCTG AACAATACGGTGCTGGGACAGAAGCTGACCGAGGAGAAGATCGGCGAGATTG ATAATCCACTGCCACGCTACGGAATGGCCTCCCGCTATTGCATCACAGGAAAG ATTGGCGACTTCTTTAACAAGCAGTTCGTGCTGTCCCGCGGACAGTTTACCTCG GAGGAGGTGGATAGTCAGGGCAACCCAATCTCGGACCAGTACGTGCGCAATAT TCTGCTGAGCTCCATGAAGCGCAACGGCCCCGTGTTCGATTTTTGGATCGACCG CGAGTCGGGAGAGCTGAAGAAGTACGATGCCGTGGAGGGCTTCGACAGTACGG TGAAGCTGAAGTGGAGCGAGGGCGTGGAGTACTTTTATAATCAGCTGGAGGAG AAGGATAAGGAGAAGAAGCTGACAGAGGCCATCGTGGCCCTGTCGCGCCCACA GAGTGTGAAGCGCGATGCCCCGATCCTGGACTTCTGCGTGCGCAACATTGGAG ATAAGGACACCCTGCTGCAGAAGCTGCTGCAGAAGGACAAGGGCGTGTACTTC CTGCTGGCCGAGCTGATCGAGAGCTGCTTCTTTGATACGGTGCACGACCTGGTG CAGTGCTGGTGCTATAAGGGCGTGTCCGCCGGAGGAGATTGCAGCGACAAGAT TTTCTCCCAGCAGGATTACGAGCTGTTTCTGTATTCGCTGAGTAACGTGATGCT GAAGAATCCAGAGCTGTCGGTGCAGGCCCCGCAGTCTGATCATGGAGATTTGGA AGTGCGAGCGCTTCGCCGAGTACCGCGAGACCAGCGTGAACACGTCCAATTAT ACAGTGCCGATCAAGTCGGTGCTGGGCGGACTGATCATTAATTGGAAGCGCGA GGATGTGTGCAAGCCAGACCGCGAGATTGAGAAGGAGGAGATCCTGGATATGA TTAGCTTCGCCAAGGGCTGCTTTCCCGAGAAGTTCGACCTGTTTAAGGAGGTCA TGATCGAGAACCTGCGCATTTGCGGACGCGAGGGCAAGCGCAAGGGAGTGGAT TACGGCAAGTTCGCCGAGGAGCTGTTTCTGCAGCTGGAGAAGGTGACGCTGCC ATCCGTGGGCGACGGACCCATGAACAATCTGCGCAGCCAGTCCAAGGTGAGCC TGCCACTGGATGGCTCCGGAGACGGACCACAGTCGGAGTTCGAGGCCCCATCG GTGAGTGGAATCAGCGGCTCCCATAAGAAGCGCCGCATTTAA (SEQ ID NO: 25) |
|---|---|
| wMel CifB optimized\|632 | ATGGACGGAGACCTGGACGGCTTTCGCCAGGAGTTTGAGAGTTTTCTGGATCAG TGCCCCTTCTTTCTGTATCATGTGAGCACGGGACGCTTTCTGCCCGTGTTCTTTT CAGCATGTTCGCCACGGCCCATGACGCCAATATTCTGAAGGCCAACGAGCGCGT GTACTTTCGCTTCGACAATACGGCATCGATACGGGCGGACGCAATCGCAACAC AGGAAACCTGAAGGTGGCCGTGTACCATGATGGCCAGCAGGTGGTGCGCTGCTA TAGCATTTCCGACCGCCTGAATAGCGATGGACTGCGCTTCTCCACGCGCGAGCG CAACGCCCTGGTGCGCGAGATCCGCGGCCAGAATCCGAACCTGCGCGAGGAGG ACCTGAACTTCGAGCAGTACAAGGTGTGCATGCACGGAAAGGGCAAGTCCCAG GGAGAGGCCATTGCCACCGTGTTTGAGGTCATCCGCGAGAAGGACTCCCAGGGA CGCGATCGCTTCGCCAAGTACTCGGCCAGTGAGATTTCGCTGCTGCGCCATATC GAGCGCAACCGCCTGAATGGCATCAACGCCCCAGCCCCACGCAGCCTGCTGACC GTGAAGGAGATTGGCAGCATCCGCCTGAATCAGGACCAGCGCGTGCAGCTGGG ACACCTGGTGAACTTCGTGCAGGTGGCCCCAGGACAGCAGGGCATCTTTAGCTT CATGGAGGTGCTGGCCTCCAATCAGAAGATCAACATTGAGCGCGGAATTAACGA GGGCATCCTGCCCTACATTACACGCATCTACCGCAGCTATCTGGGCTCCCTGCAG AATGATATTCAGAACCGCAGCCAGAAGTTTGAGTCCCACGGATTTTTCCTGGGC CTGCTGGCCAATTTCATCCATCTGTACACCATCGATATTGACCTGGATCTGTCGC CGGGCAACAGTTATGTGGCCTTCCTGATTTGCCACCAGGCCGAGCGCGAGAATA TCCCAATTGTGATCAACGTGACCCGCTGGCGCACGAGCTCCGACATCGCCCTGA ACCGCGCCCGCGCCGATGCCAAGCGCCTGCACGTGTCGAGTTTCATTTCGATCC ATACCGAGAGTCGCAACGCCGTGTGCATCGGCCTGAATTTTAACCTGAATATTG ACCCCTTCAGCATCGATACGGTGGAGTTTCTGGAGAATCGCTTCCCGCTGGTGC |

TABLE 7-continued

Codon Optimized Sequences of CI Factors

|  |  |
|---|---|
|  | AGCGCCTGTTTGAGTGCCTGGAGGACGAGGGCATTCGCGAGAACATCCGCGATT<br>TCCTGCTGCAGCACCTGCCGAATGAGATCCCACGCAACGCCGAGAACTACAATC<br>GCATTTTCGACTGCATCACCGGATTTGCCTTCGGCAATTCCATTCTGGAGGAGTT<br>CCGCCTGGTGAACGCCGTGCAGCAGCGCGTGCGCAAGTACATCTTTCGCTATGG<br>AGATGAGAACCACGCCCTGACAATGGTGTTCCATACCCAGGGCTCGGATATTGT<br>GATCCTGCATATTCGCGACAACAATGCCGTGCAGCAGGGAGCCATCAATCTGCA<br>GGACCTGAACGTGGATGGCAACAATGTGCACGTGCGCGAGGTGTCCTGCACACT<br>GAACAATCAGCTGGGACTGAATATCCACACCGATAACCTGGGCCTGTACCATAA<br>CTACCAGAACAACAACGCCAACAACTTCCTGGGCGGAAACCTGGTGCAGGTGCC<br>CAATGCCGGAAACGTGCACAATGCCCTGAACCAGGTCATGAATGACGGCTGGC<br>AGGATCGCTTTCAGCATCAGGAGCTGTTCCGCAACATCAGCGCCGTGCTGATGC<br>CAGAGGACACCCACGGCAATATGATCATTGACGTGAACTCGAAGGATAAGTTTC<br>GCAGTATCCTGCACGGCACGTTCTACGCCTCGGATAACCCATATAAGGTGCTGG<br>CCATGTACAAAGTGGGACAGACATATAGCCTGAAGCGCTGGCAGGAGGAGGAG<br>GGAGAGCGCGTGATTCTGACACGCGTGACCGAGCAGCGCCTGGGACTGCTGCTG<br>CTGCGCCAGCCCACGGCCGACACACACCCGATCGGATACGTGCTGGGCTTCGCC<br>GACAACGCCGAGGAGGTGGAGCAGGAGCAGGATGAGGCCCGCTACAAGATTAC<br>AGAGCTGATGAGCAAGCAGCGCGGATATCTGCCCATCACCTCGGGCAATGAGGT<br>GGTGCTGAGTTACGCCGTGTTTAACCGCGGAGCCCAGCGCGCCGAGGATTTCAT<br>CTCCCTGCCGCAGCAGGCCGTGTATGTGCACCGCCTGGACCGCCGCGGACATGA<br>TTCGCGCCCAGAGGTGCTGGTGGGACCAGAGAGTGTGATCGACGAGAATCCCCC<br>GGAGAACCTGCTGAGCGATCAGACGCGCGAGAACTTTCGCCGCTTCTACATGGA<br>GAAGCGCCCAGGCCAGAATAGCATTTTTCTGCTGGACATCGATGACAACCTGCA<br>CGTGCCCTTCTCCTATCTGCAGGGCACCCGCGCCCAGGCCATTGAGACGCTGCG<br>CAGCCGCATCCGGAGGAGGCACCTCCACGGCCCAGGGCATTCTGCAGCAGAT<br>TAATACCATCCTGCGCCGCAATAACGCCCGCGAGATCGAGGATGTGCATAACCT<br>GCTGGCCCTGGACTTTGCCACGGAGAACCAGAATTTCCGCTACTGGCTGCAGAC<br>ACACGATATGTTTTCGCCGCCCGCCAGTATACATTTCACGATGACCGCTCGAAT<br>CCCACCAACGACCGCCATGATTCGCCATTACGAGCGTGGGAGTGGACGGCAAC<br>CAGAATGATCCAACCGGACGCGACCTGCTGAGCTCCAATATCGACAACTTCAAG<br>CAGAAGGTGGATTCCGGAGAGAAGGACCGCCTGACCGCCATCATTAATGTGGG<br>CAACCGCCACTGGGTGACGCTGGTCATCGTGCATCAGAACGGAAATTACTATGG<br>CTACTATGCCGATAGCCTGGGACCGGACTCCCGCATTGATAATAACATCCGCGG<br>CGCCCTGCGCGAGTGCGATATTTCGGATGACAATGTGCACGACGTTAGTGTGCA<br>TCAGCAGACGGATGGACACAACTGCGGCATCTGGGCCTACGAGAATGCCCGCG<br>ATATTAACCAGGCCATCGACCAGGCCCTGCAGGGAAACTCCAATTTCGGCGAGA<br>AGGGAGAGGGCATCATTGGATACATTCGCGGCCTGCTGTCGGCCGGAATCGGCA<br>ATGATACCCGCCAGCCGCAGCGCAACGAGCAGTATTTTCGCAATCGCCGCCGCA<br>ACATTAGCCAGCTGTTCCAGAACGACTCCCTGTCGAGTCCACGCGGACGCCTGA<br>TCCAGGGACGCCCAGGCATTCAGCATGAGATCGATCCACTGCTGCTGCAGTTCC<br>TGGAGCTGCAGTACCCACAGCCGGCGGAGGAGGAGCCCTGCAGCTGGGAGGC<br>GAGCGCGTGATTTCGATCGACTTCGGACCCCAGAGTGTGCTGGACGAGATCGAT<br>GGCGTGAATCGCGTGTACGATCACTCGAACGGACGCGGCAGTCGCTAA (SEQ ID<br>NO: 26) |
| cidAwPip<br>(codon<br>optimized) | ATGCCAACACAGAAGGAGCTGCGCGATACCATGTCGAAGAAGCTGCAGGAGGC<br>CATTAAGCACCCAGACCCCGCCGTGGTGGCCGGACGCAAGAGTGCCATCAAGC<br>GCTGGGTGGGAGTGCTGCAGGATAACTTCATGGAGCACATTAAGTACTTTAAGG<br>GCGACAAGCTGAAGTTCCTGCATAATGTGTTTCAGGATGAGGGATGCTGGTCCG<br>GCGTGCGCCTGGATAATGCCGCCCTGGGACAGCGCTTCACCGAGGAGAAGATTG<br>GCGGAATCGATAACCCGCTGCGCAAGTACGAGATGGCCTGCTCGTATTGCGTGG<br>TGGACAAGATCCACCCACTGTTTCAGAAGCGCTTCGAGAGTTACCGCAATAAGT<br>TCCCGCCCGGAGCCTTTGATGGCAAGACAGAGACCGAGTTCGGCAAGTATGTGC<br>GCAACTCGCTGCTGGACAGTATTAAGCGCAAGGGACCAGTGTTTGACTTCTGGA<br>TCGATCGCGAGTCCGGCGAGCTGAAGAAGTACGACGCCGTGGAGGGATTTGATT<br>CGGCCGTGAAGCTGAAGTGGAGTGAGGGCGTGGAGTACTTCTATAATCACCTGA<br>AGGAGGAGGATAAGGAGAAGAAGCTGACCGAGGCCATTCTGGGCCCTGTCGCGC<br>GTGCAGTCGGTGGAGAAGGATGCCCCGATTCTGGATTTCTGCGTGAACAAGATC<br>GTGGATAAGGACACCCTGCTGCAGAAGCTGTCGCAGAAGGACAAGGGCGTGTA<br>CAGTCTGTTCGCCGAGCTGATCGAGAGCTGCTTCTTTGACACGGTGCACGATCTG<br>GTGCAGTGCTGGTGCTACAAGGAGGTGTCGGCCGGCGGAGACCATAGCGAGAA<br>GATTTTCTCCCAGCGCGATTATGAGCTGTTTCTGAGCTCCCTGAGCGACGTGATG<br>CTGAAGAATCCGGAGTCGAACGTGCAGGCCCGCAGTCTGATCATGGAGTTCTGG<br>GAGTGCGGCAGCCTGTACCAGTATCGCAAGGCCGCCGTGAACACGAGCAATTAC<br>ACAGTGCCAACCTCCGGCGTGTTCGCCGAGCTGATTGTGAACTGGCGCCGCGAG<br>GACATCTATAAGACAGATGAGGAGAAGGAGATTGAGAAGAAGGAGATCCTGGA<br>CATGATGTCGTTCGCCAAGGATTGCTTTCCCGAGAAGTTTGAGCTGTTCAAGAA<br>GCTGATCATTCGCGATCTGCCCTGTGCGGACGCGAGGGCAAGCGCGTGAATGT<br>GGACTACGGCCTGTTCGCCGAGGAGCTGTTTAGCGAGCTGGAGAAGACCATTCT<br>GCCACCCGGACCCGTGGGAGATGGACCATGCTCCAATCTGCGCTCCCGCAGTAA<br>GGCCCACGGCTCGAAGAAGACCACCCTGCCGGTGGATGACAGCCCGCAGTCGG<br>AGCTGGGAACCCCAGCGTGTCCGGAGTGTCGAGTTACAAGAAGAAGAGCGTG<br>TTCACGCTGAGTGGCAATAAG (SEQ ID NO: 27) |
| cidBwPip<br>(codon<br>optimized) | ATGTCCAACGGAGATGGCCTGATCCGCTCGCTGGTGGATGGAGACCTGGAGGGC<br>TTCCGCCAGGGATTTGAGTCGTTCCTGGACCAGTGCCCGAGCTTCCTGTACCACG<br>TGTCCGCCGGCCGCTTTCTGCCAGTGTTCTTTTTCTCGATGTTCAGTACAGCCCA<br>CGATGCCAATATCCTGAACGCCAATGAGCGCGTGTATTTTCGCTTCGACAACCA |

TABLE 7-continued

| Codon Optimized Sequences of CI Factors |
|---|
| TGGCGTGAACCCACGCAATGGAGAGAACCGCAATACCGCCAATCTGAAGGTGG |
| CCGTGTACCGCGATGGCCAGCAGGTGGTGCGCTGCTATTCGATCAGTGACCGCC |
| CCAACTCGGATGGACTGCGCTTCAGTGAGCGCGAGCGCGATTTTCTGGTGCAGG |
| AGATCATTCGCCAGAATCAGGGCCTGATGGAGGAGGACCTGAACTTTGAGCAGT |
| ACAAGGTGTGCATGCACGGAAAGGGCAAGTCCCAGGGCGAGGCCATTGCCACC |
| GTGTTCGAGGTCATCCGCGAGAAGGACTTCCGCGGACGCGATAAGTTTGCCAAG |
| TACTCGGCCTCGGAGGTGCACTTCCTGCGCCAGCTGTTTCGCAACCATCGCCTGA |
| CGATTAAGGAGATCGAGGGCCGCCAGCTGAACCAGAATCAGCGCCGCCAGCTG |
| GGACGCCTGGTGAATTTTGCCCAGGTGGCCCAGGGACAGCAGGGAATCGACAA |
| CTTCATGGAGATGCTGGCCTCGGATCGCCGCCAGGATGTGCGCGATCGCATTCG |
| CCGCGAGATCCTGCCCTACATTACCGATATCTACAACAATTATCGCCAGGTGCT |
| GGAGAACAATATCGAGAACCGCAATCAGCGCTTCGAGGGACACGGCTTTCTGCT |
| GGGCTTCCTGGCCAATTTTTCCCATCTGTGCACGATCGATATTGACCTGGATCTG |
| TCGCCCCGCAACAGTCACGTGGCCTTCCTGGTGCGCCATCAGGTGGAGCGCGAG |
| AATATCCCGATTGTGATCAACCTGGCCACACGCGCCCCGCCATACATCGCCCTG |
| AATCGCGCCCGCTCCCACGCCGAGCGCCTGCATGTGTTTAGTTTCATTCCCATCC |
| ACACCGAGAGCCGCAACACCGTGTGCGTGGGACTGAACTTCAATCTGAACCTGG |
| ACCCCTTTTCGGTGGATACGGTGGGACTGCAGCAGGATCGCTTCCCGCTGGTGC |
| AGCGCCTGTTTGAGTGCCTGGAGAATGAGGGCATTCGCGAGAACATCCGCGACT |
| TCCTGCTGCACCATCTGCCCGCCGAGATCCCACGCAATGCCGAGAATTACGACC |
| GCATTTTTGATTGCATCACCGGCTTTGCCTTCGGAAACAGCGCCTTCGATCGCGA |
| GTATCTGGAGCTGGAGGAGGGAGAGGACCGCGTGCGCGTGCGCAAGTACATCT |
| TTCGCTATGGAGACGGCGATCTGCGCCGCCACACCCTGACAATGGTGTTCCATG |
| CCGAGGGCAGCGATATTGTGATCCTGCACATTCGCGCCCATGATGCCCAGCAGC |
| AGGGAGCCATCAATCTGCAGACCCTGAATGTGAACGGAAATGATGTGCACGTGT |
| GGGAGGTGTCCTGCACGCTGAACAATCAGCTGGAGCTGGACATCGATCTGCCGA |
| ACGACCTGGGCCTGTACCATGATTATCAGAACAATAACGCCAATAACTTCCTGG |
| CCGGAGATCTGGTGCAGGTGCCAAACACAGAGAATGTGCACAACACCCTGAAT |
| CAGGTGGTGAATGACGGCTGGAAGAACATTGCCCAGCATCGCGGCCTGTTCCAG |
| GAGATCTCCGGAGCCCTGATGCCCCTGGTGGACACAATTAACGTGAATAGCGAG |
| GATAAGTTCCGCTCCATCCTGCACGGCACCTTCTACGCCAGCGATAACCCGTAT |
| AAGGTGCTGGCCATGTACAAAGTGGGCCAGACATATTCGCTGAAGCGCGGACA |
| GGAGGAGGAGGGAGAGCGCGTGATTCTGACGCGCATCACAGAGCAGCGCCTGG |
| ATCTGCTGCTGCTGCGCCAGCCCCGCGAGAATGACCTGGATACCCACCCCATTG |
| GATACGTGCTGCGCCTGGCCAATAACAGCGAGGAAGTGGGACAGCAGCAGAAT |
| GATGCCCGCCAGGAGATTGGACGCCTGAAGAAGCAGCATCGCGGCTTCATTCCA |
| ATCACGTCCGGAAATGAGGTGGTGCTGTTCCCGCTGGTGTTTAATGCCGGAGCC |
| GGACGCGTGGAGGGACTGATTTCGATCCCCGAGGGAATTGGCCGCGAGGAGTA |
| CGTGCACATCCTGGATCGCGGCGGACGCGATAGTCGCCCAGGCGGACTGGTGGG |
| ACCGGAGAGCGTGATCGATGAGAATCCCCCGGAGGGACTGCTGTCGGACCAGA |
| CCCGCGAGAACTTTCGCCGCTTCTACGAGGAGAAGGCCCCAGGCCAGAATAGTA |
| TTTTTCTGCTGGACATCGGAGATAACCTGCATGTGCCCTTCAGCTATCTGCAGGG |
| AACCCGCGCCCAGGTCATCGAGACACTGAAGTCCCGCATCCGCGGCGGAGGCA |
| CCCCCACCGCCCAGGGCATCCTGCAGCAGATTAACGCCATCCTGCGCCGCAATA |
| ACGCCCGCGAGATTGAGGACGTGCACGATCTGCTGGCCCTGGACTTCGCCACAG |
| ATAACCAGAATTACCGCTATTGGCTGCAGACCCATGATATGTTTTTCGCCGCCCG |
| CCAGTACACCTTTCTGGACAATCAGTCGCACAGTACGAACGATCATTATGGCTT |
| CGAGATCACATCGGTGGGAGTGGACGGCAACCAGAATGATCCGACCGGACGCG |
| GACTGCTGAGCTCCCACATTACGAACTTCAAGCAGAAGGTGGACAGCGGCGAG |
| AAGGATCGCCTGATCGCCATCATTAACGTGGGAAATCGCCACTGGGTGACGCTG |
| GTCATCGTGCATCAGAACGGCAATTACTATGGATACTATGCCGATAGCCTGGGC |
| CCGGACTCCGGAATTGATAATAACATCCGCGGAGCCCTGCGCGAGTGCGATATT |
| AACGATGACAATGTGCACAACATCAGCGTGCATCAGCAGACCGACGGCCATAA |
| CTGCGGAATCTGGGTGTACGAGAATGCCCGCGACATTAACCAGGCCATCGATCA |
| GGCCCTGCAGGGCAATAACAATTTCGGAGAGAAGGGAGAGGGCATCATTGGCT |
| ACATTCGCGGACTGCTGAGCGCCGGAATTGGAAATGATACCCGCCAGCCACGCC |
| GCAATGAGCAGTATTTCGAGGACCGCCGCCGCGATATCTCCCAGCTGCTGCAGA |
| ATGACCCAAACCTGCCCAGCCGCCGCTCCGATCTGATTCAGGCCCACCCGGGCA |
| TTCAGCATGAGATCGATCCACTGCTGCTGCAGTTCCTGGGACTGCAGTACCCAC |
| AGCGCGGAGGCGGAGGCGCCCTGCAGCTGGGAGGCGAGCGCGTGATTTCCATC |
| GACTTCGGCAACCCCCAGTCGGCCCTGGATAAGATTGATGGAGTGTCCCGCGTG |
| TATAACCACAGTAACAGTCGCGGCAGTCGC (SEQ ID NO: 28) |

We claim:

1. A genetically modified arthropod, said arthropod comprising:
    (i) a bacterial operon or two independent chromosomal insertions encoding at least two cytoplasmic incompatibility factors, wherein the bacterial operon or the two independent chromosomal insertions is from *Wolbachia*;
    wherein the bacterial operon or the two independent chromosomal insertions encode: the cytoplasmic incompatibility factors WD0631 and WD0632; and
    wherein WD0631 is encoded by SEQ ID NO: 25; and
    (ii) a promoter operably linked to the bacterial operon or the two independent chromosomal insertions;
    wherein the expression of the cytoplasmic incompatibility factors in a male arthropod causes a reduction in viable offspring in comparison to a male arthropod lacking the cytoplasmic incompatibility factors.

2. A genetically modified arthropod, said arthropod comprising:
    (i) a bacterial operon or two independent chromosomal insertions encoding at least two cytoplasmic incompatibility factors, wherein the bacterial operon or the two independent chromosomal insertions is from *Wolbachia*;
    wherein the bacterial operon or the two independent chromosomal insertions encode:
    the cytoplasmic incompatibility factors WD0631 and WD0632; and
    wherein WD0632 is encoded by SEQ ID NO: 26; and
    (ii) a promoter operably linked to the bacterial operon or the two independent chromosomal insertions;
    wherein the expression of the cytoplasmic incompatibility factors in a male arthropod causes a reduction in viable offspring in comparison to a male arthropod lacking the cytoplasmic incompatibility factors.

3. A genetically modified arthropod, said arthropod comprising:
    (i) a bacterial operon or two independent chromosomal insertions encoding at least two cytoplasmic incompatibility factors, wherein the bacterial operon or the (wo independent chromosomal insertions is from *Wolbachia*;
    wherein the bacterial operon or the two independent chromosomal insertions encode:
    the cytoplasmic incompatibility factors $CidA^{wPip}$ and $CidB^{wPip}$; and
    wherein $CidA^{wPip}$ is encoded by SEQ ID NO: 27; and
    (ii) a promoter operably linked to the bacterial operon or the two independent chromosomal insertions;

wherein the expression of the cytoplasmic incompatibility factors in a male arthropod causes a reduction in viable offspring in comparison to a male arthropod Jacking the cytoplasmic incompatibility factors.

4. A genetically modified arthropod, said arthropod comprising:
(i) a bacterial operon or two independent chromosomal insertions encoding at least two cytoplasmic incompatibility factors, wherein the bacterial operon or the two independent chromosomal insertions is from *Wolbachia*;
wherein the bacterial operon or the two independent chromosomal insertions encode:
the cytoplasmic incompatibility factors $CidA^{wPip}$ and $CidB^{wPip}$; and
wherein $CidB^{wPip}$ is encoded by SEQ ID NO: 28; and
(ii) a promoter operably linked to the bacterial operon or the two independent chromosomal insertions:
wherein the expression of the cytoplasmic incompatibility factors in a male arthropod causes a reduction in viable offspring in comparison to a male arthropod lacking the cytoplasmic incompatibility factors.

* * * * *

SEQUENCE LISTING

<160> NUMBER OF SEQ ID NOS: 28

<210> SEQ ID NO 1
<211> LENGTH: 1425
<212> TYPE: DNA
<213> ORGANISM: Wolbachia pipientis

<400> SEQUENCE: 1

```
atgccaatag aaacaaaacg tcaggctgaa gtgcttaaaa agctacaaga tgtgataaaa      60
catacagatc gtgacattgc ggctggaaga aagttagcta ttaaaaggtg ggtcgagacc     120
tatatagagt atatcaaact ttttaaggat gataagctgg aattcttata taatgttttt     180
cgagatgaag gttgttggtt aggtacaagg ttaaataata ctgttttagg tcagaaattg     240
actgaagaga aaataggaga aatcgataac ccactaccaa ggtatggtat ggcatctagg     300
tactgtataa cgggcaagat aggtgatttt ttcaacaaac agtttgtact ctctagaggt     360
caatttactt cagaagaggt agatagtcaa ggtaatccga tcagtgatca atatgtaaga     420
aacattctgc tatcatccat gaagagaaat ggtcctgtgt tgatttctg gatcgataga      480
gaatctgggg aattaaagaa gtatgatgca gtagaaggtt ttgacagtac tgtaaaactt     540
aagtggagcg aaggggtaga gtatttttat aatcagttag aggaaaaaga taaggagaag     600
aagcttacag aagctattgt tgctctttct cgtcctcaat ctgttaagag agacgctcct     660
attttagatt tttgtgtaag gaatataggc gataaagata ctcttttaca gaaattattg     720
cagaaagata agggagtata tttccttctt gctgaattaa tagagtcatg ttttttttgat    780
acggttcatg atttggtaca gtgctggtgt tataaaggcg tttcagcagg aggagactgt     840
tcggacaaga tattctcaca gcaagactat gaactttttc tttattcact ttcaaatgtg     900
atgttgaaaa atcctgagtt aagtgttcaa gctagatccc ttattatgga gatttggaaa     960
tgtgaacgct ttgctgaata cagagagacc tctgttaata cttctaatta tacagttcct    1020
ataaagagtg tacttggggg attaatcatt aattggaaac gagaagatgt ttgtaagccc    1080
gatagggaaa tagagaaaga agaaatatta gatatgattt catttgccaa aggttgcttt    1140
cctgaaaagt ttgacctttt taagaagtc atgatagaaa atcttagaat atgtggtagg     1200
gaaggaaaga ggaaaggtgt agattacggc aagtttgcag aagagttatt tcttcagtta    1260
gagaaagtaa ctttaccttc tgtaggtgat ggtccttgga ataatttgcg gtctcaatct    1320
aaggtatctt tgccacttga tggttctggt gatggcccac agtctgagtt tgaagctcct    1380
agtgtgagtg gtatttctgg ttctcataag aaaagaagaa tctag                    1425
```

<210> SEQ ID NO 2
<211> LENGTH: 474
<212> TYPE: PRT
<213> ORGANISM: Wolbachia pipientis

<400> SEQUENCE: 2

```
Met Pro Ile Glu Thr Lys Arg Gln Ala Glu Val Leu Lys Lys Leu Gln
1               5                   10                  15

Asp Val Ile Lys His Thr Asp Arg Asp Ile Ala Ala Gly Arg Lys Leu
            20                  25                  30

Ala Ile Lys Arg Trp Val Glu Thr Tyr Ile Glu Tyr Ile Lys Leu Phe
        35                  40                  45

Lys Asp Asp Lys Leu Glu Phe Leu Tyr Asn Val Phe Arg Asp Glu Gly
    50                  55                  60

Cys Trp Leu Gly Thr Arg Leu Asn Asn Thr Val Leu Gly Gln Lys Leu
65                  70                  75                  80

Thr Glu Glu Lys Ile Gly Glu Ile Asp Asn Pro Leu Pro Arg Tyr Gly
                85                  90                  95

Met Ala Ser Arg Tyr Cys Ile Thr Gly Lys Ile Gly Asp Phe Phe Asn
            100                 105                 110

Lys Gln Phe Val Leu Ser Arg Gly Gln Phe Thr Ser Glu Glu Val Asp
```

```
            115                 120                 125
Ser Gln Gly Asn Pro Ile Ser Asp Gln Tyr Val Arg Asn Ile Leu Leu
130                 135                 140

Ser Ser Met Lys Arg Asn Gly Pro Val Phe Asp Phe Trp Ile Asp Arg
145                 150                 155                 160

Glu Ser Gly Glu Leu Lys Lys Tyr Asp Ala Val Glu Gly Phe Asp Ser
                165                 170                 175

Thr Val Lys Leu Lys Trp Ser Glu Gly Val Glu Tyr Phe Tyr Asn Gln
            180                 185                 190

Leu Glu Glu Lys Asp Lys Glu Lys Leu Thr Glu Ala Ile Val Ala
        195                 200                 205

Leu Ser Arg Pro Gln Ser Val Lys Arg Asp Ala Pro Ile Leu Asp Phe
210                 215                 220

Cys Val Arg Asn Ile Gly Asp Lys Asp Thr Leu Leu Gln Lys Leu Leu
225                 230                 235                 240

Gln Lys Asp Lys Gly Val Tyr Phe Leu Leu Ala Glu Leu Ile Glu Ser
                245                 250                 255

Cys Phe Phe Asp Thr Val His Asp Leu Val Gln Cys Trp Cys Tyr Lys
                260                 265                 270

Gly Val Ser Ala Gly Gly Asp Cys Ser Asp Lys Ile Phe Ser Gln Gln
            275                 280                 285

Asp Tyr Glu Leu Phe Leu Tyr Ser Leu Ser Asn Val Met Leu Lys Asn
        290                 295                 300

Pro Glu Leu Ser Val Gln Ala Arg Ser Leu Ile Met Glu Ile Trp Lys
305                 310                 315                 320

Cys Glu Arg Phe Ala Glu Tyr Arg Glu Thr Ser Val Asn Thr Ser Asn
                325                 330                 335

Tyr Thr Val Pro Ile Lys Ser Val Leu Gly Gly Leu Ile Ile Asn Trp
                340                 345                 350

Lys Arg Glu Asp Val Cys Lys Pro Asp Arg Glu Ile Glu Lys Glu Glu
            355                 360                 365

Ile Leu Asp Met Ile Ser Phe Ala Lys Gly Cys Phe Pro Glu Lys Phe
370                 375                 380

Asp Leu Phe Lys Glu Val Met Ile Glu Asn Leu Arg Ile Cys Gly Arg
385                 390                 395                 400

Glu Gly Lys Arg Lys Gly Val Asp Tyr Gly Lys Phe Ala Glu Glu Leu
                405                 410                 415

Phe Leu Gln Leu Glu Lys Val Thr Leu Pro Ser Val Gly Asp Gly Pro
            420                 425                 430

Trp Asn Asn Leu Arg Ser Gln Ser Lys Val Ser Leu Pro Leu Asp Gly
        435                 440                 445

Ser Gly Asp Gly Pro Gln Ser Glu Phe Glu Ala Pro Ser Val Ser Gly
    450                 455                 460

Ile Ser Gly Ser His Lys Lys Arg Arg Ile
465                 470

<210> SEQ ID NO 3
<211> LENGTH: 3501
<212> TYPE: DNA
<213> ORGANISM: Wolbachia pipientis

<400> SEQUENCE: 3
gtggatggag atcttgatgg ttttagacaa gagtttgaat ccttttttaga tcaatgtcca      60 ttttttcttgt atcatgtaag tacaggacgt ttccttcctg tattcttttt cagtatgttt    120
```

```
gctactgctc atgatgctaa tatcttaaaa gcaaatgaga gagtgtattt tcgttttgat    180
aatcatggta ttgatacagg tggtagaaat agaaatacag ggaacctaaa agtcgctgtt    240
tatcatgacg gacagcaagt tgtcagatgc tacagtattt ctgatcgtct taatagtgat    300
gggttaaggt tcagtacaag ggaaagaaat gctctagtgc gagagattag agggcaaaat    360
ccaaatttaa gggaagaaga cctaaatttt gagcaataca agtatgcat gcatggaaag     420 ggcaagagtc agggagaggc gattgcaaca gtattcgagg tgattcgtga aaagattct     480 caaggtagag atagatttgc taaatattca gcgtctgaga ttagccttct taggcatata    540
gaacgcaata ggcttaatgg gattaatgcg cctgcgccac gcagtttgtt gacagttaag    600
gaaataggaa gtatacgact caatcaagat cagagagtac agcttggtca tttggtcaat    660
tttgtgcaag ttgcaccggg tcagcaaggg attttcagtt ttatggaagt gctagcaagt    720
aaccaaaaaa taaatataga acgtggaata aatgaaggaa ttttgccata cataactcga    780
atctatcgta gttacctagg cagcctacaa aatgacattc aaaatcgcag tcaaaagttt    840
gagagtcacg gattttctct taggtttgttg gcaaatttta ttcatctcta cacaatagat    900
attgaccttg acttgtctcc tggaaattca tatgttgctt ttcttatatg tcatcaggca    960
gagagagaaa acattcctat cgttattaat gttactagat ggaggacatc gtctgatatt   1020
gcattaaacc gcgctagagc tgatgctaaa agattacatg tttcttcatt tatatctatt   1080
cacactgaat caagaaatgc tgtttgtatt ggattaaatt ttaatctgaa tatagatcct   1140
tttagtattg atacagtaga gttttttagag aatagatttc ctttggtaca agattattt   1200 gagtgtttgg aggatgaagg aattagagaa atattagag atttcttgct tcaacatctt    1260
cctaacgaaa taccaagaaa tgcagagaat tataacagaa tatttgattg cataactggt   1320
tttgcttttg ggaatagtat tttagaagag ttcagattag taaacgcagt tcaacaacgt   1380
gtaagaaagt atatatttag atatggtgat gagaatcatg ctttaaccat ggtcttccat   1440
actcaaggtt ctgatatagt tatacttcat attagagata caacgctgt acaacaagga    1500 gccatcaatt tacaagatct taatgttgac ggaaataatg ttcatgtacg ggaagtttca   1560
tgcacactta ataatcaact tggccttaat attcatacag ataaccttgg tttatatcac   1620
aattaccaaa ataataatgc aaataatttt cttggtggta atcttgtgca agtgcctaat   1680
gctgaaaatg tgcataatgc tttaaatcaa gttatgaatg atggctggca agatagattt   1740
cagcatcaag aattatttag aaacatttct gcagtattaa tgccagaaga tacgcatggc   1800
aatatgataa tagatgtaaa tagcaaagat aagtttcgct ctatactaca tggtacattt   1860
tatgctagtg ataatcctta taaagtgctt gctatgtata agttggtca acatatagt    1920 ttaaaaggt ggcaggaaga agaaggagaa agggtaatac ttacaagagt tacagaacag    1980
agactaggtc ttctattatt aagacaacct acagcagata ctcacccaat tggatatgta    2040
ttaggatttg ctgataatgc agaagaagta gaacaggagc aagacgaggc aaggtacaaa    2100
ataacagaat tgatgagcaa acaaagggga tatttgccta ttacttctgg aaatgaggtg    2160
gttttgtctt atgctgtatt taatagaggt gcacagagag cagaagactt tatatctctt    2220
ccacaacaag cagtgtatgt acatagactt gatcgtcgtg gtcatgactc aagaccagaa    2280
gtattagtgg gacctgaaag tgttattgat gaaaatccac cagaaaatct attgtcagat   2340
caaactcgtg aaaatttcag gcgctttttac atggaaaaaa gaccaggaca gaactcgatt   2400 ttttgcttg atatagatga taatctgcac gttccattta gttacttgca aggtactaga    2460
```

| | | |
|---|---|---|
| gcacaggcaa tagaaacatt aaggtcaaga ataaggggag gtggtacttc tacagcacaa | 2520 | |
| ggaatattac aacaaataaa cactatcctt cgtagaaaca acgctcgtga aatagaagat | 2580 | |
| gtgcataatc tacttgcact agactttgca acagaaaatc aaaatttccg ttattggcta | 2640 | |
| caaactcatg acatgttttt cgctgcacga caatatactt tccatgatga tcgatctaat | 2700 | |
| ccaactaatg atcgtcatga ttttgcaata acttcagtag gagtcgatgg aaatcaaaat | 2760 | |
| gatccaacag gtagggactt attaagtagt aacatagata actttaaaca aaagtagat | 2820 | |
| tcgggtgaaa aagatagatt aactgctatt attaatgtag gtaatcgtca ttgggttaca | 2880 | |
| ttagttattg tccaccaaaa tggaaattat tatgggtatt atgctgattc acttggtcca | 2940 | |
| gatagtcgta ttgacaataa tattcgagga gctttaagag aatgtgatat tagcgatgat | 3000 | |
| aatgtccatg atgtttccgt tcatcagcaa acagatggcc ataattgtgg catatgggca | 3060 | |
| tacgaaaatg ctagggatat taaccaagct attgatcaag ctttacaggg aaatagtaac | 3120 | |
| tttggagaga aaggtgaagg tattataggt tatatacgtg gtcttcttag tgcaggaatt | 3180 | |
| ggaaatgaca ctagacaacc tcaaagaaat gaacaatact ttagaaatcg gagaagaaat | 3240 | |
| atttcacaat tattccaaaa tgattctcta tcttctccta ggggtagatt gattcaaggt | 3300 | |
| cgtccaggaa ttcaacatga aattgatcca ttactattac aattttttaga actccaatat | 3360 | |
| ccacagcgtg gaggtggggg agcattgcaa ttaggcggag aaagagtgat atcaattgat | 3420 | |
| tttggtccgc aatctgtatt ggatgaaatt gatggagtga atagagttta tgatcatagc | 3480 | |
| aatggtagag gcagtaggta g | 3501 | |

<210> SEQ ID NO 4
<211> LENGTH: 1166
<212> TYPE: PRT
<213> ORGANISM: Wolbachia pipientis

<400> SEQUENCE: 4

```
Met Asp Gly Asp Leu Asp Gly Phe Arg Gln Glu Phe Glu Ser Phe Leu
1               5                   10                  15

Asp Gln Cys Pro Phe Phe Leu Tyr His Val Ser Thr Gly Arg Phe Leu
            20                  25                  30

Pro Val Phe Phe Phe Ser Met Phe Ala Thr Ala His Asp Ala Asn Ile
        35                  40                  45

Leu Lys Ala Asn Glu Arg Val Tyr Phe Arg Phe Asp Asn His Gly Ile
    50                  55                  60

Asp Thr Gly Gly Arg Asn Arg Asn Thr Gly Asn Leu Lys Val Ala Val
65                  70                  75                  80

Tyr His Asp Gly Gln Gln Val Val Arg Cys Tyr Ser Ile Ser Asp Arg
                85                  90                  95

Leu Asn Ser Asp Gly Leu Arg Phe Ser Thr Arg Glu Arg Asn Ala Leu
            100                 105                 110

Val Arg Glu Ile Arg Gly Gln Asn Pro Asn Leu Arg Glu Glu Asp Leu
        115                 120                 125

Asn Phe Glu Gln Tyr Lys Val Cys Met His Gly Lys Gly Lys Ser Gln
    130                 135                 140

Gly Glu Ala Ile Ala Thr Val Phe Glu Val Ile Arg Glu Lys Asp Ser
145                 150                 155                 160

Gln Gly Arg Asp Arg Phe Ala Lys Tyr Ser Ala Ser Glu Ile Ser Leu
                165                 170                 175

Leu Arg His Ile Glu Arg Asn Arg Leu Asn Gly Ile Asn Ala Pro Ala
            180                 185                 190
```

```
Pro Arg Ser Leu Leu Thr Val Lys Glu Ile Gly Ser Ile Arg Leu Asn
        195                 200                 205

Gln Asp Gln Arg Val Gln Leu Gly His Leu Val Asn Phe Val Gln Val
    210                 215                 220

Ala Pro Gly Gln Gln Gly Ile Phe Ser Phe Met Glu Val Leu Ala Ser
225                 230                 235                 240

Asn Gln Lys Ile Asn Ile Glu Arg Gly Ile Asn Glu Gly Ile Leu Pro
            245                 250                 255

Tyr Ile Thr Arg Ile Tyr Arg Ser Tyr Leu Gly Ser Leu Gln Asn Asp
                260                 265                 270

Ile Gln Asn Arg Ser Gln Lys Phe Glu Ser His Gly Phe Phe Leu Gly
        275                 280                 285

Leu Leu Ala Asn Phe Ile His Leu Tyr Thr Ile Asp Ile Asp Leu Asp
    290                 295                 300

Leu Ser Pro Gly Asn Ser Tyr Val Ala Phe Leu Ile Cys His Gln Ala
305                 310                 315                 320

Glu Arg Glu Asn Ile Pro Ile Val Ile Asn Val Thr Arg Trp Arg Thr
            325                 330                 335

Ser Ser Asp Ile Ala Leu Asn Arg Ala Arg Ala Asp Ala Lys Arg Leu
                340                 345                 350

His Val Ser Ser Phe Ile Ser Ile His Thr Glu Ser Arg Asn Ala Val
        355                 360                 365

Cys Ile Gly Leu Asn Phe Asn Leu Asn Ile Asp Pro Phe Ser Ile Asp
    370                 375                 380

Thr Val Glu Phe Leu Glu Asn Arg Phe Pro Leu Val Gln Arg Leu Phe
385                 390                 395                 400

Glu Cys Leu Glu Asp Glu Gly Ile Arg Glu Asn Ile Arg Asp Phe Leu
            405                 410                 415

Leu Gln His Leu Pro Asn Glu Ile Pro Arg Asn Ala Glu Asn Tyr Asn
                420                 425                 430

Arg Ile Phe Asp Cys Ile Thr Gly Phe Ala Phe Gly Asn Ser Ile Leu
        435                 440                 445

Glu Glu Phe Arg Leu Val Asn Ala Val Gln Gln Arg Val Arg Lys Tyr
    450                 455                 460

Ile Phe Arg Tyr Gly Asp Glu Asn His Ala Leu Thr Met Val Phe His
465                 470                 475                 480

Thr Gln Gly Ser Asp Ile Val Ile Leu His Ile Arg Asp Asn Asn Ala
            485                 490                 495

Val Gln Gln Gly Ala Ile Asn Leu Gln Asp Leu Asn Val Asp Gly Asn
                500                 505                 510

Asn Val His Val Arg Glu Val Ser Cys Thr Leu Asn Asn Gln Leu Gly
        515                 520                 525

Leu Asn Ile His Thr Asp Asn Leu Gly Leu Tyr His Asn Tyr Gln Asn
    530                 535                 540

Asn Asn Ala Asn Asn Phe Leu Gly Gly Asn Leu Val Gln Val Pro Asn
545                 550                 555                 560

Ala Gly Asn Val His Asn Ala Leu Asn Gln Val Met Asn Asp Gly Trp
            565                 570                 575

Gln Asp Arg Phe Gln His Gln Glu Leu Phe Arg Asn Ile Ser Ala Val
                580                 585                 590

Leu Met Pro Glu Asp Thr His Gly Asn Met Ile Ile Asp Val Asn Ser
        595                 600                 605
```

```
Lys Asp Lys Phe Arg Ser Ile Leu His Gly Thr Phe Tyr Ala Ser Asp
    610             615                 620
Asn Pro Tyr Lys Val Leu Ala Met Tyr Lys Val Gly Gln Thr Tyr Ser
625             630                 635                 640
Leu Lys Arg Trp Gln Glu Glu Gly Glu Arg Val Ile Leu Thr Arg
            645                 650                 655
Val Thr Glu Gln Arg Leu Gly Leu Leu Leu Arg Gln Pro Thr Ala
            660                 665                 670
Asp Thr His Pro Ile Gly Tyr Val Leu Gly Phe Ala Asp Asn Ala Glu
        675                 680                 685
Glu Val Glu Gln Glu Gln Asp Glu Ala Arg Tyr Lys Ile Thr Glu Leu
    690                 695                 700
Met Ser Lys Gln Arg Gly Tyr Leu Pro Ile Thr Ser Gly Asn Glu Val
705             710                 715                 720
Val Leu Ser Tyr Ala Val Phe Asn Arg Gly Ala Gln Arg Ala Glu Asp
            725                 730                 735
Phe Ile Ser Leu Pro Gln Gln Ala Val Tyr Val His Arg Leu Asp Arg
            740                 745                 750
Arg Gly His Asp Ser Arg Pro Glu Val Leu Val Gly Pro Glu Ser Val
        755                 760                 765
Ile Asp Glu Asn Pro Pro Glu Asn Leu Leu Ser Asp Gln Thr Arg Glu
770             775                 780
Asn Phe Arg Arg Phe Tyr Met Glu Lys Arg Pro Gly Gln Asn Ser Ile
785             790                 795                 800
Phe Leu Leu Asp Ile Asp Asp Asn Leu His Val Pro Phe Ser Tyr Leu
            805                 810                 815
Gln Gly Thr Arg Ala Gln Ala Ile Glu Thr Leu Arg Ser Arg Ile Arg
            820                 825                 830
Gly Gly Gly Thr Ser Thr Ala Gln Gly Ile Leu Gln Gln Ile Asn Thr
            835                 840                 845
Ile Leu Arg Arg Asn Asn Ala Arg Glu Ile Glu Asp Val His Asn Leu
        850                 855                 860
Leu Ala Leu Asp Phe Ala Thr Glu Asn Gln Asn Phe Arg Tyr Trp Leu
865             870                 875                 880
Gln Thr His Asp Met Phe Phe Ala Ala Arg Gln Tyr Thr Phe His Asp
            885                 890                 895
Asp Arg Ser Asn Pro Thr Asn Asp Arg His Asp Phe Ala Ile Thr Ser
        900                 905                 910
Val Gly Val Asp Gly Asn Gln Asn Asp Pro Thr Gly Arg Asp Leu Leu
        915                 920                 925
Ser Ser Asn Ile Asp Asn Phe Lys Gln Lys Val Asp Ser Gly Glu Lys
    930                 935                 940
Asp Arg Leu Thr Ala Ile Ile Asn Val Gly Asn Arg His Trp Val Thr
945             950                 955                 960
Leu Val Ile Val His Gln Asn Gly Asn Tyr Tyr Gly Tyr Tyr Ala Asp
            965                 970                 975
Ser Leu Gly Pro Asp Ser Arg Ile Asp Asn Asn Ile Arg Gly Ala Leu
        980                 985                 990
Arg Glu Cys Asp Ile Ser Asp Asp Asn Val His Asp Val Ser Val His
        995                 1000                1005
Gln Gln Thr Asp Gly His Asn Cys Gly Ile Trp Ala Tyr Glu Asn
    1010                1015                1020
Ala Arg Asp Ile Asn Gln Ala Ile Asp Gln Ala Leu Gln Gly Asn
```

```
                   1025                1030                1035
Ser Asn Phe Gly Glu Lys Gly Glu Gly Ile Ile Gly Tyr Ile Arg
        1040                1045                1050

Gly Leu Leu Ser Ala Gly Ile Gly Asn Asp Thr Arg Gln Pro Gln
        1055                1060                1065

Arg Asn Glu Gln Tyr Phe Arg Asn Arg Arg Asn Ile Ser Gln
        1070                1075                1080

Leu Phe Gln Asn Asp Ser Leu Ser Ser Pro Arg Gly Arg Leu Ile
        1085                1090                1095

Gln Gly Arg Pro Gly Ile Gln His Glu Ile Asp Pro Leu Leu Leu
        1100                1105                1110

Gln Phe Leu Glu Leu Gln Tyr Pro Gln Arg Gly Gly Gly Gly Ala
        1115                1120                1125

Leu Gln Leu Gly Gly Glu Arg Val Ile Ser Ile Asp Phe Gly Pro
        1130                1135                1140

Gln Ser Val Leu Asp Glu Ile Asp Gly Val Asn Arg Val Tyr Asp
        1145                1150                1155

His Ser Asn Gly Arg Gly Ser Arg
        1160                1165

<210> SEQ ID NO 5
<211> LENGTH: 1476
<212> TYPE: DNA
<213> ORGANISM: Wolbachia pipientis

<400> SEQUENCE: 5
atgccaacac agaaagagct tcgggatacg atgtccaaaa aattacagga agctattaaa      60
catccagatc cagcagttgt tgccgggagg aagtcagcta tcaagagatg ggtgggagtc     120
cttcaagata actttatgga gcacataaaa tactttaagg gtgataagtt gaagttttg     180 cacaatgtat ttcaagatga aggttgctgg tcaggtgtaa ggttggataa tgctgcttta     240
ggtcaaaggt ttactgaaga aaaaatatggt ggaatagata tcccacttcg caaatatgag     300
atggcttgta gttactgtgt ggtggataaa attcatcctc tctttcaaaa aagatttgaa     360
tcttatagga acaagtttcc tcctggtgca tttgatggta aaactgaaac tgaatttggc     420
aaatacgtac gaaactcgtt actagatagc ataagagga aaggtcctgt atttgatttc     480
tggattgata gagaatctgg ggaattaaag aagtatgatg cagtagaagg ttttgacagt     540
gctgtaaaat ttaagtggag tgaaggggta gagtattttt ataatcattt aaaagaagaa     600
gataaggaaa agaagctcac agaagctatt cttgctcttt ctcgcgttca atctgttgag     660
aaagacgccc ctattttaga ttttttgtgta aataagatag tcgataaaga tactctttta     720
cagaaattat cacagaaaga taaggagta tattcccttt ttgctgaatt aatagagtca     780
tgtttttttg atacggttca tgatttggta cagtgctggt gttataaaga gtttcagca     840 ggaggagacc attcagagaa atattctca cagcagagact atgagctttt tctttcctct     900
ctttcagaca caatgttgaa aaatcctgag ttaagcgttc aagctagatc tcttattatg     960
gaattttggg aatgtggtag cttgtatcaa tacagaaaag ctgctgttaa tacttctaat    1020
tatacagttc ctacaagtgg tgtatttgca gagttaatag tcaattggag acgagaagac    1080
atttataaga ctgatgaaga aaagagaata gagaaaaaag aaatattaga tatgatgtca    1140
tttgccaaag attgctttcc tgaaaagttt gagctcttta aaaaactaat aataagagac    1200
cttagattat gcggtaggga aggtaaaaga gtaaatgtag attacggtct gtttgcagaa    1260
```

```
gaattattct ctgagttaga gaaaacaatt ttaccacctg gtcctgtagg tgatggtcct    1320
tgcagtaatt tgcgatcacg atctaaagct catggtagta agaaaacaac tttgccagtt    1380
gatgatagtc cgcagtctga gcttggaact cctagtgtaa gtggtgtttc ttcttataag    1440
aaaaaaagcg tctttacgct tagtggtaat aagtaa                              1476
```

<210> SEQ ID NO 6
<211> LENGTH: 491
<212> TYPE: PRT
<213> ORGANISM: Wolbachia pipientis

<400> SEQUENCE: 6

```
Met Pro Thr Gln Lys Glu Leu Arg Asp Thr Met Ser Lys Lys Leu Gln
1               5                   10                  15

Glu Ala Ile Lys His Pro Asp Pro Ala Val Val Ala Gly Arg Lys Ser
            20                  25                  30

Ala Ile Lys Arg Trp Val Gly Val Leu Gln Asp Asn Phe Met Glu His
        35                  40                  45

Ile Lys Tyr Phe Lys Gly Asp Lys Leu Lys Phe Leu His Asn Val Phe
    50                  55                  60

Gln Asp Glu Gly Cys Trp Ser Gly Val Arg Leu Asp Asn Ala Ala Leu
65                  70                  75                  80

Gly Gln Arg Phe Thr Glu Glu Lys Ile Gly Gly Ile Asp Asn Pro Leu
                85                  90                  95

Arg Lys Tyr Glu Met Ala Cys Ser Tyr Cys Val Val Asp Lys Ile His
            100                 105                 110

Pro Leu Phe Gln Lys Arg Phe Glu Ser Tyr Arg Asn Lys Phe Pro Pro
        115                 120                 125

Gly Ala Phe Asp Gly Lys Thr Glu Thr Glu Phe Gly Lys Tyr Val Arg
    130                 135                 140

Asn Ser Leu Leu Asp Ser Ile Lys Arg Lys Gly Pro Val Phe Asp Phe
145                 150                 155                 160

Trp Ile Asp Arg Glu Ser Gly Glu Leu Lys Lys Tyr Asp Ala Val Glu
                165                 170                 175

Gly Phe Asp Ser Ala Val Lys Phe Lys Trp Ser Glu Gly Val Glu Tyr
            180                 185                 190

Phe Tyr Asn His Leu Lys Glu Glu Asp Lys Glu Lys Lys Leu Thr Glu
        195                 200                 205

Ala Ile Leu Ala Leu Ser Arg Val Gln Ser Val Glu Lys Asp Ala Pro
    210                 215                 220

Ile Leu Asp Phe Cys Val Asn Lys Ile Val Asp Lys Asp Thr Leu Leu
225                 230                 235                 240

Gln Lys Leu Ser Gln Lys Asp Lys Gly Val Tyr Ser Leu Phe Ala Glu
                245                 250                 255

Leu Ile Glu Ser Cys Phe Phe Asp Thr Val His Asp Leu Val Gln Cys
            260                 265                 270

Trp Cys Tyr Lys Glu Val Ser Ala Gly Gly Asp His Ser Glu Lys Ile
        275                 280                 285

Phe Ser Gln Arg Asp Tyr Glu Leu Phe Leu Ser Ser Leu Ser Asp Thr
    290                 295                 300

Met Leu Lys Asn Pro Glu Leu Ser Val Gln Ala Arg Ser Leu Ile Met
305                 310                 315                 320

Glu Phe Trp Glu Cys Gly Ser Leu Tyr Gln Tyr Arg Lys Ala Ala Val
                325                 330                 335
```

```
Asn Thr Ser Asn Tyr Thr Val Pro Thr Ser Gly Val Phe Ala Glu Leu
            340                 345                 350

Ile Val Asn Trp Arg Arg Glu Asp Ile Tyr Lys Thr Asp Glu Glu Lys
    355                 360                 365

Glu Ile Glu Lys Lys Glu Ile Leu Asp Met Met Ser Phe Ala Lys Asp
    370                 375                 380

Cys Phe Pro Glu Lys Phe Glu Leu Phe Lys Lys Leu Ile Ile Arg Asp
385                 390                 395                 400

Leu Arg Leu Cys Gly Arg Glu Gly Lys Arg Val Asn Val Asp Tyr Gly
            405                 410                 415

Leu Phe Ala Glu Glu Leu Phe Ser Glu Leu Glu Lys Thr Ile Leu Pro
            420                 425                 430

Pro Gly Pro Val Gly Asp Gly Pro Cys Ser Asn Leu Arg Ser Arg Ser
            435                 440                 445

Lys Ala His Gly Ser Lys Lys Thr Thr Leu Pro Val Asp Asp Ser Pro
    450                 455                 460

Gln Ser Glu Leu Gly Thr Pro Ser Val Ser Gly Val Ser Ser Tyr Lys
465                 470                 475                 480

Lys Lys Ser Val Phe Thr Leu Ser Gly Asn Lys
            485                 490

<210> SEQ ID NO 7
<211> LENGTH: 3525
<212> TYPE: DNA
<213> ORGANISM: Wolbachia pipientis

<400> SEQUENCE: 7
atgagtaatg gtgatggact tattaggagt ttggtggatg agatcttga aggattcaga      60
caaggatttg aatctttttt agatcaatgt ccatctttct tgtatcatgt aagtgcaggt     120
cgtttccttc ctgtattctt ttttagtatg ttttctactg cacatgatgc taatatctta     180
aatgcaaatg agagagtcta ttttcgtttt gataaccatg tgttaatcc acgtaatggt     240
gaaaatcgaa atacggcaaa cctaaaagtt gctgtttatc gtgacggaca gcaagttgtc     300
agatgctaca gtatttctga tcgtcctaat agtgatgggt tgaggttcag tacaagggag     360
agaaatgctc tagtacaaga gattagacgg caaaatccaa atttaaggga agaagaccta     420
aattttgagc aatacaaagt atgcatgcac ggaaagggca agtcagggg agaggcaatt     480
gcaacggtat tcgaggtaat tcgtgaaaaa gatcgtcaag gtagggataa atttgccaaa     540
tattcagcat ctgaggttca tttcttgagg caactcttta gaaatcacag attaacaatt     600
aaggaaatag aaggaagaca actcaatcaa aatcagctca gacaacttgg taggtcagtc     660
aattttacac gagtagaacc aggtcagcag aggattgaca actttatgga aatgctagca     720
agtaaccaaa gacaagatgt aagggattct ctccgaggag atattttaga atatgtaact     780
gatacctata caattatag ggcacagata gaaaataata ttgaaggtcg cagtcaaaag     840
tttgagagtc atgggttttt attaggtttc ttagcaaatt ttagtcatcg ctacacaata     900
ggcgtcgatc ttgacttatc tcctagaaac tcacatgttg catttcttgt acgtcatcaa     960
gtagaaagag aaaatattcc tattgttatt aatcttgcta caagggcacc gccctatatc    1020
gcattaaacc gcgccagaag tcacgctgaa agattgcatg tttttcatt tataccctatc    1080
catactgaat caagaaatac tgtctgtgtt ggattaaatt ttaatttaaa tctagatcct    1140
tttagtgttg atacagtagg gcttcaacag gatagatttc ctttagtaca agattatttt    1200
gagtgtttgg agaatgaagg aattagagaa atattagag atttcttgct tcaccatctt    1260
```

```
cctgctgaaa taccaagaaa tgcagagaat tatgatagaa tatttgattg cataactggt    1320
tttgcttttg ggaatagtgc tttttgatagg caccctttag aactagaaga ggaagacgaa    1380
gcacctataa caaagtacat atttagacat ggtgatgagg gtttaagatg tttaactatg    1440
gtctttcatg ctgaaggttc tgatatagtt atacttcata ttagagctca cgatgcgcaa    1500
caacaaggag ccatcaattt acagactctt aatgttaatg gaaatgatgt tcatgtgtgg    1560
gaagtttcat gcacacttaa taatcaactt gaactagata ttgatctacc aaatgacctt    1620
ggtttatatc acgattacca aaataataat gcaaataatt ttcttgctgg tgatcttgta    1680
caagtgccca atactgaaaa tgtacataat actttaaatc aagttgtgaa tgatggctgg    1740
aaaaatatag ctcagcatag aggattattt caagagatct ctggagcatt gatgccgctt    1800
gtggatacaa taaatgttaa tagtgaggat aagttccgtt ctatactaca tggtacattt    1860
tatgctagtg ataatcctta taaagtgctt gctatgtata agttggtca aacatatagt    1920 ttaaaagggg ggcaggaaga agaaggagaa agggtaatac tcacaagaat tacagaacag    1980
agattagatc ttttattatt aagacaacct agagagaatg acctagatac tcacccaatt    2040
ggatatgtgt taagacttgc taataatgca gaagaagtag gacaacagca aaatgatgcg    2100
agacaagaaa tcggaagact taagaaacaa cacagaggat ttatacctat tacttctgga    2160
aatgaggtgg ttttgtttcc tattgtgttt aatagagatg cacacgaagc aggtaatctt    2220
atacttttcc cagaagggat aggaagagaa gagcatgtac acaggcttga tcgtcatgtt    2280
cgcagctcaa gaccaggagg attagtggga cctgaaagtg ttattgatga aaatccacca    2340
gaaggtctat tatcagatca gactcgtgaa aactttaggc gttttacga agaaaaagca    2400 ccaggacaaa attcgatttt tttgcttgat ataggcgaca atctacatgt tccctttagt    2460
tacttgcaag gtactagagc acaggtaata gaaacattaa agtcaagaat aaggggaggt    2520
ggtactccta cagcacaagg aatattacaa caaataaatg ctatccttcg tagaaacaac    2580
gctcgtgaga tagaagatgt gcatgatcta cttgcactag actttgcaac agataatcaa    2640
aattatcgtt attggctaca aactcatgac atgttttcg ctgcacgaca atatactttc    2700
cttgataatc aatctcattc aactaatgat cattatggtt ttgaaataac ttcagtagga    2760
gtcgatggaa atcaaaatga tccaacaggt aggggcttat taagtagtca cataactaac    2820
tttaaacaaa aagtagattc gggtgaaaaa gatagattaa ttgctattat taatgtaggt    2880
aatcgtcatt gggttacatt agttattgta caccaaaatg gaaattatta tgggtattat    2940
gctgattcac ttggtccaga tagtggtatt gacaataata ttcgaggagc tttaagagaa    3000
tgtgatatta cgatgataa tgtccataat atttccgttc atcagcaaac agatggccat    3060
aattgtggca tatgggtata cgaaaatgct agggatatta ccaagctat tgatcaagct    3120 ttacagggaa ataataactt tggagagaaa ggtgaaggta ttataggtta tatacgtggt    3180
cttcttagtg caggcattgg aaatgacact agacaacctc gaagaaatga acaatacttt    3240
gaagatcgga gaagagatat ttcacaatta ctccaaaatg atcctaactt accttctcgc    3300
cggagtgatt taattcaagc tcatccagga attcaacatg aaattgatcc attactatta    3360
caatttttag gactccaata cccacagcgt ggaggtggag gagcattaca attaggcgga    3420
gaaagagtga tatcaattga ttttggtaac ccgcagtctg cattagataa aattgatgga    3480
gtgagtagag tttataacca tagcaatagt agaggtagta ggtag             3525
```

<210> SEQ ID NO 8

```
<211> LENGTH: 1174
<212> TYPE: PRT
<213> ORGANISM: Wolbachia pipientis

<400> SEQUENCE: 8

Met Ser Asn Gly Asp Gly Leu Ile Arg Ser Leu Val Asp Gly Asp Leu
1               5                   10                  15

Glu Gly Phe Arg Gln Gly Phe Glu Ser Phe Leu Asp Gln Cys Pro Ser
            20                  25                  30

Phe Leu Tyr His Val Ser Ala Gly Arg Phe Leu Pro Val Phe Phe Phe
        35                  40                  45

Ser Met Phe Ser Thr Ala His Asp Ala Asn Ile Leu Asn Ala Asn Glu
    50                  55                  60

Arg Val Tyr Phe Arg Phe Asp Asn His Gly Val Asn Pro Arg Asn Gly
65                  70                  75                  80

Glu Asn Arg Asn Thr Ala Asn Leu Lys Val Ala Val Tyr Arg Asp Gly
                85                  90                  95

Gln Gln Val Val Arg Cys Tyr Ser Ile Ser Asp Arg Pro Asn Ser Asp
            100                 105                 110

Gly Leu Arg Phe Ser Thr Arg Glu Arg Asn Ala Leu Val Gln Glu Ile
        115                 120                 125

Arg Arg Gln Asn Pro Asn Leu Arg Glu Glu Asp Leu Asn Phe Glu Gln
130                 135                 140

Tyr Lys Val Cys Met His Gly Lys Gly Lys Ser Gln Gly Glu Ala Ile
145                 150                 155                 160

Ala Thr Val Phe Glu Val Ile Arg Glu Lys Asp Arg Gln Gly Arg Asp
                165                 170                 175

Lys Phe Ala Lys Tyr Ser Ala Ser Glu Val His Phe Leu Arg Gln Leu
            180                 185                 190

Phe Arg Asn His Arg Leu Thr Ile Lys Glu Ile Glu Gly Arg Gln Leu
        195                 200                 205

Asn Gln Asn Gln Leu Arg Gln Leu Gly Arg Ser Val Asn Phe Thr Arg
    210                 215                 220

Val Glu Pro Gly Gln Gln Arg Ile Asp Asn Phe Met Glu Met Leu Ala
225                 230                 235                 240

Ser Asn Gln Arg Gln Asp Val Arg Asp Ser Leu Arg Gly Asp Ile Leu
                245                 250                 255

Glu Tyr Val Thr Asp Thr Tyr Asn Asn Tyr Arg Ala Gln Ile Glu Asn
            260                 265                 270

Asn Ile Glu Gly Arg Ser Gln Lys Phe Glu Ser His Gly Phe Leu Leu
        275                 280                 285

Gly Phe Leu Ala Asn Phe Ser His Arg Tyr Thr Ile Gly Val Asp Leu
    290                 295                 300

Asp Leu Ser Pro Arg Asn Ser His Val Ala Phe Leu Val Arg His Gln
305                 310                 315                 320

Val Glu Arg Glu Asn Ile Pro Ile Val Ile Asn Leu Ala Thr Arg Ala
                325                 330                 335

Pro Pro Tyr Ile Ala Leu Asn Arg Ala Arg Ser His Ala Glu Arg Leu
            340                 345                 350

His Val Phe Ser Phe Ile Pro Ile His Thr Glu Ser Arg Asn Thr Val
        355                 360                 365

Cys Val Gly Leu Asn Phe Asn Leu Asn Leu Asp Pro Phe Ser Val Asp
    370                 375                 380

Thr Val Gly Leu Gln Gln Asp Arg Phe Pro Leu Val Gln Arg Leu Phe
```

```
385                 390                 395                 400
Glu Cys Leu Glu Asn Glu Gly Ile Arg Glu Asn Ile Arg Asp Phe Leu
                405                 410                 415
Leu His His Leu Pro Ala Glu Ile Pro Arg Asn Ala Glu Asn Tyr Asp
                420                 425                 430
Arg Ile Phe Asp Cys Ile Thr Gly Phe Ala Phe Gly Asn Ser Ala Phe
                435                 440                 445
Asp Arg His Pro Leu Glu Leu Glu Glu Asp Glu Ala Pro Ile Thr
        450                 455                 460
Lys Tyr Ile Phe Arg His Gly Asp Glu Gly Leu Arg Cys Leu Thr Met
465                 470                 475                 480
Val Phe His Ala Glu Gly Ser Asp Ile Val Ile Leu His Ile Arg Ala
                485                 490                 495
His Asp Ala Gln Gln Gln Gly Ala Ile Asn Leu Gln Thr Leu Asn Val
                500                 505                 510
Asn Gly Asn Asp Val His Val Trp Glu Val Ser Cys Thr Leu Asn Asn
                515                 520                 525
Gln Leu Glu Leu Asp Ile Asp Leu Pro Asn Asp Leu Gly Leu Tyr His
        530                 535                 540
Asp Tyr Gln Asn Asn Asn Ala Asn Asn Phe Leu Ala Gly Asp Leu Val
545                 550                 555                 560
Gln Val Pro Asn Thr Glu Asn Val His Asn Thr Leu Asn Gln Val Val
                565                 570                 575
Asn Asp Gly Trp Lys Asn Ile Ala Gln His Arg Gly Leu Phe Gln Glu
                580                 585                 590
Ile Ser Gly Ala Leu Met Pro Leu Val Asp Thr Ile Asn Val Asn Ser
        595                 600                 605
Glu Asp Lys Phe Arg Ser Ile Leu His Gly Thr Phe Tyr Ala Ser Asp
        610                 615                 620
Asn Pro Tyr Lys Val Leu Ala Met Tyr Lys Val Gly Gln Thr Tyr Ser
625                 630                 635                 640
Leu Lys Arg Gly Gln Glu Glu Gly Glu Arg Val Ile Leu Thr Arg
                645                 650                 655
Ile Thr Glu Gln Arg Leu Asp Leu Leu Leu Arg Gln Pro Arg Glu
                660                 665                 670
Asn Asp Leu Asp Thr His Pro Ile Gly Tyr Val Leu Arg Leu Ala Asn
        675                 680                 685
Asn Ala Glu Glu Val Gly Gln Gln Gln Asn Asp Ala Arg Gln Glu Ile
        690                 695                 700
Gly Arg Leu Lys Lys Gln His Arg Gly Phe Ile Pro Ile Thr Ser Gly
705                 710                 715                 720
Asn Glu Val Val Leu Phe Pro Ile Val Phe Asn Arg Asp Ala His Glu
                725                 730                 735
Ala Gly Asn Leu Ile Leu Phe Pro Glu Gly Ile Gly Arg Glu Glu His
                740                 745                 750
Val His Arg Leu Asp Arg His Val Arg Ser Arg Pro Gly Gly Leu
                755                 760                 765
Val Gly Pro Glu Ser Val Ile Asp Glu Asn Pro Pro Glu Gly Leu Leu
        770                 775                 780
Ser Asp Gln Thr Arg Glu Asn Phe Arg Arg Phe Tyr Glu Glu Lys Ala
785                 790                 795                 800
Pro Gly Gln Asn Ser Ile Phe Leu Leu Asp Ile Gly Asp Asn Leu His
                805                 810                 815
```

Val Pro Phe Ser Tyr Leu Gln Gly Thr Arg Ala Gln Val Ile Glu Thr
            820                 825                 830

Leu Lys Ser Arg Ile Arg Gly Gly Thr Pro Thr Ala Gln Gly Ile
    835                 840                 845

Leu Gln Gln Ile Asn Ala Ile Leu Arg Arg Asn Asn Ala Arg Glu Ile
850                 855                 860

Glu Asp Val His Asp Leu Leu Ala Leu Asp Phe Ala Thr Asp Asn Gln
865                 870                 875                 880

Asn Tyr Arg Tyr Trp Leu Gln Thr His Asp Met Phe Phe Ala Ala Arg
                885                 890                 895

Gln Tyr Thr Phe Leu Asp Asn Gln Ser His Ser Thr Asn Asp His Tyr
            900                 905                 910

Gly Phe Glu Ile Thr Ser Val Gly Val Asp Gly Asn Gln Asn Asp Pro
        915                 920                 925

Thr Gly Arg Gly Leu Leu Ser Ser His Ile Thr Asn Phe Lys Gln Lys
    930                 935                 940

Val Asp Ser Gly Glu Lys Asp Arg Leu Ile Ala Ile Asn Val Gly
945                 950                 955                 960

Asn Arg His Trp Val Thr Leu Val Ile Val His Gln Asn Gly Asn Tyr
                965                 970                 975

Tyr Gly Tyr Tyr Ala Asp Ser Leu Gly Pro Asp Ser Gly Ile Asp Asn
            980                 985                 990

Asn Ile Arg Gly Ala Leu Arg Glu Cys Asp Ile Asn Asp Asp Asn Val
        995                 1000                1005

His Asn Ile Ser Val His Gln Gln Thr Asp Gly His Asn Cys Gly
    1010                1015                1020

Ile Trp Val Tyr Glu Asn Ala Arg Asp Ile Asn Gln Ala Ile Asp
    1025                1030                1035

Gln Ala Leu Gln Gly Asn Asn Asn Phe Gly Glu Lys Gly Glu Gly
    1040                1045                1050

Ile Ile Gly Tyr Ile Arg Gly Leu Leu Ser Ala Gly Ile Gly Asn
    1055                1060                1065

Asp Thr Arg Gln Pro Arg Arg Asn Glu Gln Tyr Phe Glu Asp Arg
    1070                1075                1080

Arg Arg Asp Ile Ser Gln Leu Leu Gln Asn Asp Pro Asn Leu Pro
    1085                1090                1095

Ser Arg Arg Ser Asp Leu Ile Gln Ala His Pro Gly Ile Gln His
    1100                1105                1110

Glu Ile Asp Pro Leu Leu Leu Gln Phe Leu Gly Leu Gln Tyr Pro
    1115                1120                1125

Gln Arg Gly Gly Gly Gly Ala Leu Gln Leu Gly Gly Glu Arg Val
    1130                1135                1140

Ile Ser Ile Asp Phe Gly Asn Pro Gln Ser Ala Leu Asp Lys Ile
    1145                1150                1155

Asp Gly Val Ser Arg Val Tyr Asn His Ser Asn Ser Arg Gly Ser
    1160                1165                1170

Arg

<210> SEQ ID NO 9
<211> LENGTH: 1371
<212> TYPE: DNA
<213> ORGANISM: Wolbachia pipientis

<400> SEQUENCE: 9

```
atgccaaaaa agatggagcg tcatgctgca gtgcttagta agttaaagag tgttattcaa    60
catacagatt ccaaggtcat ggctgaaagg cgttcagcta ttgaaagatg ggtaaaaact   120
tacattaggc aggtagaata tcttaaagat gataagctac aattcttata acacatattt   180
cgcgatgaaa gttgttggtc aggtacgaga ttgaacaata caatcttagg acagaggttt   240
actgaagaaa aaataggcga aataaagaac cctcttccta tatatgatat ggcatgtcga   300
tactgcgtga tagataaaat tcctttgctc tttcagaagc agtttgaatc ttacaaaagt   360
agcttctctt ctgaagagat agatgatgat ggtaagcctg caactagcaa taacaaatat   420
gtaaagagtg agttgttggg ttatatgaag agtcaagacc ctgtatttag cttttgggtt   480
gataaaaaat ctggagaatt taagaagcat gtcagcgcaa cagaaggatt taagaaagct   540
atagaactta agtggagcga aggagtagaa tattttttata gccttctaaa tgaaaaagaa   600
agagaaagag aaaggaaaat tactgatgca gttactatat tatcctctgt tcaatgtgac   660
cataatggtg ctgttacttt agacttttgt cttagtaaaa tgagcgatca agcaaaaaac   720
aagctgttta agattctga gctatcaaaa aaagataaag gagtgtactc tctctttagc   780
gcgttgatac atcaaggttt ttttgatacg atgcaagcta tacttccgat gtttaaagat   840
aaaatactgg aggataagat actttcacct aggagttata ctcttcttct ctcctcactt   900
tcggacatga tgctcgaaaa ttctgagtca actattcaag ctagggaagc tataatgaac   960
cttataaagt gtggtaattt caataatcat gagggggcgtg aggaaaaagc tgcggtattt  1020
ttttctaatg aagggggttcc gattaagcgt gcgcttgcag gattgattgt cgattggcaa  1080
cttggttgta caaaaaagga agaggtgtta aaggtactac agtttgccaa agagtttttgt  1140
gcagttgaaa gttttatgta tttttaaaaaa tctgttgttg ataacctaaa atggttggt   1200
agggatggta tgagaaaaaa tatagactat ggtaaattag cagaaaagtt gtttgctgaa  1260
ttagatacgg tatccgtgcc taacggaaga ggtgattttg gtggagctgg tgacccacag  1320
tctacactag gaagcactga agttagtagt ttttctggtc gcaataagta g           1371
```

<210> SEQ ID NO 10
<211> LENGTH: 456
<212> TYPE: PRT
<213> ORGANISM: Wolbachia pipientis

<400> SEQUENCE: 10

```
Met Pro Lys Lys Met Glu Arg His Ala Ala Val Leu Ser Lys Leu Lys
1               5                   10                  15

Ser Val Ile Gln His Thr Asp Ser Lys Val Met Ala Glu Arg Arg Ser
            20                  25                  30

Ala Ile Glu Arg Trp Val Lys Thr Tyr Ile Arg Gln Val Glu Tyr Leu
        35                  40                  45

Lys Asp Asp Lys Leu Gln Phe Leu Tyr Asn Ile Phe Arg Asp Glu Ser
    50                  55                  60

Cys Trp Ser Gly Thr Arg Leu Asn Asn Thr Ile Leu Gly Gln Arg Phe
65                  70                  75                  80

Thr Glu Glu Lys Ile Gly Glu Ile Lys Asn Pro Leu Pro Ile Tyr Asp
                85                  90                  95

Met Ala Cys Arg Tyr Cys Val Ile Asp Lys Ile Pro Leu Leu Phe Gln
            100                 105                 110

Lys Gln Phe Glu Ser Tyr Lys Ser Ser Phe Ser Glu Glu Ile Asp
        115                 120                 125
```

Asp Asp Gly Lys Pro Ala Thr Ser Asn Asn Lys Tyr Val Lys Ser Glu
        130                 135                 140

Leu Leu Gly Tyr Met Lys Ser Gln Asp Pro Val Phe Ser Phe Trp Val
145                 150                 155                 160

Asp Lys Lys Ser Gly Glu Phe Lys Lys His Val Ser Ala Thr Glu Gly
                165                 170                 175

Phe Lys Lys Ala Ile Glu Leu Lys Trp Ser Glu Gly Val Glu Tyr Phe
                180                 185                 190

Tyr Ser Leu Leu Asn Glu Lys Glu Arg Glu Arg Glu Lys Ile Thr
            195                 200                 205

Asp Ala Val Thr Ile Leu Ser Ser Val Gln Cys Asp His Asn Gly Ala
        210                 215                 220

Val Thr Leu Asp Phe Cys Leu Ser Lys Met Ser Asp Gln Ala Lys Asn
225                 230                 235                 240

Lys Leu Phe Lys Asp Ser Glu Leu Ser Lys Lys Asp Lys Gly Val Tyr
                245                 250                 255

Ser Leu Phe Ser Ala Leu Ile His Gln Gly Phe Phe Asp Thr Met Gln
            260                 265                 270

Ala Ile Leu Pro Met Phe Lys Asp Lys Ile Leu Glu Asp Lys Ile Leu
        275                 280                 285

Ser Pro Arg Ser Tyr Thr Leu Leu Ser Ser Leu Ser Asp Met Met
290                 295                 300

Leu Glu Asn Ser Glu Ser Thr Ile Gln Ala Arg Glu Ala Ile Met Asn
305                 310                 315                 320

Leu Ile Lys Cys Gly Asn Phe Asn Asn His Glu Gly Arg Glu Lys
                325                 330                 335

Ala Ala Val Phe Phe Ser Asn Gly Arg Val Pro Ile Lys Arg Ala Leu
                340                 345                 350

Ala Gly Leu Ile Val Asp Trp Gln Leu Gly Cys Thr Lys Lys Glu Glu
            355                 360                 365

Val Leu Lys Val Leu Gln Phe Ala Lys Glu Phe Cys Ala Val Glu Ser
        370                 375                 380

Phe Met Tyr Phe Lys Lys Ser Val Val Asp Asn Leu Lys Met Val Gly
385                 390                 395                 400

Arg Asp Gly Met Arg Lys Asn Ile Asp Tyr Gly Lys Leu Ala Glu Lys
                405                 410                 415

Leu Phe Ala Glu Leu Asp Thr Val Ser Val Pro Asn Gly Arg Gly Asp
            420                 425                 430

Phe Gly Gly Ala Gly Asp Pro Gln Ser Thr Leu Gly Ser Thr Glu Val
        435                 440                 445

Ser Ser Phe Ser Gly Arg Asn Lys
    450                 455

<210> SEQ ID NO 11
<211> LENGTH: 2265
<212> TYPE: DNA
<213> ORGANISM: Wolbachia pipientis

<400> SEQUENCE: 11
atgcatgggt tagttagaag tttaataaat ggaaattgtg gagaattcac ggaaaagttt    60
gaatatttct tggattcatg tccatctttt ctgcattcag ttggcaaaga tcacttttt   120 cctgcgttct tttttggcat gtttgctact gcacatgatt ctggtgttgc aaacaatgat   180
gaaagaatct tctttcgttt tgataatgat ccaggtagtc ctggaagggg aaatctaaag   240

-continued

| | |
|---|---|
| gttgcaattc taacaactga tggaaataac agaagagttg taaggtgcta tactattgct | 300 |
| gacagagaga atagctacgg ttctaggttt agccagcagg aaagggagca gctggaaggt | 360 |
| atcctgcgag atgaagagct tgaatggcaa gagtataaaa catttatatg gcggataat | 420 |
| caaggtgaag atgaagaaga ggaagcagta agatgtagga tatttcaggc aggacaaggg | 480 |
| ccgtttactg gaaatcatgc atcttattta actcgtagac atagttttca agagattacc | 540 |
| agaacacctg gctgcaaaaa taattattta ccggatttga tgaatcagct agaaagtgat | 600 |
| gatgcagatg atgtacacga cactactgag gaagtgtttc agcatattat tggtgtctac | 660 |
| gatagatata gtcaggcatt ggacttctat ggtagagagt ctgactatca tggttttgtt | 720 |
| tccggtgttt tgatgcattt tagatatcgc aatgtagcca atatttacct tgagctgttt | 780 |
| gtaggtggtg gatatgcaga tattacttct attgtacgtg gtacacagag gttaattaat | 840 |
| tctgttccct gtgtaactga acttaaggca ggcagaagag cagataggaa tgctggccgt | 900 |
| gcattagagc aggctggaaa ttatgttaat ggatgtcccg tttcatccat atctattcca | 960 |
| acattatcac caagagctgt ctccgctgga gtgaatttcg attttggtaa cccaggacgt | 1020 |
| ttacagcttg gtgtgagggc tttttttagca aaaggttctt ctttaatgga aagattattt | 1080 |
| gaacctgtag aggatgagga gattggagaa atgttaggg attatctact ccatccagcc | 1140 |
| tttggtgtac ctgctgtacc aggtattagg aataggggtg gtgttaacgc tagagataga | 1200 |
| agaatatttc tctatacaag tggatttgct ttcgcaagta ttgcatttgc aaaaggaact | 1260 |
| gtgccaatag aaggaaatcg tgcaatagta gataagcact gtttcacta tgacggtaat | 1320 |
| gcaaaaatgt tagatgagca aagatacaat acacaagtaa atattggaga tcgtgctttg | 1380 |
| actatggttt tgcatgtatc acgaggtaga gaccagaagg aggaggtgat cgtatttcat | 1440 |
| gttcgccacg tattggctaa tcaactttt ccggacaatg gattggatct atcgcgttgg | 1500 |
| ccgaatgcta tggtacatga agtggtgtgt aatttgacca taaatagaag gacaagagga | 1560 |
| gtaaatgata atcttggttt aactgttaat gtagaaacat ttgactcgcc tgctgactac | 1620 |
| ctgcttgata gaggtaatca gccttttcaa ggtgagcttt tacgaatagg tggcgttagt | 1680 |
| aatgtgcatc gcgctgcaaa tgtaatgatg aatactggct gggaaaatga agatccagac | 1740 |
| agtcatgaac ggttttacca agcaatttcc aacgtgctaa atccacccca gccaaataat | 1800 |
| gcaggactcc aatcattagc atgggtagtg aacagagata tgctagaga agctgggttt | 1860 |
| catgctgcat tgcatggatt attttacact tgcgataatc ctgctagggt agttagtgaa | 1920 |
| tttcaggttg gaggaggagg aaagttagac ttagtattgt cacgagctat aggaaggatg | 1980 |
| ggaggtactt atccgattgg aacagagcta agtttgctg ccactgaagc agacgtacaa | 2040 |
| aatagagaag aagaagcaga tgaacaggtg gagggttatc tgcagagtag agggtttgat | 2100 |
| cgcattactg atggagataa aatggttttc tcgtatgccg tatttaatga tcaagcgcca | 2160 |
| gcaccagcac aaaatgtccc aaatacccctt atagcagtta gtaatgttct acgcataaaa | 2220 |
| gataacttag gaattgacac tgtggacgac tttccttata gataa | 2265 |

<210> SEQ ID NO 12
<211> LENGTH: 754
<212> TYPE: PRT
<213> ORGANISM: Wolbachia pipientis

<400> SEQUENCE: 12

Met His Gly Leu Val Arg Ser Leu Ile Asn Gly Asn Cys Gly Glu Phe
1               5                   10                  15

```
Thr Glu Lys Phe Glu Tyr Phe Leu Asp Ser Cys Pro Ser Phe Leu His
             20                  25                  30

Ser Val Gly Lys Asp His Phe Pro Ala Phe Phe Gly Met Phe
         35                  40                  45

Ala Thr Ala His Asp Ser Gly Val Ala Asn Asn Asp Glu Arg Ile Phe
     50                  55                  60

Phe Arg Phe Asp Asn Asp Pro Gly Ser Pro Gly Arg Gly Asn Leu Lys
 65                  70                  75                  80

Val Ala Ile Leu Thr Thr Asp Gly Asn Asn Arg Arg Val Val Arg Cys
                 85                  90                  95

Tyr Thr Ile Ala Asp Arg Glu Asn Ser Tyr Gly Ser Arg Phe Ser Gln
             100                 105                 110

Gln Glu Arg Glu Gln Leu Glu Gly Ile Leu Arg Asp Glu Glu Leu Glu
         115                 120                 125

Trp Gln Glu Tyr Lys Thr Phe Ile Trp Ala Asp Asn Gln Gly Glu Asp
 130                 135                 140

Glu Glu Glu Glu Ala Val Arg Cys Arg Ile Phe Gln Ala Gly Gln Gly
145                 150                 155                 160

Pro Phe Thr Gly Asn His Ala Ser Tyr Leu Thr Arg Arg His Ser Phe
             165                 170                 175

Gln Glu Ile Thr Arg Thr Pro Gly Leu Gln Asn Asn Tyr Leu Pro Asp
         180                 185                 190

Leu Met Asn Gln Leu Glu Ser Asp Asp Ala Asp Asp Val His Asp Thr
     195                 200                 205

Thr Glu Glu Val Phe Gln His Ile Ile Gly Val Tyr Asp Arg Tyr Ser
210                 215                 220

Gln Ala Leu Asp Phe Tyr Gly Arg Glu Ser Asp Tyr His Gly Phe Val
225                 230                 235                 240

Ser Gly Val Leu Met His Phe Arg Tyr Arg Asn Val Ala Asn Ile Tyr
             245                 250                 255

Leu Glu Leu Phe Val Gly Gly Tyr Ala Asp Ile Thr Ser Ile Val
         260                 265                 270

Arg Gly Thr Gln Arg Leu Ile Asn Ser Val Pro Cys Val Thr Glu Leu
     275                 280                 285

Lys Ala Gly Arg Arg Ala Asp Arg Asn Ala Gly Arg Ala Leu Glu Gln
290                 295                 300

Ala Gly Asn Tyr Val Asn Gly Cys Pro Val Ser Ile Ser Ile Pro
305                 310                 315                 320

Thr Leu Ser Pro Arg Ala Val Ser Ala Gly Val Asn Phe Asp Phe Gly
             325                 330                 335

Asn Pro Gly Arg Leu Gln Leu Gly Val Arg Ala Phe Leu Ala Lys Gly
         340                 345                 350

Ser Ser Leu Met Glu Arg Leu Phe Glu Pro Val Glu Asp Glu Ile
     355                 360                 365

Gly Glu Asn Val Arg Asp Tyr Leu Leu His Pro Ala Phe Gly Val Pro
370                 375                 380

Ala Val Pro Gly Ile Arg Asn Arg Gly Val Asn Ala Arg Asp Arg
385                 390                 395                 400

Arg Ile Phe Leu Tyr Thr Ser Gly Phe Ala Phe Ala Ser Ile Ala Phe
             405                 410                 415

Ala Lys Gly Thr Val Pro Ile Glu Gly Asn Arg Ala Ile Val Asp Lys
         420                 425                 430

His Leu Phe His Tyr Asp Gly Asn Ala Lys Met Leu Asp Glu Gln Arg
```

Tyr Asn Thr Gln Val Asn Ile Gly Asp Arg Ala Leu Thr Met Val Leu
435                 440                 445
                450                                 455                 460

His Val Ser Arg Gly Arg Asp Gln Lys Glu Glu Val Ile Val Phe His
465                 470                 475                 480

Val Arg His Val Leu Ala Asn Gln Leu Phe Pro Asp Asn Gly Leu Asp
                485                 490                 495

Leu Ser Arg Trp Pro Asn Ala Met Val His Glu Val Val Cys Asn Leu
                500                 505                 510

Thr Ile Asn Arg Arg Thr Arg Gly Val Asn Asp Asn Leu Gly Leu Thr
                515                 520                 525

Val Asn Val Glu Thr Phe Asp Ser Pro Ala Asp Tyr Leu Leu Asp Arg
530                 535                 540

Gly Asn Gln Pro Phe Gln Gly Glu Leu Leu Arg Ile Gly Gly Val Ser
545                 550                 555                 560

Asn Val His Arg Ala Ala Asn Val Met Met Asn Thr Gly Trp Glu Asn
                565                 570                 575

Glu Asp Pro Asp Ser His Glu Arg Phe Tyr Gln Ala Ile Ser Asn Val
                580                 585                 590

Leu Asn Pro Pro Gln Pro Asn Asn Ala Gly Leu Gln Ser Leu Ala Trp
                595                 600                 605

Val Val Asn Arg Asp Asn Ala Arg Glu Ala Gly Phe His Ala Ala Leu
610                 615                 620

His Gly Leu Phe Tyr Thr Cys Asp Asn Pro Ala Arg Val Val Ser Glu
625                 630                 635                 640

Phe Gln Val Gly Gly Gly Lys Leu Asp Leu Val Leu Ser Arg Ala
                645                 650                 655

Ile Gly Arg Met Gly Gly Thr Tyr Pro Ile Gly Thr Glu Leu Lys Phe
                660                 665                 670

Ala Ala Thr Glu Ala Asp Val Gln Asn Arg Glu Glu Ala Asp Glu
                675                 680                 685

Gln Val Glu Gly Tyr Leu Gln Ser Arg Gly Phe Asp Arg Ile Thr Asp
690                 695                 700

Gly Asp Lys Met Val Phe Ser Tyr Ala Val Phe Asn Asp Gln Ala Pro
705                 710                 715                 720

Ala Pro Ala Gln Asn Val Pro Asn Thr Leu Ile Ala Val Ser Asn Val
                725                 730                 735

Leu Arg Ile Lys Asp Asn Leu Gly Ile Asp Thr Val Asp Asp Phe Pro
                740                 745                 750

Tyr Arg

<210> SEQ ID NO 13
<211> LENGTH: 1473
<212> TYPE: DNA
<213> ORGANISM: Wolbachia pipientis

<400> SEQUENCE: 13
atgccaaaaa gtaaaactaa acgtggaacg gaagatttga agggtaatgc aggcccaagc      60
aaaagatctc gtctcagttc tgatcctaaa aaaaataaag agattatctc tagcaaagta     120
ataagtaagc tgaaggatgt tgttaaaggt gatagaactt cagctattga ggaatgggtc     180
aaggctcacc ctgtcacagt agagggtcta atcgttgagc aatcggacct cttatgtaat     240
gcgtttcgtg atgaatcttg ttggtcaggt gcgacactag atgttgctaa attggtagga     300

-continued

```
gaattagcta aatcaggtgt gttgaatcca tttgctatat ataaaatagc atgtattgag      360
tgtgtagaga gtgaaattaa gcaattattt gacaaggcgt tagagtcttt tagatctgac      420
ttatctcata aaggtgcatg tgaggaagat aggaatttag cttgcagtga taagcttgca      480
agagttgaat tgttaagttc catgggaaga cgtgatcctg ttttcaattt ctggattgat      540
caagaatcag gtaaccttag agaaaatata gaagcagaag atggatttaa taaggctgta      600
gatttcaagt ggagtaaggg agtggaacac ttctataatc gtctgtgttc tgaagaaaaa      660
ttagtgaaag aagagagaga aaaattgcta gtttctgcta ttgcaaaatt atctccattg      720
caatctagct ataaacttgc ttctacctta aattcccttc taggtaaagt cataagcgca      780
aaagtagatc ataagtcact acttgggcta ccgaataaga gagatagggg tgtgatctat      840
cgtcctctta gttacttagt agagcacggt tttctttgca caactaagta tgttatccag      900
tacttgagcg agggatgttc aagatctgaa gtagagaaaa tgctttcacc tagaggatat      960
gcacatcttc tctcatcgct ttcatttgtt gtagtttcta agattatga cttggataac     1020 aggaatgaag caaggtcagc tattagcagt ctttgggaat ctagtgtatt taaccaaaat     1080
aaaataaatg ttgtcgatcc ttttaaagat aggattgctt tgttgcaat ggaaaatgca     1140 atttcaaatt tgattgtaga tcaggagaac agtaaggata ctcaaagtgc tggcgatggt     1200
gaaaaagttg atttggtctt gagtatttta agtttgcta aagattgttg ttcagacaaa     1260
agctttaaat cattaaaagc gaggatagca aatagtttag ataaaacaag gaattctaag     1320
atgatagatg caactagctc ctgcaattta atagaagagt tgtgtaagtc agcgagaaat     1380
ttgaatttat tctctgctag cactgaaggt cctcaatcta cgttagtggg tactaatgtt     1440
agtatttcgc ctgctgcagt tgttaacaaa tag                                  1473
```

```
<210> SEQ ID NO 14
<211> LENGTH: 490
<212> TYPE: PRT
<213> ORGANISM: Wolbachia pipientis

<400> SEQUENCE: 14

Met Pro Lys Ser Lys Thr Lys Arg Gly Thr Glu Asp Leu Lys Gly Asn
1               5                   10                  15

Ala Gly Pro Ser Lys Arg Ser Arg Leu Ser Ser Asp Pro Lys Lys Asn
            20                  25                  30

Lys Glu Ile Ile Ser Ser Lys Val Ile Ser Lys Leu Lys Asp Val Val
        35                  40                  45

Lys Gly Asp Arg Thr Ser Ala Ile Glu Glu Trp Val Lys Ala His Pro
    50                  55                  60

Val Thr Val Glu Gly Leu Ile Val Glu Gln Ser Asp Leu Leu Cys Asn
65                  70                  75                  80

Ala Phe Arg Asp Glu Ser Cys Trp Ser Gly Ala Thr Leu Asp Val Ala
                85                  90                  95

Lys Leu Val Gly Glu Leu Ala Lys Ser Gly Val Leu Asn Pro Phe Ala
            100                 105                 110

Ile Tyr Lys Ile Ala Cys Ile Glu Cys Val Glu Ser Glu Ile Lys Gln
        115                 120                 125

Leu Phe Asp Lys Ala Leu Glu Ser Phe Arg Ser Asp Leu Ser His Lys
    130                 135                 140

Gly Ala Cys Glu Glu Asp Arg Asn Leu Ala Cys Ser Asp Lys Leu Ala
145                 150                 155                 160

Arg Val Glu Leu Leu Ser Ser Met Gly Arg Arg Asp Pro Val Phe Asn
```

```
                 165                 170                 175
Phe Trp Ile Asp Gln Glu Ser Gly Asn Leu Arg Glu Asn Ile Glu Ala
            180                 185                 190

Glu Asp Gly Phe Asn Lys Ala Val Asp Phe Lys Trp Ser Lys Gly Val
        195                 200                 205

Glu His Phe Tyr Asn Arg Leu Cys Ser Glu Glu Lys Leu Val Lys Glu
    210                 215                 220

Glu Arg Glu Lys Leu Leu Val Ser Ala Ile Ala Lys Leu Ser Pro Leu
225                 230                 235                 240

Gln Ser Ser Tyr Lys Leu Ala Ser Thr Leu Asn Ser Leu Leu Gly Lys
                245                 250                 255

Val Ile Ser Ala Lys Val Asp His Lys Ser Leu Leu Gly Leu Pro Asn
            260                 265                 270

Lys Arg Asp Arg Gly Val Ile Tyr Arg Pro Leu Ser Tyr Leu Val Glu
        275                 280                 285

His Gly Phe Leu Cys Thr Thr Lys Tyr Val Ile Gln Tyr Leu Ser Glu
    290                 295                 300

Gly Cys Ser Arg Ser Glu Val Glu Lys Met Leu Ser Pro Arg Gly Tyr
305                 310                 315                 320

Ala His Leu Leu Ser Ser Leu Ser Phe Val Val Ser Lys Asp Tyr
                325                 330                 335

Asp Leu Asp Asn Arg Asn Glu Ala Arg Ser Ala Ile Ser Ser Leu Trp
            340                 345                 350

Glu Ser Ser Val Phe Asn Gln Asn Lys Ile Asn Val Val Asp Pro Phe
        355                 360                 365

Lys Asp Arg Ile Ala Phe Val Ala Met Glu Asn Ala Ile Ser Asn Leu
    370                 375                 380

Ile Val Asp Gln Glu Asn Ser Lys Asp Thr Gln Ser Ala Gly Asp Gly
385                 390                 395                 400

Glu Lys Val Asp Leu Val Leu Ser Ile Leu Lys Phe Ala Lys Asp Cys
                405                 410                 415

Cys Ser Asp Lys Ser Phe Lys Ser Leu Lys Ala Arg Ile Ala Asn Ser
            420                 425                 430

Leu Asp Lys Thr Arg Asn Ser Lys Met Ile Asp Ala Thr Ser Ser Cys
        435                 440                 445

Asn Leu Ile Glu Glu Leu Cys Lys Ser Ala Arg Asn Leu Asn Leu Phe
    450                 455                 460

Ser Ala Ser Thr Glu Gly Pro Gln Ser Thr Leu Val Gly Thr Asn Val
465                 470                 475                 480

Ser Ile Ser Pro Ala Ala Val Val Asn Lys
                485                 490

<210> SEQ ID NO 15
<211> LENGTH: 2091
<212> TYPE: DNA
<213> ORGANISM: Wolbachia pipientis

<400> SEQUENCE: 15
atgcatggta ataatgaaga tcgtgaatta gttagggctt tattaagtgg aggttgtgat      60
gagtttagta gacaatttgt aggtttttta aacaactgtc catcttttttt gcattcggct    120 aataagcctg gctttttttcc tacattcttt tttggtatgt tttctactgc acatgatgca    180
ggtatattag ttgaaggtga agagtctat tttcgttttg acaattatgg aaatctaaaa     240
gttgctgttc tcactaataa agaaaataga agaatagtca ggtgttatac tgttgctgat    300
```

```
aatgagaaca gccctgggtc aaggtttagt gcagaagaga agcagcaggt agaagagaat    360
cttccacaag aattacagga agatgaggat ctggattggg aagagtataa aatatttcgg    420
tttggagaag aatgtaggtt tattcatgaa atagatagat ttcctcaacg tgatgaacct    480
ggagctccaa tttttcatga aattaaccca atcagagaac aaggtgaatt gttagacctg    540
atgagtgagt tggcaaatga cgatacagga gaagtgcgta ctaatgttaa agaatttttg    600
gaatatgtta ttgatatcca tgatgaacat gaagatagct tagtgtttcg tgcagagtct    660
gactaccacg gttttctgtg tgggtttta gtaaatttta gataccgagc tttggctgat    720
ttctacccag agctacttat aggaaaaggt tatgcagatg ttgttttgct tgttcgtggt    780
gttgatcaga caaatgattc ggttccaatt ataattgagt tgaaggttgg tgatgaggaa    840
ggattagagc aagctaaaga ttatgctaaa agttgttctg tttcgtcttt gcctattcat    900
acctcatcac caagtgctgt ttgtgtagcg ttaaattttc aattacgtgg aggtgctggt    960
ctccgaactt ctgtgcaggc ttttcagaa ggtggtcttt ccttaatacc gggtttacta   1020
catcctcatg gaaatggagt taggggaaat gtaaaacgtt tttacaacc catagcatca   1080
gagttcactc aatcgcctca ttgtaacact ttttcctgta cttcatcgtt tgttttggga   1140
aatgttttat ctacaaggag ggacttagaa acaaatgatg gcgggaggt aagggttacc   1200
aagtatctat ttaaccactc tcagggagag aaaatgaaac gtacaggtgg tagaggagat   1260
gcagcagata ttgtaagcca tgcgttaact ttagctctat ttttatcaaa tattggtttt   1320
gttgtgcttc acatttttcg tcgtttaaag tggcagactt taccagacaa ggcattgaac   1380
ctgtcgttac tgcctcaagc cacagatgat gctaaggtgc gtcaagtact ttgtgaagta   1440
gatgtccagg gtcatctgga agtggcttct gcaagaaat tcgaatcact acgtgcttac   1500
tcacgttctc atagtgaagg ttatttcgag ggaaggtttt cagaacaaat gggtaatgtt   1560
aggaatttac atcaacttgc agatcagttg atgagtgctg agcctaattt tggtaatgat   1620
ggtaatgtta atggtgagta cagggctagg tatgaagttt atttaatga gatttctcgt   1680
ctgttgtctc cgttattaaa tggaaaccgt ctactcgtga acaatgaagc taaatttcag   1740
gctttgttgc gtggaatatt tcaaaattgc gataatcctg ccaaggtaat tattgagttc   1800
cagctacaga gaggaaggaa atagaccta gtattatcaa aatctgcgga aaatgatgat   1860
actcatccaa ttggaataga gttgaagtat gctaacaccg cagaacaagt tgaacgaaaa   1920
agggtggagg caaatcgaca gttaagtgaa tacgaatttt gtggaggatg caagcgtatt   1980
actggggag atgcgatggt tttgttatac gctatattaa atgctgtagg acaagagcag   2040
gatctgatat tgattggtgg gcttcgtaga gcatctgggt tttctagatg a              2091
```

<210> SEQ ID NO 16
<211> LENGTH: 696
<212> TYPE: PRT
<213> ORGANISM: Wolbachia pipientis

<400> SEQUENCE: 16

```
Met His Gly Asn Asn Glu Asp Arg Glu Leu Val Arg Ala Leu Leu Ser
 1               5                  10                  15

Gly Gly Cys Asp Glu Phe Ser Arg Gln Phe Val Gly Phe Leu Asn Asn
                20                  25                  30

Cys Pro Ser Phe Leu His Ser Ala Asn Lys Pro Gly Phe Phe Pro Thr
            35                  40                  45

Phe Phe Phe Gly Met Phe Ser Thr Ala His Asp Ala Gly Ile Leu Val
```

-continued

```
         50                  55                  60
Glu Gly Glu Arg Val Tyr Phe Arg Phe Asp Asn Tyr Gly Asn Leu Lys
 65                  70                  75                  80

Val Ala Val Leu Thr Asn Lys Glu Asn Arg Arg Ile Val Arg Cys Tyr
                 85                  90                  95

Thr Val Ala Asp Asn Glu Asn Ser Pro Gly Ser Arg Phe Ser Ala Glu
                100                 105                 110

Glu Lys Gln Gln Val Glu Glu Asn Leu Pro Gln Glu Leu Gln Glu Asp
            115                 120                 125

Glu Asp Leu Asp Trp Glu Glu Tyr Lys Ile Phe Arg Phe Gly Glu Glu
        130                 135                 140

Cys Arg Phe Ile His Glu Ile Asp Arg Phe Pro Gln Arg Asp Glu Pro
145                 150                 155                 160

Gly Ala Pro Ile Phe His Glu Ile Asn Pro Ile Arg Glu Gln Gly Glu
                165                 170                 175

Leu Leu Asp Leu Met Ser Glu Leu Ala Asn Asp Asp Thr Gly Glu Val
                180                 185                 190

Arg Thr Asn Val Lys Arg Ile Leu Glu Tyr Val Ile Asp Ile His Asp
            195                 200                 205

Glu His Glu Asp Ser Leu Val Phe Arg Ala Glu Ser Asp Tyr His Gly
    210                 215                 220

Phe Leu Cys Gly Phe Leu Val Asn Phe Arg Tyr Arg Ala Leu Ala Asp
225                 230                 235                 240

Phe Tyr Pro Glu Leu Leu Ile Gly Lys Gly Tyr Ala Asp Val Val Leu
                245                 250                 255

Leu Val Arg Gly Val Asp Gln Thr Asn Asp Ser Val Pro Ile Ile Ile
            260                 265                 270

Glu Leu Lys Val Gly Asp Glu Gly Leu Glu Gln Ala Lys Asp Tyr
        275                 280                 285

Ala Lys Ser Cys Ser Val Ser Ser Leu Pro Ile His Thr Ser Ser Pro
290                 295                 300

Ser Ala Val Cys Val Ala Leu Asn Phe Gln Leu Arg Gly Gly Ala Gly
305                 310                 315                 320

Leu Arg Thr Ser Val Gln Ala Phe Ser Glu Gly Leu Ser Leu Ile
                325                 330                 335

Pro Gly Leu Leu His Pro His Gly Asn Gly Val Arg Gly Asn Val Lys
            340                 345                 350

Arg Phe Leu Gln Pro Ile Ala Ser Glu Phe Thr Gln Ser Pro His Cys
        355                 360                 365

Asn Thr Phe Ser Cys Thr Ser Ser Phe Val Phe Gly Asn Val Leu Ser
    370                 375                 380

Thr Arg Arg Asp Leu Glu Thr Asn Asp Gly Arg Glu Val Arg Val Thr
385                 390                 395                 400

Lys Tyr Leu Phe Asn His Ser Gln Gly Glu Lys Met Lys Arg Thr Gly
                405                 410                 415

Gly Arg Gly Asp Ala Ala Asp Ile Val Ser His Ala Leu Thr Leu Ala
            420                 425                 430

Leu Phe Leu Ser Asn Ile Gly Phe Val Val Leu His Ile Phe Arg Arg
        435                 440                 445

Leu Lys Trp Gln Thr Leu Pro Asp Lys Ala Leu Asn Leu Ser Leu Leu
    450                 455                 460

Pro Gln Ala Thr Asp Asp Ala Lys Val Arg Gln Val Leu Cys Glu Val
465                 470                 475                 480
```

```
Asp Val Gln Gly His Leu Glu Val Ala Ser Ala Lys Phe Glu Ser
                485                 490                 495
Leu Arg Ala Tyr Ser Arg Ser His Ser Glu Gly Tyr Phe Glu Gly Arg
            500                 505                 510
Phe Ser Glu Gln Met Gly Asn Val Arg Asn Leu His Gln Leu Ala Asp
            515                 520                 525
Gln Leu Met Ser Ala Glu Pro Asn Phe Gly Asn Asp Gly Asn Val Asn
        530                 535                 540
Gly Glu Tyr Arg Ala Arg Tyr Glu Val Leu Phe Asn Glu Ile Ser Arg
545                 550                 555                 560
Leu Leu Ser Pro Leu Leu Asn Gly Asn Arg Leu Leu Val Asn Asn Glu
                565                 570                 575
Ala Lys Phe Gln Ala Leu Leu Arg Gly Ile Phe Gln Asn Cys Asp Asn
            580                 585                 590
Pro Ala Lys Val Ile Ile Glu Phe Gln Leu Gln Arg Gly Arg Lys Ile
        595                 600                 605
Asp Leu Val Leu Ser Lys Ser Ala Glu Asn Asp Asp Thr His Pro Ile
    610                 615                 620
Gly Ile Glu Leu Lys Tyr Ala Asn Thr Ala Glu Gln Val Glu Arg Lys
625                 630                 635                 640
Arg Val Glu Ala Asn Arg Gln Leu Ser Glu Tyr Glu Phe Cys Gly Gly
                645                 650                 655
Cys Lys Arg Ile Thr Gly Gly Asp Ala Met Val Leu Leu Tyr Ala Ile
            660                 665                 670
Leu Asn Ala Val Gly Gln Glu Gln Asp Leu Ile Leu Ile Gly Gly Leu
        675                 680                 685
Arg Arg Ala Ser Gly Phe Ser Arg
    690                 695

<210> SEQ ID NO 17
<211> LENGTH: 1338
<212> TYPE: DNA
<213> ORGANISM: Wolbachia pipientis

<400> SEQUENCE: 17
atggaatctg gtttggatca caattacaat aaaatacttg atatattaaa aggtgctatt      60
aaaggcgacg ataatcaagt taaagcaaga aaacacctta gagtagaaag atggttgagg     120
gcttatattc aattaattga agattttgat gaggaaaaac taattttttt ttctgatata     180
ttctctgata attcttgttg ggatggaata aaattaaaga ataaagctgt tggtgaaagg     240
ctaactgaag aaaaaaataa aaatggaaaa gaaaatccgc ttgatcttgc agatagatat     300
tacttggcat gtaaatattg tctagaagat aagattcctg gattatttga acaagtattt     360
atgagattta agagaagtgc ctttgaagaa gatggatctg atgatgatct gagaagagaa     420
ttattggaaa atatcgaaga aactagccct atagaagctt tctggtcttt tcttattgat     480
aagcagattg gaaaactaaa cgaatataaa tcagttgaag gtttgcaaaa atccatacag     540
ataaattcta ataaaaactg gaagaaggt atagagttct tctataataa attacacaat     600
gattccagta tttctagtca agataaagat gatctgttaa ttgaagcagc tttatctgca     660
gtaaagggtt acaagaagt agacaccata gagttttgcc tgtctaaaat ggatgatgag     720
caaaagaaaa aattactaga tagagattat aaggaaaata cttattatgc agtgttgaat     780
gtgctagtag gtcagtatta ctttgattct tttatggaat taagccgatt gtgtagtcag     840
```

-continued

```
attgaatgtg aacgttacac aactttttta tcttcattat cagatcaagt actgaagaat    900
ccagatctgt ctgaagaaac aaaaaaatgt atgatgaatg tttgggaacg tataataaaa    960
ttaaaaactc aagaccgcgg ggagcaatct atttcctcta tttttgtaga ctattcagtt   1020
acatatacaa tagcaaattt aattgtggat ccaagtagac aagggtaag taaagaagaa    1080 atattaggga agatattaaa gcacgtaaaa gaaatgagtg gtgaagagat gataaaggtt   1140
aaagattctg tattaagtaa aattcagtta tttcatgggg gtaaaaaatt gcagttagga   1200
gaacaagtat tttctaaatt agctcaagaa gcttctaaag aatcaatttt gcgtgaagct   1260
ggtgatactt tgccacagtc aagtctcagt acgactgata ccccatataa tataaaatct   1320
ttaagccata gcaaatag                                                 1338
```

<210> SEQ ID NO 18
<211> LENGTH: 445
<212> TYPE: PRT
<213> ORGANISM: Wolbachia pipientis

<400> SEQUENCE: 18

```
Met Glu Ser Gly Leu Asp His Asn Tyr Asn Lys Ile Leu Asp Ile Leu
1               5                   10                  15

Lys Gly Ala Ile Lys Gly Asp Asp Asn Gln Val Lys Ala Arg Lys His
                20                  25                  30

Leu Arg Val Glu Arg Trp Leu Arg Ala Tyr Ile Gln Leu Ile Glu Asp
            35                  40                  45

Phe Asp Glu Glu Lys Leu Ile Phe Phe Ser Asp Ile Phe Ser Asp Asn
        50                  55                  60

Ser Cys Trp Asp Gly Ile Lys Leu Lys Asn Lys Ala Val Gly Glu Arg
65                  70                  75                  80

Leu Thr Glu Glu Lys Asn Lys Asn Gly Lys Glu Asn Pro Leu Asp Leu
                85                  90                  95

Ala Asp Arg Tyr Tyr Leu Ala Cys Lys Tyr Cys Leu Glu Asp Lys Ile
            100                 105                 110

Pro Gly Leu Phe Glu Gln Val Phe Met Arg Phe Lys Arg Ser Ala Phe
        115                 120                 125

Glu Glu Asp Gly Ser Asp Asp Leu Arg Arg Glu Leu Leu Glu Asn
    130                 135                 140

Ile Glu Glu Thr Ser Pro Ile Glu Ala Phe Trp Ser Phe Leu Ile Asp
145                 150                 155                 160

Lys Gln Ile Gly Lys Leu Asn Glu Tyr Lys Ser Val Glu Gly Leu Gln
                165                 170                 175

Lys Ser Ile Gln Ile Asn Ser Asn Lys Asn Trp Glu Glu Gly Ile Glu
            180                 185                 190

Phe Phe Tyr Asn Lys Leu His Asn Asp Ser Ser Ile Ser Ser Gln Asp
        195                 200                 205

Lys Asp Asp Leu Leu Ile Glu Ala Ala Leu Ser Ala Val Lys Gly Tyr
    210                 215                 220

Lys Glu Val Asp Thr Ile Glu Phe Cys Leu Ser Lys Met Asp Asp Glu
225                 230                 235                 240

Gln Lys Lys Lys Leu Leu Asp Arg Asp Tyr Lys Glu Asn Thr Tyr Tyr
                245                 250                 255

Ala Val Leu Asn Val Leu Val Gly Gln Tyr Tyr Phe Asp Ser Phe Met
            260                 265                 270

Glu Leu Ser Arg Leu Cys Ser Gln Ile Glu Cys Glu Arg Tyr Thr Thr
        275                 280                 285
```

```
Phe Leu Ser Ser Leu Ser Asp Gln Val Leu Lys Asn Pro Asp Leu Ser
        290                 295                 300
Glu Glu Thr Lys Lys Cys Met Met Asn Val Trp Glu Arg Ile Ile Lys
305                 310                 315                 320
Leu Lys Thr Gln Asp Arg Gly Glu Gln Ser Ile Ser Ser Ile Phe Val
                325                 330                 335
Asp Tyr Ser Val Thr Tyr Thr Ile Ala Asn Leu Ile Val Asp Pro Ser
                340                 345                 350
Arg Gln Gly Val Ser Lys Glu Glu Ile Leu Gly Lys Ile Leu Lys His
            355                 360                 365
Val Lys Glu Met Ser Gly Glu Glu Met Ile Lys Val Lys Asp Ser Val
        370                 375                 380
Leu Ser Lys Ile Gln Leu Phe His Gly Gly Lys Lys Leu Gln Leu Gly
385                 390                 395                 400
Glu Gln Val Phe Ser Lys Leu Ala Gln Glu Ala Ser Lys Glu Ser Ile
                405                 410                 415
Leu Arg Glu Ala Gly Asp Thr Leu Pro Gln Ser Ser Leu Ser Thr Thr
            420                 425                 430
Asp Thr Pro Tyr Asn Ile Lys Ser Leu Ser His Ser Lys
        435                 440                 445

<210> SEQ ID NO 19
<211> LENGTH: 2199
<212> TYPE: DNA
<213> ORGANISM: Wolbachia pipientis

<400> SEQUENCE: 19
atgccaagta atgtcaagcc gcttgagttg gtacagcttc tgttaatgag aaataaatca    60
aaagacgagt tcctagattt tcaaaaaagg ttccaatcgt ttatcaatca atctccttct   120
tttttgcatt cagttggaaa gccaggcttt tccctagtt tcttttttgg tatgtttgct   180
actgtattag acacagaact tgctactaaa attggtatta aaaaacttca ttttcgtttt   240
gatgataata gaactttaaa aatagctata ttaactaatg agggacttaa gtgtataacg   300
atgtctgatc aagttgatgg taacatgcat ctaaagttct ctcaaggaga gttagaaaaa   360
atagcacaga atggaaaat gggagcagag tttgataaac tagaaaaaga gagcatgaa    420
ataacaatta caggaaaaga agtaaagcac ggaaaggttg atccagcttt tagtaaaaag   480
actgattatt cacaaaaagg ttttacagaa atagaaaaag atcgtgacca acaagaccta   540
gagagcttaa tttcaaaatt gagtaatcaa gatttcgaag aagtaaaaaa gaacgctaga   600
agaatgttta attatattac aaatgtctat aagaaatatg aaaaagaaac tctatttagc   660
ggtaaagaat caagtcatca tgggttttta gctgggtttt tgataaattt taagtatcgt   720
tttcacctaa aactttatct cgaattattt gctggaaaag gttacgcaga cattattttg   780
cttgtgcgcg gttctgataa gtcgctaagc tctattccta ttattattga gcttaaagca   840
ggtactggtg agataagtac agtgataaaa gcattgaagc aagcacaaga ttatgttaag   900
ggctcttttt ctaactctat aagaatgatt actatagcta atgaagctat tgtgtagga    960
ttaaattttg acatggttca tcacgaaaat gttaaaattg atgtagaaaa ttttcttagt  1020
cgagaaggta attctgtaat agaaaagtta cttggcactg aagcaacgaa tgctgaggtg  1080
ataagaacac agctagagta tctttactat ggaattgttt ggagcaatgg tggaagtgat  1140
aatattaatt atgtcagcag aatgatctta ggtcagctag tacttatttc taatattatt  1200
```

```
aagcgtgaaa agttaggtaa acatattttt atttatgatc aaaatgataa aatggttact   1260
ggatcacaga aacgcccaga agcagcaaaa gaaagtattg aggattgtgt tacaactata   1320
gtgctaactt taggtaagaa ggtgcttata ctcaacataa atgaaaaaaa tgaatttgca   1380
ttgagagtgc cagataataa aggaattcct attgaaaata ttaggagaat tcaaaacgtc   1440
aatgacataa agatacaaga ataaacctgt aacttataca gtacgcctag taataagaat   1500
ccatttgatc agtactgtaa taagaataag ggaattacag taaatacgta tgactcattg   1560
gacaaataca aagaggtaa agaaattta caaggtaatt ttactcgaat tgtggaaaat    1620
aaaaaattta aagcagcttt gagcaaagct atagaatctg gtaaatatga tgattacaaa   1680
aaactatttg aagaaatttc tcatatacta catcctttca aatcattaat aagcaatgag   1740
gctacatttc aagctgtatt gcatggttta tttagtagct acggagaaga taatataaaa   1800
gttattactg aatttcaaat aggtggtgga gagaagttgg atgttatgtt ggttataaat   1860
gctactgatc aaaaaaaaga ataccccca gttggaatag agctaaaatt tgctaagaaa   1920
ggagaattgg ataaaaaaga aaaagatgct aaggaccagt tgaaaagata taagaaggt   1980 gaagcgtata aggtaattac tgatgctggc aaagtgaaac tgatatatgc tgtttttaat   2040
aaaggtgcaa cagatgaagg ttcccttata aaaattggta atgagtttgt agaggtagat   2100
gtaagacata gctctgtggt tgcttttggt caacagccag gtagtctcca acaaccttat   2160
gttaaacaag caggtctatc tcgagcagtt aatcagtga                         2199
```

<210> SEQ ID NO 20
<211> LENGTH: 732
<212> TYPE: PRT
<213> ORGANISM: Wolbachia pipientis

<400> SEQUENCE: 20

```
Met Pro Ser Asn Val Lys Pro Leu Glu Leu Val Gln Leu Leu Leu Met
1               5                   10                  15

Arg Asn Lys Ser Lys Asp Glu Phe Leu Asp Phe Gln Lys Arg Phe Gln
                20                  25                  30

Ser Phe Ile Asn Gln Ser Pro Ser Phe Leu His Ser Val Gly Lys Pro
            35                  40                  45

Gly Phe Phe Pro Ser Phe Phe Gly Met Phe Ala Thr Val Leu Asp
        50                  55                  60

Thr Glu Leu Ala Thr Lys Ile Gly Ile Lys Lys Leu His Phe Arg Phe
65                  70                  75                  80

Asp Asp Asn Arg Thr Leu Lys Ile Ala Ile Leu Thr Asn Glu Gly Leu
                85                  90                  95

Lys Cys Ile Thr Met Ser Asp Gln Val Asp Gly Asn Met His Leu Lys
            100                 105                 110

Phe Ser Gln Gly Glu Leu Glu Lys Ile Ala Gln Lys Trp Lys Met Gly
        115                 120                 125

Ala Glu Phe Asp Lys Leu Glu Lys Glu His Glu Ile Thr Ile Thr
    130                 135                 140

Gly Lys Glu Val Lys His Gly Lys Val Asp Pro Ala Phe Ser Lys Lys
145                 150                 155                 160

Thr Asp Tyr Ser Gln Lys Gly Phe Thr Glu Ile Glu Lys Asp Arg Asp
                165                 170                 175

Gln Gln Asp Leu Glu Ser Leu Ile Ser Lys Leu Ser Asn Gln Asp Phe
            180                 185                 190

Glu Glu Val Lys Lys Asn Ala Arg Arg Met Phe Asn Tyr Ile Thr Asn
```

```
            195                 200                 205
Val Tyr Lys Lys Tyr Glu Lys Glu Thr Leu Phe Ser Gly Lys Glu Ser
210                 215                 220

Ser His His Gly Phe Leu Ala Gly Phe Leu Ile Asn Phe Lys Tyr Arg
225                 230                 235                 240

Phe His Leu Lys Leu Tyr Leu Glu Leu Phe Ala Gly Lys Gly Tyr Ala
                    245                 250                 255

Asp Ile Ile Leu Leu Val Arg Gly Ser Asp Lys Ser Leu Ser Ser Ile
                260                 265                 270

Pro Ile Ile Ile Glu Leu Lys Ala Gly Thr Gly Glu Ile Ser Thr Val
            275                 280                 285

Ile Lys Ala Leu Lys Gln Ala Gln Asp Tyr Val Lys Gly Ser Phe Ser
        290                 295                 300

Asn Ser Ile Arg Met Ile Thr Ile Ala Asn Glu Ala Ile Cys Val Gly
305                 310                 315                 320

Leu Asn Phe Asp Met Val His His Glu Asn Val Lys Ile Asp Val Glu
                    325                 330                 335

Asn Phe Leu Ser Arg Glu Gly Asn Ser Val Ile Glu Lys Leu Leu Gly
                340                 345                 350

Thr Glu Ala Thr Asn Ala Glu Val Ile Arg Thr Gln Leu Glu Tyr Leu
            355                 360                 365

Tyr Tyr Gly Ile Val Trp Ser Asn Gly Gly Ser Asp Asn Ile Asn Tyr
        370                 375                 380

Val Ser Arg Met Ile Leu Gly Gln Leu Val Leu Ile Ser Asn Ile Ile
385                 390                 395                 400

Lys Arg Glu Lys Leu Gly Lys His Ile Phe Ile Tyr Asp Gln Asn Asp
                    405                 410                 415

Lys Met Val Thr Gly Ser Gln Lys Arg Pro Glu Ala Ala Lys Glu Ser
                420                 425                 430

Ile Glu Asp Cys Val Thr Thr Ile Val Leu Thr Leu Gly Lys Lys Val
            435                 440                 445

Leu Ile Leu Asn Ile Asn Glu Lys Asn Glu Phe Ala Leu Arg Val Pro
        450                 455                 460

Asp Asn Lys Gly Ile Pro Ile Glu Asn Ile Arg Arg Ile Gln Asn Val
465                 470                 475                 480

Asn Asp Ile Lys Ile Gln Glu Ile Thr Cys Asn Leu Tyr Ser Thr Pro
                    485                 490                 495

Ser Asn Lys Asn Pro Phe Asp Gln Tyr Cys Asn Lys Asn Lys Gly Ile
                500                 505                 510

Thr Val Asn Thr Tyr Asp Ser Leu Asp Lys Tyr Lys Arg Gly Lys Glu
            515                 520                 525

Ile Leu Gln Gly Asn Phe Thr Arg Ile Val Glu Asn Lys Lys Phe Lys
        530                 535                 540

Ala Ala Leu Ser Lys Ala Ile Glu Ser Gly Lys Tyr Asp Asp Tyr Lys
545                 550                 555                 560

Lys Leu Phe Glu Glu Ile Ser His Ile Leu His Pro Phe Lys Ser Leu
                    565                 570                 575

Ile Ser Asn Glu Ala Thr Phe Gln Ala Val Leu His Gly Leu Phe Ser
                580                 585                 590

Ser Tyr Gly Glu Asp Asn Ile Lys Val Ile Thr Glu Phe Gln Ile Gly
            595                 600                 605

Gly Gly Glu Lys Leu Asp Val Met Leu Val Ile Asn Ala Thr Asp Gln
610                 615                 620
```

-continued

```
Lys Lys Glu Tyr Pro Pro Val Gly Ile Glu Leu Lys Phe Ala Lys Lys
625                 630                 635                 640

Gly Glu Leu Asp Lys Glu Lys Asp Ala Lys Asp Gln Leu Lys Arg
            645                 650                 655

Tyr Lys Glu Gly Glu Ala Tyr Lys Val Ile Thr Asp Ala Gly Lys Val
            660                 665                 670

Lys Leu Ile Tyr Ala Val Phe Asn Lys Gly Ala Thr Asp Glu Gly Ser
            675                 680                 685

Leu Ile Lys Ile Gly Asn Glu Phe Val Glu Val Asp Val Arg His Ser
690                 695                 700

Ser Val Val Ala Phe Gly Gln Gln Pro Gly Ser Leu Gln Gln Pro Tyr
705                 710                 715                 720

Val Lys Gln Ala Gly Leu Ser Arg Ala Val Asn Gln
                725                 730

<210> SEQ ID NO 21
<211> LENGTH: 22
<212> TYPE: DNA
<213> ORGANISM: Artificial Sequence
<220> FEATURE:
<223> OTHER INFORMATION: Synthetic Construct

<400> SEQUENCE: 21
gggcgtgccc ttgagttctc tc                                    22

<210> SEQ ID NO 22
<211> LENGTH: 21
<212> TYPE: DNA
<213> ORGANISM: Artificial Sequence
<220> FEATURE:
<223> OTHER INFORMATION: Synthetic Construct

<400> SEQUENCE: 22
cgaggatcgc ataccgcact g                                     21

<210> SEQ ID NO 23
<211> LENGTH: 22
<212> TYPE: DNA
<213> ORGANISM: Artificial Sequence
<220> FEATURE:
<223> OTHER INFORMATION: Synthetic Construct

<400> SEQUENCE: 23
gggcgtgccc ttgagttctc tc                                    22

<210> SEQ ID NO 24
<211> LENGTH: 20
<212> TYPE: DNA
<213> ORGANISM: Artificial Sequence
<220> FEATURE:
<223> OTHER INFORMATION: Synthetic Construct

<400> SEQUENCE: 24
aacgctttgc tttctcgctg                                       20

<210> SEQ ID NO 25
<211> LENGTH: 1425
<212> TYPE: DNA
<213> ORGANISM: Artificial Sequence
<220> FEATURE:
<223> OTHER INFORMATION: Synthetic construct

<400> SEQUENCE: 25
```

```
atgcccattg agacaaagcg ccaggccgag gtgctgaaga agctgcagga tgtgattaag      60
catacagacc gcgatattgc cgccggacgc aagctggcca tcaagcgctg ggtggagaca     120
tacatcgagt atattaagct gttcaaggat gacaagctgg agttcctgta caacgtgttt     180
cgcgacgagg atgctggct gggcacccgc ctgaacaata cggtgctggg acagaagctg      240
accgaggaga gatcggcga gattgataat ccactgccac gctacggaat ggcctcccgc      300
tattgcatca caggaaagat tggcgacttc tttaacaagc agttcgtgct gtcccgcgga     360
cagtttacct cggaggaggt ggatagtcag ggcaacccaa tctcggacca gtacgtgcgc     420
aatattctgc tgagctccat gaagcgcaac ggccccgtgt tcgattttg gatcgaccgc      480
gagtcgggag agctgaagaa gtacgatgcc gtggagggct cgacagtac ggtgaagctg      540
aagtggagcg agggcgtgga gtacttttat aatcagctgg aggagaagga taaggagaag     600
aagctgacag aggccatcgt ggccctgtcg cgcccacaga gtgtgaagcg cgatgccccg     660
atcctggact tctgcgtgcg caacattgga gataaggaca ccctgctgca gaagctgctg     720
cagaaggaca agggcgtgta cttcctgctg gccgagctga tcgagagctg cttctttgat    780
acggtgcacg acctggtgca gtgctggtgc tataagggcg tgtccgccgg aggagattgc     840
agcgacaaga tttttctccca gcaggattac gagctgtttc tgtattcgct gagtaacgtg    900
atgctgaaga atccagagct gtcggtgcag gcccgcagtc tgatcatgga gatttggaag    960
tgcgagcgct tcgccgagta ccgcgagacc agcgtgaaca cgtccaatta tacagtgccg   1020
atcaagtcgg tgctgggcgg actgatcatt aattggaagc gcgaggatgt gtgcaagcca   1080
gaccgcgaga ttgagaagga ggagatcctg gatatgatta gcttcgccaa gggctgcttt   1140
cccgagaagt tcgacctgtt taaggaggtc atgatcgaga acctgcgcat tgcggacgc    1200
gagggcaagc gcaagggagt ggattacggc aagttcgccg aggagctgtt tctgcagctg   1260
gagaaggtga cgctgccatc cgtgggcgac ggaccatgga caatctgcg cagccagtcc   1320
aaggtgagcc tgccactgga tggctccgga gacggaccac agtcggagtt cgaggcccca   1380
tcggtgagtg gaatcagcgg ctcccataag aagcgccgca tttaa                   1425
```

<210> SEQ ID NO 26
<211> LENGTH: 3500
<212> TYPE: DNA
<213> ORGANISM: Artificial Sequence
<220> FEATURE:
<223> OTHER INFORMATION: Synthetic construct

<400> SEQUENCE: 26

```
atggacggag acctggacgg ctttcgccag gagtttgaga gttttctgga tcagtgcccc     60
ttctttctgt atcatgtgag cacgggacgc tttctgcccg tgttctttt cagcatgttc     120
gccacggccc atgacgccaa tattctgaag gccaacgagc gcgtgtactt cgcttcgac     180
aatcacggca tcgatacggg cggacgcaat cgcaacacag aaaacctgaa ggtggccgtg    240
taccatgatg gccagcaggt ggtgcgctgc tatagcattt ccgaccgcct gaatagcgat    300
ggactgcgct ctccacgcg cgagcgcaac gccctggtgc gcgagatccg cggccagaat    360
ccgaacctgc gcgaggagga cctgaacttc gagcagtaca aggtgtgcat gcacggaaag    420
ggcaagtccc agggagaggc cattgccacc gtgtttgagg tcatccgcga aaggactcc    480
cagggacgcg atcgcttcgc caagtactcg gccagtgaga tttcgctgct gcgccatatc    540
gagcgcaacc gcctgaatgg catcaacgcc ccagccccac gcagcctgct gaccgtgaag   600
```

```
gagattggca gcatccgcct gaatcaggac cagcgcgtgc agctgggaca cctggtgaac     660
ttcgtgcagg tggccccagg acagcagggc atctttagct tcatggaggt gctggcctcc    720
aatcagaaga tcaacattga gcgcggaatt aacgagggca tcctgcccta cattacacgc    780
atctaccgca gctatctggg ctccctgcag aatgatattc agaaccgcag ccagaagttt    840
gagtcccacg atttttcct gggcctgctg gccaatttca tccatctgta caccatcgat     900
attgacctgg atctgtcgcc gggcaacagt tatgtggcct tcctgatttg ccaccaggcc    960
gagcgcgaga atatcccaat tgtgatcaac gtgacccgct ggcgcacgag ctccgacatc   1020
gccctgaacc gcgcccgcgc cgatgccaag cgcctgcacg tgtcgagttt catttcgatc   1080
cataccgaga gtcgcaacgc cgtgtgcatc ggcctgaatt ttaacctgaa tattgacccc   1140
ttcagcatcg atacggtgga gtttctggag aatcgcttcc cgctggtgca gcgcctgttt   1200
gagtgcctgg aggacgaggg cattcgcgag aacatccgcg atttcctgct gcagcacctg   1260
ccgaatgaga tcccacgcaa cgccgagaac tacaatcgca ttttcgactg catcaccgga   1320
tttgccttcg gcaattccat tctggaggag ttccgcctgg tgaacgccgt gcagcagcgc   1380
gtgcgcaagt acatctttcg ctatggagat gagaaccacg ccctgacaat ggtgttccat   1440
acccagggct cggatattgt gatcctgcat attcgcgaca caatgccgt gcagcaggga    1500 gccatcaatc tgcaggacct gaacgtggat ggcaacaatg tgcacgtgcg cgaggtgtcc   1560
tgcacactga acaatcagct gggactgaat atccacaccg ataacctggg cctgtaccat   1620
aactaccaga caacaacgc caacaacttc ctgggcggaa acctggtgca ggtgcccaat     1680
gccgaaaacg tgcacaatgc cctgaaccag gtcatgaatg acggctggca ggatcgcttt   1740
cagcatcagg agctgttccg caacatcagc gccgtgctga tgccagagga cacccacggc   1800
aatatgatca ttgacgtgaa ctcgaaggat aagtttcgca gtatcctgca cggcacgttc   1860
tacgcctcgg ataacccata aggtgctg gccatgtaca agtgggaca gacatatagc      1920 ctgaagcgct ggcaggagga ggagggagag cgcgtgattc tgacacgcgt gaccgagcag   1980
cgcctgggac tgctgctgct gcgccagccc acggccgaca cacccgat cggatacgtg     2040 ctgggcttcg ccgacaacgc cgaggaggtg gagcaggagc aggatgaggc ccgctacaag   2100
attacagagc tgatgagcaa gcagcgcgga tatctgccca tcacctcggg caatgaggtg   2160
gtgctgagtt acgccgtgtt taaccgcgga gcccagcgcg ccgaggattt catctccctg   2220
ccgcagcagg ccgtgtatgt gcaccgcctg gaccgccgcg gacatgattc gcgcccagag   2280
gtgctggtgg gaccagagag tgtgatcgac gagaatcccc cggagaacct gctgagcgat   2340
cagacgcgcg agaactttcg ccgcttctac atggagaagc gcccaggcca gaatagcatt   2400
tttctgctgg acatcgatga caacctgcac gtgcccttct cctatctgca gggcacccgc   2460
gcccaggcca ttgagacgct gcgcagccgc atccgcggag gaggcacctc cacggcccag   2520
ggcattctgc agcagattaa taccatcctg cgccgcaata cgcccgcga gatcgaggat    2580 gtgcataacc tgctggccct ggactttgcc acggagaacc agaatttccg ctactggctg   2640
cagacacacg atatgttttt cgccgcccgc cagtatacat ttcacgatga ccgctcgaat   2700
cccaccaacg accgccatga tttcgccatt acgagcgtgg gagtggacgg caaccagaat   2760
gatccaaccg gacgcgacct gctgagctcc aatatcgaca acttcaagca gaaggtggat   2820
tccggagaga aggaccgcct gaccgccatc attaatgtgg gcaaccgcca ctgggtgacg   2880
ctggtcatcg tgcatcagaa cggaaattac tatggctact atgccgatag cctgggaccg   2940
gactcccgca ttgataataa catccgcggc gccctgcgcg agtgcgatat ttcggatgac   3000
```

| | |
|---|---|
| aatgtgcacg acgttagtgt gcatcagcag acggatggac acaactgcgg catctgggcc | 3060 |
| tacgagaatg cccgcgatat taaccaggcc atcgaccagg ccctgcaggg aaactccaat | 3120 |
| ttcggcgaga agggagaggg catcattgga tacattcgcg gcctgctgtc ggccggaatc | 3180 |
| ggcaatgata cccgccagcc gcagcgcaac gagcagtatt ttcgcaatcg ccgccgcaac | 3240 |
| attagccagc tgttccagaa cgactccctg tcgagtccac gcggacgcct gatccaggga | 3300 |
| cgcccaggca ttcagcatga gatcgatcca ctgctgctgc agttcctgga gctgcagtac | 3360 |
| ccacagcgcg gcggaggagg agccctgcag ctgggaggcg agcgcgtgat ttcgatcgac | 3420 |
| ttcggacccc agagtgtgct ggacgagatc gatggcgtga atcgcgtgta cgatcactcg | 3480 |
| aacggacgcg gcagtcgcta | 3500 |

<210> SEQ ID NO 27
<211> LENGTH: 1473
<212> TYPE: DNA
<213> ORGANISM: Artificial Sequence
<220> FEATURE:
<223> OTHER INFORMATION: Synthetic construct

<400> SEQUENCE: 27

| | |
|---|---|
| atgccaacac agaaggagct gcgcgatacc atgtcgaaga agctgcagga ggccattaag | 60 |
| cacccagacc ccgccgtggt ggccggacgc aagagtgcca tcaagcgctg ggtgggagtg | 120 |
| ctgcaggata acttcatgga gcacattaag tactttaagg gcgacaagct gaagttcctg | 180 |
| cataatgtgt ttcaggatga gggatgctgg tccggcgtgc gcctggataa tgccgccctg | 240 |
| ggacagcgct tcaccgagga gaagattggc ggaatcgata cccgctgcg caagtacgag | 300 |
| atggcctgct cgtattgcgt ggtggacaag atccacccac tgtttcagaa gcgcttcgag | 360 |
| agttaccgca ataagttccc gcccggagcc tttgatggca gacagagac cgagttcggc | 420 |
| aagtatgtgc gcaactcgct gctggacagt attaagcgca agggaccagt gtttgacttc | 480 |
| tggatcgatc gcgagtccgg cgagctgaag aagtacgacg ccgtggaggg atttgattcg | 540 |
| gccgtgaagc tgaagtggag tgagggcgtg gagtacttct ataatcacct gaaggaggag | 600 |
| gataaggaga agaagctgac cgaggccatt ctggccctgt cgcgcgtgca gtcggtggag | 660 |
| aaggatgccc cgattctgga tttctgcgtg aacaagatcg tggataagga caccctgctg | 720 |
| cagaagctgt cgcagaagga caagggcgtg tacagtctgt tcgccgagct gatcgagagc | 780 |
| tgcttctttg acacggtgca cgatctggtg cagtgctggt gctacaagga ggtgtcggcc | 840 |
| ggcggagacc atagcgagaa gatttttctcc cagcgcgatt atgagctgtt tctgagctcc | 900 |
| ctgagcgacg tgatgctgaa gaatccggag tcgaacgtgc aggcccgcag tctgatcatg | 960 |
| gagttctggg agtgcggcag cctgtaccag tatcgcaagg ccgccgtgaa cacgagcaat | 1020 |
| tacacagtgc caacctccgg cgtgttcgcc gagctgattg tgaactggcg ccgcgaggac | 1080 |
| atctataaga cagatgagga aaggagatt gagaagaagg agatcctgga catgatgtcg | 1140 |
| ttcgccaagg attgctttcc cgagaagttt gagctgttca agaagctgat cattcgcgat | 1200 |
| ctgcgcctgt gcgacgcga gggcaagcgc gtgaatgtgg actacggcct gttcgccgag | 1260 |
| gagctgtttta gcgagctgga gaagaccatt ctgccacccg gacccgtggg agatggacca | 1320 |
| tgctccaatc tgcgctcccg cagtaaggcc cacggctcga agaagaccac cctgccggtg | 1380 |
| gatgacagcc cgcagtcgga gctgggaacc cccagcgtgt ccggagtgtc gagttacaag | 1440 |
| aagaagagcg tgttcacgct gagtggcaat aag | 1473 |

<210> SEQ ID NO 28
<211> LENGTH: 3531
<212> TYPE: DNA
<213> ORGANISM: Artificial Sequence
<220> FEATURE:
<223> OTHER INFORMATION: Synthetic construct

<400> SEQUENCE: 28

| | | | | | |
|---|---|---|---|---|---|
| atgtccaacg | agatggcct | gatccgctcg | ctggtggatg | gagacctgga | gggcttccgc | 60 |
| cagggatttg | agtcgttcct | ggaccagtgc | ccgagcttcc | tgtaccacgt | gtccgccggc | 120 |
| cgctttctgc | cagtgttctt | tttctcgatg | ttcagtacag | cccacgatgc | caatatcctg | 180 |
| aacgccaatg | agcgcgtgta | ttttcgcttc | gacaaccatg | gcgtgaaccc | acgcaatgga | 240 |
| gagaaccgca | ataccgccaa | tctgaaggtg | ccgtgtacc | cgcatggcca | gcaggtggtg | 300 |
| cgctgctatt | cgatcagtga | ccgccccaac | tcggatggac | tgcgcttcag | tgagcgcgag | 360 |
| cgcgattttc | tggtgcagga | gatcattcgc | cagaatcagg | gcctgatgga | ggaggacctg | 420 |
| aactttgagc | agtacaaggt | gtgcatgcac | ggaaagggca | gtcccaggg | cgaggccatt | 480 |
| gccaccgtgt | cgaggtcat | ccgcgagaag | gacttccgcg | gacgcgataa | gtttgccaag | 540 |
| tactcggcct | cggaggtgca | cttcctgcgc | cagctgtttc | gcaaccatcg | cctgacgatt | 600 |
| aaggagatcg | agggccgcca | gctgaaccag | aatcagcgcc | gccagctggg | acgcctggtg | 660 |
| aattttgccc | aggtggccca | gggacagcag | ggaatcgaca | acttcatgga | gatgctggcc | 720 |
| tcggatcgcc | gccaggatgt | gcgcgatcgc | attcgccgcg | agatcctgcc | ctacattacc | 780 |
| gatatctaca | caattatcg | ccaggtgctg | gagaacaata | tcgagaaccg | caatcagcgc | 840 |
| ttcgagggac | acggctttct | gctgggcttc | ctggccaatt | tttcccatct | gtgcacgatc | 900 |
| gatattgacc | tggatctgtc | gccccgcaac | agtcacgtgg | ccttcctggt | gcgccatcag | 960 |
| gtggagcgcg | agaatatccc | gattgtgatc | aacctggcca | cacgcgcccc | gccatacatc | 1020 |
| gccctgaatc | gcgcccgctc | ccacgccgag | cgcctgcatg | tgtttagttt | cattcccatc | 1080 |
| cacaccgaga | gccgcaacac | cgtgtgcgtg | ggactgaact | tcaatctgaa | cctggacccc | 1140 |
| ttttcggtgg | atacggtggg | actgcagcag | gatcgcttcc | cgctggtgca | gcgcctgttt | 1200 |
| gagtgcctgg | agaatgaggg | cattcgcgag | aacatccgcg | acttcctgct | gcaccatctg | 1260 |
| cccgccgaga | tcccacgcaa | tgccgagaat | tacgaccgca | ttttttgattg | catcaccggc | 1320 |
| tttgccttcg | gaaacagcgc | cttcgatcgc | gagtatctgg | agctggagga | gggagaggac | 1380 |
| cgcgtgcgcg | tgcgcaagta | catctttcgc | tatggagacg | gcgatctgcg | ccgccacacc | 1440 |
| ctgacaatgg | tgttccatgc | cgagggcagc | gatattgtga | tcctgcacat | tcgcgcccat | 1500 |
| gatgcccagc | agcagggagc | catcaatctg | cagaccctga | atgtgaacgg | aaatgatgtg | 1560 |
| cacgtgtggg | aggtgtcctg | cacgctgaac | aatcagctgg | agctggacat | cgatctgccg | 1620 |
| aacgacctgg | gcctgtacca | tgattatcag | aacaataacg | ccaataactt | cctggccgga | 1680 |
| gatctggtgc | aggtgccaaa | cacagagaat | gtgcacaaca | ccctgaatca | ggtggtgaat | 1740 |
| gacggctgga | agaacattgc | ccagcatcgc | ggcctgttcc | aggagatctc | cggagccctg | 1800 |
| atgcccctgg | tggacacaat | taacgtgaat | agcgaggata | agttccgctc | catcctgcac | 1860 |
| ggcaccttct | acgccagcga | taacccgtat | aaggtgctgg | ccatgtacaa | agtgggccag | 1920 |
| acatattcgc | tgaagcgcgg | acaggaggag | gagggagagc | gcgtgattct | gacgcgcatc | 1980 |
| acagagcagc | gcctggatct | gctgctgctg | cgccagcccc | gcgagaatga | cctggatacc | 2040 |
| cacccccattg | gatacgtgct | gcgcctggcc | aataacagcg | aggaagtggg | acagcagcag | 2100 |

-continued

```
aatgatgccc gccaggagat tggacgcctg aagaagcagc atcgcggctt cattccaatc    2160
acgtccggaa atgaggtggt gctgttccecg ctggtgttta atgccggagc cggacgcgtg    2220
gagggactga tttcgatccc cgagggaatt ggccgcgagg agtacgtgca catcctggat    2280
cgcggcggac gcgatagtcg cccaggcgga ctggtgggac cggagagcgt gatcgatgag    2340
aatcccccgg agggactgct gtcggaccag acccgcgaga actttcgccg cttctacgag    2400
gagaaggccc caggccagaa tagtattttt ctgctggaca tcggagataa cctgcatgtg    2460
cccttcagct atctgcaggg aacccgcgcc caggtcatcg agacactgaa gtcccgcatc    2520
cgcggcggag gcaccccecac cgcccagggc atcctgcagc agattaacgc catcctgcgc    2580
cgcaataacg cccgcgagat tgaggacgtg cacgatctgc tggccctgga cttcgccaca    2640
gataaccaga attaccgcta ttggctgcag acccatgata tgtttttcgc cgcccgccag    2700
tacacctttc tggacaatca gtcgcacagt acgaacgatc attatggctt cgagatcaca    2760
tcggtgggag tggacggcaa ccagaatgat ccgaccggac gcggactgct gagctcccac    2820
attacgaact tcaagcagaa ggtggacagc ggcgagaagg atcgcctgat cgccatcatt    2880
aacgtgggaa atcgccactg ggtgacgctg gtcatcgtgc atcagaacgg caattactat    2940
ggatactatg ccgatagcct gggcccggac tccggaattg ataataacat ccgcggagcc    3000
ctgcgcgagt gcgatattaa cgatgacaat gtgcacaaca tcagcgtgca tcagcagacc    3060
gacggccata actgcggaat ctgggtgtac gagaatgccc gcgacattaa ccaggccatc    3120
gatcaggccc tgcagggcaa taacaatttc ggagagaagg gagagggcat cattggctac    3180
attcgcggac tgctgagcgc cggaattgga aatgataccc gccagccacg ccgcaatgag    3240
cagtatttcg aggaccgccg ccgcgatatc tcccagctgc tgcagaatga cccaaacctg    3300
cccagccgcc gctccgatct gattcaggcc caccecgggca ttcagcatga gatcgatcca    3360
ctgctgctgc agttcctggg actgcagtac ccacagcgcg gaggcggagg cgccctgcag    3420
ctgggaggcg agcgcgtgat ttccatcgac ttcggcaacc cccagtcggc cctggataag    3480
attgatggag tgtcccgcgt gtataaccac agtaacagtc gcggcagtcg c              3531
```